(12) United States Patent
Pedersen

(10) Patent No.: US 6,958,217 B2
(45) Date of Patent: Oct. 25, 2005

(54) SINGLE-STRANDED POLYNUCLEOTIDE TAGS

(75) Inventor: Morten Lorentz Pedersen, Taastrup (DK)

(73) Assignee: Genomic Expression APS, Taastrup (DK)

(*) Notice: Subject to any disclaimer, the term of this patent is extended or adjusted under 35 U.S.C. 154(b) by 285 days.

(21) Appl. No.: 10/053,883

(22) Filed: Jan. 24, 2002

(65) Prior Publication Data

US 2003/0113737 A1 Jun. 19, 2003

Related U.S. Application Data

(60) Provisional application No. 60/267,704, filed on Feb. 12, 2001.

(51) Int. Cl.[7] .............................. C12Q 1/68; C12P 19/34
(52) U.S. Cl. .......................... 435/6; 435/91.1; 435/91.2
(58) Field of Search ........................... 435/6, 91.1, 91.2

(56) References Cited

U.S. PATENT DOCUMENTS

| 6,191,267 B1 | 2/2001 | Kong et al. | |
| 6,660,475 B2 * | 12/2003 | Jack et al. | 435/6 |
| 2003/0022317 A1 | 1/2003 | Jack et al. | |
| 2003/0194736 A1 * | 10/2003 | Bitinaite | 435/6 |

FOREIGN PATENT DOCUMENTS

| WO | 0023619 | 4/2000 |
| WO | 0053744 | 9/2000 |

OTHER PUBLICATIONS

Dong–Jing Fu et al., *Efficient preparation of short DNA sequence ladders potentially suitable for MALDI–TQF DNA sequencing*, Genetic Analysis: Biomolecular Engineering, vol. 12, pp. 137–142, 1996.

* cited by examiner

*Primary Examiner*—Kenneth R. Horlick
(74) *Attorney, Agent, or Firm*—Iver P. Cooper

(57) ABSTRACT

It is one objective of the present invention to obtain reproducible representations of expressed mRNA molecules by exploiting a novel technique that relies on short, single stranded polynucleotide tags. In one preferred embodiment, only one polynucleotide tag is obtained from each mRNA molecule, and relatively simple counting statistics can thus be applied after identification and sampling of the different tags, or a subset of tags being present in the population of representative tags. The tags according to the present invention are preferably single stranded polynucleotide tags obtained by subjecting genetic material derived from a biological sample to at least one site-specific nicking endonuclease capable of i) recognizing a predetermined nucleotide motif comprising complementary nucleotide strands and ii) cleaving only one of said complementary strands in the process of generating the at least one single stranded polynucleotide tag. Accordingly, the present invention demonstrates that nicking endonucleases may advantageously be used for obtaining and isolating ssDNA tags. This novel approach in one embodiment eliminates the occurrence of any linker sequence in the ssDNA tag, and it eliminates the presence of a complementary strand in the isolated polynucleotide tag. The lack of linker sequence in the tag and the lack of any complementary strand serves to reduce the huge complexities associated with the analysis of expressed molecules in a biological sample.

100 Claims, 69 Drawing Sheets

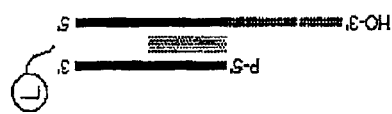
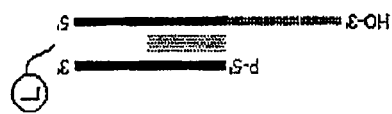
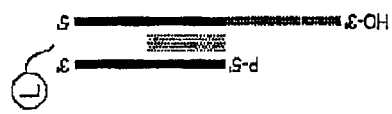
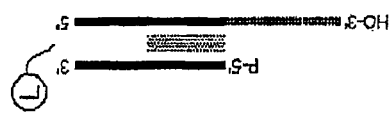
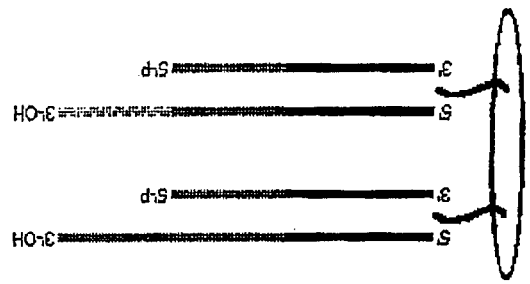
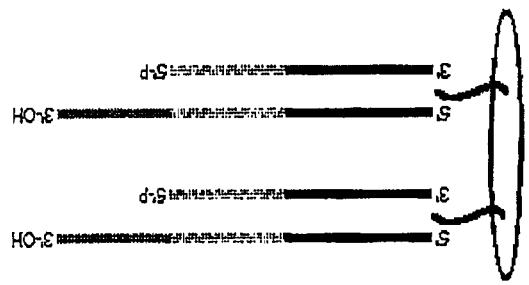
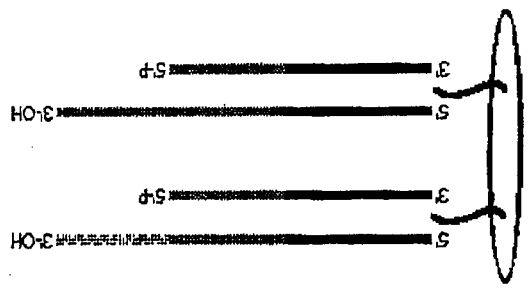
Fig. 23  A  B

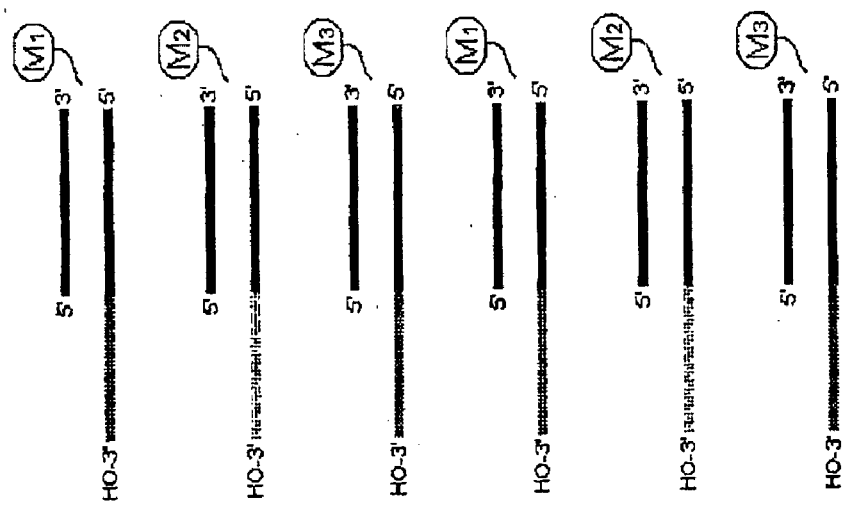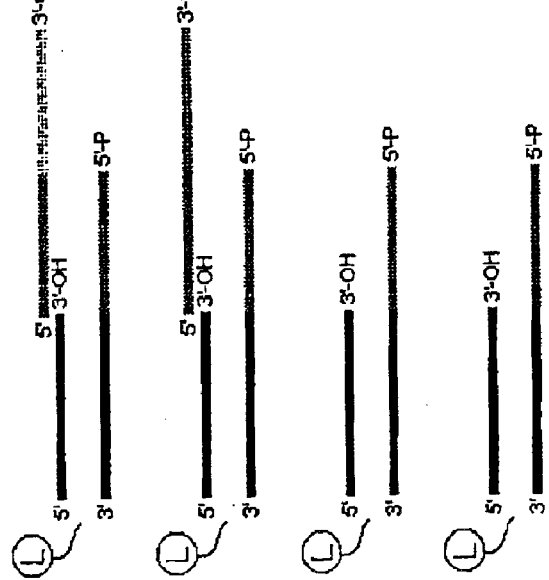
Fig. 58

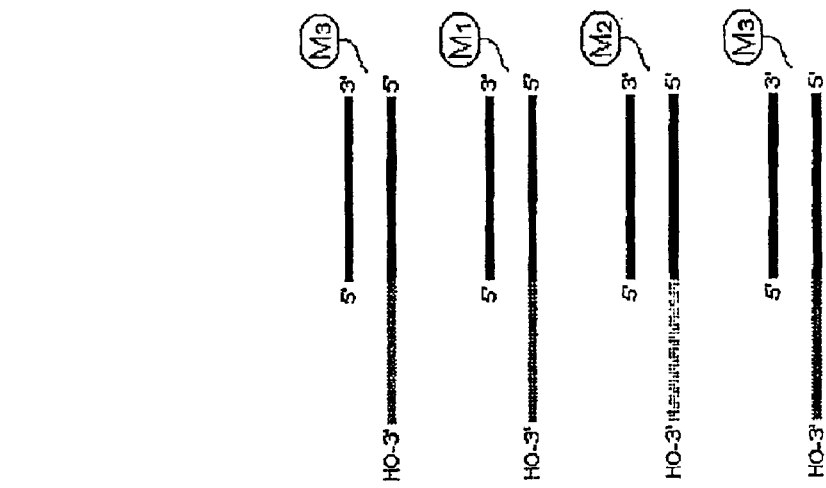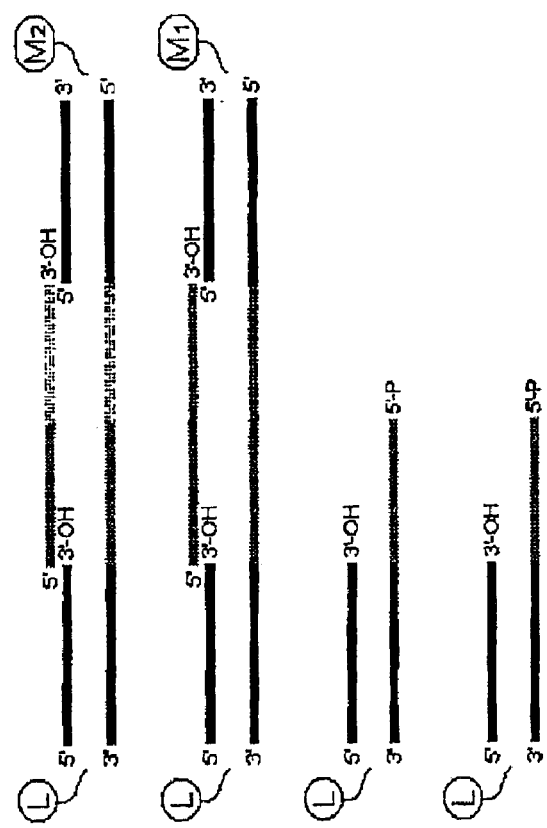
Fig. 59

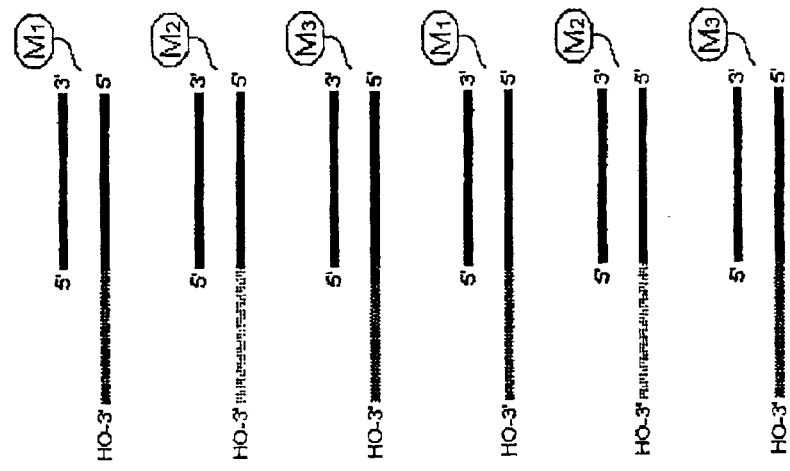
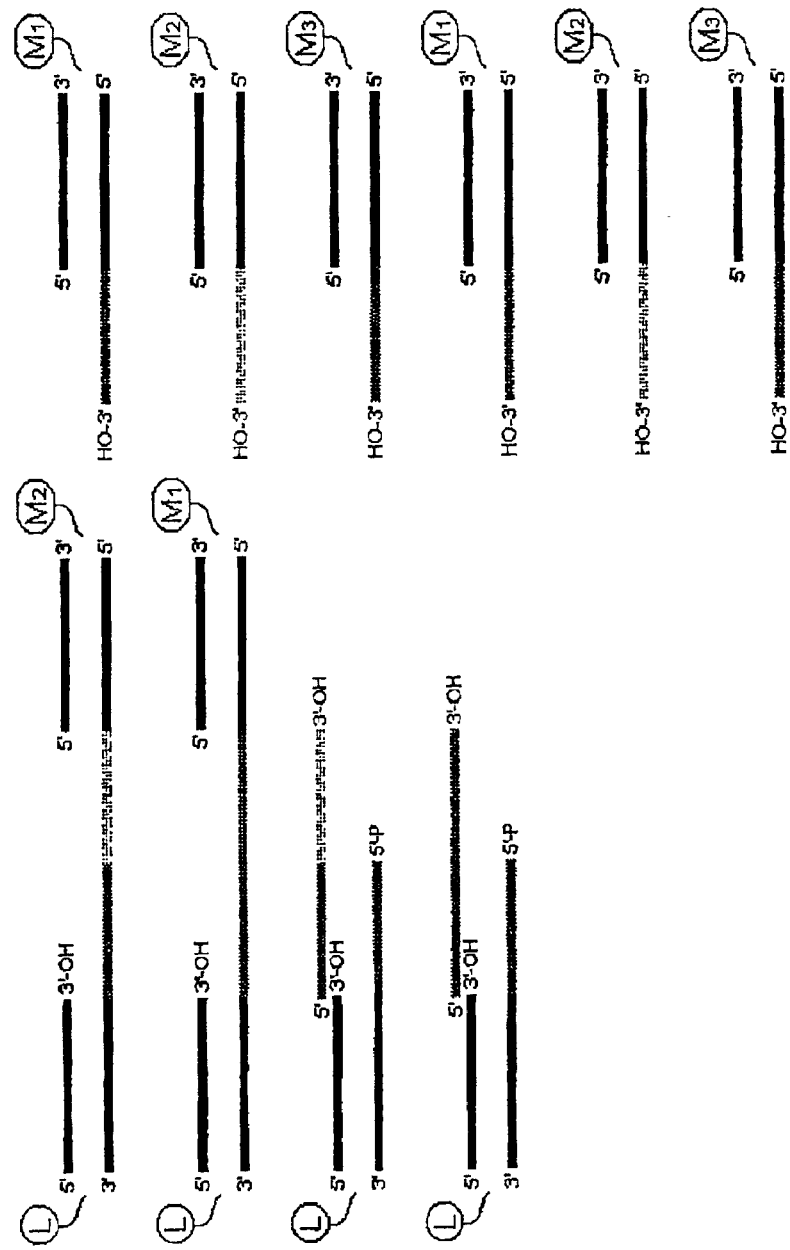
Fig. 61

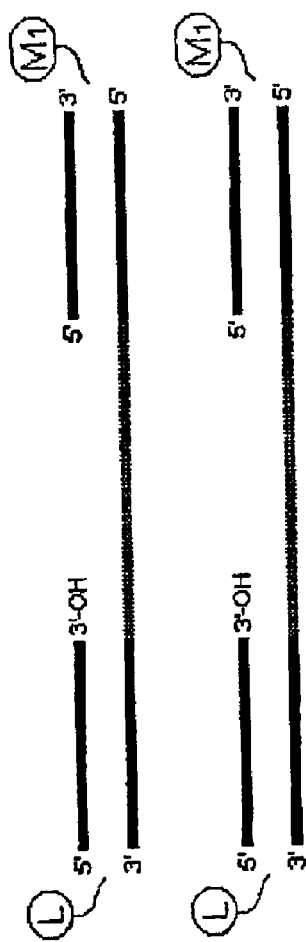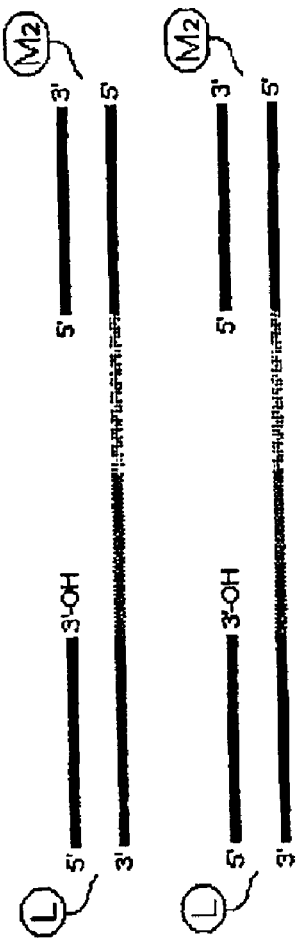
Fig. 63

SEQUENCE LISTING

<160> NUMBER OF SEQ ID NOS: 148

<210> SEQ ID NO 1
<211> LENGTH: 14
<212> TYPE: DNA
<213> ORGANISM: Artificial Sequence
<220> FEATURE:
<223> OTHER INFORMATION: synthetic

<400> SEQUENCE: 1
gcttggatcc aagc                                                         14

<210> SEQ ID NO 2
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(16)
<223> OTHER INFORMATION: n is a, c, g or t

<400> SEQUENCE: 2
gagtcggatc nnnnnn                                                       16

<210> SEQ ID NO 3
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 3
nnnnnngatc cgactc                                                       16

<210> SEQ ID NO 4
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(23)
<223> OTHER INFORMATION: n is a, c, g or t

<400> SEQUENCE: 4
gagtcgcagc nnnnnnnnnn nnn                                               23

<210> SEQ ID NO 5
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: n is a, c, g or t

<400> SEQUENCE: 5
nnnnnnnnnn nnngctgcga ctc                                               23

```
<210> SEQ ID NO 6
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(18)
<223> OTHER INFORMATION: n is a, c, g or t

<400> SEQUENCE: 6
gagtcgtatc cnnnnnnn                                              18

<210> SEQ ID NO 7
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(7)
<223> OTHER INFORMATION: n is a, c, g or t

<400> SEQUENCE: 7 nnnnnnnga tacgactc                                               18

<210> SEQ ID NO 8
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(17)
<223> OTHER INFORMATION: n is a, c, g or t

<400> SEQUENCE: 8
gagtcactgg gnnnnnn                                               17

<210> SEQ ID NO 9
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 9
nnnnnnccca gtgactc                                               17

<210> SEQ ID NO 10
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(29)
<223> OTHER INFORMATION: n is a, c, g or t

<400> SEQUENCE: 10
```
gagtcctgga gnnnnnnnnn nnnnnnnn                                                29

<210> SEQ ID NO 11
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(18)
<223> OTHER INFORMATION: n is a, c, g or t

<400> SEQUENCE: 11
nnnnnnnnnn nnnnnnnnct ccaggactc                                              29

<210> SEQ ID NO 12
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(27)
<223> OTHER INFORMATION: n is a, c, g or t

<400> SEQUENCE: 12
gagtctggag nnnnnnnnnn nnnnnnn                                                27

<210> SEQ ID NO 13
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(17)
<223> OTHER INFORMATION: n is a, c, g or t

<400> SEQUENCE: 13
nnnnnnnnnn nnnnnnnctc cagactc                                                27

<210> SEQ ID NO 14
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(22)
<223> OTHER INFORMATION: n is a, c, g or t

<400> SEQUENCE: 14
gagtcgagga gnnnnnnnnn nn                                                     22

<210> SEQ ID NO 15
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(11)
<223> OTHER INFORMATION: n is a, c, g or t

<400> SEQUENCE: 15

-continued nnnnnnnnnn nctcctcgac tc                                    22

<210> SEQ ID NO 16
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(28)
<223> OTHER INFORMATION: n is a, c, g or t

<400> SEQUENCE: 16
gagtcgtgca gnnnnnnnnn nnnnnnn                               28

<210> SEQ ID NO 17
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(17)
<223> OTHER INFORMATION: n is a, c, g or t

<400> SEQUENCE: 17
nnnnnnnnnn nnnnnnnctg cacgactc                              28

<210> SEQ ID NO 18
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(23)
<223> OTHER INFORMATION: n is a, c, g or t

<400> SEQUENCE: 18
gtgcaggagt cnnnnnnnnn nnn                                   23

<210> SEQ ID NO 19
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g or t

<400> SEQUENCE: 19
nnnnnnnnnn nngactcctg cac                                   23

<210> SEQ ID NO 20
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(23)
<223> OTHER INFORMATION: n is a, c, g or t

```
<400> SEQUENCE: 20
gtgcagagtc nnnnnnnnnn nnn                                          23

<210> SEQ ID NO 21
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: n is a, c, g or t

<400> SEQUENCE: 21
nnnnnnnnnn nnngactctg cac                                          23

<210> SEQ ID NO 22
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(25)
<223> OTHER INFORMATION: n is a, c, g or t

<400> SEQUENCE: 22
gagtcgggac nnnnnnnnnn nnnnn                                        25

<210> SEQ ID NO 23
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(15)
<223> OTHER INFORMATION: n is a, c, g or t

<400> SEQUENCE: 23
nnnnnnnnnn nnnnngtccc gactc                                        25

<210> SEQ ID NO 24
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(20)
<223> OTHER INFORMATION: n is a, c, g or t

<400> SEQUENCE: 24
gagtcacctg cnnnnnnnnn                                              20

<210> SEQ ID NO 25
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t
```

-continued

```
<400> SEQUENCE: 25
nnnnnnnnng caggtgactc                                              20

<210> SEQ ID NO 26
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(23)
<223> OTHER INFORMATION: n is a, c, g or t

<400> SEQUENCE: 26
gagtcggcgg annnnnnnn nnn                                           23

<210> SEQ ID NO 27
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g or t

<400> SEQUENCE: 27
nnnnnnnnnn nntccgccga ctc                                          23

<210> SEQ ID NO 28
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(17)
<223> OTHER INFORMATION: n is a, c, g or t

<400> SEQUENCE: 28
gagtccccgc nnnnnnn                                                 17

<210> SEQ ID NO 29
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(7)
<223> OTHER INFORMATION: n is a, c, g or t

<400> SEQUENCE: 29
nnnnnnngcg gggactc                                                 17

<210> SEQ ID NO 30
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(24)
```

<223> OTHER INFORMATION: n is a, c, g or t

<400> SEQUENCE: 30
gagtcggatg nnnnnnnnnn nnnn                                                24

<210> SEQ ID NO 31
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g or t

<400> SEQUENCE: 31
nnnnnnnnnn nnnncatccg actc                                                24

<210> SEQ ID NO 32
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(21)
<223> OTHER INFORMATION: n is a, c, g or t

<400> SEQUENCE: 32
gagtcgacgc nnnnnnnnnn n                                                   21

<210> SEQ ID NO 33
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(11)
<223> OTHER INFORMATION: n is a, c, g or t

<400> SEQUENCE: 33
nnnnnnnnnn ngcgtcgact c                                                   21

<210> SEQ ID NO 34
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(19)
<223> OTHER INFORMATION: n is a, c, g or t

<400> SEQUENCE: 34
gagtcggtga nnnnnnnnn                                                      19

<210> SEQ ID NO 35
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature

```
<222> LOCATION: (1)..(9)
<223> OTHER INFORMATION: n is a, c, g or t

<400> SEQUENCE: 35
nnnnnnnnnt caccgactc                                              19

<210> SEQ ID NO 36
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(19)
<223> OTHER INFORMATION: n is a, c, g or t

<400> SEQUENCE: 36
gagtcgaaga nnnnnnnnn                                              19

<210> SEQ ID NO 37
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t

<400> SEQUENCE: 37
nnnnnnnnnt cttcgactc                                              19

<210> SEQ ID NO 38
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(16)
<223> OTHER INFORMATION: n is a, c, g or t

<400> SEQUENCE: 38
gagtcgagtc nnnnnn                                                 16

<210> SEQ ID NO 39
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 39
nnnnnngact cgactc                                                 16

<210> SEQ ID NO 40
<211> LENGTH: 16
<212> TYPE: DNA
<213> ORGANISM: Artificial Sequence
<220> FEATURE:
<223> OTHER INFORMATION: synthetic
<220> FEATURE:
```

```
<221> NAME/KEY: misc_feature
<222> LOCATION: (11)..(16)
<223> OTHER INFORMATION: n is a, c, g or t

<400> SEQUENCE: 40
gagtcgagtc nnnnnn                                                    16

<210> SEQ ID NO 41
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 41
nnnnnngact cgactc                                                    16

<210> SEQ ID NO 42
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(20)
<223> OTHER INFORMATION: n is a, c, g or t

<400> SEQUENCE: 42
gagtcgcatc nnnnnnnnnn                                                20

<210> SEQ ID NO 43
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g or t

<400> SEQUENCE: 43
nnnnnnnnnn gatgcgactc                                                20

<210> SEQ ID NO 44
<211> LENGTH: 35
<212> TYPE: DNA
<213> ORGANISM: Artificial Sequence
<220> FEATURE:
<223> OTHER INFORMATION: synthetic

<400> SEQUENCE: 44
cgcggatccg ccgccatgga tcattcccac catat                               35

<210> SEQ ID NO 45
<211> LENGTH: 30
<212> TYPE: DNA
<213> ORGANISM: Artificial Sequence
<220> FEATURE:
<223> OTHER INFORMATION: synthetic

<400> SEQUENCE: 45
gctctagaac tgcaatcgat aaggccacgc                                     30
```

```
<210> SEQ ID NO 46
<211> LENGTH: 34
<212> TYPE: DNA
<213> ORGANISM: Artificial Sequence
<220> FEATURE:
<223> OTHER INFORMATION: synthetic

<400> SEQUENCE: 46
cgcggatccg ccgccatggc gatgcatttc atct                          34

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
gctctagagc ttcagctcaa agtttccagg                               30

<210> SEQ ID NO 48
<211> LENGTH: 33
<212> TYPE: DNA
<213> ORGANISM: Artificial Sequence
<220> FEATURE:
<223> OTHER INFORMATION: synthetic

<400> SEQUENCE: 48
cgcggatccg ccgccatgcc gaagcacgag ttc                           33

<210> SEQ ID NO 49
<211> LENGTH: 30
<212> TYPE: DNA
<213> ORGANISM: Artificial Sequence
<220> FEATURE:
<223> OTHER INFORMATION: synthetic

<400> SEQUENCE: 49
gctctagaac tgccaagtcc caggtctgtc                               30

<210> SEQ ID NO 50
<211> LENGTH: 22
<212> TYPE: DNA
<213> ORGANISM: Artificial Sequence
<220> FEATURE:
<223> OTHER INFORMATION: synthetic

<400> SEQUENCE: 50
acccactgtt tactggctta tc                                       22

<210> SEQ ID NO 51
<211> LENGTH: 18
<212> TYPE: DNA
<213> ORGANISM: Artificial Sequence
<220> FEATURE:
<223> OTHER INFORMATION: synthetic

<400> SEQUENCE: 51 gagggcaaa cagatggc                                             18

<210> SEQ ID NO 52
<211> LENGTH: 46
<212> TYPE: DNA
<213> ORGANISM: Artificial Sequence
<220> FEATURE:
```

<210> SEQ ID NO 52
<211> LENGTH: 46
<212> TYPE: DNA
<213> ORGANISM: Artificial Sequence
<220> FEATURE:
<223> OTHER INFORMATION: synthetic

<400> SEQUENCE: 52
ccatctgttg tttgcccctc aaaaaaaaaa aaaaaaaaa aaaaaa                46

<210> SEQ ID NO 53
<211> LENGTH: 26
<212> TYPE: DNA
<213> ORGANISM: Artificial Sequence
<220> FEATURE:
<223> OTHER INFORMATION: synthetic

<400> SEQUENCE: 53
tttttttttt tttttttttt tttttt                                     26

<210> SEQ ID NO 54
<211> LENGTH: 46
<212> TYPE: DNA
<213> ORGANISM: Artificial Sequence
<220> FEATURE:
<223> OTHER INFORMATION: synthetic

<400> SEQUENCE: 54
tttttttttt tttttttttt tttttttgagg ggcaaacaac agatgg              46

<210> SEQ ID NO 55
<211> LENGTH: 29
<212> TYPE: DNA
<213> ORGANISM: Artificial Sequence
<220> FEATURE:
<223> OTHER INFORMATION: synthetic

<400> SEQUENCE: 55
tcagactcca gacacccaca caaccacaa                                  29

<210> SEQ ID NO 56
<211> LENGTH: 32
<212> TYPE: DNA
<213> ORGANISM: Artificial Sequence
<220> FEATURE:
<223> OTHER INFORMATION: synthetic

<400> SEQUENCE: 56 tttttttttgt ggttgtgtgg gtgtctggag tc                             32

<210> SEQ ID NO 57
<211> LENGTH: 41
<212> TYPE: DNA
<213> ORGANISM: Artificial Sequence
<220> FEATURE:
<223> OTHER INFORMATION: synthetic

<400> SEQUENCE: 57
tgagctttcc tcacctcctg caaacagtgc tgcacatcat c                    41

<210> SEQ ID NO 58
<211> LENGTH: 41
<212> TYPE: DNA
<213> ORGANISM: Artificial Sequence
<220> FEATURE:
<223> OTHER INFORMATION: synthetic

<400> SEQUENCE: 58
tagttgccag ccatctgttg tttgcccctc ccccgtgcct t                    41

```
<210> SEQ ID NO 59
<211> LENGTH: 56
<212> TYPE: DNA
<213> ORGANISM: Artificial Sequence
<220> FEATURE:
<223> OTHER INFORMATION: synthetic

<400> SEQUENCE: 59
tttttttttt tttttttttt tttttgagg ggcaaacaac agatggctgg caacta        56

<210> SEQ ID NO 60
<211> LENGTH: 38
<212> TYPE: DNA
<213> ORGANISM: Artificial Sequence
<220> FEATURE:
<223> OTHER INFORMATION: synthetic

<400> SEQUENCE: 60
gatgatgtgc agcactgttt ggacgaggtg ggaaaagc                            38

<210> SEQ ID NO 61
<211> LENGTH: 64
<212> TYPE: DNA
<213> ORGANISM: Artificial Sequence
<220> FEATURE:
<223> OTHER INFORMATION: synthetic

<400> SEQUENCE: 61
ttttttttgt ggttgtgtgg gtgtctggag tctgagcttt cctcacctcc tgcaaacagt    60
gctg                                                                 64

<210> SEQ ID NO 62
<211> LENGTH: 35
<212> TYPE: DNA
<213> ORGANISM: Artificial Sequence
<220> FEATURE:
<223> OTHER INFORMATION: synthetic

<400> SEQUENCE: 62
ccagccatct gttgtttgcc cctcccccgt gcctt                               35

<210> SEQ ID NO 63
<211> LENGTH: 50
<212> TYPE: DNA
<213> ORGANISM: Artificial Sequence
<220> FEATURE:
<223> OTHER INFORMATION: synthetic

<400> SEQUENCE: 63
tttttttttt tttttttttt tttttgagg ggcaaacaac agatggctgg               50

<210> SEQ ID NO 64
<211> LENGTH: 58
<212> TYPE: DNA
<213> ORGANISM: Artificial Sequence
<220> FEATURE:
<223> OTHER INFORMATION: synthetic

<400> SEQUENCE: 64
cagcactgtt tgcaggaggt gaggaaagct cagactccac acacccacac aaccacaa      58

<210> SEQ ID NO 65
<211> LENGTH: 46
<212> TYPE: DNA
<213> ORGANISM: Artificial Sequence
<220> FEATURE:
```

<223> OTHER INFORMATION: synthetic

<400> SEQUENCE: 65 tttttttttgt ggttgtgtgg gtgtctggag tctgagctttt cctcac     46

<210> SEQ ID NO 66
<211> LENGTH: 38
<212> TYPE: DNA
<213> ORGANISM: Artificial Sequence
<220> FEATURE:
<223> OTHER INFORMATION: synthetic

<400> SEQUENCE: 66
gaggaaagct cagactccac acacccacac aaccacaa     38

<210> SEQ ID NO 67
<211> LENGTH: 36
<212> TYPE: DNA
<213> ORGANISM: Artificial Sequence
<220> FEATURE:
<223> OTHER INFORMATION: synthetic

<400> SEQUENCE: 67 tttttttttgt ggttgtgtgg gtgtctggag tctgag     36

<210> SEQ ID NO 68
<211> LENGTH: 10
<212> TYPE: DNA
<213> ORGANISM: Artificial Sequence
<220> FEATURE:
<223> OTHER INFORMATION: synthetic

<400> SEQUENCE: 68
ctttcctcac     10

<210> SEQ ID NO 69
<211> LENGTH: 10
<212> TYPE: DNA
<213> ORGANISM: Artificial Sequence
<220> FEATURE:
<223> OTHER INFORMATION: synthetic

<400> SEQUENCE: 69
gctggaggga     10

<210> SEQ ID NO 70
<211> LENGTH: 10
<212> TYPE: DNA
<213> ORGANISM: Artificial Sequence
<220> FEATURE:
<223> OTHER INFORMATION: synthetic

<400> SEQUENCE: 70
cacagcatgg     10

<210> SEQ ID NO 71
<211> LENGTH: 56
<212> TYPE: DNA
<213> ORGANISM: Artificial Sequence
<220> FEATURE:
<223> OTHER INFORMATION: synthetic

<400> SEQUENCE: 71
ctcactaagg ttcaaaggtt caaacggatc caaaaaaaaa aaaaaaaaaa aaaaaa     56

```
<210> SEQ ID NO 72
<211> LENGTH: 56
<212> TYPE: DNA
<213> ORGANISM: Artificial Sequence
<220> FEATURE:
<223> OTHER INFORMATION: synthetic

<400> SEQUENCE: 72
agggataagg ttcaaaggtt caaacggatc caaaaaaaaa aaaaaaaaaa aaaaaa        56

<210> SEQ ID NO 73
<211> LENGTH: 56
<212> TYPE: DNA
<213> ORGANISM: Artificial Sequence
<220> FEATURE:
<223> OTHER INFORMATION: synthetic

<400> SEQUENCE: 73
catggtaagg ttcaaaggtt caaacggatc caaaaaaaaa aaaaaaaaaa aaaaaa        56

<210> SEQ ID NO 74
<211> LENGTH: 33
<212> TYPE: DNA
<213> ORGANISM: Artificial Sequence
<220> FEATURE:
<223> OTHER INFORMATION: synthetic

<400> SEQUENCE: 74
taaggttcaa aggttcaaac ggatccaaaa aaa                                 33

<210> SEQ ID NO 75
<211> LENGTH: 33
<212> TYPE: DNA
<213> ORGANISM: Artificial Sequence
<220> FEATURE:
<223> OTHER INFORMATION: synthetic

<400> SEQUENCE: 75
taaggttcaa aggttcaaac ggatccaaaa aaa                                 33

<210> SEQ ID NO 76
<211> LENGTH: 57
<212> TYPE: DNA
<213> ORGANISM: Artificial Sequence
<220> FEATURE:
<223> OTHER INFORMATION: synthetic

<400> SEQUENCE: 76
tttttttttt tttttttttt tttttggat ccgtttgaac ctttgaacct tagtgag        57

<210> SEQ ID NO 77
<211> LENGTH: 33
<212> TYPE: DNA
<213> ORGANISM: Artificial Sequence
<220> FEATURE:
<223> OTHER INFORMATION: synthetic

<400> SEQUENCE: 77
taaggttcaa aggttcaaac ggatccaaaa aaa                                 33

<210> SEQ ID NO 78
<211> LENGTH: 57
<212> TYPE: DNA
<213> ORGANISM: Artificial Sequence
<220> FEATURE:
<223> OTHER INFORMATION: synthetic
```

```
<400> SEQUENCE: 78
tttttttttt tttttttttt ttttttggat ccgtttgaac ctttgaacct tatccct        57

<210> SEQ ID NO 79
<211> LENGTH: 33
<212> TYPE: DNA
<213> ORGANISM: Artificial Sequence
<220> FEATURE:
<223> OTHER INFORMATION: synthetic

<400> SEQUENCE: 79
taaggttcaa aggttcaaac ggatccaaaa aaa                                  33

<210> SEQ ID NO 80
<211> LENGTH: 57
<212> TYPE: DNA
<213> ORGANISM: Artificial Sequence
<220> FEATURE:
<223> OTHER INFORMATION: synthetic

<400> SEQUENCE: 80
tttttttttt tttttttttt ttttttggat ccgtttgaac ctttgaacct taccatg        57

<210> SEQ ID NO 81
<211> LENGTH: 52
<212> TYPE: DNA
<213> ORGANISM: Artificial Sequence
<220> FEATURE:
<223> OTHER INFORMATION: synthetic

<400> SEQUENCE: 81
gaaagtccct ggaatgccgg tttcgttttt ttcgaaacct tcattccagg ga             52

<210> SEQ ID NO 82
<211> LENGTH: 62
<212> TYPE: DNA
<213> ORGANISM: Artificial Sequence
<220> FEATURE:
<223> OTHER INFORMATION: synthetic

<400> SEQUENCE: 82
ccagcggaag gtttggtccc aatttcgtgt tttttttaca cgaaattggg accaaacctt     60
cc                                                                   62

<210> SEQ ID NO 83
<211> LENGTH: 72
<212> TYPE: DNA
<213> ORGANISM: Artificial Sequence
<220> FEATURE:
<223> OTHER INFORMATION: synthetic

<400> SEQUENCE: 83
ctgtgggtgt tgtgtggaat tcgtgtaag gtccctttt ttgggacctt acacgaaatt       60
ccacacaaca cc                                                        72

<210> SEQ ID NO 84
<211> LENGTH: 43
<212> TYPE: DNA
<213> ORGANISM: Artificial Sequence
<220> FEATURE:
<223> OTHER INFORMATION: synthetic

<400> SEQUENCE: 84
ctttcctcac taaggttcaa aggttcaaac ggatccaaaa aaa                       43
```

```
<210> SEQ ID NO 85
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(10)
<223> OTHER INFORMATION: n is a, c, g or t

<400> SEQUENCE: 85 gagtcnnnnn                                                           10

<210> SEQ ID NO 86
<211> LENGTH: 10
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: n is a, t, c or g

<400> SEQUENCE: 86 nnnnngactc                                                           10

<210> SEQ ID NO 87
<211> LENGTH: 131
<212> TYPE: DNA
<213> ORGANISM: Artificial Sequence
<220> FEATURE:
<223> OTHER INFORMATION: synthetic

<400> SEQUENCE: 87 tttttttggat ccgtttgaac ctttgaacct tagtgaggaa agtccctgga atgaaggttt    60 cgttttttc gaaaccttca ttccagggac tttcctcact aaggttcaaa ggttcaaacg    120
gatccaaaaa a                                                        131

<210> SEQ ID NO 88
<211> LENGTH: 113
<212> TYPE: DNA
<213> ORGANISM: Artificial Sequence
<220> FEATURE:
<223> OTHER INFORMATION: synthetic

<400> SEQUENCE: 88
gatccgtttg aacctttgaa ccttagtgag gaaagtccct ggaatgaagg tttcgttttt    60
ttcgaaacct tcattccagg gactttcctc actaaggttc aaaggttcaa acg           113

<210> SEQ ID NO 89
<211> LENGTH: 32
<212> TYPE: DNA
<213> ORGANISM: Artificial Sequence
<220> FEATURE:
<223> OTHER INFORMATION: synthetic

<400> SEQUENCE: 89 tttttttttgt ggttgtgtgg gtgtctggag tc                                 32

<210> SEQ ID NO 90
<211> LENGTH: 29
<212> TYPE: DNA
```

```
<213> ORGANISM: Artificial Sequence
<220> FEATURE:
<223> OTHER INFORMATION: synthetic

<400> SEQUENCE: 90
tcagactcca cacacccaca caaccacaa                                       29

<210> SEQ ID NO 91
<211> LENGTH: 24
<212> TYPE: DNA
<213> ORGANISM: Artificial Sequence
<220> FEATURE:
<223> OTHER INFORMATION: synthetic

<400> SEQUENCE: 91
ttttcgaaac cttcattcca ggga                                            24

<210> SEQ ID NO 92
<211> LENGTH: 28
<212> TYPE: DNA
<213> ORGANISM: Artificial Sequence
<220> FEATURE:
<223> OTHER INFORMATION: synthetic

<400> SEQUENCE: 92
gaaagtccct ggaatgaagg tttcgttt                                        28

<210> SEQ ID NO 93
<211> LENGTH: 29
<212> TYPE: DNA
<213> ORGANISM: Artificial Sequence
<220> FEATURE:
<223> OTHER INFORMATION: synthetic

<400> SEQUENCE: 93
ttttacacga aattgggacc aaaccttcc                                       29

<210> SEQ ID NO 94
<211> LENGTH: 33
<212> TYPE: DNA
<213> ORGANISM: Artificial Sequence
<220> FEATURE:
<223> OTHER INFORMATION: synthetic

<400> SEQUENCE: 94
ccagcggaag gtttggtccc aatttcgtgt ttt                                  33

<210> SEQ ID NO 95
<211> LENGTH: 34
<212> TYPE: DNA
<213> ORGANISM: Artificial Sequence
<220> FEATURE:
<223> OTHER INFORMATION: synthetic

<400> SEQUENCE: 95
ttttgggacc ttacacgaaa ttccacacaa cacc                                 34

<210> SEQ ID NO 96
<211> LENGTH: 38
<212> TYPE: DNA
<213> ORGANISM: Artificial Sequence
<220> FEATURE:
<223> OTHER INFORMATION: synthetic

<400> SEQUENCE: 96
ctgtgggtgt tgtgtggaat tcgtgtaag gtcccttt                              38
```

```
<210> SEQ ID NO 97
<211> LENGTH: 10
<212> TYPE: DNA
<213> ORGANISM: Artificial Sequence
<220> FEATURE:
<223> OTHER INFORMATION: synthetic

<400> SEQUENCE: 97
ctttcctcac                                                           10

<210> SEQ ID NO 98
<211> LENGTH: 33
<212> TYPE: DNA
<213> ORGANISM: Artificial Sequence
<220> FEATURE:
<223> OTHER INFORMATION: synthetic

<400> SEQUENCE: 98
taaggttcaa aggttcaaac ggatccaaaa aaa                                 33

<210> SEQ ID NO 99
<211> LENGTH: 66
<212> TYPE: DNA
<213> ORGANISM: Artificial Sequence
<220> FEATURE:
<223> OTHER INFORMATION: synthetic

<400> SEQUENCE: 99
ttttcgaaac cttcattcca gggactttcc tcactaaggt tcaaaggttc aaacggatcc    60
aaaaaa                                                               66

<210> SEQ ID NO 100
<211> LENGTH: 65
<212> TYPE: DNA
<213> ORGANISM: Artificial Sequence
<220> FEATURE:
<223> OTHER INFORMATION: synthetic

<400> SEQUENCE: 100 tttttttggat ccgtttgaac ctttgaacct tagtgaggaa agtccctgga atgaaggttt   60
cgttt                                                                65

<210> SEQ ID NO 101
<211> LENGTH: 55
<212> TYPE: DNA
<213> ORGANISM: Artificial Sequence
<220> FEATURE:
<223> OTHER INFORMATION: synthetic

<400> SEQUENCE: 101
ttttcgaaac cttcattcca gggactttcc tcactaaggt tcaaaggttc aaacg         55

<210> SEQ ID NO 102
<211> LENGTH: 58
<212> TYPE: DNA
<213> ORGANISM: Artificial Sequence
<220> FEATURE:
<223> OTHER INFORMATION: synthetic

<400> SEQUENCE: 102
gatccgtttg aacctttgaa ccttagtgag gaaagtccct ggaatgaagg tttcgttt      58

<210> SEQ ID NO 103
```

```
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(11)
<223> OTHER INFORMATION: n  is a, c, g or t

<400> SEQUENCE: 103
ggatcnnnnn n                                                           11

<210> SEQ ID NO 104
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n  is a, c, g or t

<400> SEQUENCE: 104
nnnnnngatc c                                                           11

<210> SEQ ID NO 105
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(18)
<223> OTHER INFORMATION: n  is a, c, g or t

<400> SEQUENCE: 105
gcagcnnnnn nnnnnnnn                                                    18

<210> SEQ ID NO 106
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: n  is a, c, g or t

<400> SEQUENCE: 106
nnnnnnnnnn nnngctgc                                                    18

<210> SEQ ID NO 107
<211> LENGTH: 13
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(13)
<223> OTHER INFORMATION: n  is a, c, g or t

<400> SEQUENCE: 107
gtatccnnnn nnn                                                         13
```

```
<210> SEQ ID NO 108
<211> LENGTH: 13
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(7)
<223> OTHER INFORMATION: n  is a, c, g or t

<400> SEQUENCE: 108
nnnnnnngga tac                                                              13

<210> SEQ ID NO 109
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(12)
<223> OTHER INFORMATION: n  is a, c, g or t

<400> SEQUENCE: 109
actgggnnnn nn                                                               12

<210> SEQ ID NO 110
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 110
nnnnnnccca gt                                                               12

<210> SEQ ID NO 111
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(23)
<223> OTHER INFORMATION: n  is a, c, g or t

<400> SEQUENCE: 111
ctggagnnnn nnnnnnnnn nnn                                                    23

<210> SEQ ID NO 112
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(17)
<223> OTHER INFORMATION: n  is a, c, g or t

<400> SEQUENCE: 112
nnnnnnnnnn nnnnnnnctc cag                                                   23
```

```
<210> SEQ ID NO 113
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(23)
<223> OTHER INFORMATION: n   is a, c, g or t

<400> SEQUENCE: 113
ctggagtcnn nnnnnnnnn nnn                                              23

<210> SEQ ID NO 114
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(15)
<223> OTHER INFORMATION: n   is a, c, g or t

<400> SEQUENCE: 114
nnnnnnnnnn nnnnngactc cag                                             23

<210> SEQ ID NO 115
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(18)
<223> OTHER INFORMATION: n   is a, c, g or t

<400> SEQUENCE: 115
gaggagnnnn nnnnnnnn                                                   18

<210> SEQ ID NO 116
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(12)
<223> OTHER INFORMATION: n   is a, c, g or t

<400> SEQUENCE: 116
nnnnnnnnnn nnctcctc                                                   18

<210> SEQ ID NO 117
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(17)
<223> OTHER INFORMATION: n   is a, c, g or t

<400> SEQUENCE: 117
gaggagtcnn nnnnnnn                                                    17
```

<210> SEQ ID NO 118
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n  is a, c, g or t

<400> SEQUENCE: 118
nnnnnnnnng actcctc                                                    17

<210> SEQ ID NO 119
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(23)
<223> OTHER INFORMATION: n  is a, c, g or t

<400> SEQUENCE: 119
gtgcagnnnn nnnnnnnnn nnn                                              23

<210> SEQ ID NO 120
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(17)
<223> OTHER INFORMATION: n  is a, c, g or t

<400> SEQUENCE: 120
nnnnnnnnnn nnnnnnnctg cac                                             23

<210> SEQ ID NO 121
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(20)
<223> OTHER INFORMATION: n  is a, c, g or t

<400> SEQUENCE: 121
gggacnnnnn nnnnnnnnnn                                                 20

<210> SEQ ID NO 122
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(15)
<223> OTHER INFORMATION: n  is a, c, g or t

<400> SEQUENCE: 122
nnnnnnnnnn nnnnngtccc                        20

<210> SEQ ID NO 123
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(15)
<223> OTHER INFORMATION: n is a, c, g or t

<400> SEQUENCE: 123
acctgcnnnn nnnnn                             15

<210> SEQ ID NO 124
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t

<400> SEQUENCE: 124
nnnnnnnnng caggt                             15

<210> SEQ ID NO 125
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(18)
<223> OTHER INFORMATION: n is a, c, g or t

<400> SEQUENCE: 125
ggcggannnn nnnnnnnn                          18

<210> SEQ ID NO 126
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g or t

<400> SEQUENCE: 126
nnnnnnnnnn nntccgcc                          18

<210> SEQ ID NO 127
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(12)
<223> OTHER INFORMATION: n is a, c, g or t

<400> SEQUENCE: 127

-continued cccgcnnnnn nn          12

<210> SEQ ID NO 128
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(7)
<223> OTHER INFORMATION: n is a, c, g or t

<400> SEQUENCE: 128
nnnnnnngcg gg          12

<210> SEQ ID NO 129
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(17)
<223> OTHER INFORMATION: n is a, c, g or t

<400> SEQUENCE: 129
gagtcccgcn nnnnnnn          17

<210> SEQ ID NO 130
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(8)
<223> OTHER INFORMATION: n is a, c, g or t

<400> SEQUENCE: 130
nnnnnnnngc gggactc          17

<210> SEQ ID NO 131
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(19)
<223> OTHER INFORMATION: n is a, c, g or t

<400> SEQUENCE: 131
ggatgnnnnn nnnnnnnn          19

<210> SEQ ID NO 132
<211> LENGTH: 19
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g or t

```
<400> SEQUENCE: 132 nnnnnnnnn nnnncatcc                                              19

<210> SEQ ID NO 133
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(16)
<223> OTHER INFORMATION: n  is a, c, g or t

<400> SEQUENCE: 133
gacgcnnnnn nnnnnn                                                16

<210> SEQ ID NO 134
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(11)
<223> OTHER INFORMATION: n is a, c, g or t

<400> SEQUENCE: 134
nnnnnnnnnn ngcgtc                                                16

<210> SEQ ID NO 135
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(14)
<223> OTHER INFORMATION: n is a, c, g or t

<400> SEQUENCE: 135
ggtgannnnn nnnn                                                  14

<210> SEQ ID NO 136
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t

<400> SEQUENCE: 136
nnnnnnnnnt cacc                                                  14

<210> SEQ ID NO 137
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(14)
<223> OTHER INFORMATION: n is a, c, g or t
```

```
<400> SEQUENCE: 137
gaagannnnn nnnn                                                14

<210> SEQ ID NO 138
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t

<400> SEQUENCE: 138
nnnnnnnnnt cttc                                                14

<210> SEQ ID NO 139
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(11)
<223> OTHER INFORMATION: n is a, c, g or t

<400> SEQUENCE: 139
gagtcnnnnn n                                                   11

<210> SEQ ID NO 140
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: n is a, c, g or t

<400> SEQUENCE: 140
nnnnnngact c                                                   11

<210> SEQ ID NO 141
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(12)
<223> OTHER INFORMATION: n is a, c, g or t

<400> SEQUENCE: 141
cctcnnnnnn nn                                                  12

<210> SEQ ID NO 142
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(8)
```

```
<223> OTHER INFORMATION: n is a, c, g or t

<400> SEQUENCE: 142
nnnnnnnnga gg                                                            12

<210> SEQ ID NO 143
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(17)
<223> OTHER INFORMATION: n is a, c, g or t

<400> SEQUENCE: 143
gagtccctcn nnnnnn                                                        17

<210> SEQ ID NO 144
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(8)
<223> OTHER INFORMATION: n is a, c, g or t

<400> SEQUENCE: 144
nnnnnnnnga gggactc                                                       17

<210> SEQ ID NO 145
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(17)
<223> OTHER INFORMATION: n is a, c, g or t

<400> SEQUENCE: 145
gagtcctcnn nnnnnn                                                        17

<210> SEQ ID NO 146
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g or t

<400> SEQUENCE: 146 nnnnnnnng aggactc                                                        17

<210> SEQ ID NO 147
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

```
-continued

<222> LOCATION: (6)..(15)
<223> OTHER INFORMATION: n is a, c, g or t

<400> SEQUENCE: 147
gcatcnnnnn nnnnn                                                          15

<210> SEQ ID NO 148
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g or t

<400> SEQUENCE: 148
nnnnnnnnnn gatgc                                                          15
```

SINGLE-STRANDED POLYNUCLEOTIDE TAGS

This application is a nonprovisional of U.S. provisional application Ser. No. 60/267,704 filed on Feb. 12, 2001, which is hereby incorporated by reference in its entirety. All patent and nonpatent references cited in the application, or in the present application, are also hereby incorporated by reference in their entirety.

TECHNICAL FIELD OF THE INVENTION

The present invention relates to methods and tools for analyzing gene expression at large. A process also known as expression profiling. In a basic scientific context, information about gene expression from one biological sample is normally correlated to the gene expression information obtained from another biological sample. This can be done in a variety of ways generally referred to as differential gene expression.

The objective of differential gene expression is to perform an analysis by determining the genes, which are expressed in a first predetermined cell, but not expressed, or expressed at a different level, in a second predetermined cell. The analysis thus facilitates a characterization of the selected cell type and differentiates said cell type from other cell types, or essentially identical cell types having a different history. The analysis also facilitates target identification, when correlating the expression from an "altered" or "aberrant" cell with the expected expression from that type of cell.

Clustering software can be used to group genes that are regulated in a similar fashion. Some of these clusters will be mutually exclusive. For example a group of the genes that prevent cell proliferation may do so by encoding proteins or non-translated RNA species capable of blocking the expression of genes necessary for DNA replication and cell division. If genes belonging to clusters that are mutually exclusive are expressed at the same time in a cell sample that normally would not express genes from mutually exclusive genes, then this is a strong indication that the cell in this sample exhibit an aberrant behaviour. In this case no direct correlation with a normal control is necessary.

As many examples of mutually exclusive gene clusters are described in the literature, it may not be necessary or convenient to do a classical differential gene expression analysis when using gene expression for diagnostic or genotyping purposes. Instead it may be more relevant just to refer to present knowledge about the behavior of the marker genes used or to refer to a database comprising the relevant data for the analysis of the sample.

BACKGROUND OF THE INVENTION

Analysis of complex nucleic acid populations is a common problem in many areas of molecular biology, nowhere more so than in the analysis of patterns of gene expression. Various methods have been developed to allow simultaneous analysis of entire mRNA populations, or their corresponding cDNA populations, in order to understand the observed patterns of gene expression.

The method of "subtractive cloning" (Lee et al, Proc. Nat. Acad. Sci. USA 88, 2825–2829) allows identification of mRNAs, or rather, their corresponding cDNAs, that are differentially expressed in two related cell types. One can selectively eliminate cDNAs common to two related cell types by hybridizing cDNAs from a library derived from one cell type to a large excess of mRNA from a related, but distinct cell type. mRNAs in the second cell type complementary to cDNAs from the first type will form double-stranded hybrids. Various enzymes exist which degrade such double-stranded hybrids allowing these to be eliminated thus enriching the remaining population in cDNAs unique to the first cell type. This method allows highly specific comparative information about differences in gene expression between related cell types to be derived and has had moderate success in isolating rare cDNAs.

The methods of "differential display" (Science 257, 967–971, 1992) sorts mRNAs using PCR primers to selectively amplify specific subsets of an mRNA population. An mRNA population is primed with a general oligo(dT) primer to amplify one strand and a specific primer, of perhaps 10 nucleotides or so to amplify the reverse strand with greater specificity. In this way only mRNAs bearing the second primer sequence are amplified; the longer the second primer the smaller a proportion of the total cDNA population is amplified or any given sequence of that length used. The resultant amplified sub-population can then be cloned for screening or sequencing or the fragments can simply be separated on a sequencing gel. Low copy number mRNAs are less likely to get lost in this sort of scheme in comparison with subtractive cloning, and it is probably more reproducible. Whilst this method is more general than subtractive cloning, time-consuming analysis is required.

The method of "molecular indexing" (PCT/GB93/01452) uses populations of adapter molecules to hybridize to the ambiguous sticky-ends generated by cleavage of a nucleic acid with a type IIs restriction endonuclease to categorize the cleavage fragments. Using specifically engineered adapters one can specifically immobilize or amplify or clone specific subsets of fragments in a manner similar to differential display but achieving a greater degree of control. Again, time-consuming analysis is required.

The method of Kato (Nucleic Acids Research 12, 3685–3690, 1995) exemplifies the above molecular indexing approach and effects cDNA population analysis by sorting terminal cDNA fragments into sub-populations followed by selective amplification of specific subsets of cDNA fragments. Sorting is effected by using type IIs restriction endonucleases and adapters. The adapters also carry primer sites, which in conjunction with general oligo(dT) primers allows selective amplification of terminal cDNA fragments as in differential display. It is possibly more precise than differential display in that it effects greater sorting: only about 100 cDNAs will be present in a given subset and sorting can be related to specific sequence features rather than using primers chosen by trial and error.

The method of "Serial Analysis of Gene Expression" or "SAGE" (Science 270, 484–487, 1995) allows identification of mRNAs, or rather, their corresponding cDNAs, that are expressed in a given cell type. The method involved a process for isolating a "tag" from every cDNA in a population using adapters and type IIs restriction endonucleases. A tag is a sample of a cDNA sequence of a fixed number of nucleotides sufficient to identify uniquely that cDNA in the population. Tags are then ligated together to create so-called di-tags consisting of two decamers from the pool of cDNA molecules under investigation ligated head-to-head and flanked by two linkers. These di-tags are then amplified using PCR, concaternerized into longer fragments, cloned and sequenced. The method gives quantitative data on gene expression and will readily identify novel cDNAs. This method was invented in 1995, but trials have since then showed that the amplification efficiency of different di-tags depends very much upon the sequence of the individual di-tags. In one trial a seven fold difference between two di-tag sequences after 20 cycles of PCR was detected even though there was no difference in abundance between these two di-tags in the starting material (NAR 27(18), e22, 1999). This makes SAGE a very bad choice if reliable quantitative data are required. The method is also extremely time-consuming in view of the large amount of sequencing required.

The method of "Tandem Arrayed Ligation of Expressed Sequence Tags" or "TAL-EST" (NAR 27(18), e22, 1999) is a modification of SAGE, where the PCR amplification step gives way to a cloning step. Each analysis then involves two cloning steps. The method is very quantitative and reproducible (P=0.99), but on the other hand approx. 15% of all genes are invisible in this assay. This means that the expression of 15% of all genes is not detected regardless how abundant their mRNA is. Thus TALEST is a very labor and time intensive technique to work with and the coverage is only 85% of all genes.

The method of "Total Gene Expression Analysis" or "TOGA" (PNAS 97(5), p. 1976–1981, 2000) makes use of a technique where the poly(T) tail of the cDNA along with the sequence 5' of the poly(T) tail is ligated into an RNA expression vector. This vector is then linarized and RNA in vitro synthesized. Then gene specific sequences are detected and quantified in approximately the same manner as with AFLP. Thus in TOGA, PCR is also used to amplify the products that are analyzed. As for SAGE, the use of PCR before the analysis step jeopardizes the quantitative aspect of the method.

The method of "Massively Parallel Signature Sequencing" or "MPSS" (Nature Biotech. 18, 630–634, 2000) uses a FACS sorting device in the data acquisition process. Like many of the other techniques MPSS depends heavily upon PCR for amplification of the tags, and hence MPSS is inflicted with all the problems that comes from using PCR.

Methods involving hybridization grids, chips and arrays are advantageous in that they avoid gel methods for sequencing and are relatively quantitative. They can be performed entirely in solution, and are thus readily automatable. These methods come in two forms.

The first involves immobilization of target nucleic aids to an array of oligonucleotides complementary to the terminal sequences of the target nucleic acid. Immobilization is followed by partial sequencing of those fragments by a single base method, e.g. using type IIs restriction endonucleases and adapters. This particular approach is advocated by Brenner in PCT/US95/12678.

The second form involves arrays of oligonucleotides. Nucleic acids are hybridized as single strands to the array. Detection of hybridization is achieved by fluorescently labeling each nucleic acid and determining from where on the grid the fluorescence arises, which determines the oligonucleotide to which the nucleic acid has bound. The fluorescent labels also give quantitative information about how much nucleic acid has hybridized to a given oligonucleotide. This information and knowledge of the relative quantities of individual nucleic acids should be sufficient to reconstruct the sequences and quantities of the hybridizing population. This approach is advocated by Lehrach in numerous papers and Nucleic Acids Research 22, 3423 contains a recent discussion. A disadvantage of this approach is that the construction of large arrays of oligonucleotides is extremely technically demanding and expensive. It is also still a very big technological challenge to hybridize between 10.000 and 20.000 different cDNA products quantitatively to a gene-chip containing between 25.000 and 100.000 different cDNA probes without getting a significant amount of mismatch hybridization. Another drawback with DNA array technology is that high quality sequence information is necessary for all the genes used on the array. Still the technology is relatively easy to use once the arrays have been designed and manufactured.

Additional methods for analyzing and demonstrating differential gene expression have been disclosed in e.g. WO 94/01582; WO 97/10363; WO 97/13877; WO 98/10095; WO 98/15652; WO 98/31380; WO 98/44152; WO 98/48047; WO 99/02725; WO 99/02726; WO 99/02727; WO 99/02728; WO 99/39001; WO 00/53806; U.S. Pat. No. 5,508,169; U.S. Pat. No. 5,658,736; U.S. Pat. No. 6,090,553; and EP 735 144 A1. Reference is also made to Cowan et al. (J. Theor. Biol., 1987, vol. 127, p. 229–245), who disclose breakage of double-stanled DNA due to single-stranded nicking. The nicking activity is not site-specific. Morgan et al. (Biol. Chem., 2000, vol. 361, p. 1123–1125) disclose a characterization of the specific DNA nicking activity of restriction endonuclease N.BstNBI.

None of the above methods are related to a method for obtaining—and optionally analyzing the sequence of—at least one single stranded polynucleotide tag originating at least partly from a biological sample and comprising a consecutive sequence of bases, wherein—prior to sequence analysis or other characterization—no part of the single stranded polynucleotide tag comprises a complementary polynucleotide strand, and wherein preferably all of the bases originate from the biological sample, such as more than 95% of the bases, for example more than 90% of the bases, such as more than 85% of the bases, for example more than 80% of the bases, such as more than 75% of the bases originating from the biological sample.

Furthermore, none the above methods exploit a cleavage agent, preferably in the form of a site-specific nicking endonuclease capable of i) recognizing a predetermined nucleotide motif comprising complementary nucleotide strands and ii) cleaving only one of said complementary strands in the process of generating at least one single stranded polynucleotide tag.

SUMMARY OF THE INVENTION

It is an objective of the present invention to obtain reproducible representations of expressed mRNA molecules by exploiting a novel technique that relies on short polynucleotide tags comprising nucleotide sequence information. In one preferred embodiment, only one polynucleotide tag is obtained from each mRNA molecule, and relatively simple counting statistics can thus be applied after identification and sampling of the different tags, or a subset of tags being present in the population of representative tags. The present invention thus provides signal-to-noise ratios sufficient for utilizing very simple counting statistics.

The information carried by the different types of polynucleotide tags lies not only in the unique sequence of each tag originating from one mRNA molecule. Other types of information includes the orientation of the tag (sense or anti-sense) and the location of the tag relative to the 3' or 5' ends or relative to internal restriction sites in the cDNA molecule. Having preferably gathered all this information in addition to the sequence of at least one specific polynucleotide tag according to the present invention, specific expressed sequence tags (ESTs) that are represented by the specific tag can readily be identified. The identification may preferably be performed by searching a database of EST sequences. Subsequently, the ESTs comprising the sequence of the tag can readily be obtained or isolated from a biological sample. It is also possible to use one identified ssDNA tag sequence directly as a primer, or a part thereof, in a gene-specific PCR reaction in order to isolate genespecific sequences.

The tags according to the present invention are preferably single stranded polynucleotide tags obtained by subjecting genetic material derived from a biological sample to at least one site-specific nicking endonuclease capable of i) recognizing a predetermined nucleotide motif comprising complementary nucleotide strands and ii) cleaving only one of said complementary strands in the process of generating the at least one single stranded polynucleotide tag. The tag may subsequently be identified and/or amplified as described herein further below.

As explained in detail herein below, the present invention provides novel and innovative solutions to the problem of how to obtain reproducible representations of molecules expressed in a biological sample.

The present invention for the first time demonstrates that nicking endonucleases may advantageously be used for obtaining and isolating ssDNA tags. This novel approach in one embodiment eliminates the occurrence of any linker sequence in the ssDNA tag and it eliminates the presence of a complementary strand in the isolated polynucleotide tag. The lack of linker sequence in the tag and the lack of any complementary strand serves to reduce the huge complexities associated with the analysis of expressed molecules in a biological sample.

It is not necessary according to the present invention to use full length cDNA for expression profiling—truncated cDNAs may also be exploited, and tags arising from the 3' end or from the 5' end of the mRNA can be analyzed at will.

In one preferred embodiment, only one ssDNA tag is isolated from each mRNA molecule. This facilitates and ensures a direct correlation between i) the abundance, i.e. relative amount, of any one ssDNA tag and ii) the expression of the corresponding mRNA molecule in a biological sample. The increased correlation between the ssDNA tag and the mRNA as well as the decreased complexity serves to achieve a higher success rate when tracking changes in gene expression.

It is possible to automate the isolation of the ssDNA tags from a biological sample by using e.g. robot technology or a microfluid device. The signal generated by a label can easily be amplified using e.g. asymmetric ligase chain reaction (LCR), thereby preserving the tight correlation between the abundance of one ssDNA tag and the expression of the corresponding mRNA molecule.

As an alternative solution, the signal can be amplified by cloning ssDNA tags into extrachromosomal replicons, including plasmids and phages, and subsequently releasing the tags after in vivo amplification, thereby preserving the tight correlation between the abundance of one ssDNA tag sequence and the expression of the corresponding mRNA molecule.

As another alternative, the signal can be amplified by using PCR. As with every other technique that uses PCR, the tight correlation between the abundance of one ssDNA tag and the expression of the corresponding mRNA molecule is likely to be jeopardized to some extent due to different amplification efficiencies of sequences having different C/G content. It is also possible to use one identified ssDNA tag sequence directly as a primer, or a part thereof, in a gene-specific PCR reaction in order to isolate genespecific sequences.

It is also possible to automate the amplification of the signal regardless of asymmetric LCR, in vivo amplification or PCR are used for the signal amplification. This may be achieved e.g. by using a robot or a microfluid device in combination with a peltier element.

The present invention used in combination with any state of the art array technology makes expression profiling experiments more cost effective to conduct. In particular, more than one display technology can be used at will or in combination. Cost effectiveness is also associated with an automated analysis of the ssDNA tags, e.g. by using a robot or a microfluid device in combination with a mass spectrometer, an array, an UV/VIS spectrometer or a fluorometer, including any combination thereof.

In one embodiment, the present invention makes it possible to concatenate the ssDNA tags by using dsDNA linkers. After cloning and sequencing, a more accurate picture of the expression profile as compared to SAGE is obtained in this way as the use of PCR can be avoided. The present invention thus provides signal-to-noise ratios sufficient for utilizing very simple counting statistics.

The invention can also be used to analyze genomic DNA, thereby moving into areas such as methylation profiling and SNP profiling (single nucleotide polymorphism). Consequently, the present invention covers such diverse areas as expression profiling, genotyping, epigenotyping, and diagnostics.

The present invention can also be used to elucidate new etiologies of disease related phenotypes and discover new modes of disease.

The present invention can also be used to discover new uses of known drugs, to pinpoint new drug targets, to monitor specific diagnostic markers, and to make diagnostic kits.

In one embodiment, the tags according to the present invention are used for expression profiling. The tags can either be concaternerized, sequenced and counted; or just used in a conventional array expression profiling experiment instead of full length mRNA or cDNA molecules. In the latter case, one significant advantage is that any background originating from a cross-hybridization between different sequences with one or more mismatches can be significantly reduced due to the more simple hybridization dynamics of shorter nucleotides compared with longer nucleotides. The dynamics is even more favorable if the tag is ligated onto the oligo probe in the array. The identity and abundance of each tag sequence can also be displayed by means of gel electrophoresis following ligation to a set of identifying linker oligonucleotides with overhang sequences that correspond to their length. In a similar fashion, mass spectroscopy or a micro-fluid device can also be employed in the process of sorting the tags and/or displaying the identity and abundance of each tag sequence. The tags are preferably linked to a suitable label that enables identification of the tag. The label may form part of the identifying linker oligonucleotide. Alternatively, the label may form part of a molecular identifier comprised by the identifying linker oligonucleotide. Accordingly, the molecular identifier may facilitate both sorting and/or detection of the tag in question. The sorting may be performed e.g. when a plurality of tags are attached to a plurality of identifying linker oligonucleotides comprising a molecular identifier. Separation preferably occurs by means of differences among molecular identifiers in terms of molecular weight, size, charge electromagnetic properties, or affinity among predetermined specific binding partners. The latter shall comprise antigens and antibodies, or binding fragments thereof, including epitopes and monoclonal antibodies, including binding fragments thereof. A further example of specific binding partners is biotin, and avidin or streptavidin, respectively.

When doing expression profiling experiments, it is not necessary to incorporate a procedure to enrich for different behavior of genes between to types of cells (commonly known as the "normal" and the "aberrant" cell) if relatively simple counting statistics (as modeled e.g. by the Poisson distribution) can be applied in the sampling procedure. If that is the case the comparison between the "normal" and the "aberrant" cells can be carried out in a database containing the expression profiles of the "normal" and the "aberrant" cells, respectively. If relatively simple counting statistics cannot be applied it may be necessary to either incorporate a procedure to enrich for differential behavior of genes or to use a large number of test samples to equal out random noise. The number of samples necessary in the latter case depends upon the signal-to-noise ratio of the method used in the expression profiling experiments.

When the present invention relates to methods for making expression profiling, the profiling is used to compare the expression of genes, or a subset of genes, in samples comprising a biological cell or a plurality of such cells, either directly or through a database comprising expression profiles.

The objective of the analysis is to elucidate which genes are expressed in a first type of cell, but not expressed, or expressed at a different level, in a second type of cell. Each expressed gene is initially identified by obtaining and identifying a unique polynucleotide tag that can be correlated to an expressed gene. The correlation enables a positive identification of each expressed gene and a very accurate assertion of the abundance of each expressed gene.

The analysis according to the present invention facilitates a characterization of the selected cell type and differentiates said cell type from other cell types, or essentially identical cell types having different histories.

The invention in further aspects relates to methods for identifying the polynucleotide tag, methods for identifying the nucleotide sequence of the tag, and methods for displaying an expression profile. The invention in further aspects also relates to using said expression profile, or a part thereof, obtained from a predetermined first cell and comparing said profile with that of a predetermined second cell.

In even further aspects the present invention relates to methods for treatment of a clinical condition or a genetic disorder in an individual, and methods for performing a diagnosis of a clinical condition or a genetic disorder in an individual, wherein said methods for treatment and/or diagnosis exploit either the method for displaying the results obtained from the analysis of the differential gene expression, or the method for analyzing an expression profile through a database comprising expression profiles.

There is also provided a kit of parts for performing the methods pertaining to the invention as described herein immediately above.

In a preferred aspect the present invention relates to a method for obtaining at least one single stranded polynucleotide tag from a biological sample, said method comprising the steps of
i) providing at least one double stranded polynucleotide, wherein the polynucleotide is selected from the group of polynucleotides consisting of polynucleotides comprising complementary DNA (cDNA), polynucleotides comprising genomic DNA, and polynucleotides comprising extra-genomic DNA, ii) contacting and cleaving at least one of the complementary strands of the double stranded polynucleotide provided in step i) with at least one cleavage agent capable of recognizing a double stranded polynucleotide comprising complementary polynucleotide strands and cleaving only one of the strands of the polynucleotide provided in step i), and iii) obtaining at least one single stranded polynucleotide tag.

In preferred embodiments the method comprises the further step(s) of i) isolating the tag and/or ii) determining the sequence of the tag and/or iii) quantifying the tag against a predetermined standard.

BRIEF DESCRIPTION OF THE DRAWINGS

As illustrated in FIGS. 15 through 18, a subset of ssDNA tags can be identified and quantified using an array. A population of ssDNA tags A) is exposed to identifying linker oligonucleotides B) attached to a solid support in an array. The identifying linker oligonucleotides are ordered in the array according to the sequence of their overhangs. 5' overhangs are indicated, but 3' overhangs may also be used, along with any suitable plurality of identifying linker oligonucleotides. Accordingly, although only three different identifying linker oligonucleotides are shown, and only in duplicates (i.e. two of each), any number of different identifying linker oligonucleotides can be used, and a comparatively large number of each identifying linker oligonucleotide may be attached closely together within the confined area defining that particular identifying linker oligonucleotide in the array. Different shading of strands illustrates different sequences. Complementary sequences are shown with the same shading. Selected 5' $PO_4$ and 3' OH groups are indicated.

FIG. 16: The ssDNA tags are ligated to the identifying linker oligonucleotides in the array. This way a part of the sequence in the ssDNA tags is used to sort the ssDNA tags. In this case this part is at the 5' end of the ssDNA tags, but the sequence in the 3' end of the ssDNA tag may also be used as well. Different shading of strands illustrates different sequences. Complementary sequences are shown with the same shading. Selected 5' $PO_4$ and 3' OH groups are indicated.

FIG. 17: A) A specific identifying linker oligonucleotide in solution with a predetermined sequence in the overhang and comprising a label A) is exposed to the population of chimeric tags B) made from ssDNA tags ligated to the identifying linker oligonucleotides in the array. Different shading of strands illustrates different sequences. Complementary sequences are shown with the same shading. Selected 5' $PO_4$ and 3' OH groups are indicated.

FIG. 18: A specific identifying linker oligonucleotide comprising a predetermined sequence in the overhang and comprising a label is contacted and ligated to the population of ssDNA tags ligated to the identifying linker oligonucleotide in the array. Then the individual intensities of all the positions in the array are recorded to determine the relative amount of the individual ssDNA tags in the subset. This completes the analysis of a panel of ssDNA tags sharing the same sequence in their 3' end. Different shading of strands illustrates different sequences. Complementary sequences are shown with the same shading. Selected 5' $PO_4$ and 3' OH groups are indicated.

As illustrated in FIGS. 15 through 22 a whole population of ssDNA tags can be identified and quantified using an array. Starting from FIG. 18 a specific identifying linker oligonucleotide in solution with a predetermined sequence in the overhang that is different from the sequence used in FIG. 17 and comprising a label A) is exposed to the population of chimeric tags B) made from ssDNA tags ligated to the identifying linker oligonucleotides in the array. Different shading of strands illustrates different sequences. Complementary sequences are shown with the same shading. Selected 5' $PO_4$ and 3' OH groups are indicated.

FIG. 20: A specific identifying linker oligonucleotide comprising a predetermined sequence in the overhang that is different from the sequence used in FIG. 17 and comprising a label is ligated to the population of chimeric tags made from ssDNA tags ligated to the identifying linker oligonucleotides in the array. Then the individual intensities of all the positions in the array are recorded. To determine the relative amount of the individual ssDNA tags in this second panel of ssDNA tags that share a common sequence in their 3' end the recordings from the previous panel (See FIG. 18) is subtracted. Different shading of strands illustrates different sequences. Complementary sequences are shown with the same shading. Selected 5' $PO_4$ and 3' OH groups are indicated.

FIG. 21: The process described in FIGS. 19 through 20 is iterated until all possible sequences in the overhang of the specific identifying linker oligonucleotide in solution with a predetermined sequence in the overhang and comprising a label have been used. Ultimately, a last specific identifying linker oligonucleotide in solution comprising a predetermined sequence in the overhang that is different from all the sequence previously used in the steps described in FIGS. 17 through 20 and comprising a label A) is exposed to the population of chimeric tags B) made from ssDNA tags ligated to the identifying linker oligonucleotide in the array. Different shading of strands illustrates different sequences. Complementary sequences are shown with the same shading. Selected 5' $PO_4$ and 3' OH groups are indicated.

FIG. 22: The last specific identifying linker oligonucleotide comprising a predetermined sequence in the overhang that is different from all the sequences previously used in the steps described in FIGS. 17 through 20 and comprising a label is ligated to the population of chimeric tags made from ssDNA tags ligated to the identifying linker oligonucleotides in the array. Then the individual intensities of all the positions in the array are recorded. To determine the relative amount of the individual ssDNA tags in this last panel of ssDNA tags that share a common sequence in their 3' end all the recordings from the previous panels are subtracted. Different shading of strands illustrates different sequences. Complementary sequences are shown with the same shading. If the identifying linker oligonucleotides in solution are comprising labels of a different color for each different sequence of their overhang, then a plurality of different identifying linker oligonucleotides in solution may be exposed, hybridized and ligated simultaneously. An optical separation can then give data for each subset. Selected 5' $PO_4$ and 3' OH groups are indicated.

FIG. 23: As illustrated in FIGS. 23 through 30 a whole population of ssDNA tags can be identified and quantified using an array in another preferred embodiment. In this embodiment both the variable end of the identifying linker oligonucleotide and the ssDNA tag is protected against cleavage with methylated bases. A specific identifying linker oligonucleotide in solution A) comprising a predetermined sequence in the overhang and comprising a label and a cleavage site for a site-specific restriction endonuclease (hatched box) is exposed to the population of chimeric tags B) made from ssDNA tags ligated to the identifying linker oligonucleotides in the array (See FIG. 16). Different shading of strands illustrates different sequences. Complementary sequences are shown with the same shading. Selected 5' $PO_4$ and 3' OH groups are indicated.

FIG. 24: A specific identifying linker oligonucleotide comprising a predetermined sequence in the overhang and comprising a label and a cleavage site for a site-specific restriction endonuclease (hatched box) is contacted and ligated to the population of chimeric tags made from ssDNA tags ligated to the identifying linker oligonucleotides in the array. Then the individual intensities of all the positions in the array are recorded to determine the relative amount of the individual ssDNA tags in the subset. This completes the analysis of a panel of ssDNA tags sharing the same sequence in their 3' end. Different shading of strands illustrates different sequences. Complementary sequences are shown with the same shading. Selected 5' $PO_4$ and 3' OH groups are indicated.

FIG. 25: The array is subsequently exposed to a restriction endonuclease recognizing and cleaving the unmethylated cleavage site introduced with the identifying linker oligonucleotide previously ligated to a subset of the chimeric tags and all the labels are cleaved from the chimeric tags and subsequently washed off of the array. Different shading of strands illustrates different sequences. Complementary sequences are shown with the same shading. Selected 5' $PO_4$ and 3' OH groups are indicated.

FIG. 26: A specific identifying linker oligonucleotide in solution A) comprising a predetermined sequence in the overhang that is different from the sequence used in FIGS. 23 and 25 and comprising a label and a cleavage site for a site-specific restriction endonuclease (hatched box) is exposed to the population of chimeric tags B) made from ssDNA tags ligated to the identifying linker oligonucleotides in the array. Different shading of strands illustrates different sequences. Complementary sequences are shown with the same shading. Selected 5' P and 3' OH groups are indicated.

FIG. 27: A specific identifying linker oligonucleotide comprising a predetermined sequence in the overhang that is different from the sequence used in FIGS. 23 and 25 and comprising a label and a cleavage site for a site-specific restriction endonuclease (hatched box) A) is ligated to the population of chimeric tags made from ssDNA tags ligated to the identifying linker oligonucleotides in the array. Then the individual intensities of all the positions in the array are recorded: Different shading of strands illustrates different sequences. Complementary sequences are shown with the same shading. Selected 5' $PO_4$ and 3' OH groups are indicated.

FIG. 28: The array is subsequently exposed to a restriction endonuclease recognizing and cleaving the unmethylated cleavage site introduced with the identifying linker oligonucleotide previously ligated to a subset of the chimeric tags in FIG. 27 and all the labels are cleaved from the chimeric tags and subsequently washed off of the array. Different shading of strands illustrates different sequences. Complementary sequences are shown with the same shading Selected 5' $PO_4$ and 3' OH groups are indicated.

FIG. 29: The process described in FIGS. 26 through 28 is iterated until all possible sequences in the overhang of the specific identifying linker oligonucleotide in solution comprising a predetermined sequence in the overhang and comprising a label and a cleavage site for a site-specific restriction endonuclease have been used. Ultimately, a last specific identifying linker oligonucleotide in solution A) comprising a predetermined sequence in the overhang that is different from all the sequence previously used in the steps described in FIGS. 23 through 28 and comprising a label and a cleavage site for a site-specific restriction endonuclease (hatched box) is exposed to the population of chimeric tags B) made from ssDNA tags ligated to the identifying linker oligonucleotides in the array. Different shading of strands illustrates different sequences. Complementary sequences are shown with the same shading. Selected 5' $PO_4$ and 3' OH groups are indicated.

FIG. 30: The last specific identifying linker oligonucleotide comprising a predetermined sequence in the overhang that is different from all the sequence previously used in the steps described in FIGS. 23 through 28 and comprising a label and a cleavage site for a site-specific restriction endonuclease (hatched box) is ligated to the population of chimeric tags made from ssDNA tags ligated to the identifying linker oligonucleotides in the array. Then the individual intensities of all the positions in the array are recorded to complete the profiling experiment. Different shading of strands illustrates different sequences. Complementary sequences are shown with the same shading. Selected 5' $PO_4$ and 3' OH groups are indicated.

As illustrated in FIGS. 39 through 43 in one embodiment a subset of ssDNA tags can be identified and quantified using two arrays. In this embodiment both the variable end of the identifying linker oligonucleotide and the ssDNA tag is protected against cleavage with methylated bases. In one embodiment an array of identifying linker oligonucleotides comprising a label and a recognition/ binding site for a site-specific cleavage agent A) is exposed to the ssDNA tags in solution B). Different shading of strands illustrates different sequences. Likewise different restriction sites are depicted with different shading. Complementary sequences are shown with the same shading. Different restriction endonuclease recognition/binding sites are illustrated with boxes of different shadings. Selected 5' $PO_4$ and 3' OH groups are indicated.

FIG. 40: The ssDNA tags are ligated to the identifying linker oligonucleotides in the array. This way a part of the sequence in the ssDNA tags is used to sort the ssDNA tags. In this illustration this part is at the 5' end of the ssDNA tags but the 3' end could have been used instead. Different shading of strands illustrates different sequences. Likewise different restriction sites are depicted with different shading. Complementary sequences are shown with the same shading. Different restriction endonuclease recognition/binding sites are illustrated with boxes of different shadings. Selected 5' $PO_4$ and 3' OH groups are indicated.

FIG. 41: A site-specific cleavage agent is used to free a predetermined subset of chimeric tags from the array A). This releases a subset of chimeric tags B) comprised of the ssDNA tags and the identifying linker oligonucleotides in the array that was cleaved. The label is released together with the chimeric tags. Different shading of strands illustrates different sequences. Likewise different restriction sites are depicted with different shading. Complementary sequences are shown with the same shading. Different restriction endonuclease recognition/binding sites are illustrated with boxes of different shadings. Selected 5' $PO_4$ and 3' OH groups are indicated.

FIG. 42: Another array A) is exposed to the released chimeric tags B). Different shading of strands illustrates different sequences. Complementary sequences are shown with the same shading. Selected 5' $PO_4$ and 3' OH groups are indicated.

FIG. 43: After ligation the second array is now ready for recording of the data. Different shading of strands illustrates different sequences. Complementary sequences are shown with the same shading. Selected 5' $PO_4$ and 3' OH groups are indicated.

As illustrated in FIGS. 44 through 51 in one embodiment a whole population of ssDNA tags can be identified and quantified using e.g. a microfluid device. In one such embodiment, both the variable end of the identifying linker oligonucleotide and the ssDNA tag is protected against cleavage with methylated bases. In a microfluid device a complete set of first identifying linker oligonucleotides in solution A) comprising every combination of sequence in the overhang, or a predetermined subset thereof, and comprising a label and a predetermined molecular identifier capable of identifying each predetermined overhang of the identifying linker oligonucleotides and comprising a recognition/binding site for a type II restriction endonucleaseis exposed to a sample of ssDNA tags B). Unique molecular identifiers are illustrated as M1, M2, M3, and any suitable plurality of molecular identifiers can be applied. The molecular identifier that makes it possible to identify each identifying linker oligonucleotide comprising a predetermined nucleotide sequence overhang can be i) a predetermined epitope, or ii) a molecule comprised of a predetermined number of subunits having the same, or almost the same charge, mass, hydrophobic properties, three dimensional structure, or any other physical or chemical property, or any combination thereof, wherein the different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy, or iii) a predetermined dsDNA or ssDNA oligonucleotide having either a different predetermined length, or a different predetermined sequence, optionally chosen from a minimal cross hybridization set, or iv) a peptide of a predetermined length or sequence, or v) a predetermined first (small) molecule capable of binding to a second (larger) molecule, e.g biotin, or vi) any combination of i)–v). In this case 5' overhangs are used, but 3' overhangs may also be used, in both cases along with any suitable plurality of identifying linker oligonucleotides. Different shading of strands illustrates different sequences. Complementary sequences are shown with the same shading. Selected 5' $PO_4$ and 3' OH groups are indicated.

FIG. 45: Following ligation the chimeric dsDNA tags are separated in the microfluid device by using molecular identifiers that makes it possible to identify each predetermined overhang of the first identifying linker oligonucleotides. Different shading of strands illustrates different sequences. Complementary sequences are shown with the same shading. Selected 5' $PO_4$ and 3' OH groups are indicated.

FIG. 46: After separation each pool of separated chimeric dsDNA tags is comprised of chimeric dsDNA tags having a variety of 3' overhangs. Different shading of strands illustrates different sequences. Complementary sequences are shown with the same shading. Selected 5' $PO_4$ and 3' OH groups are indicated.

FIG. 47: A site-specific cleavage agent is used to remove the part of the chimeric dsDNA comprising a molecular identifier that makes it possible to identify each predetermined overhang of the first identifying linker oligonucleotides. Different shading of strands illustrates different sequences. Complementary sequences are shown with the same shading. Selected 5' $PO_4$ and 3' OH groups are indicated.

FIG. 48: The chimeric dsDNA tags A) are exposed to complete set of second identifying linker oligonucleotides in solution B) comprising every combination of sequence in the overhang or a preselected subset thereof and comprising a molecular identifier that makes it possible to identify each predetermined overhang of the identifying linker oligonucleotides. If 5' overhangs are used for the first set of identifying linker oligonucleotides in solution, then 3' overhangs are used for the second set of identifying linker oligonucleotides in solution and vice versa. Different shading of strands illustrates different sequences. Complementary sequences are shown with the same shading. Selected 5' $PO_4$ and 3' OH groups are indicated.

FIG. 49: After ligation a set of chimeric dsDNA tags each comprising a label and a molecular identifier that makes it possible to identify each predetermined overhang of the second identifying linker oligonucleotides is obtained. Different shading of strands illustrates different sequences. Complementary sequences are shown with the same shading. Selected 5' $PO_4$ and 3' OH groups are indicated.

FIG. 50: Using a microfluid device the chimeric dsDNA tags are seperated. Different shading of strands illustrates different sequences. Complementary sequences are shown with the same shading. Selected 5' $PO_4$ and 3' OH groups are indicated.

FIG. 51: Before quantification of each chimeric dsDNA tag the molecular identifier that makes it possible to identify each predetermined overhang of the identifying linker oligonucleotides is optionally removed by cleaving with a site-specific cleavage agent. Different shading of strands illustrates different sequences. Complementary sequences are shown with the same shading. Selected 5' $PO_4$ and 3' OH groups are indicated.

FIG. 58: The conditions are manipulated so that the ssDNA tags hybridizes to the 5' overhangs of the first identifying linker nucleotides comprising a label A). After hybridization the ssDNA tags together with the first identifying linker oligonucleotides comprising a label exposes a 3' overhang that the second identifying linker oligonucleotides comprising a molecular identifier B) can hybridize to. Different shading of strands illustrates different sequences. Complementary sequences are shown with the same shading. Selected 5' $PO_4$ and 3' OH groups are indicated.

FIG. 59: Concurrently the second identifying linker oligonucleotides comprising a molecular identifier hybridize to the exposed 3' end of the ssDNA tags hybridized to the first identifying linker oligonucleotides comprising a label. This complex is a substrate for ligase, but because the ssDNA tags and the second identifying linker oligonucleotides in solution had their 5' end blocked, only the two identifying linker oligonucleotides can be ligated together. Different shading of strands illustrates different sequences. Complementary sequences are shown with the same shading. Selected 5' $PO_4$ and 3' OH groups are indicated.

FIG. 61: Again the conditions are changed; for example by cooling down; making the ssDNA tags hybridize to the first identifying linker oligonucleotides again A). Because the concentration of the first identifying linker oligonucleotides in solution exceeds the number of ssDNA tags having the same complementary 5' end, the chances a tag hybridizes to a first identifying linker oligonucleotide that is already ligated to one of the second identifying linker oligonucleotides in solution is very small. After hybridization the ssDNA tags together with the first identifying linker oligonucleotides comprising a label exposes a 3' overhang that the second identifying linker oligonucleotides comprising a molecular identifier B) can hybridize to. Different shading of strands illustrates different sequences. Complementary sequences are shown with the same shading. Selected 5' $PO_4$ and 3' OH groups are indicated.

FIG. 63: After a number of cycles of the steps In FIGS. 60 through 62 the signal from a subset of the ssDNA tags have been amplified without consuming the ssDNA tags in the process. Due to the molecular identifier on the second identifying linker oligonucleotide a separation can be carried out so that each subset of amplification products from the asymmetric LCR can be quantified without interference from the other subsets of amplification products. In this case two subset of amplification products are shown in A) and B). Different shading of strands illustrates different sequences. Selected 5' $PO_4$ and 3' OH groups are indicated.

DEFINITIONS

Adapter oligonucleotide: Generally speaking an adapter oligonucleotide is an oligonucleotide, either double stranded or single stranded, that is capable of being linked to a polynucleotide, preferably by means of ligation or PCR, for a specific purpose. In the present context an adapter oligonucleotide is an oligonucleotide comprising a recognition/binding motif or a part thereof, wherein the recognition/binding motif is capable of being recognized by a cleavage agent. Unless otherwise stated, the adapter oligonucleotide comprises a recognition motif for a cleavage agent capable of recognizing a predetermined motif of a double stranded polynucleotide and cleaving only one strand of the double stranded nucleotide. Optionally the adapter oligonucleotide also comprises one or more recognition motifs for one or more cleavage agents capable of cleaving both strands of a double stranded polynucleotide. Such cleavage agents are known in the art and described herein as site specific nicking endonucleases and site-specific restriction endonucleases respectively. Examples are site-specific nicking endonucleases of the N. BstNB I type, and site-specific restriction endonucleases of type II and of type IIs. The recognition motif may be a hybrid motif, wherein part of the motif is recognized by more than one cleavage agent. See FIGS. 10–13 for a number of examples of an adapter. When present in single stranded form the adapter comprises one nucleotide strand, which, together with the complementary strand, comprises the motif. Single stranded adapters are preferably ligated to single stranded polynucleotides, such as RNA species. The resulting single stranded chimeric polynucleotide is subsequently converted into a double stranded polynucleotide. Double stranded adapters are capable of being ligated directly to a double stranded polynucleotide with compatible sticky ends or optionally a blunt end, if the adapter is blunt ended.

Amplification: Process whereby more copies are generated of a tag sequence or a sequence complementary thereto, or both. The product of an amplification may also include flanking sequences not included in the tag sequence.

Figure 15:
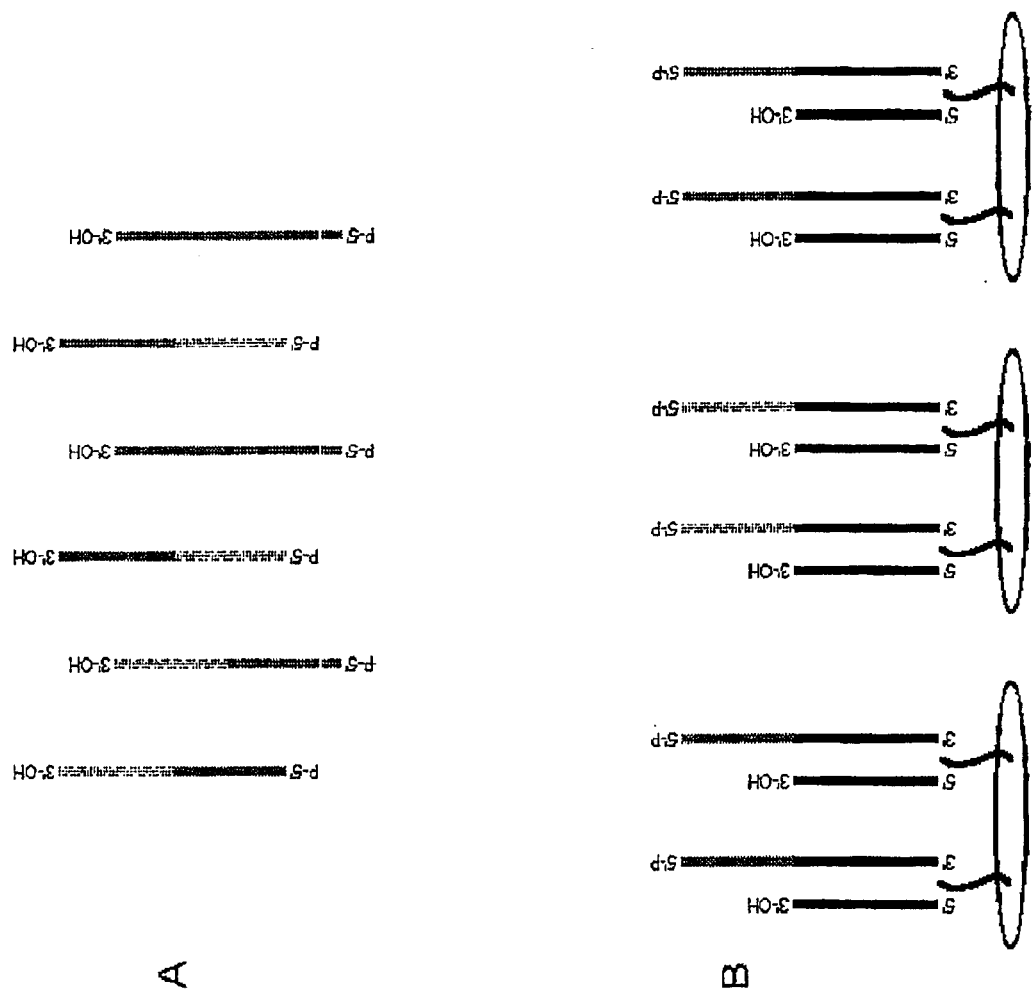
FIG. 15.
Figure 16:
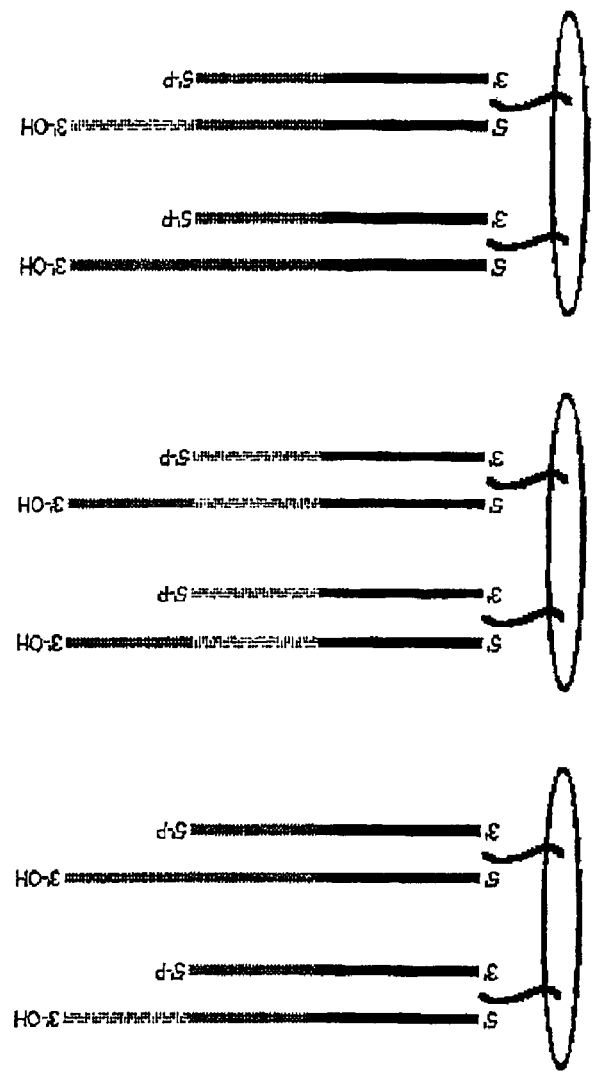
Figure 17:
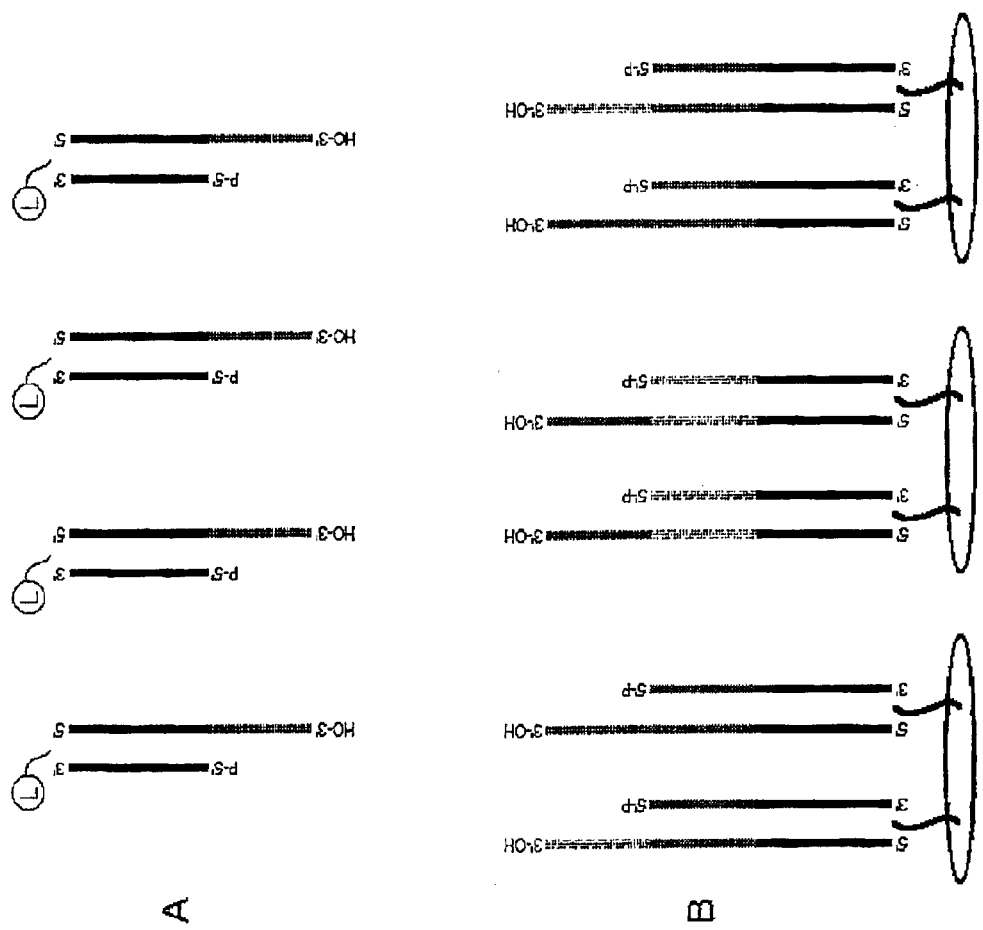
Figure 18:
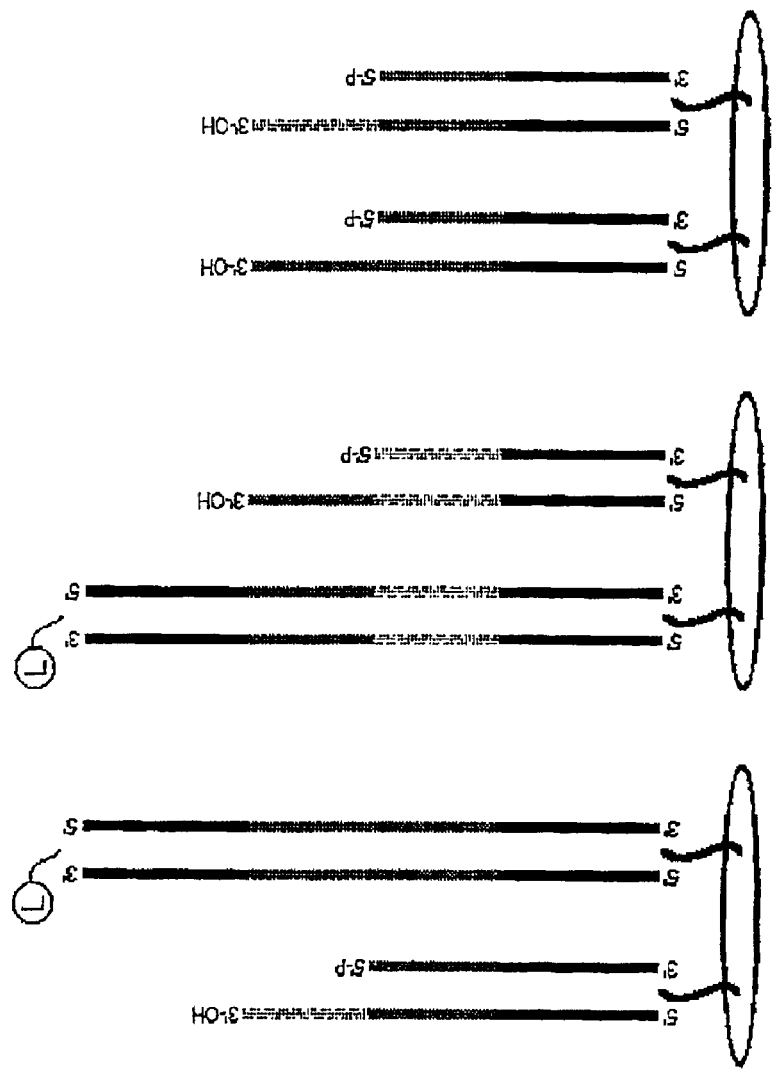
Figure 19:
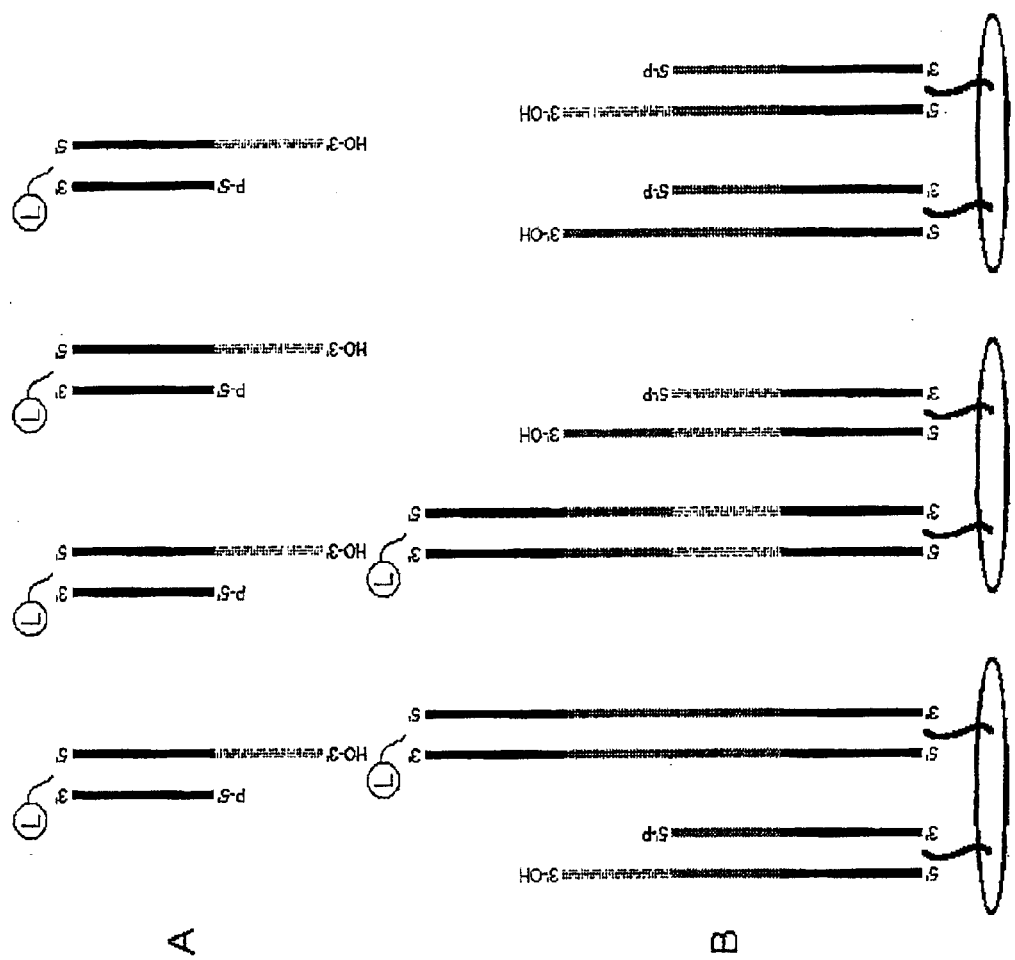
FIG. 19.
Figure 20:
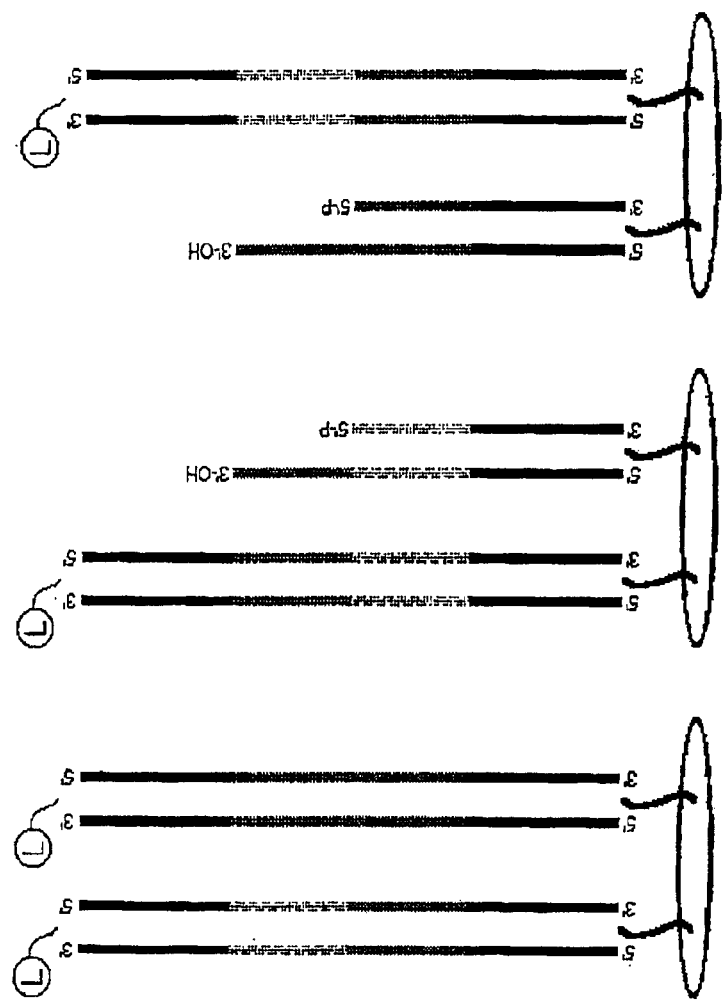
Figure 21:
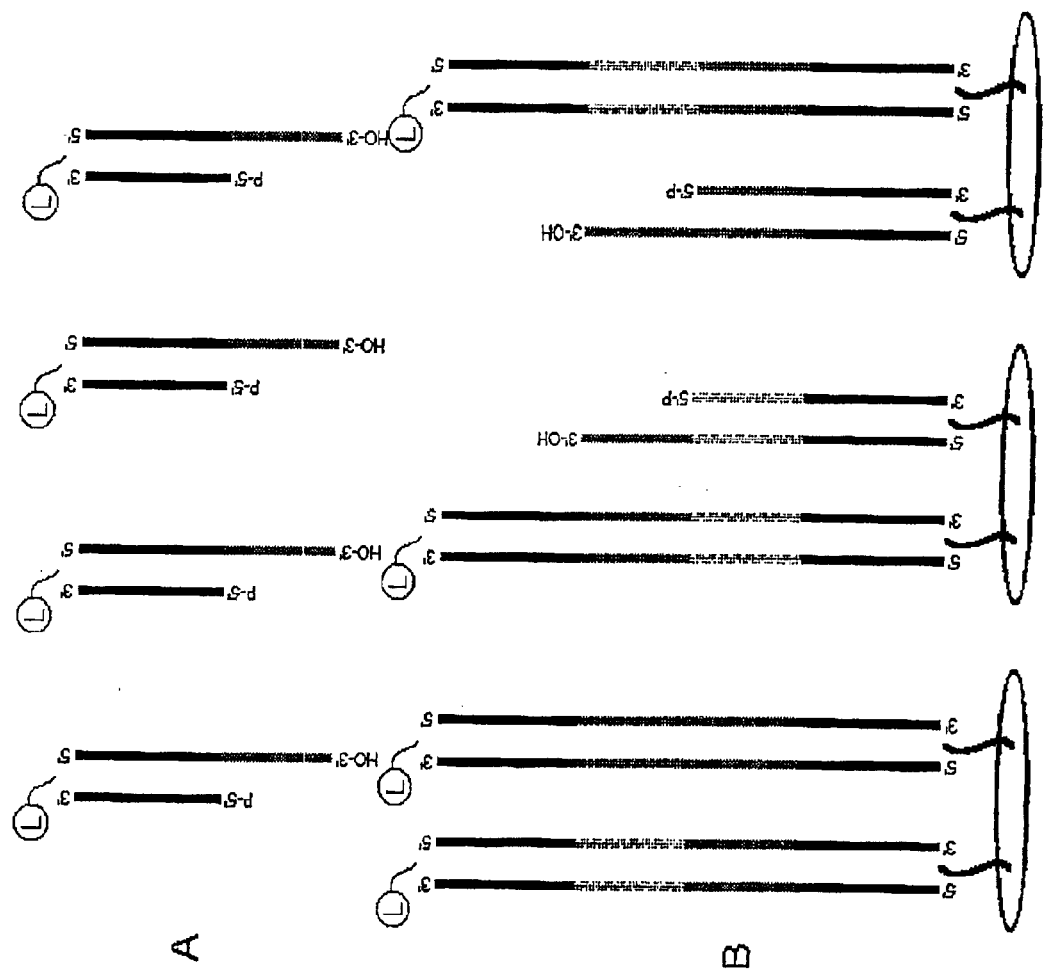
Figure 22:
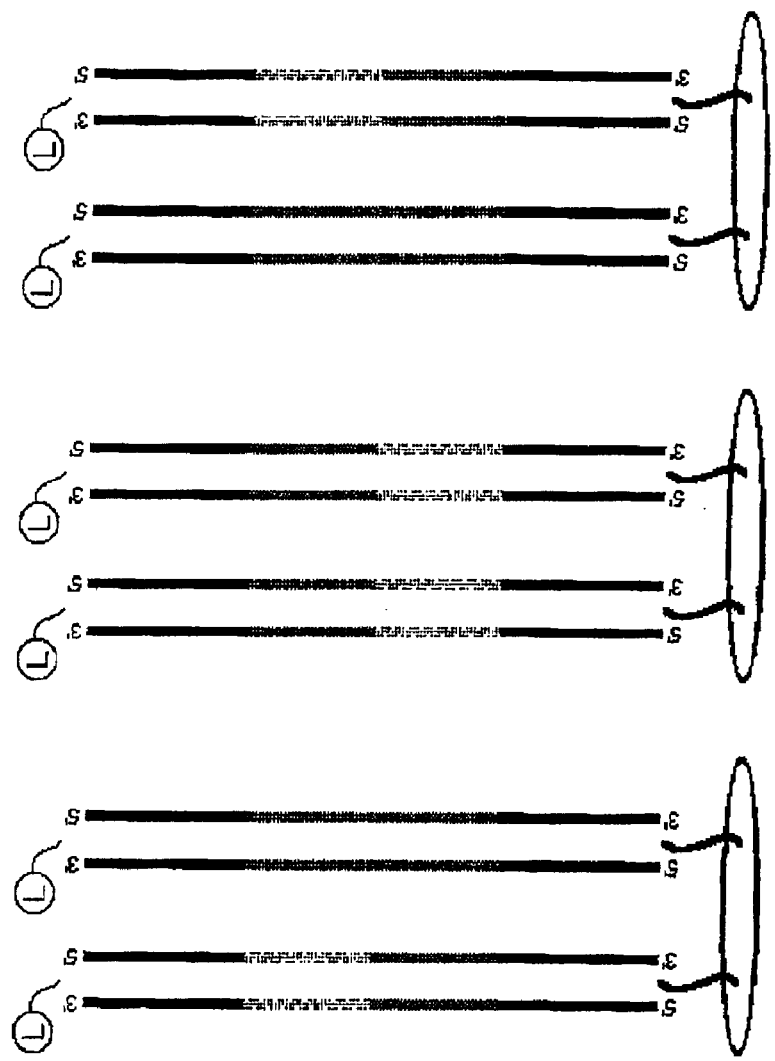
Figure 24:
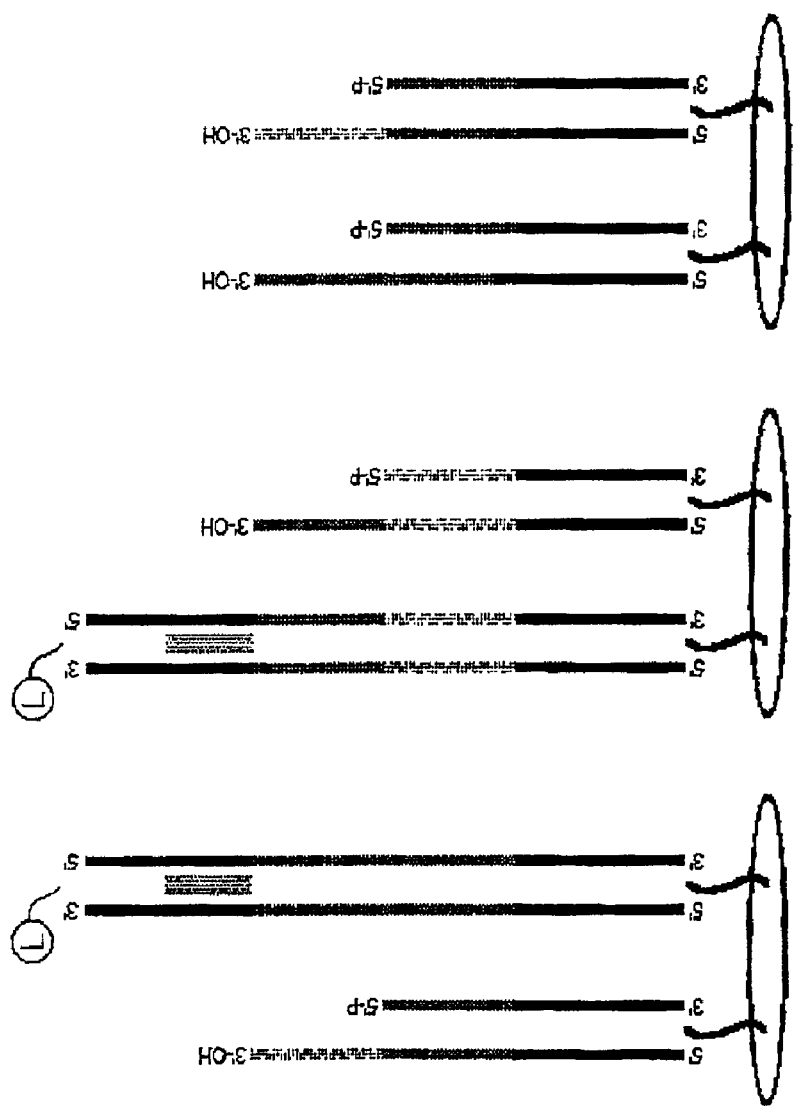
Figure 25:
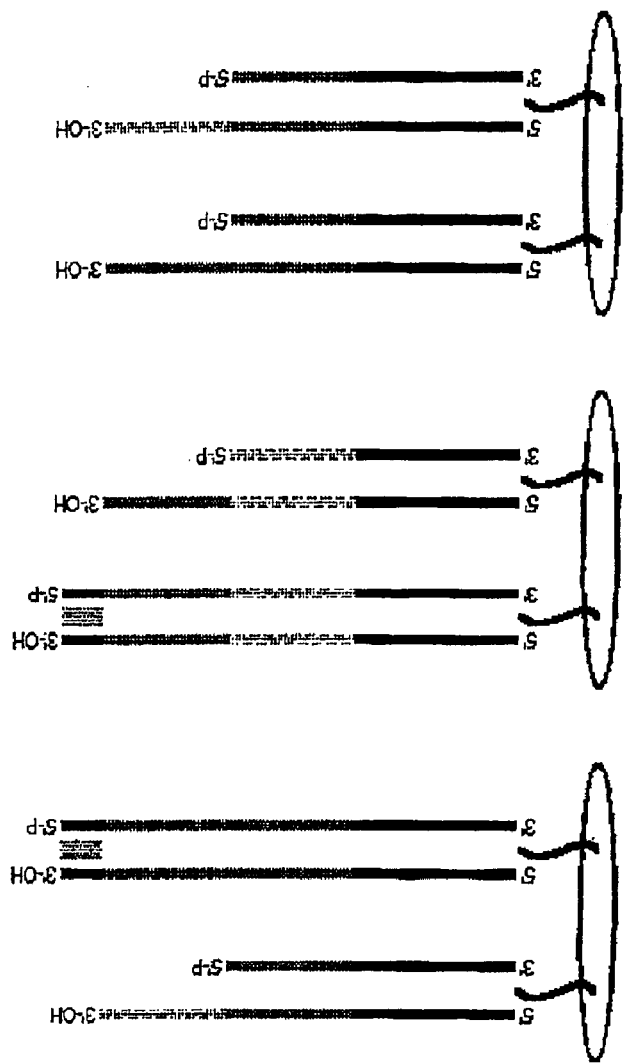
Figure 26:
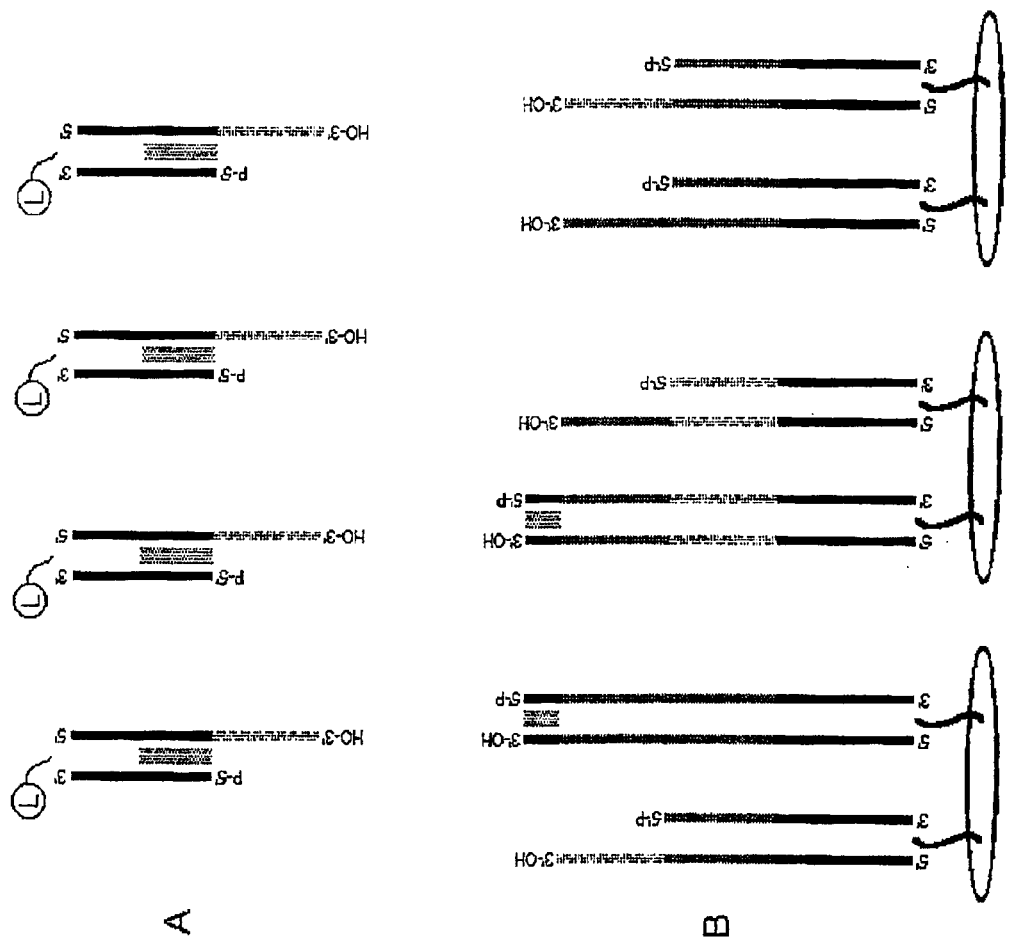
Figure 27:
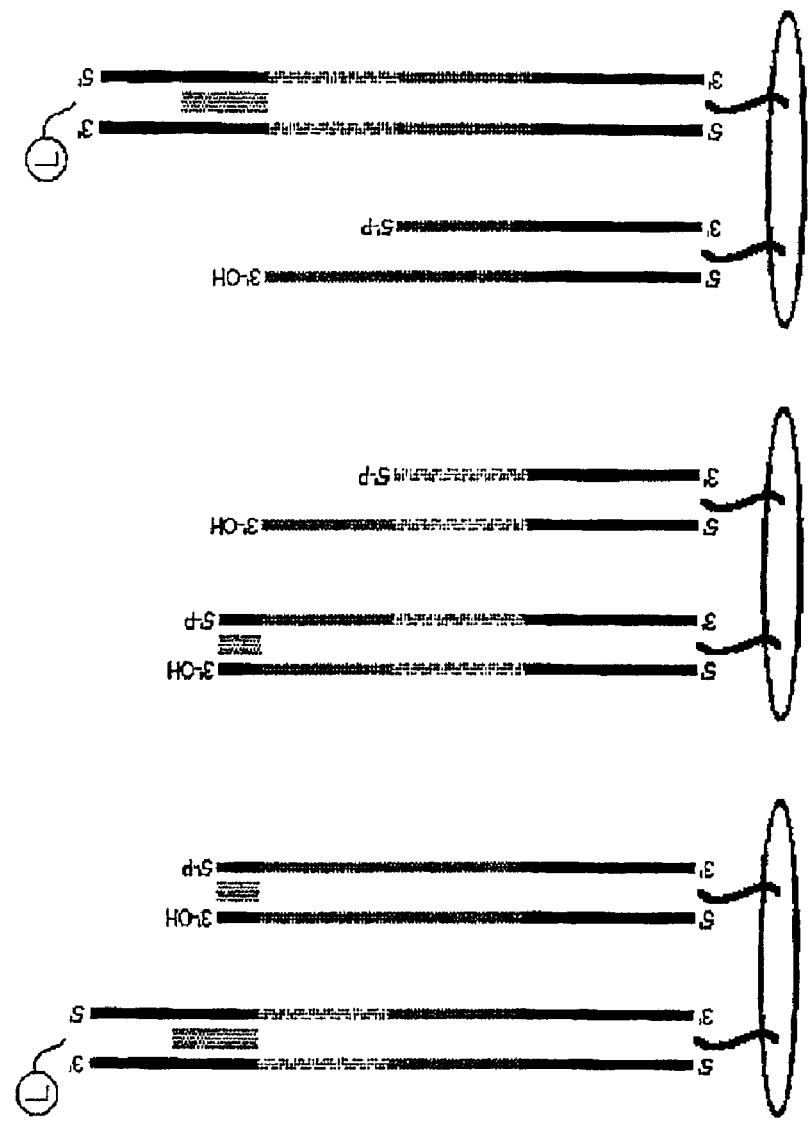
Figure 28:
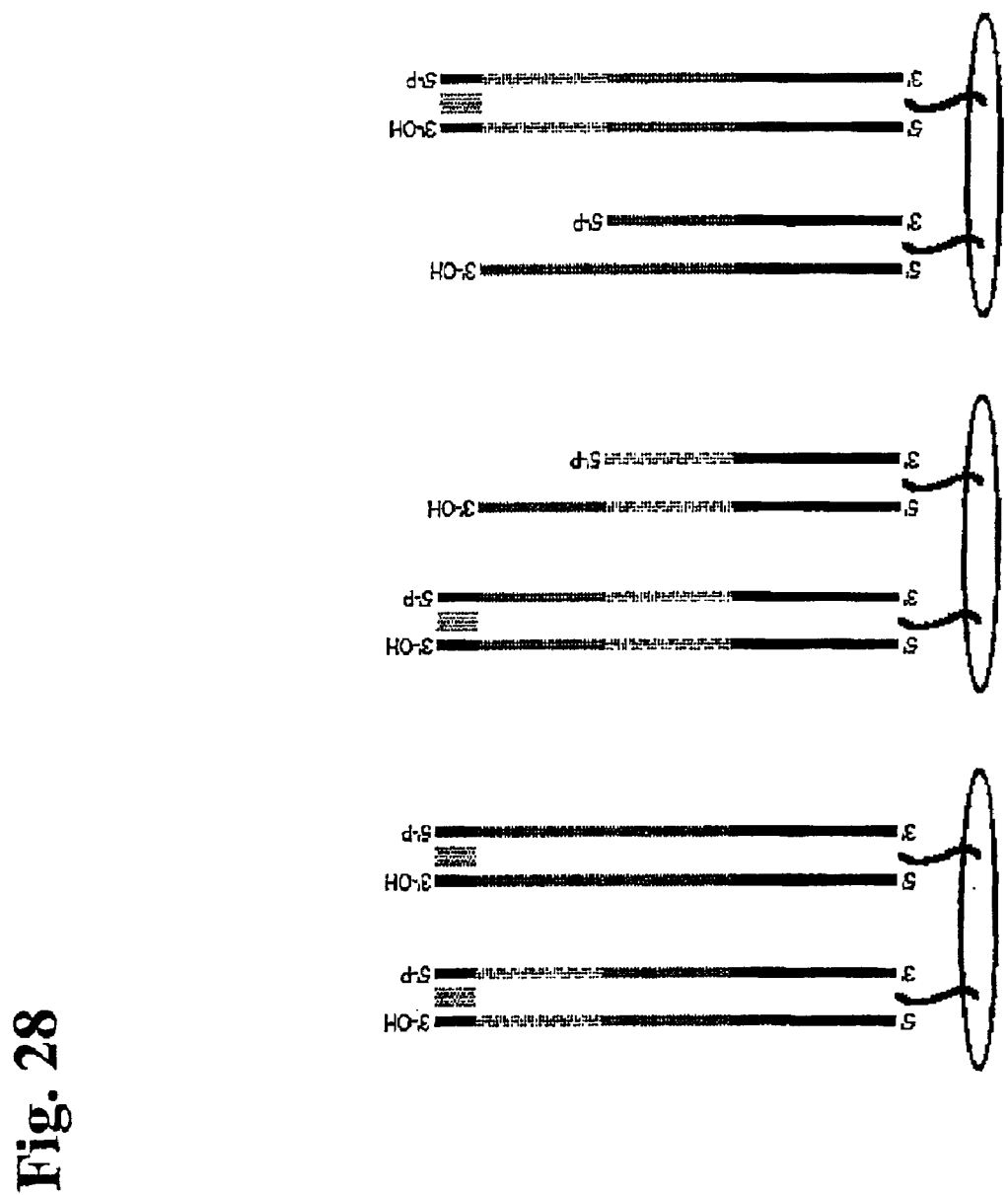
Figure 29:
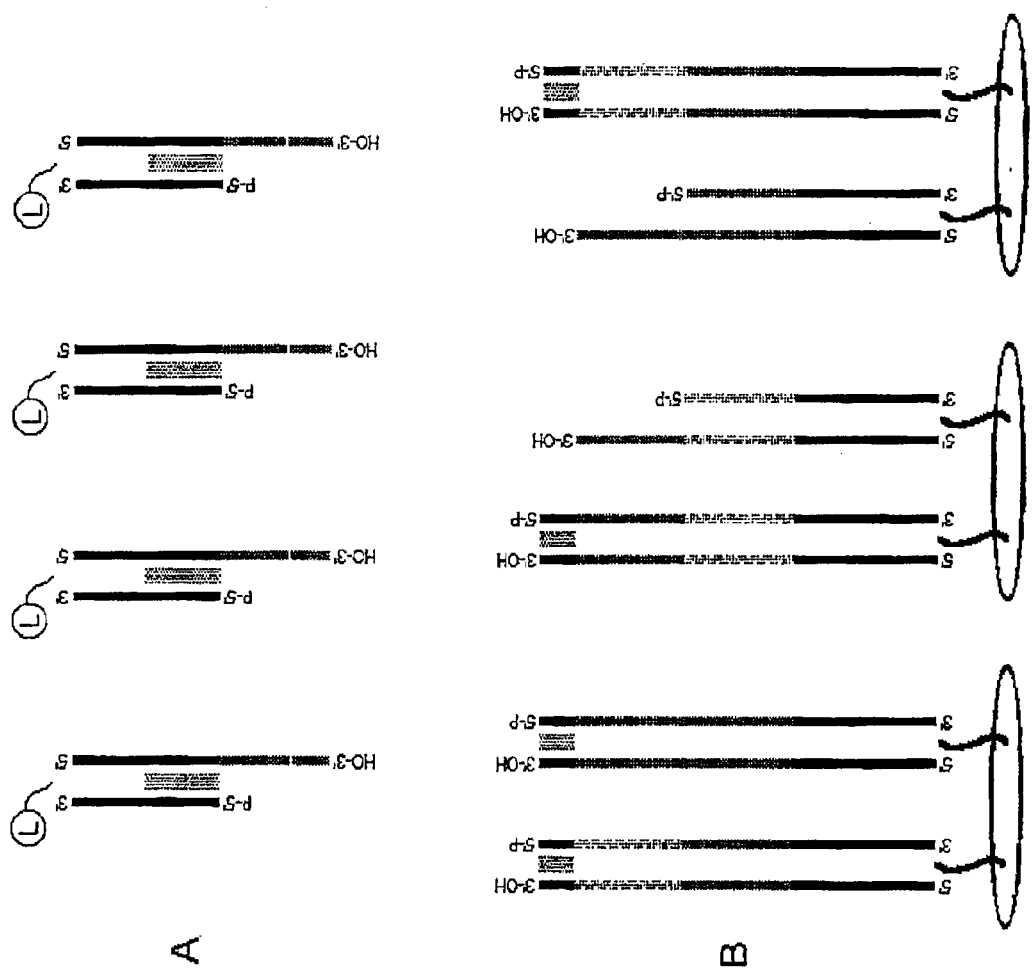
Figure 30:
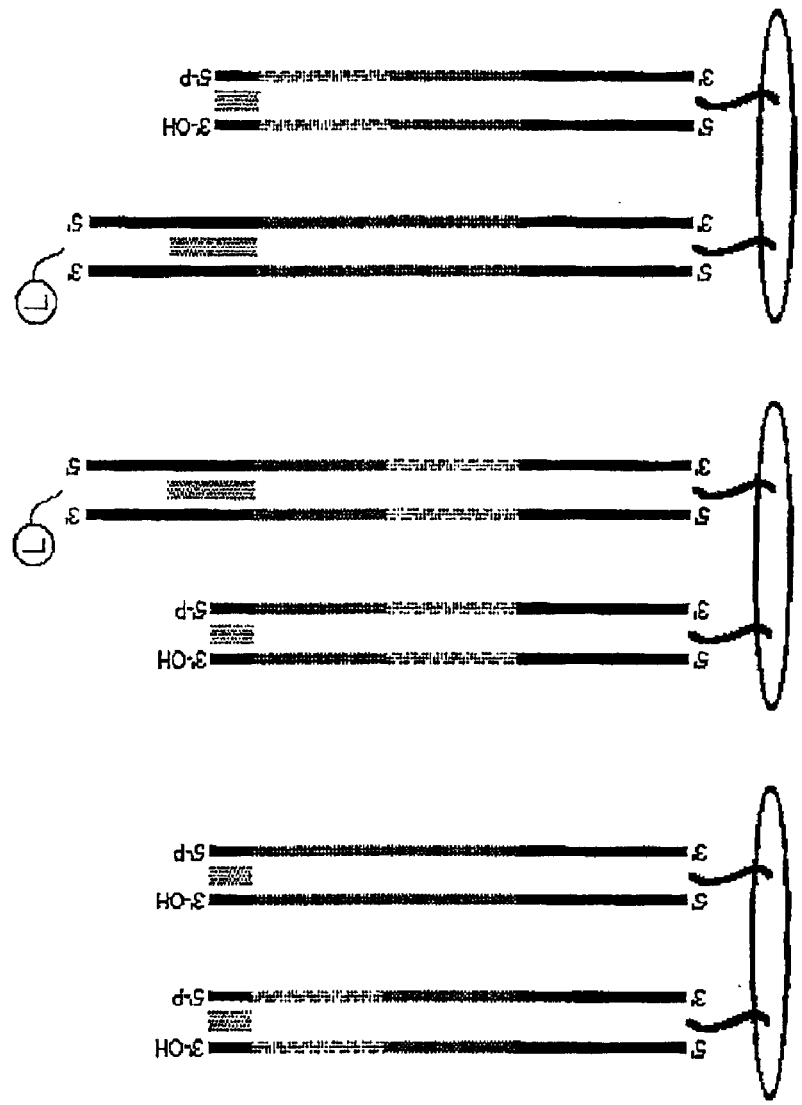
Figure 31:
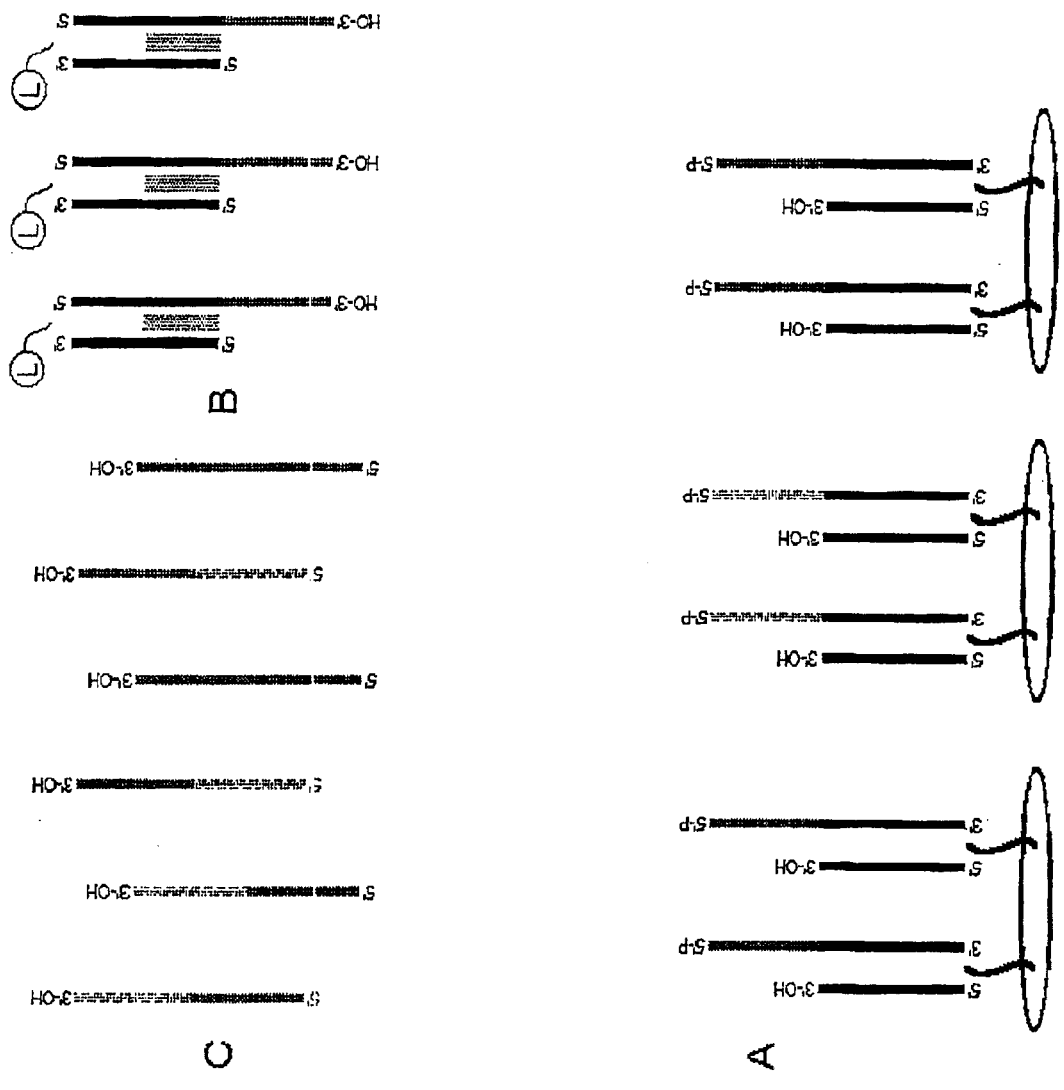
FIG. 31: In one preferred embodiment asymmetric LCR amplification of the signal from each ssDNA tag can be carried out as illustrated in FIGS. 31 through 37. As a first step the ssDNA tags are blocked in one end, for example by removing the 5' phosphate group. These blocked ssDNA tags are then used in an asymmetric ligase chain reaction (LCR) directly on an array to amplify the signal derived from each ssDNA tag. An array similar to that used in FIG. 15A) and a linker in solution B) comprising a predetermined sequence in the overhang and comprising a label and having the 5' end next to the 3' end overhang blocked; for example by removing the 5' phosphate group; is exposed to the ssDNA tags C) having a blocked 5' end. In this case 5' overhangs are used on the array, but 3' overhangs may also be used, in both cases along with any suitable plurality of identifying linker oligonucleotides. Accordingly, although only three different identifying linker oligonucleotides are shown, and only in duplicates (i.e. two of each), any number of different identifying linker oligonucleotides can be used, and a comparatively large number of each identifying linker oligonucleotide may be attached closely together within the confined area defining that particular identifying linker oligonucleotide in the array. Different shading of strands illustrates different sequences. Complementary sequences are shown with the same shading. Selected 5' $PO_4$ and 3' OH groups are indicated.
Figure 32:
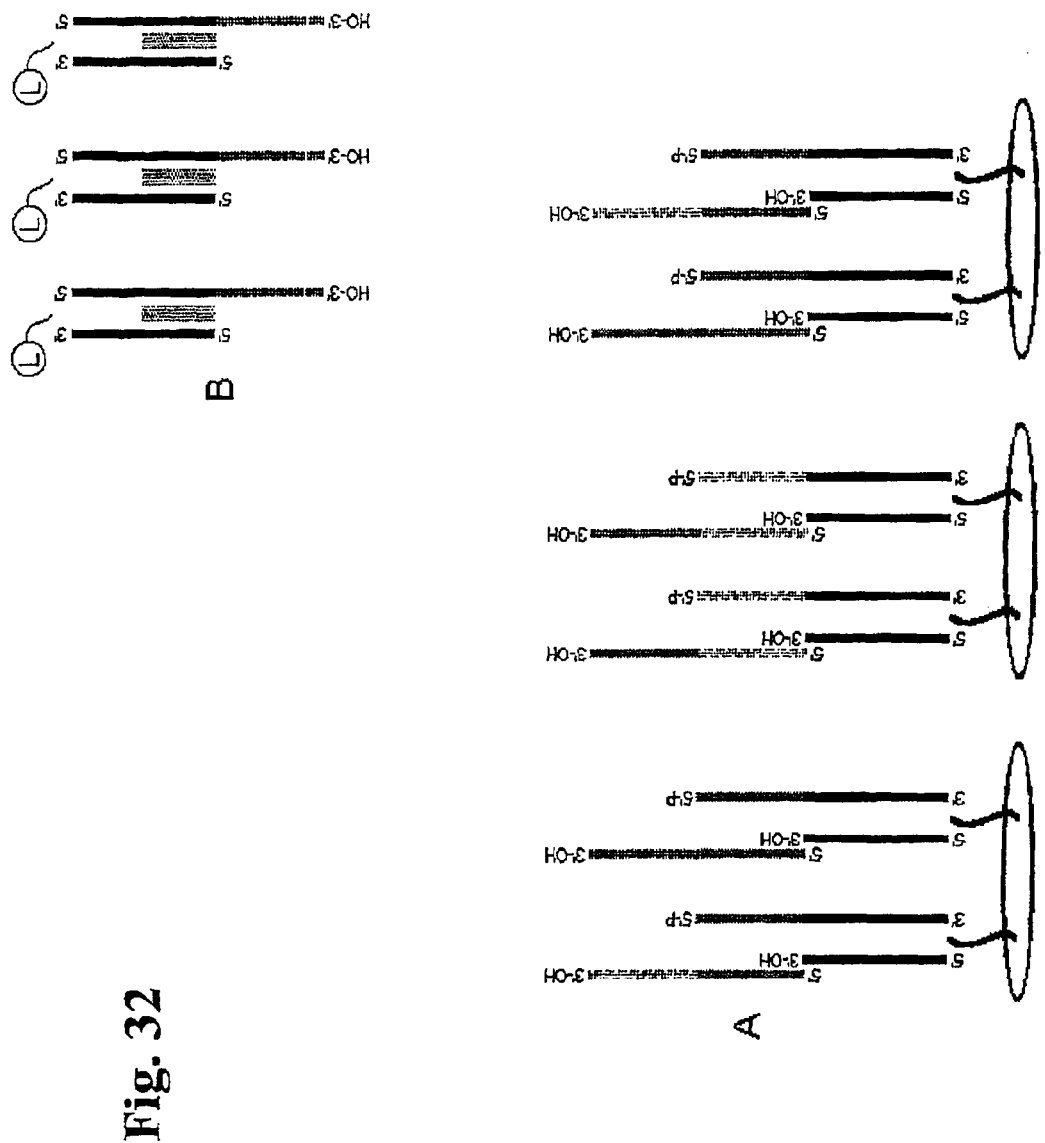
FIG. 32: The conditions are manipulated so that the ssDNA tags hybridize to the 5' overhangs of the linkers in the array A). After hybridization the ssDNA tags together with the identifying linker oligonucleotides in the array exposes a 3' overhang that the identifying linker oligonucleotides in solution B) can hybridize to. Different shading of strands illustrates different sequences. Complementary sequences are shown with the same shading. Selected 5' $PO_4$ and 3' OH groups are indicated.
Figure 33:
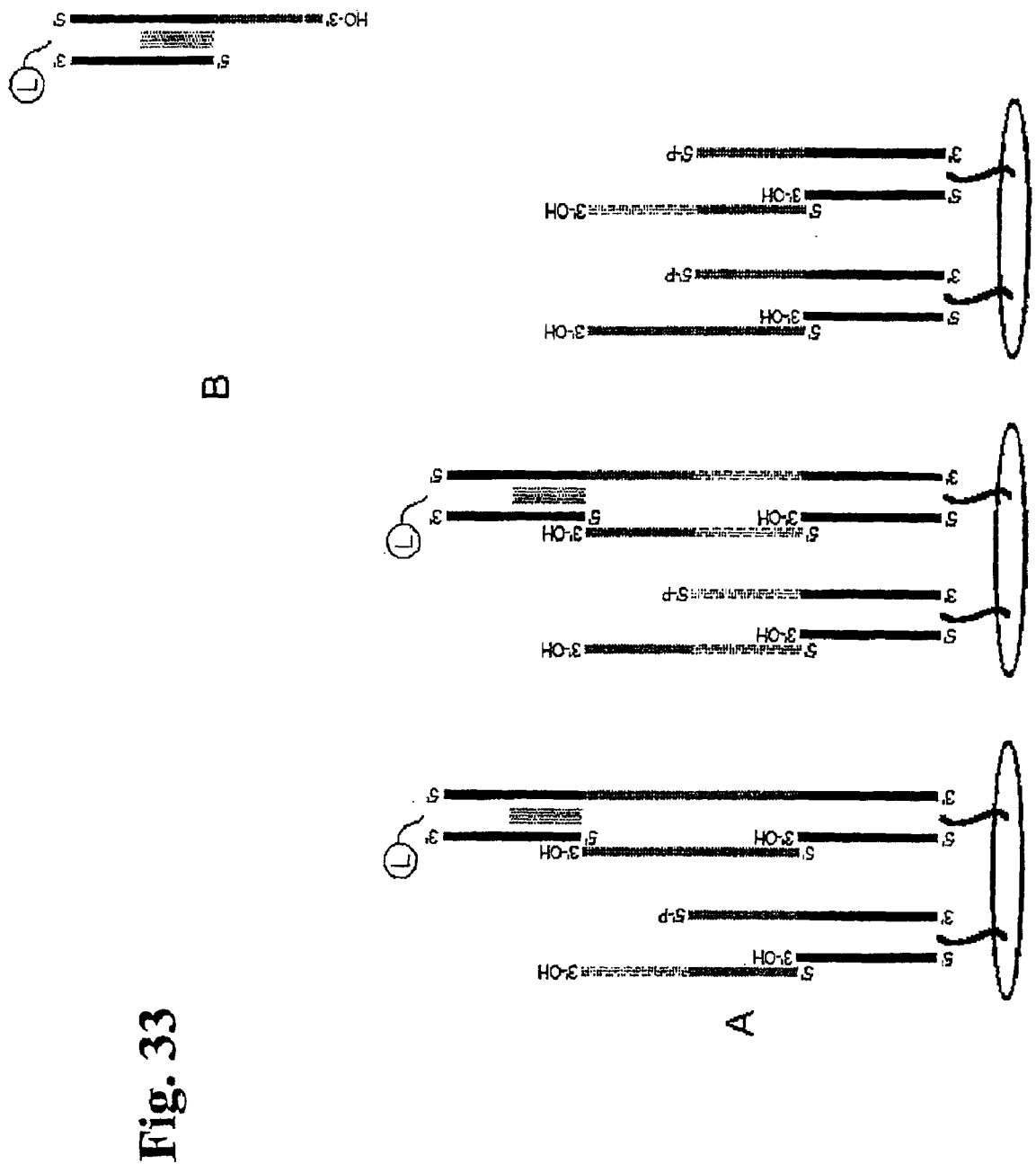
FIG. 33: Concurrently the identifying linker oligonucleotides comprising a label hybridizes to the exposed 3' end of the ssDNA tags hybridized to the identifying linker oligonucleotides in the array A). This complex is a substrate for ligase, but because the ssDNA tags and the identifying linker oligonucleotides in solution had their 5' end blocked only the two identifying linker oligonucleotides can be ligated together. Different shading of strands illustrates different sequences. Complementary sequences are shown with the same shading. Selected 5' $PO_4$ and 3' OH groups are indicated.
Figure 34:
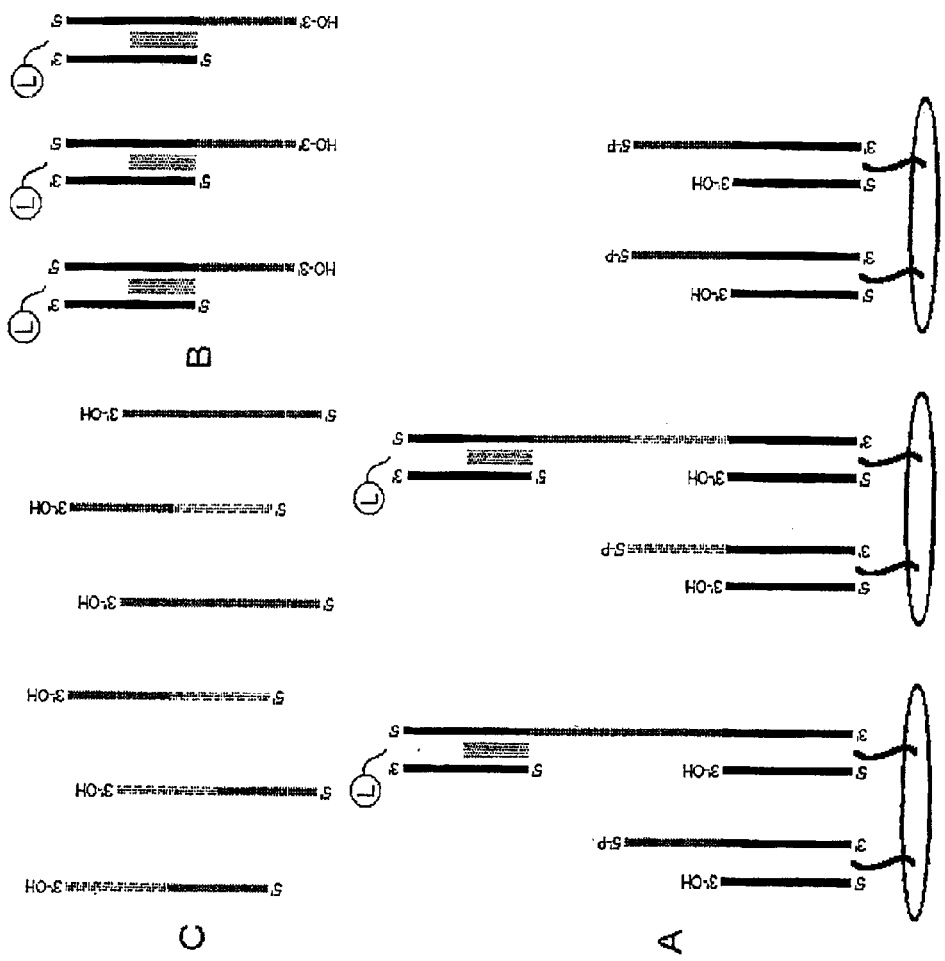
FIG. 34: The conditions are changed again; for example by heating; leaving a number of identifying linker oligonucleotides covalently attached to some of the linkers in the array A). If necessary the concentration of the identifying linker oligonucleotides in solution B) is adjusted to restore the initial concentration. The ssDNA tags C) are restored in solution by the changing of the conditions. Different shading of strands illustrates different sequences. Complementary sequences are shown with the same shading. Selected 5' $PO_4$ and 3' OH groups are indicated.
Figure 35:
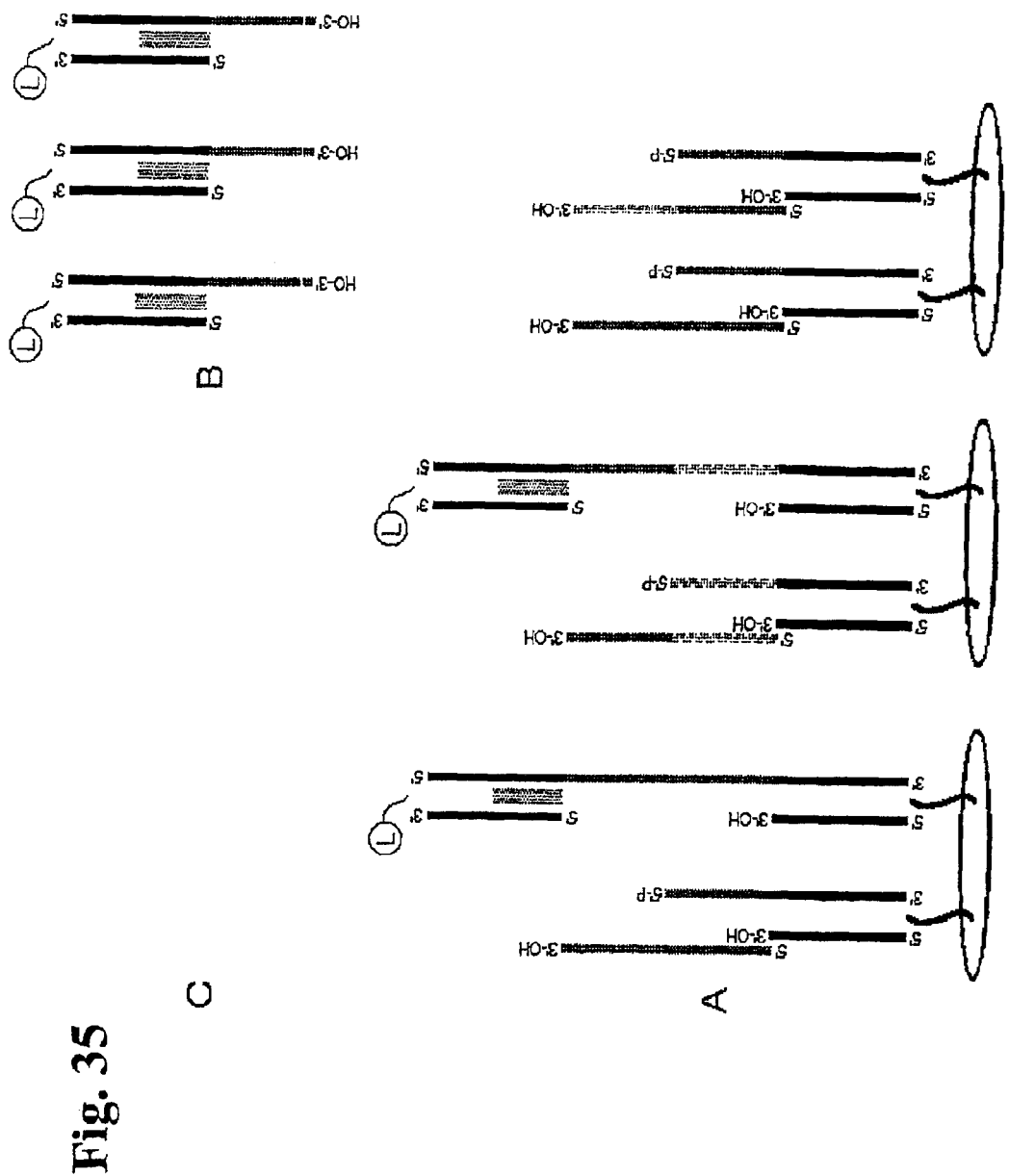
FIG. 35: Again the conditions are changed; for example by cooling down the array; making the ssDNA tags hybridize to the identifying linker oligonucleotides in the array again A). Because the number of identifying linker oligonucleotides in each spot in the array exceeds the number of ssDNA tags having the same complementary 5' end, the chances a tag hybridizes to an identifying linker oligonucleotide that is already ligated to one of the identifying linker oligonucleotides in solution is very small. After hybridization the ssDNA tags together with the identifying linker oligonucleotides in the array exposes a 3' overhang that the identifying linker oligonucleotides in solution B) can hybridize to. Different shading of strands illustrates different sequences. Complementary sequences are shown with the same shading. Selected 5' $PO_4$ and 3' OH groups are indicated.
Figure 36:
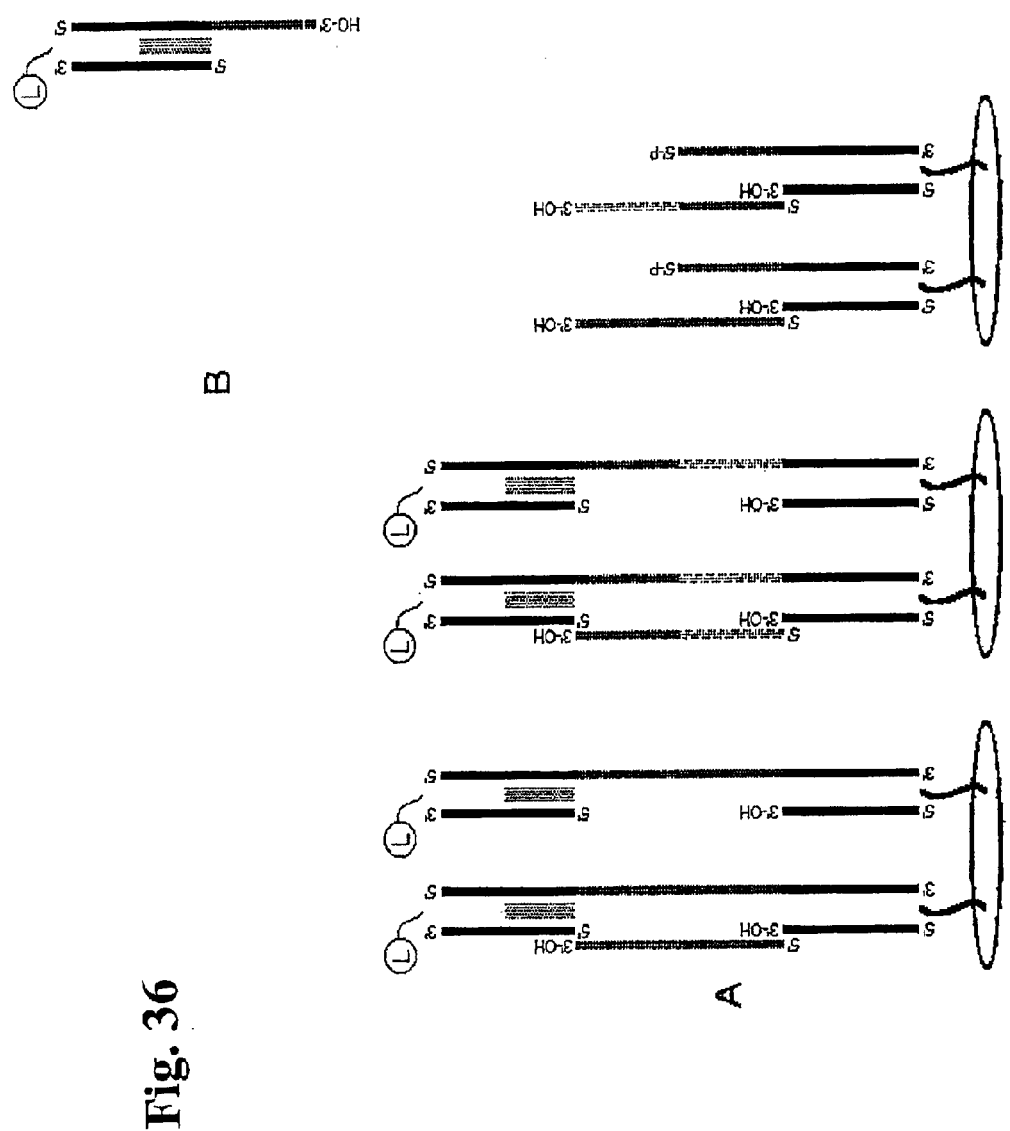
FIG. 36: Concurrently the identifying linker oligonucleotides comprising a label hybridizes to the exposed 3' end of the ssDNA tags hybridized to the identifying linker oligonucleotides in the array. This complex is a substrate for ligase, but because the ssDNA tags and the linker in solution had their 5' end blocked only the two linkers can be ligated together. Different shading of strands illustrates different sequences. Complementary sequences are shown with the same shading. Selected 5' $PO_4$ and 3' OH groups are indicated.
Figure 37:
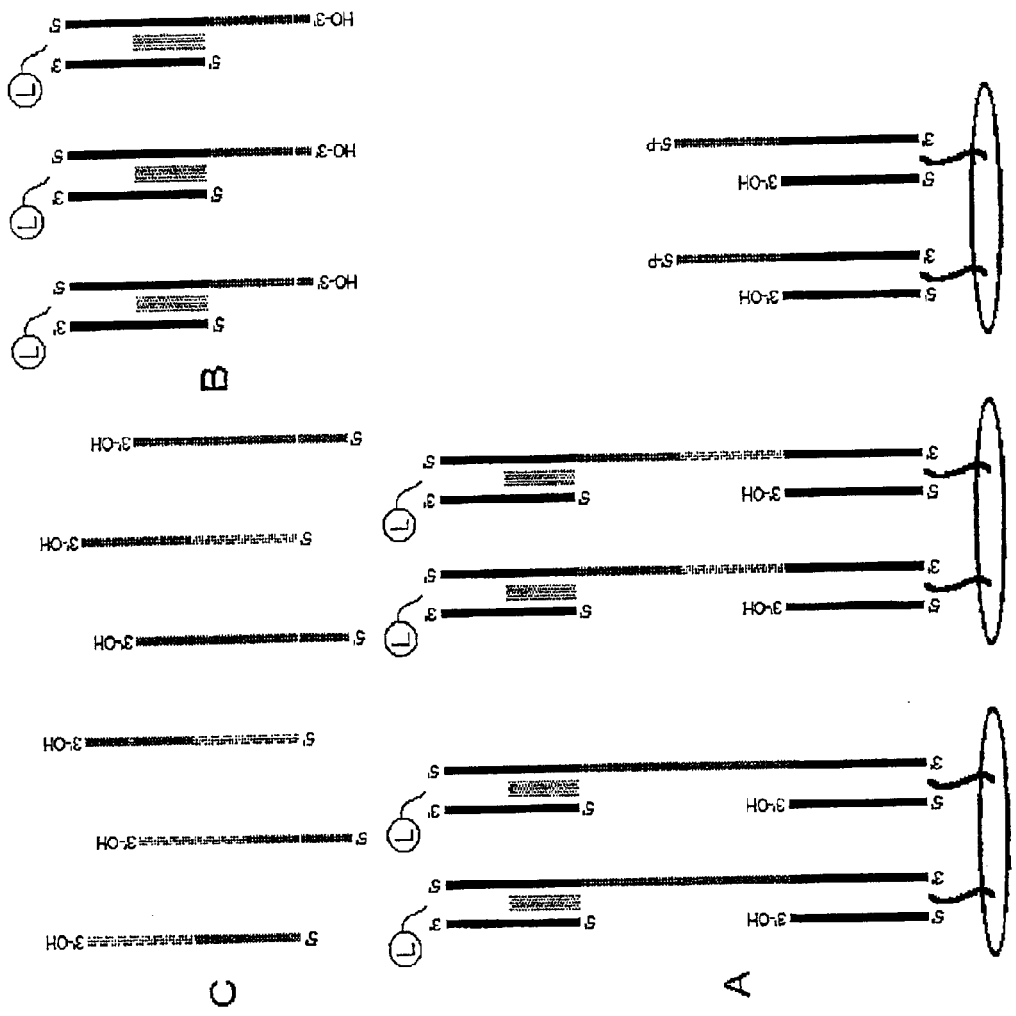
FIG. 37: After a number of cycles of the steps in FIGS. 34 through 36 the signal from a subset of the ssDNA tags have been amplified without consuming the ssDNA tags in the process. The amplification products from the asymmetric LCR A) can now be recorded after removal of the remaining linkers B) in solution. The ssDNA tags C) can be separated from the linkers in solution and used in a similar LCR with the next linker in solution with a predetermined sequence in the overhang and comprising a label. Different shading of strands illustrates different sequences. Complementary sequences are shown with the same shading. Selected 5' $PO_4$ and 3' OH groups are indicated.
Figure 38:
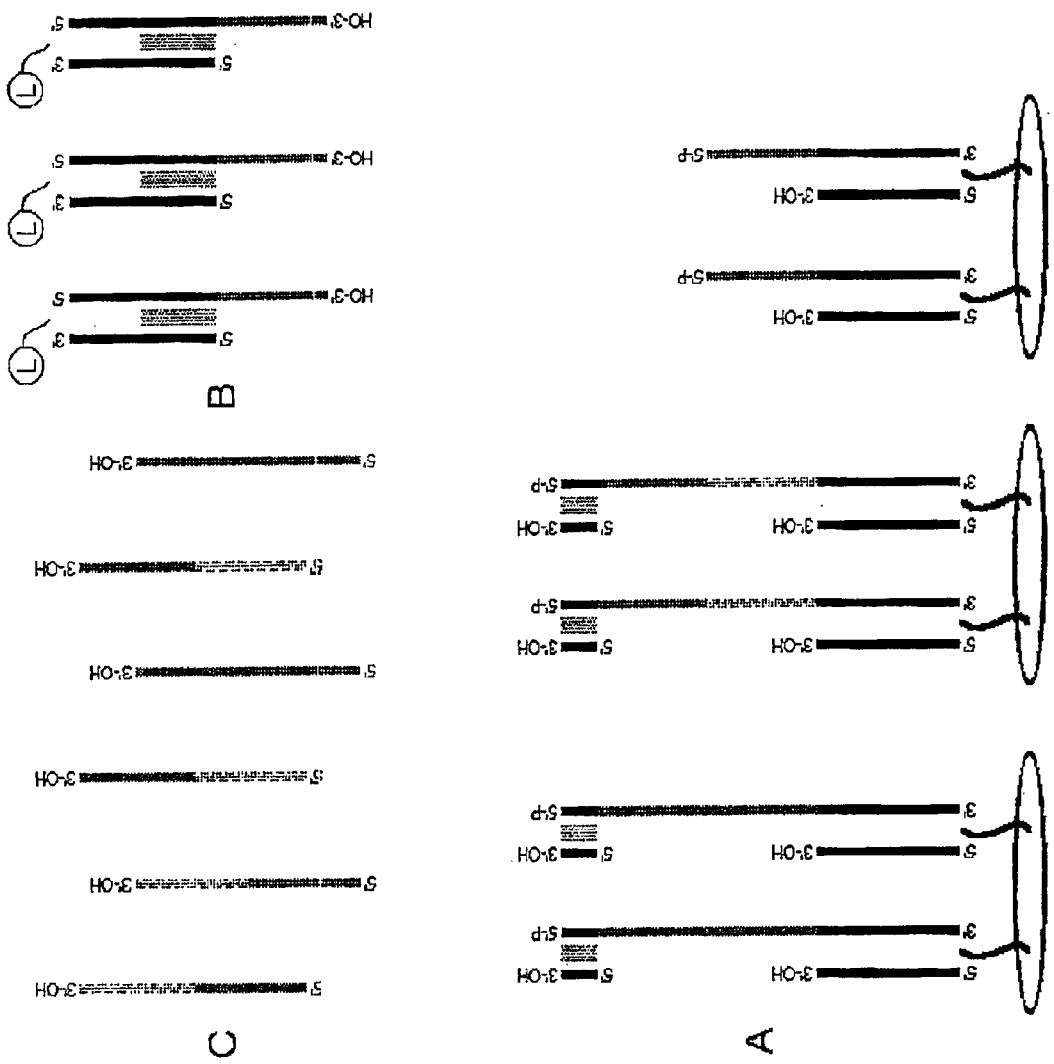
FIG. 38: In one embodiment labels from the first LCR are removed by cleaving the unmethylated recognition/binding site for a type II restriction endonuclease on the second identifying linker oligonucleotide with a methylation sensitive type II restriction endonuclease, thereby eliminating the label that is subsequently washed away A). A new identifying linker oligonucleotide in solution B) comprising a predetermined sequence in the overhang and comprising a label is introduced with the ssDNA tags C) that is regenerated from the previous LCR. This whole process is repeated with all the possible $4^n$ sequence combinations of the identifying linker oligonucleotide in solution. However, the process may also be repeated using only a predetermined subset of such combinations. Different shading of strands illustrates different sequences. Complementary sequences are shown with the same shading. Selected 5' $PO_4$ and 3' OH groups are indicated.
Figure 39:
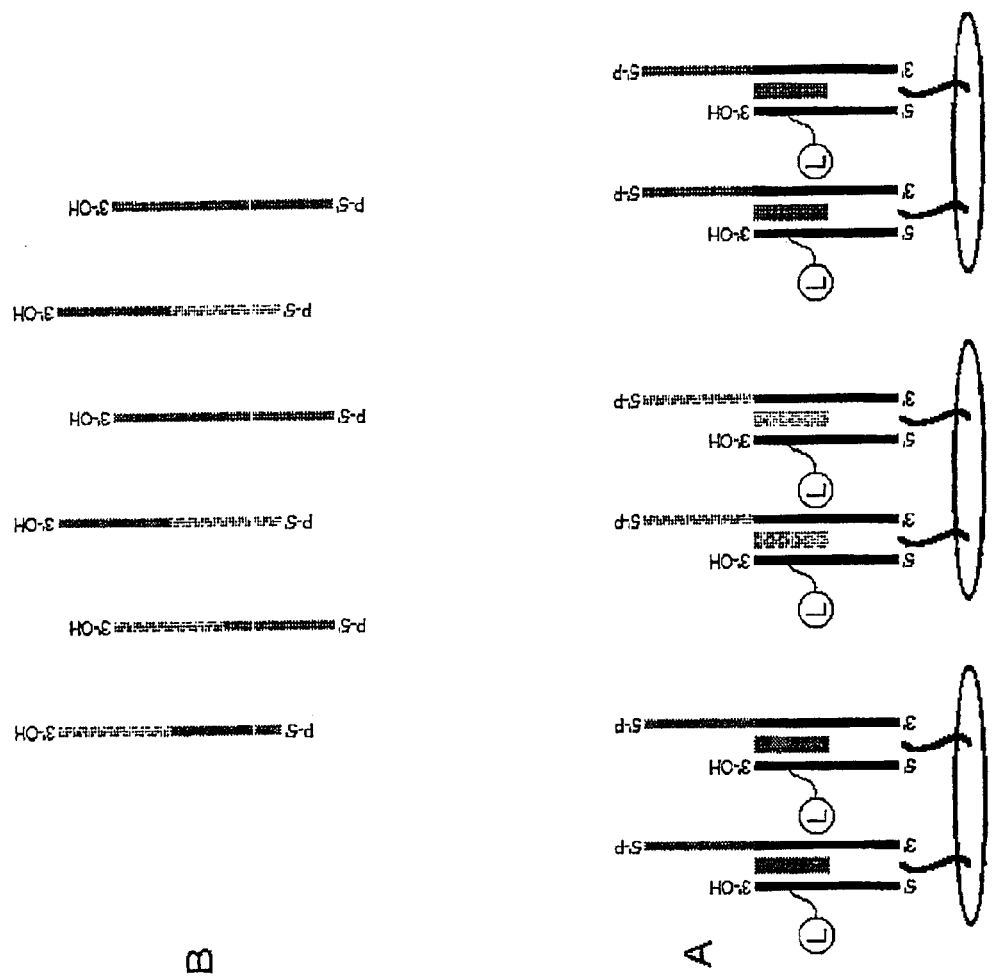
FIG. 39.
Figure 40:
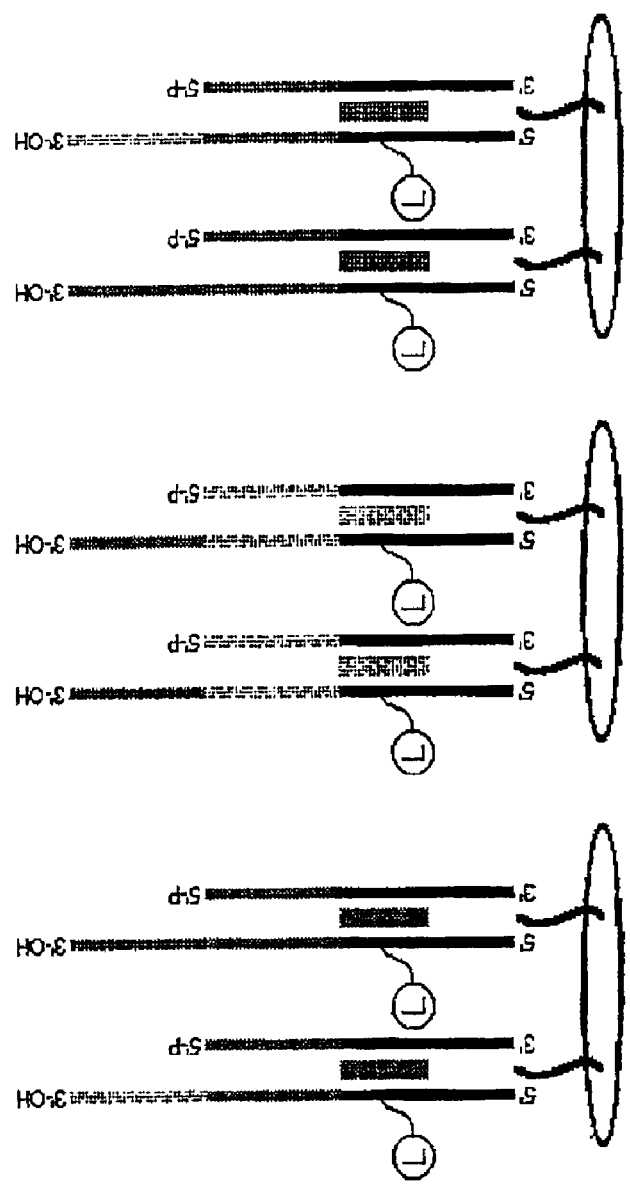
Figure 41:
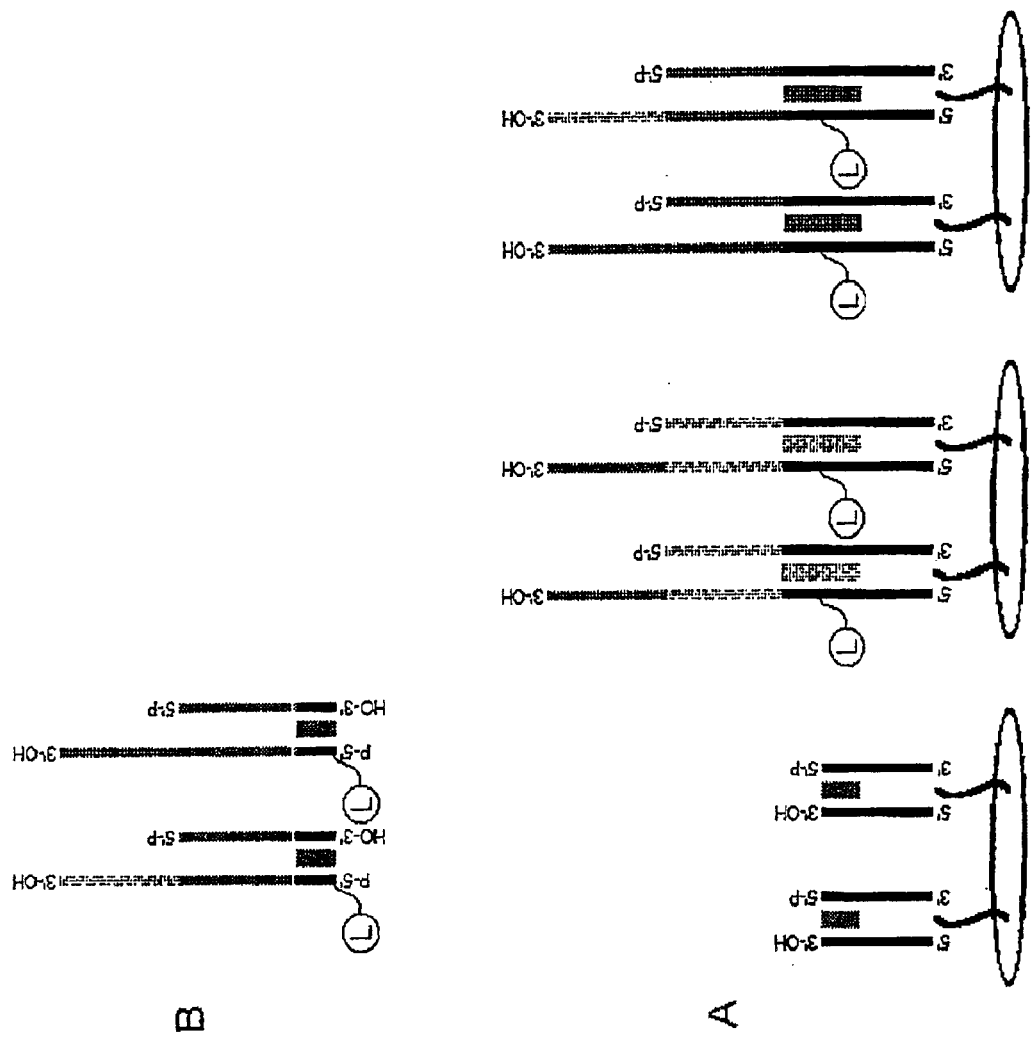
Figure 42:
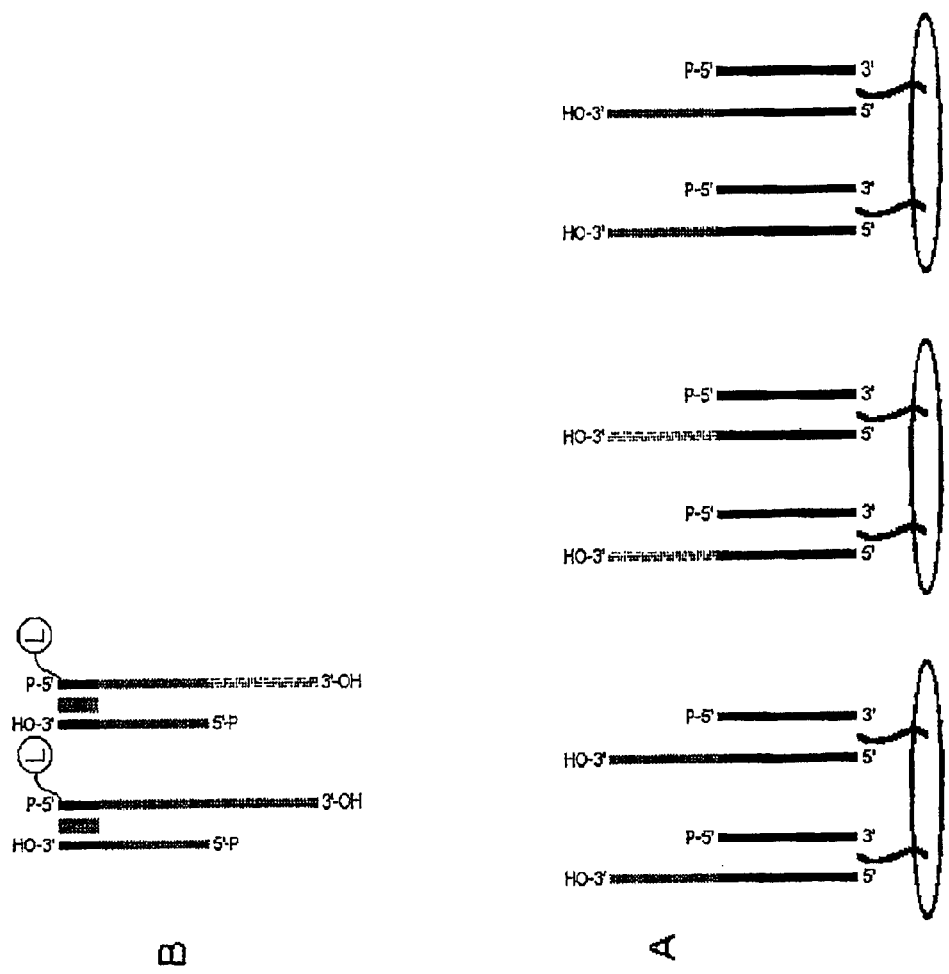
Figure 43:
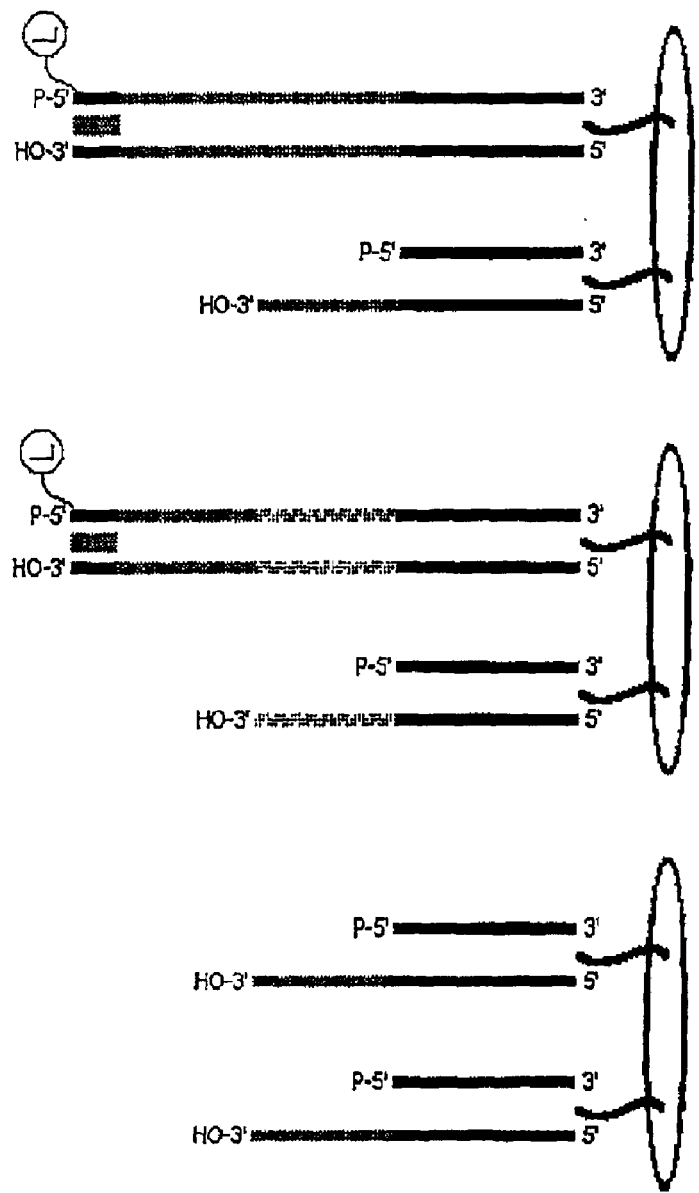

Array: In the present context an array means an ordered plurality of molecules. Mostly consisting of a plurality of dsDNA or ssDNA fragments covalently attached to a slide or a similar solid support, said DNA fragments being identified by their two dimensional position in the array. See FIG. 15 for an example of an array.

Asymmetric LCR: LCR using only two oligonucleotides instead of four. Asymmetric LCR can be carried out on ssDNA. As with asymmetric PCR the amplification in LCR is linear instead of exponential. See FIGS. 31–38 for an example of asymmetric LCR.

Base: In this context a base refers to one of the bases in nucleic acid or modified nucleic acid unless otherwise noted. The bases of DNA, for example are adenosine, cytidine, guanosine, and thymidine.

Biological sample: Any sample comprising genetic material in the form of DNA or RNA.

cDNA: See "complementary DNA"

Chimeric polynucleotide: Polynucleotide comprising an adapter oligonucleotide part that is ligated to a polynucleotide derived from a biological sample. A chimeric polynucleotide can also be a single stranded polynucleotide. The polynucleotide derived from a biological sample can also be a truncated part of a polynucleotide obtained from a biological sample. Chimeric polynucleotide also denotes any cDNA copy of a chimeric RNA polynucleotide. See FIGS. 10–13 for a number of examples of a chimeric polynucleotide.

Figure 1:
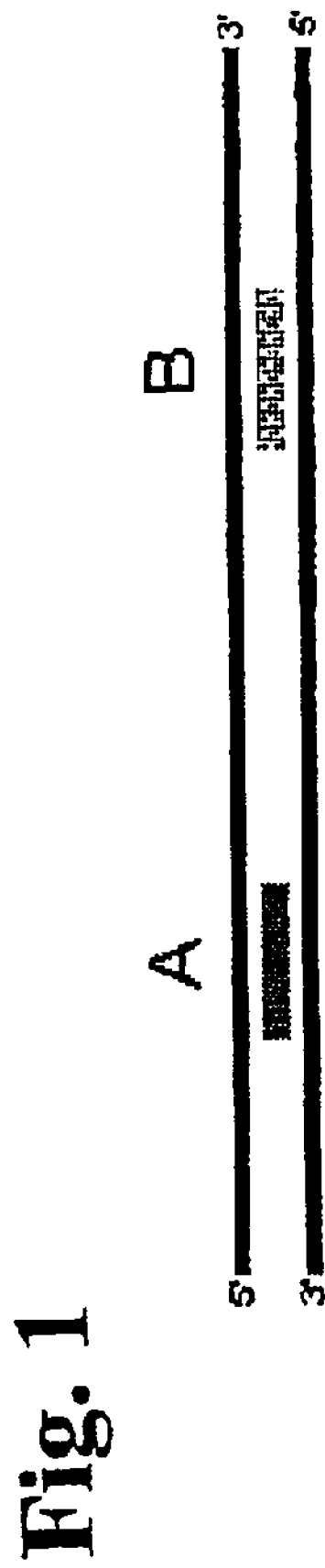
FIG. 1: Common features of type IIs restriction endonucleases and nicking endonucleases. A) Recognition/binding site. B) Cleavage site. 5' $PO_4$ and 3' OH groups are not shown.
Figure 2:
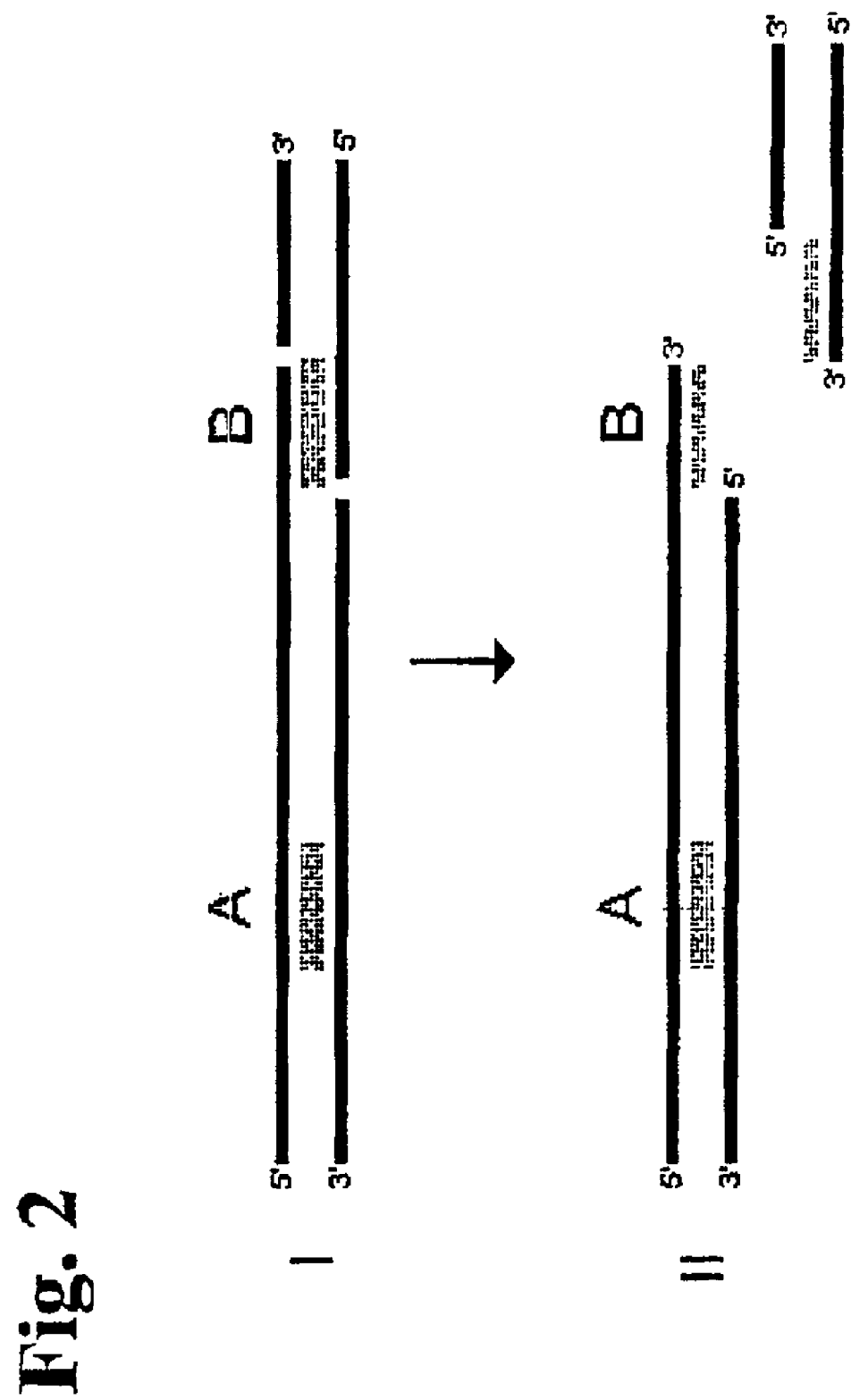
FIG. 2: dsDNA after treatment with type IIs restriction endonuclease producing 3' overhangs. A) Recognition/binding site. B) Cleavage site. I) Just after cleavage. II) Fragments after separation. 5' $PO_4$ and 3' OH groups are not shown.
Figure 3:
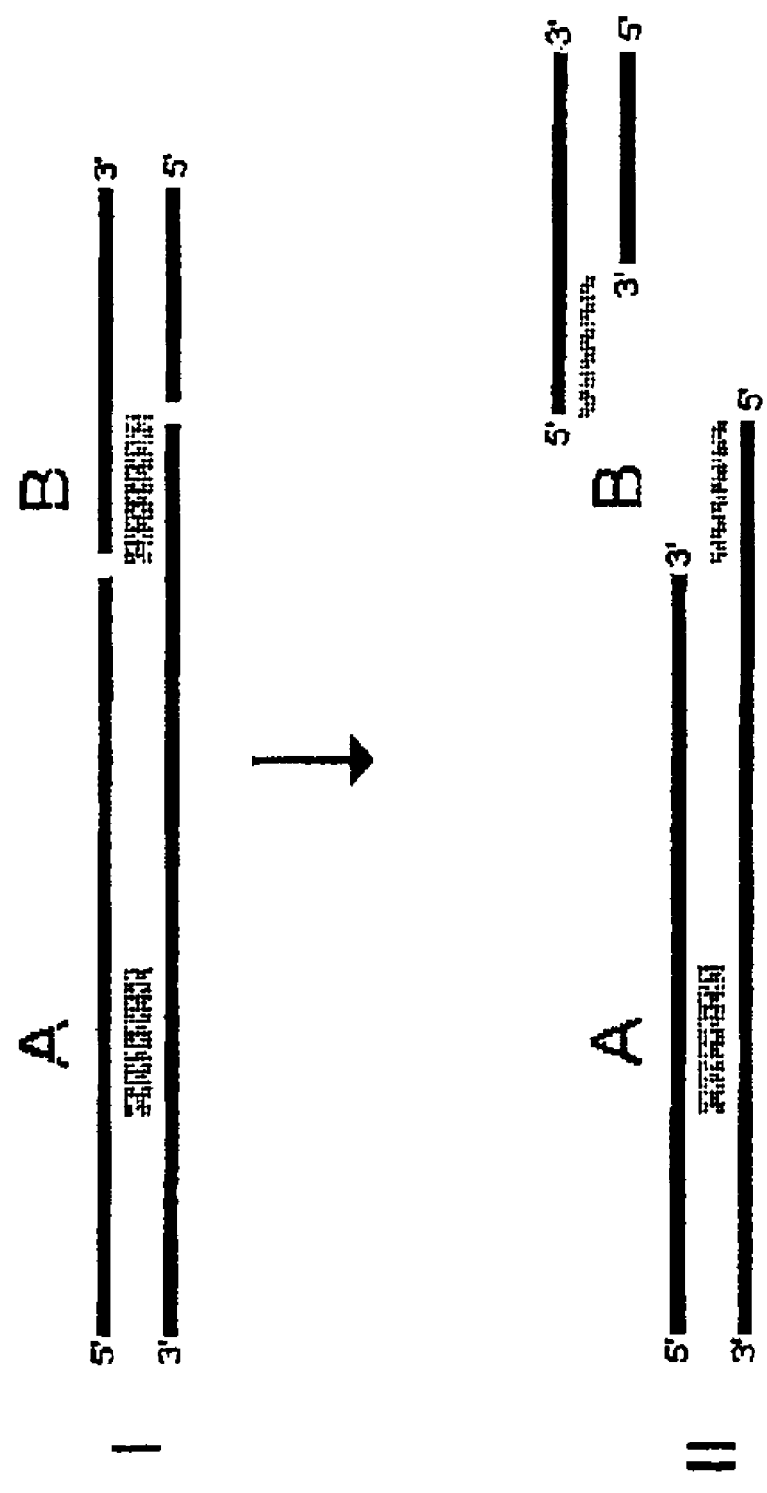
FIG. 3: dsDNA after treatment with type IIs restriction endonuclease producing 5' overhangs. A) Recognition/binding site. B) Cleavage site. I) Just after cleavage. II) Fragments after separation. 5' $PO_4$ and 3' OH groups are not shown.
Figure 4:
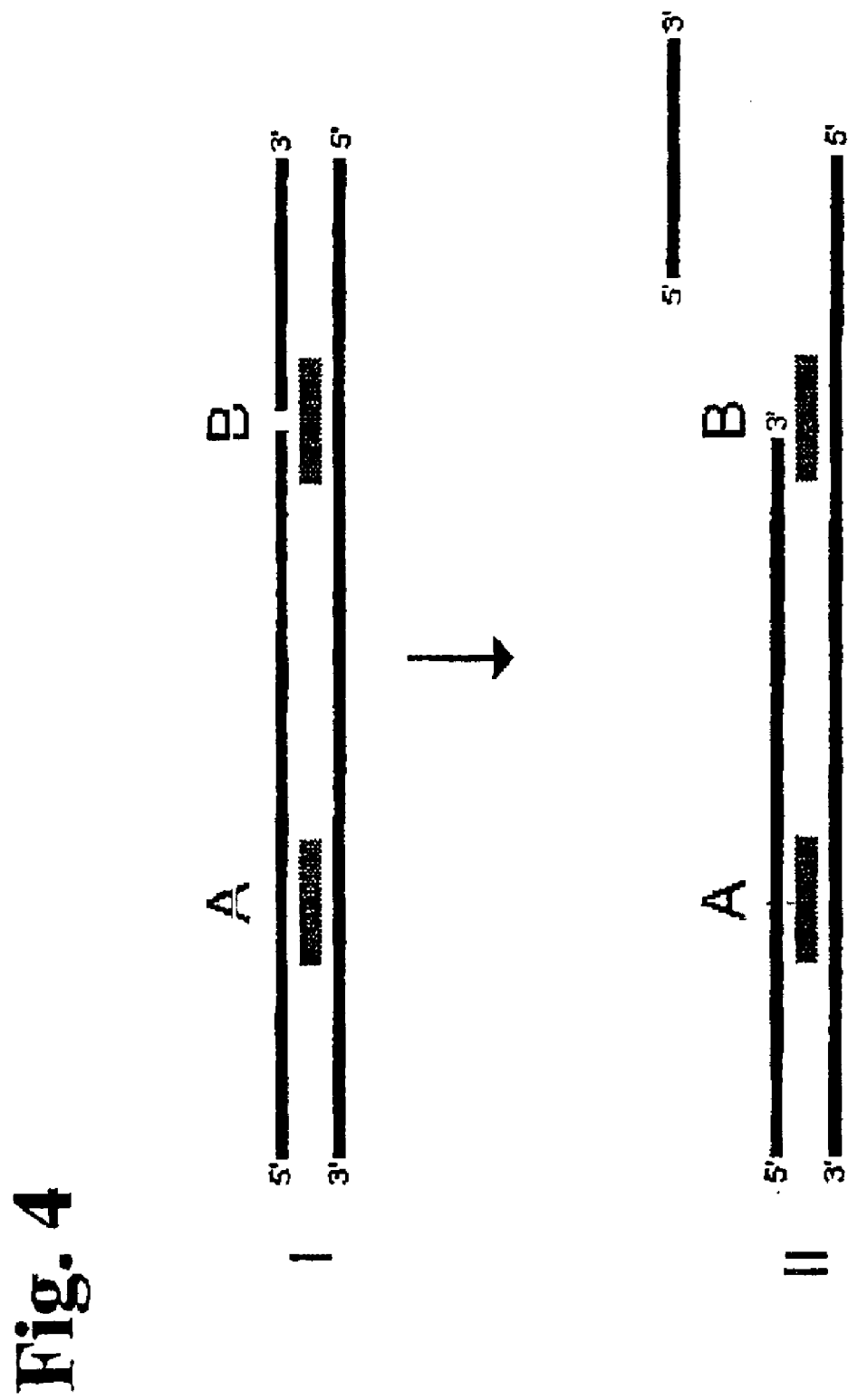
FIG. 4: dsDNA after treatment with nicking endonuclease cleaving the sense string downstream from recognition/binding site. A) Recognition/binding site. B) Cleavage site. I) Just after cleavage. II) Fragments after separation. 5' $PO_4$ and 3' OH groups are not shown.
Figure 5:
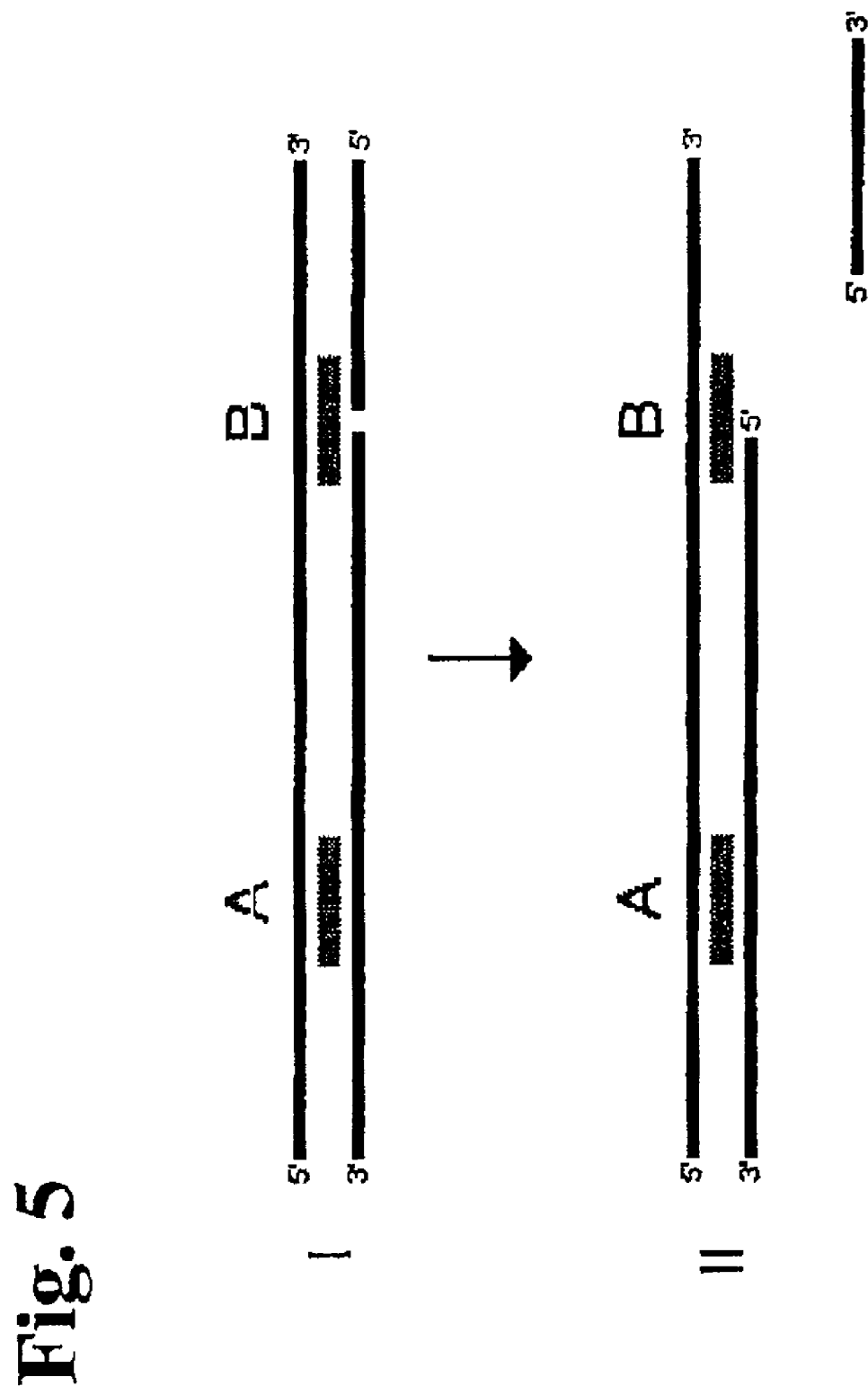
FIG. 5: dsDNA after treatment with nicking endonuclease cleaving the anti-sense string downstream from recognition/binding site. A) Recognition/binding site. B) Cleavage site. I) Just after cleavage. II) Fragments after separation. 5' $PO_4$ and 3' OH groups are not shown.
Figure 6:
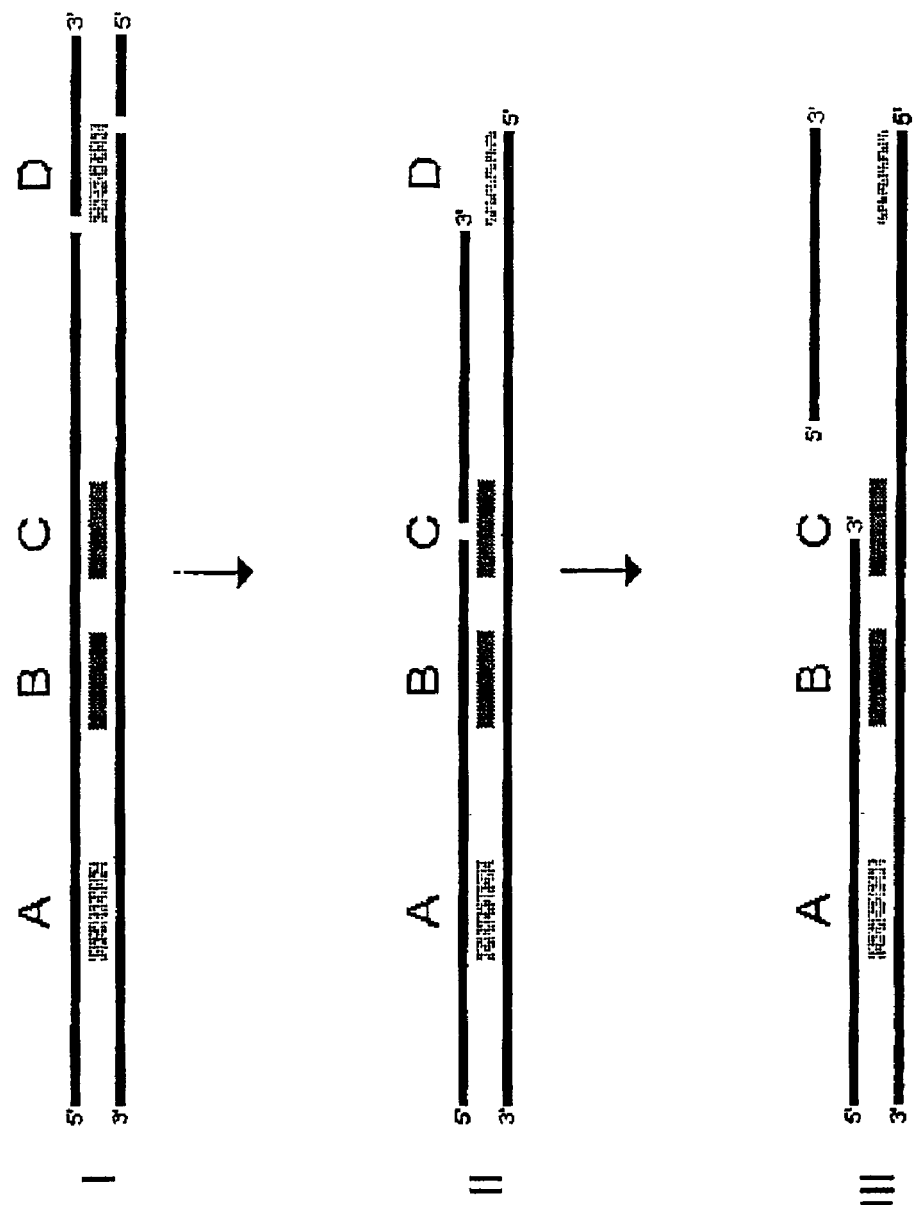
FIG. 6: Creation of an ssDNA tag from dsDNA comprising a nicking endonuclease recognition/binding site between a type IIs restriction endonuclease recognition/binding site and the cleavage site for said type IIs restriction endonuclease, when said type IIs restriction endonuclease produces 5' overhangs. A) Recognition/binding site for type IIs restriction endonuclease. B) Recognition/binding site for nicking endonuclease. C) Cleavage site for nicking endonuclease. D) Cleavage site for type IIs restriction endonuclease. I) The dsDNA after cleavage with type IIs restriction endonuclease producing 5' overhangs. II) Downstream fragments are discarded and the remaining fragment is cleaved with nicking endonuclease. III) The ssDNA tag is separated from the remaining dsDNA fragment 5' $PO_4$ and 3' OH groups are not shown.
Figure 7:
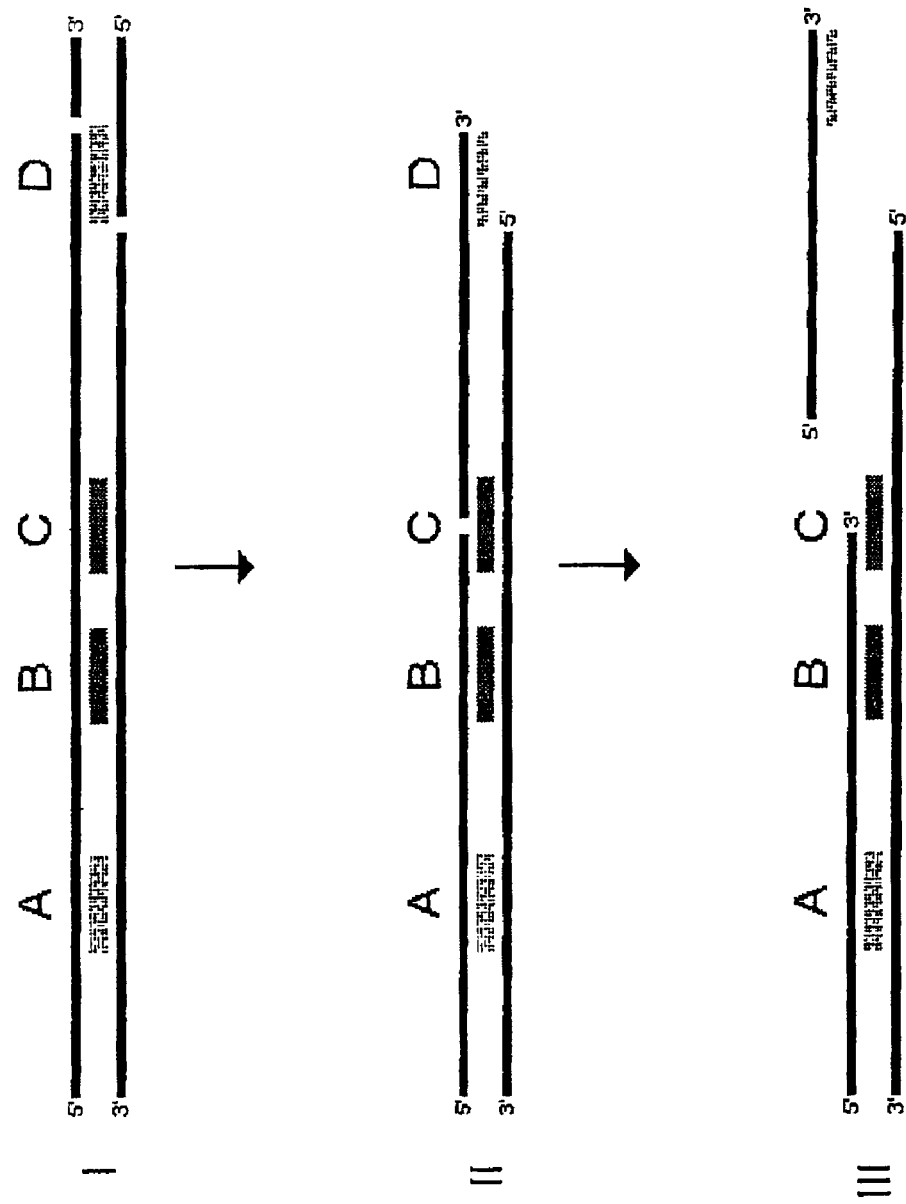
FIG. 7: Creation of an ssDNA tag from dsDNA comprising a nicking endonuclease recognition/binding site between a type IIs restriction endonuclease recognition/binding site and the cleavage site for said type IIs restriction endonuclease, when said type IIs restriction endonuclease produces 3' overhangs. A) Recognition/binding site for type IIs restriction endonuclease. B) Recognition/binding site for nicking endonuclease. C) Cleavage site for nicking endonuclease. D) Cleavage site for type IIs restriction endonuclease. I) The dsDNA after cleavage with type IIs restriction endonuclease producing 3' overhangs. II) Downstream fragments are discarded and the remaining fragment is cleaved with nicking endonuclease. III) The ssDNA tag is separated from the remaining dsDNA fragment. 5' P and 3' OH groups are not shown.
Figure 8:
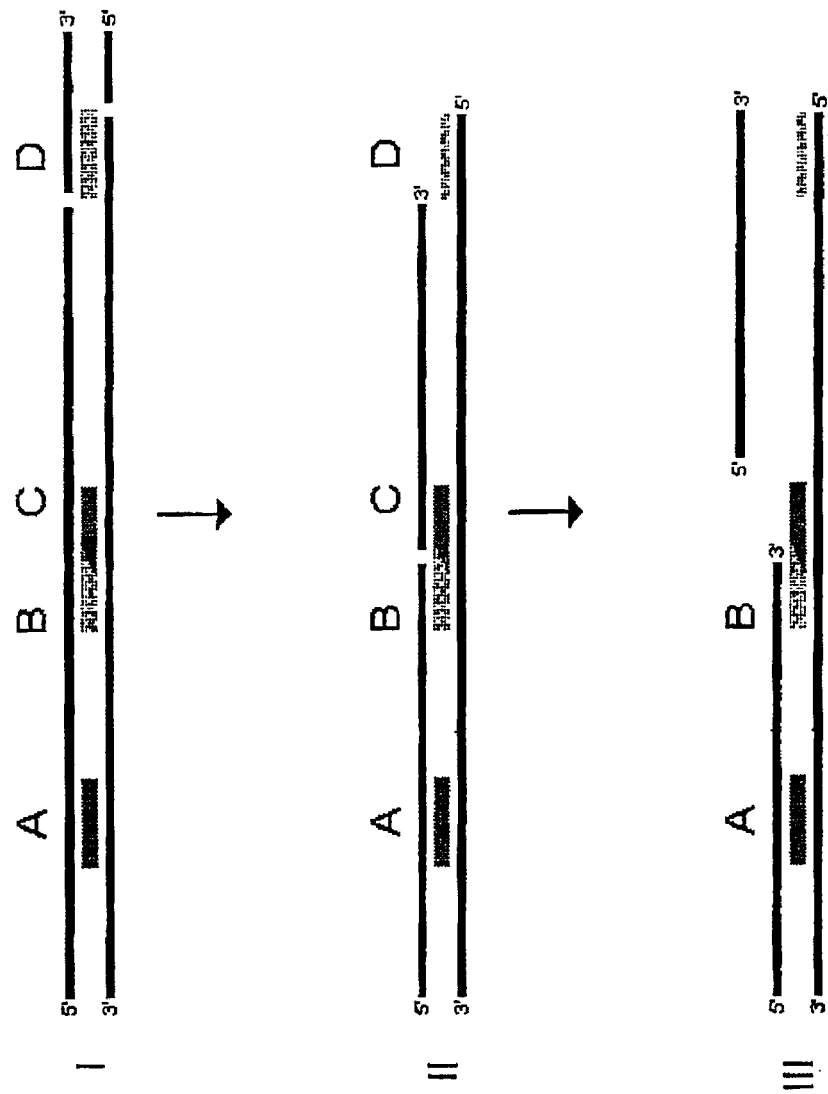
FIG. 8: Creation of an ssDNA tag from dsDNA comprising a nicking endonuclease recognition/binding site, that is situated proximal to a type IIs restriction endonuclease recognition/binding site as the cleavage site for said type IIs restriction endonuclease is distal to said type IIs restriction endonuclease recognition/binding site. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. The situation depicted is when said type IIs restriction endonuclease produces 5' overhangs. A) Recognition/binding site for nicking endonuclease. B) Recognition/binding site for type IIs restriction endonuclease. C) Cleavage site for nicking endonuclease. D) Cleavage site for type IIs restriction endonuclease. I) The dsDNA is cleaved with type IIs restriction endonuclease producing 5' overhangs. II) Downstream fragments are discarded and the remaining fragment is cleaved with nicking endonuclease. III) The ssDNA tag is separated from the remaining dsDNA fragment. 5' $PO_4$ and 3' OH groups are not shown.
Figure 9:
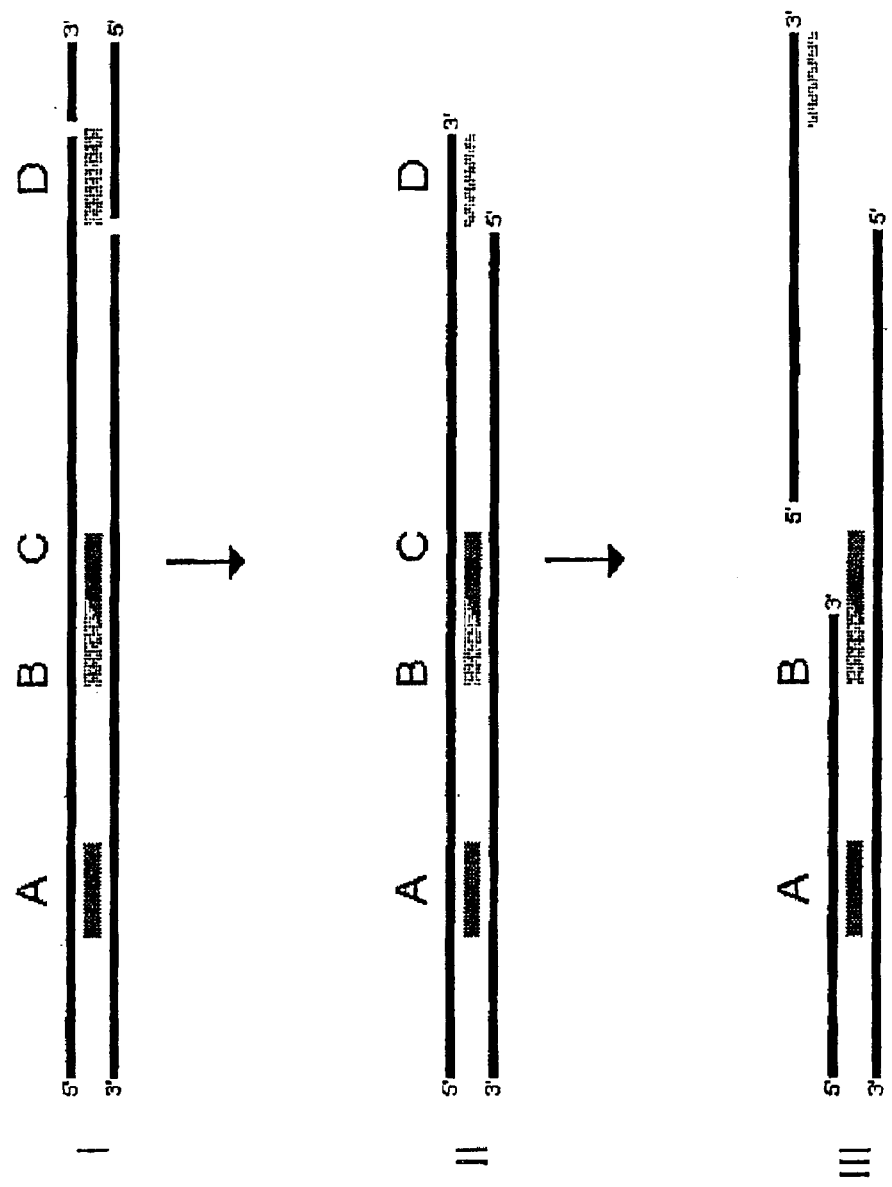
FIG. 9: Creation of a ssDNA tag from dsDNA comprising a nicking endonuclease recognition/binding site, that is situated proximal to a type IIs restriction endonuclease recognition/binding site as the cleavage site for said type IIs restriction endonuclease is distal to said type IIs restriction endonuclease recognition/binding site. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. The situation depicted is when said type IIs restriction endonuclease produces 3' overhangs. A) Recognition/binding site for nicking endonuclease. B) Recognition/binding site for type IIs restriction endonuclease. C) Cleavage site for nicking endonuclease. D) Cleavage site for type IIs restriction endonuclease. I) The dsDNA is cleaved with type IIs restriction endonuclease producing 3' overhangs. II) Downstream fragments are discarded and the remaining fragment is cleaved with nicking endonuclease. III) The ssDNA tag is separated from the remaining dsDNA fragment. 5' $PO_4$ and 3' OH groups are not shown.
Figure 10:
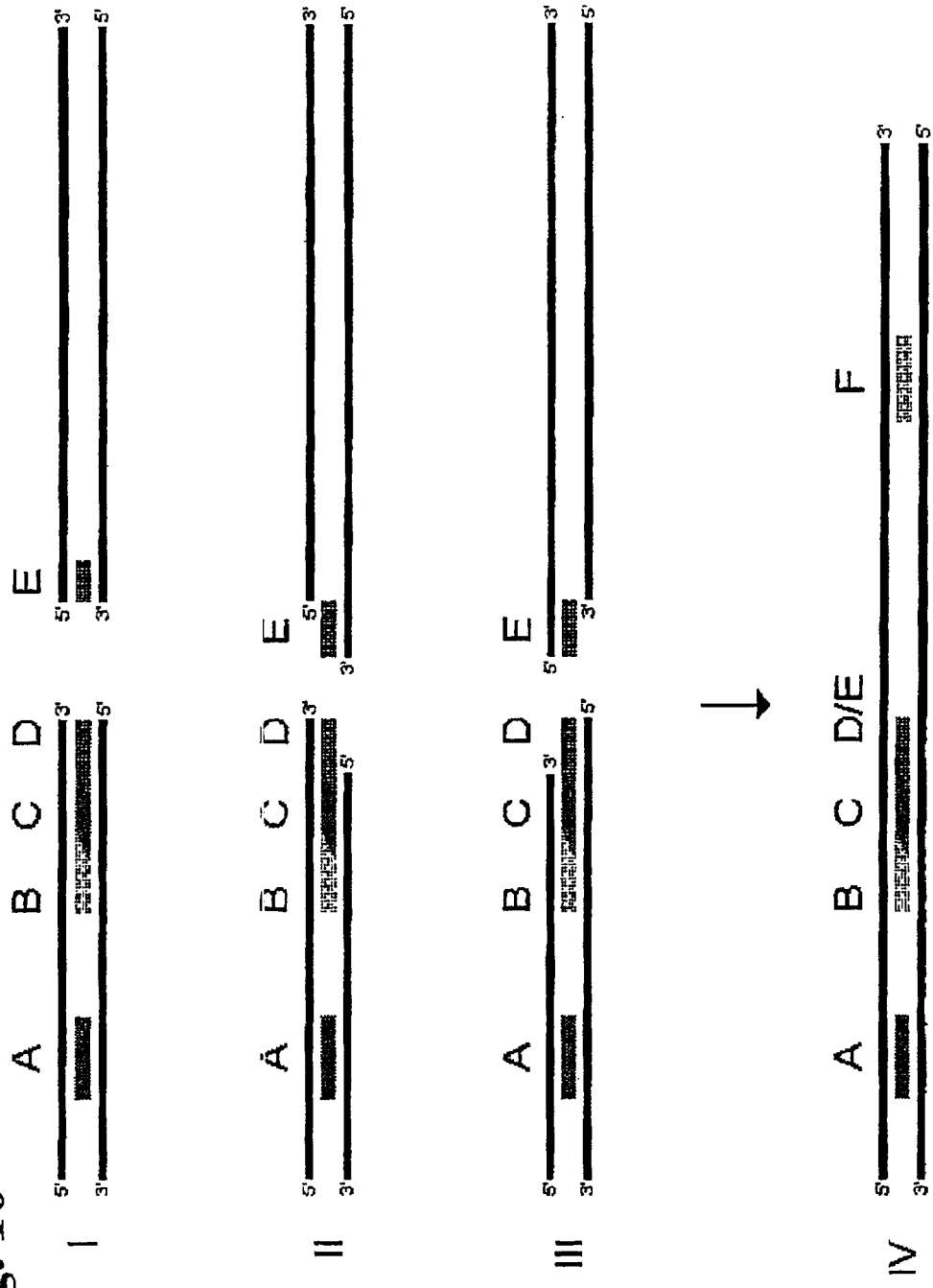
FIG. 10: Creation of chimeric dsDNA using either a blunt ended adapter or an adapter with 3' or 5' overhangs respectively. The adapter comprises a nicking endonuclease recognition/binding site, that is situated proximal to a type IIs restriction endonuclease recognition/binding site as the cleavage site for said type IIs restriction endonuclease is distal to the cleavage site for said nicking endonuclease. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. A) Recognition/binding site for nicking endonuclease. B) Recognition/binding site for type IIs restriction endonuclease. C) Cleavage site for nicking endonuclease. D) Overhang or blunt end of adapter corresponding to the specific cleavage overhang of the type II restriction endonuclease used for cleavage of the dsDNA that is used in the creation of the chimeric dsDNA. E) Recognition/binding and cleavage site for type II restriction endonuclease after cleavage of dsDNA. F) Cleavage site for type IIs restriction endonuclease. I) Ligation of blunt ended adapter to dsDNA after cleavage of dsDNA with type II restriction endonuclease. II) Ligation of adapter to dsDNA with 3' overhangs after cleavage of dsDNA with type II restriction endonuclease. III) Ligation of adapter to dsDNA with 5' overhangs after cleavage of dsDNA with type II restriction endonuclease. IV) After ligation using either I) blunt end II) 3', or III) 5' overhangs the resulting chimeric dsDNA has a cleavage site for a nicking endonuclease immediately 3' of a type IIs restriction endonuclease recognition/binding site and a cleavage site for said type IIs restriction endonuclease 3' of the cleavage site for said nicking endonuclease. 5' $PO_4$ and 3' OH groups are not shown.
Figure 11:
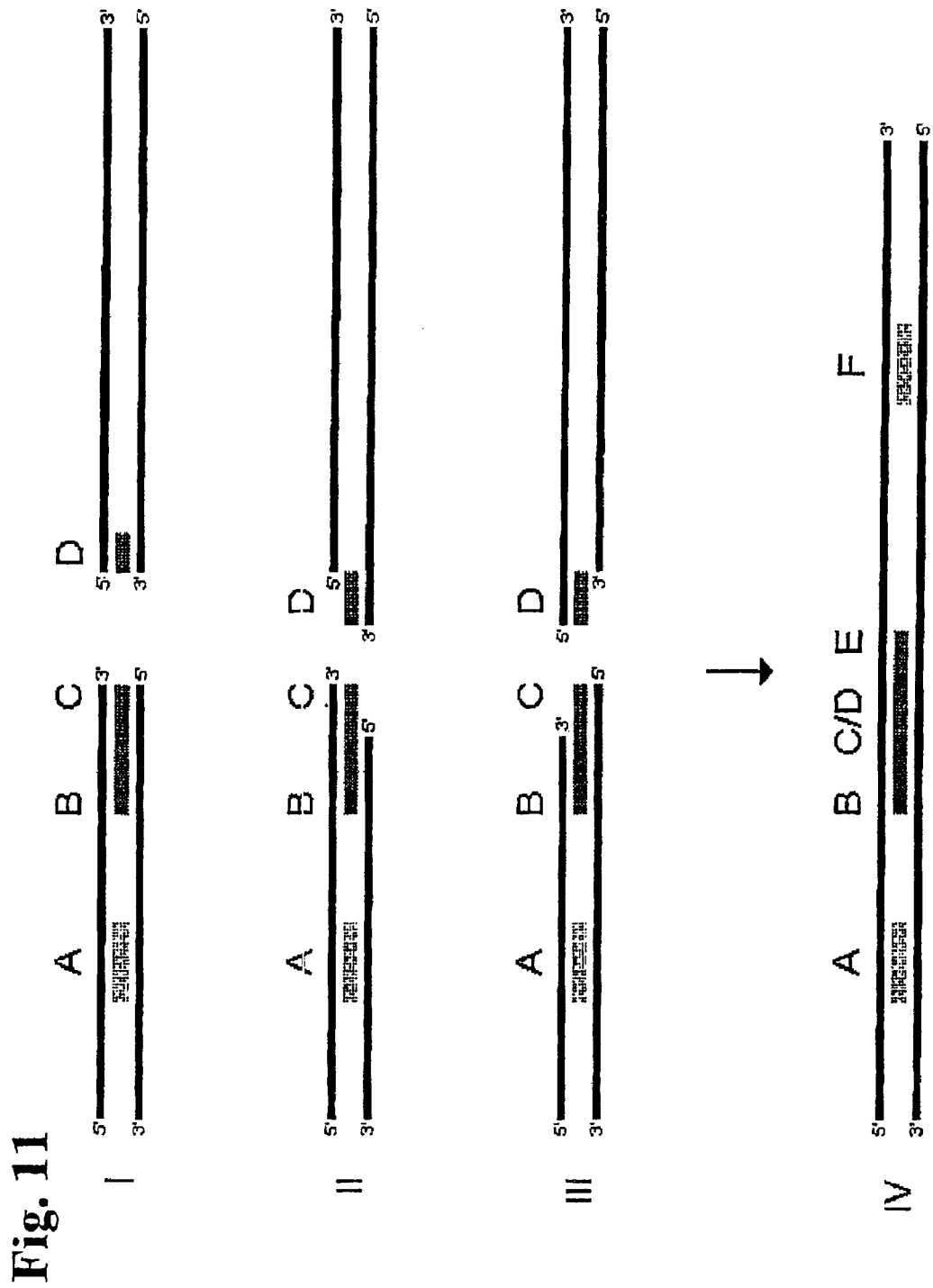
FIG. 11: Creation of chimeric dsDNA using either a blunt ended adapter or an adapter with 3' or 5' overhangs respectively. The adapter has a type IIs restriction endonuclease recognition/binding site that is situated proximal to a nicking endonuclease recognition/binding site as the cleavage site for said type IIs restriction endonuclease is distal to said type IIs restriction endonuclease recognition/binding site. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. A) Recognition/binding site for type IIs restriction endonuclease. B) Recognition/binding site for nicking endonuclease. C) Overhang or blunt end of adapter corresponding to the specific cleavage overhang of the type II restriction endonuclease used for cleavage of the dsDNA that is used in the creation of the chimeric dsDNA. D) Recognition/binding and cleavage site for type II restriction endonuclease after cleavage of dsDNA. E) Cleavage site for nicking endonuclease. F) Cleavage site for type IIs restriction endonuclease. I) Ligation of blunt ended adapter to dsDNA after cleavage of dsDNA with type II restriction endonuclease. II) Ligation of adapter with 3' overhang to dsDNA with 3' overhangs after cleavage of dsDNA with type II restriction endonuclease. III) Ligation of adapter with 5' overhang to dsDNA with 5' overhangs after cleavage of dsDNA with type II restriction endonuclease. IV) After ligation using either I) blunt end II) 3', or III) 5' overhangs the resulting chimeric dsDNA has a recognition/binding site for a nicking endonuclease immediately 3' of a type IIs restriction endonuclease recognition/binding site and a cleavage site for said type IIs restriction endonuclease 3' of the cleavage site for said nicking endonuclease. 5' $PO_4$ and 3' OH groups are not shown.
Figure 12:
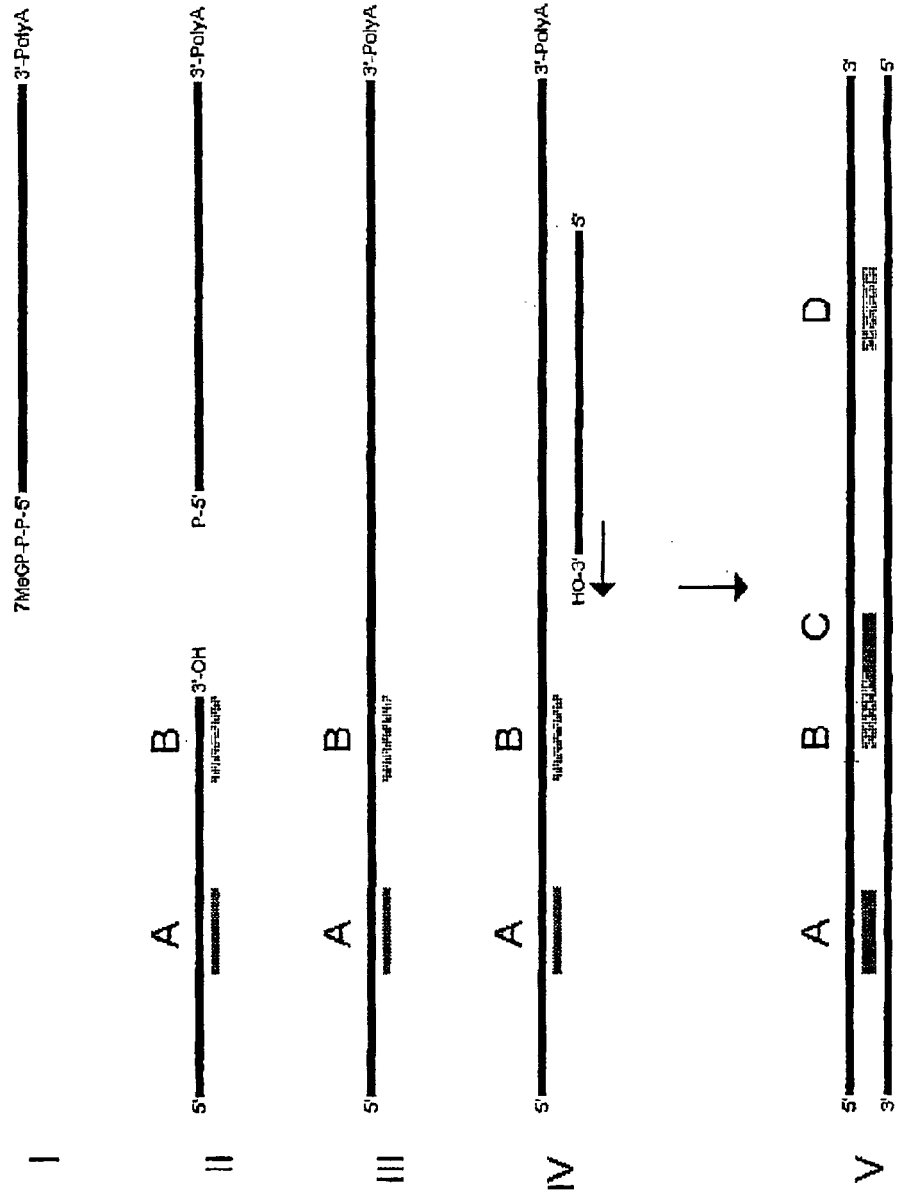
FIG. 12: Creation of chimeric dsDNA using ligation of an adapter to mRNA before reverse transcription. Said adapter harboring part of a nicking endonuclease recognition/binding site, that is situated proximal to a type IIs restriction endonuclease recognition/binding site as the cleavage site for said type IIs restriction endonuclease is distal to the cleavage site of said nicking endonuclease. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. A) Recognition/binding site for nicking endonuclease. B) Recognition/binding site for type IIs restriction endonuclease. C) Cleavage site for nicking endonuclease. D) Cleavage site for type IIs restriction endonuclease. I) mRNA contains a 5' cap. Contamination from degraded mRNA, tRNA, rRNA and DNA is eliminated by treating the RNA sample with phosphatase II) A pyrophosphatase is used to remove the 5' cap on the mRNA and the adapter is mixed with the decapped mRNA. III) The adapter is ligated to the 5' end of the mRNA. IV) Reverse transcription is carried out using random decamers. V) After second strand synthesis is carried out using a primer with the sequence of the adapter the resulting chimeric dsDNA has a cleavage site for a nicking endonuclease immediately 3' of a type IIs restriction endonuclease recognition/binding site and a cleavage site for said type IIs restriction endonuclease 3' of the cleavage site for said nicking endonuclease. Selected 5' $PO_4$ and 3' OH groups are indicated.
Figure 13:
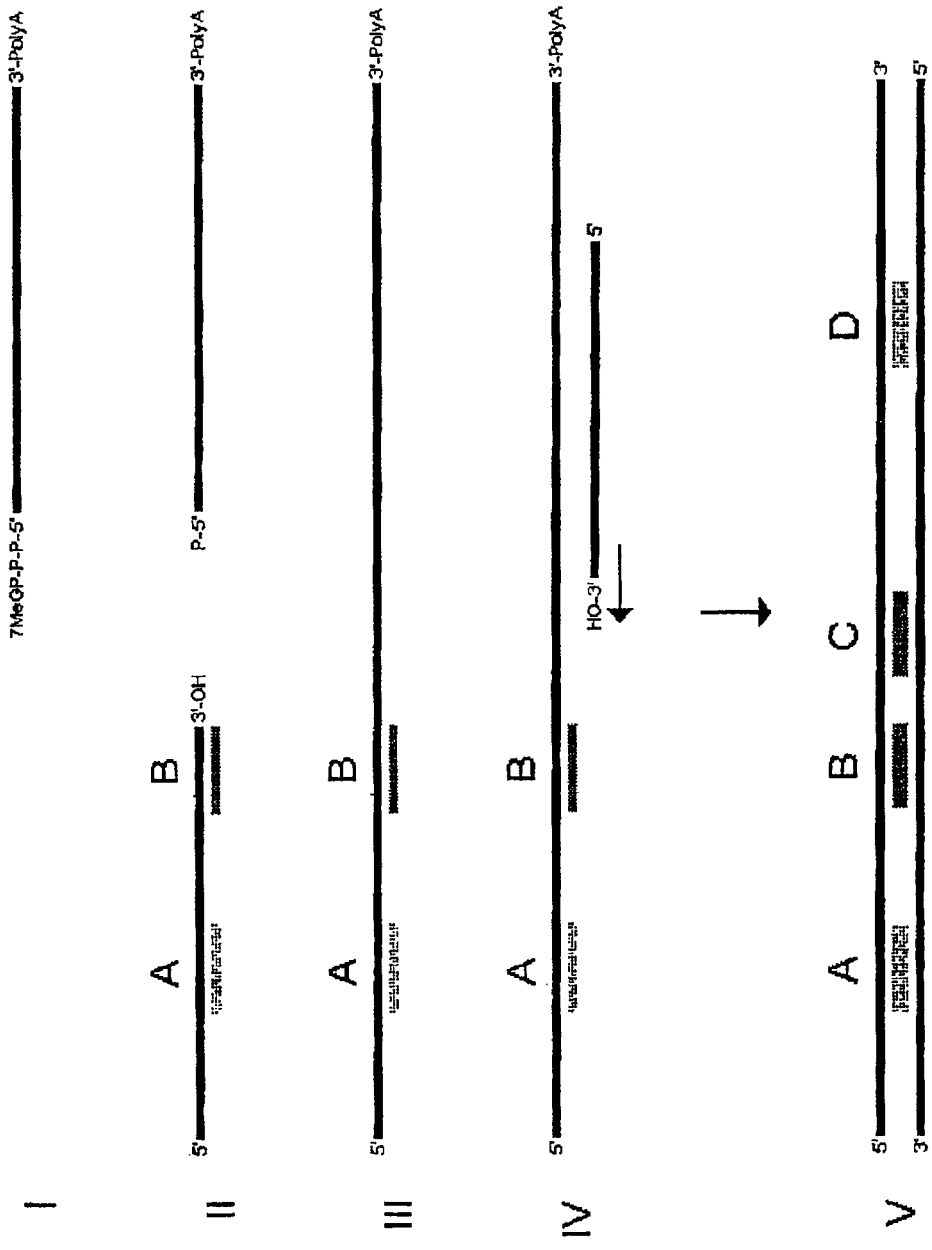
FIG. 13: Creation of chimeric dsDNA using ligation of an adapter to mRNA before reverse transcription. Said adapter harboring part of a type IIs restriction endonuclease recognition/binding site, that is situated proximal to a nicking endonuclease recognition/binding site as the cleavage site for said type IIs restriction endonuclease is distal to the cleavage site of said nicking endonuclease. This is illustrated with hatched boxes having different shadings. Some of the sites are drawn as if they were overlapping each other. In fact for as long as the general order of the recognition/binding sites and the corresponding cleavage sites is maintained, any number of depicted recognition/binding sites may overlap with neighbouring sites. A) Recognition/binding site for type IIs restriction endonuclease. B) Recognition/binding site for nicking endonuclease. C) Cleavage site for nicking endonuclease. D) Cleavage site for type IIs restriction endonuclease. I) mRNA contains a 5' cap. Contamination from degraded mRNA, tRNA, rRNA and DNA is eliminated by treating the RNA sample with phosphatase. II) A pyrophosphatase is used to remove the 5' cap on the mRNA and the adapter is mixed with the decapped mRNA. III) The adapter is ligated to the 5' end of the mRNA. IV) Reverse transcription is carried out using random decamers. V) After second strand synthesis is carried out using a primer with the sequence of the adapter the resulting chimeric dsDNA has a recognition/binding site for a nicking endonuclease immediately 3' of a type IIs restriction endonuclease recognition/ binding site and a cleavage site for said type IIs restriction endonuclease 3' of the cleavage site for said nicking endonuclease. Selected 5' $PO_4$ and 3' OH groups are indicated.
Figure 14:
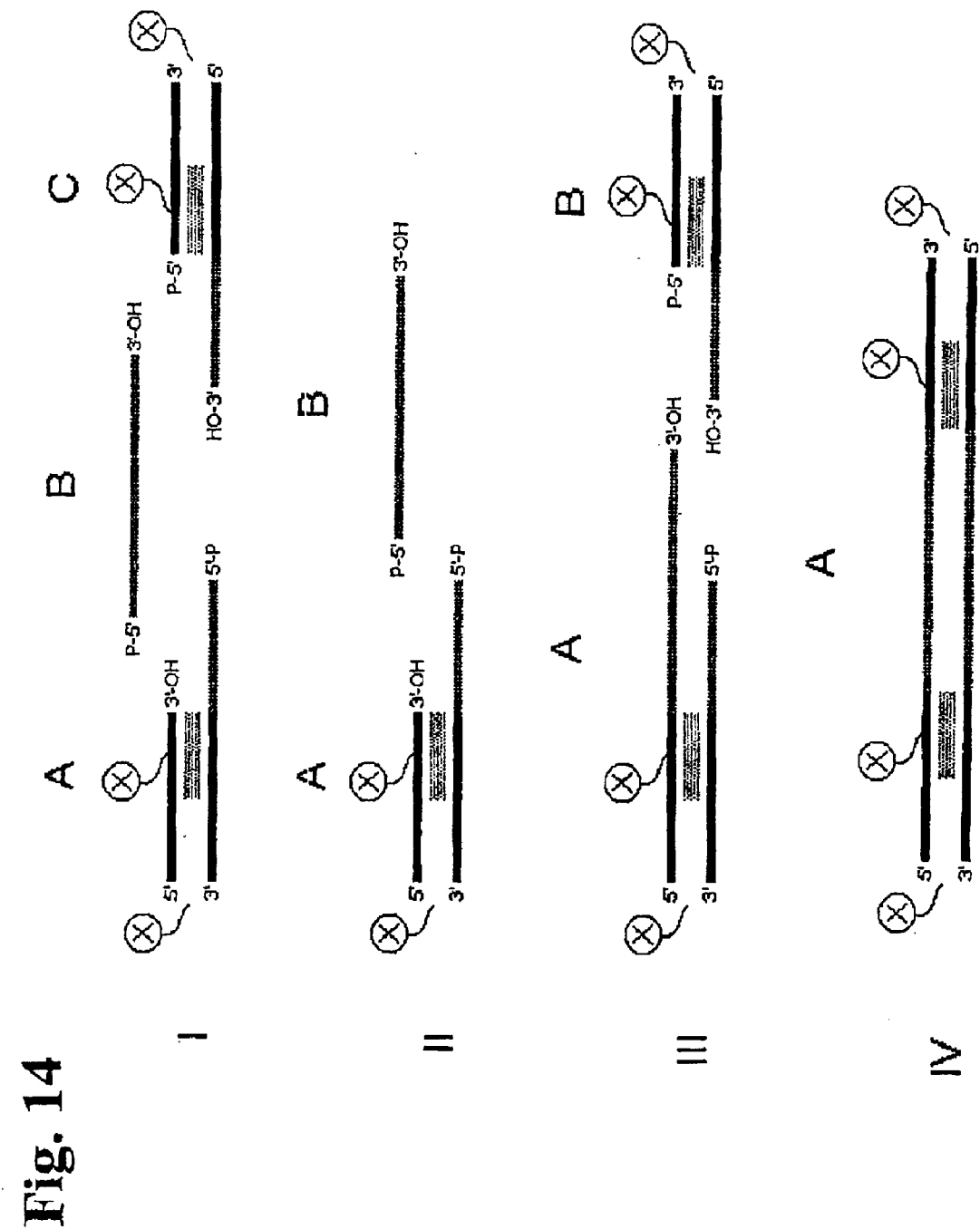
FIG. 14: Every ssDNA tag in the population of ssDNA tags is analyzed as illustrated with only one ssDNA tag in this figure. Different shading of strands illustrates different sequences. Complementary sequences are shown with the same shading. I) A first identifying linker oligonucleotide A) is in this example comprising a 5' overhang with a sequence complementary to the 5' end of an ssDNA tag. The identifying linker is either attached to a predetermined position in an array or it is optionally comprising one or more molecular identifiers or labels, or any combination thereof that are used in the identification and quantification steps. The ssDNA tag B) illustrated here has a 5' end complementary to the 5' overhang of the first identifying linker oligonucleotide and a 3' end complementary to the 3' overhang of the second identifying linker oligonucleotide C). The second identifying linker-oligonucleotide is either attached to a predetermined position in an array or it is optionally comprising one or more molecules or labels or any combination thereof, that are used in the identification and quantification steps. Both the first and the second identifying linker oligonucleotide can optionally comprise a recognition/binding site for one or more site-specific endonucleases including restriction endonucleases and/or nicking endonucleases. The X in the circle can either be a solid support or a molecule that is used to identify and/or quantify the ssDNA tag linked to a first identifying linker oligonucleotide; optionally in combination with the X on a second identifying linker oligonucleotide attached to the same ssDNA tag. Attached shall in this respect denote attached by means of ligation or hybridization. X can be linked to the 3' or to the 5' end of one or both of the two DNA strands in an identifying linker oligonucleotide or it can be linked to any of the bases or to the backbone structure at any position(s) serving the purpose, including any combination thereof. See the definition of identifying linker oligonucleotide for further examples of X. II) The steps involved includes providing at least one identifying linker oligonucleotide A) having a 3' or 5' overhang complementary to an ssDNA tag or a part of an ssDNA tag (In this example an identifying linker oligonucleotide having a 5' overhang is used and only one identifying linker oligonucleotide is shown, but 3' overhangs may also be used along with any suitable plurality of identifying linker oligonucleotides); B) exposing the ssDNA tags to the linker. III) After contacting and hybridizing said identifying linker to an ssDNA tag forming a hybrid oligonucleotide tag, the ssDNA tag is preferably ligated to the identifying linker thereby producing a chimeric polynucleotide tag A) comprising an ssDNA tag derived from a biological sample and a synthetic, identifying linker oligonucleotide. This chimeric polynucleotide is capable of being linked to the second identifying linker B) having a complementary overhang opposite to that of the first identifying linker oligonucleotide (e.g. when the first identifying linker oligonucleotide has a 5' overhang, the second identifying linker oligonucleotide has a 3' overhang, and vice versa). IV) After a second ligation step the chimeric polynucleotide tag A) becomes double stranded along the entire length of the original ssDNA tag. It is possible to quantify each double stranded chimeric tag by employing a combination of a solid support and/or a molecule attached to one or both of the two identifying linker oligonucleotides. Such molecules are termed "molecular identifiers" and it will be understood that any unique identifying linker oligonucleotide may comprise at least one unique molecular identifier. The molecular identifier makes it possible to identify the identifying linker oligonucleotide capable of identifying the single stranded nucleotide tag according to the invention. Examples of molecular identifiers are listed under "Definitions" herein. The identifying linker oligonucleotides themselves can be blocked in any end of the two DNA strands. For example by not having a 5' $PO_4$ group or a 3' OH group or any combination thereof. Furthermore the two DNA strands in one linker can be covalently linked together in one end or at any point along the length of the linker. For example by making the linker out of one palindromic DNA strand looping back onto itself. The combined length of the two overhangs can either be equal to or shorter than the ssDNA tag that is being identified by the combination of the two overhangs of the first and second identifying linker. The two overhangs of the first and the second identifying linker oligonucleotide do not have to be of equal length. Furthermore, double stranded linkers are only required if they are to be ligated to the ssDNA tag or if a fixed offset is required. In other instances single stranded linkers can be used as well. Selected 6' $PO_4$ and 3' OH groups are indicated.

Chimeric tag: Double stranded oligonucleotide linker comprising a single stranded oligonucleotide overhang that is ligated to a complementary single stranded oligonucleotide tag following hybridization between the overhang of the oligonucleotide linker and the single stranded oligonucleotide tag. See also FIG. 14.

Cleavage agent: Agent capable of recognizing a predetermined motif of a double stranded polynucleotide and cleaving only one strand of the double stranded polynucleotide, or capable of cleaving both strands of the double stranded polynucleotide. Examples of cleavage agents in the present context is type If restriction endonucleases, type IIs restriction endonucleases, and nicking endonucleases having activities as outlined e.g. in New England BioLabs' catalog for 2000–01.

Complementary DNA: Any DNA obtained by means of reverse transcriptase acting on RNA as a substrate. Complementary DNA is also termed copy DNA.

Complementary strand: Double stranded polynucleotide contains two strands that are complementary in sequence and capable of hybridizing to one another.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Selective hybridization conditions include, but is not limited to, stringent hybridization conditions. Selective hybridization occurs in one embodiment when there is at least about 65% complementarity over a stretch of at least 14 to 25 nucleotides, preferably at least about 75%, more preferably at least about 90% complementarity. See, M. Kanehisa (Nucleic Acids Res. 12, 203, 1984), incorporated herein by reference. For shorter nucleotide sequences selective hybridization occurs when there is at least about 65% complementarity over a stretch of at least 8 to 12 nucleotides, preferably at least about 75%, more preferably at least about 90% complementarity. Stringent hybridization conditions will typically include salt concentrations of less than about 1 M, more usually less than about 500 mM and preferably less than about 200 mM. Hybridization temperatures can be as low as 5° C. and are preferably lower than about 30° C. However, longer fragments may require higher hybridization temperatures for specific hybridization. Hybridization temperatures are generally about 2° C. to 6° C. lower than melting temperatures ($T_m$), which for polynucleotides comprising less than about 20 nucleotides can be calculated as $T_m=4\times(G+C \text{ content})+2\times(A+T \text{ content})$. As other factors may affect the stringency of hybridization, including base composition and length of the complementary strands, presence of organic solvents and extent of base mismatching, the combination of parameters is more important than the absolute measure of any one alone.

DNA: deoxyribonucleic acid.

Double stranded polynucleotide: Polynucleotide comprising complementary strands.

Double stranded tag source: Sources selected from cDNA, genomic DNA and extra-genomic DNA, including plasmids and other extra-chromosomal replicons.

dsDNA. Double stranded DNA.

Epitope: Epitope in this context covers any epitope capable of being recognised by an antibody or a binding fragment thereof. Therefore a unique epitope can identify a unique identifying linker.

Hybrid motif: In the present context a hybrid motif is one binding/recognition motif for a site-specific endonuclease that is overlapping with another binding/recognition motif for another site-specific endonuclease so that some of the bases in the hybrid motif is used by both site-specific endonuclease. A hybrid motif can also comprise binding/recognition motifs for more than two site-specific endonucleases.

Hybrid oligonucleotide tag: Single stranded or double stranded oligonucleotide linker comprising a single stranded oligonucleotide overhang that is hybridized to a complementary single stranded oligonucleotide tag. A hybrid oligonucleotide tag can be a substrate for ligase if a 3' and a 5' end of two polynucleotides are adjacent to each other. See FIG. 32 for an example.

Identifying linker oligonucleotide: An oligonucleotide, preferably comprising either a double stranded part comprising complementary nucleotide strands and/or comprising at least one single stranded part, such as two single stranded parts. The identifying linker oligonucleotide may thus in one preferred embodiment be exclusively single stranded. Identifying linker nucleotides are used in the process of identifying at least one single stranded polynucleotide tag. The double stranded part may be obtained by hybridization of a first nucleotide strand to a second, complementary nucleotide strand, or by a "hairpin" structure obtained by folding a first single stranded nucleotide strand to a part of itself. In one embodiment a double stranded linker oligonucleotide is used having a 3' or 5' overhang comprising or essentially consisting of a predetermined sequence capable of hybridizing under suitable conditions to a single stranded polynucleotide tag comprising a sequence that is complementary to the predetermined sequence of the overhang of the identifying linker oligonucleotide. The identifying linker oligonucleotide may be linked to a solid support, or it may, in another embodiment, comprise one or more molecules, that makes it possible to link an ssDNA tag; or any other polynucleotide comprising a part that is complementary to the overhang of the identifying oligonucleotide; to for example i) one predetermined position out of a plurality of predetermined positions in an array, or ii) one predetermined epitope out of a plurality of predetermined epitopes, or iii) one predetermined label out of a plurality of predetermined labels, that can be either a fluorochrome, an epitope, an enzyme, a DNA tag, or a first (small) molecule that can bind to a second (larger) molecule for example, but not limited to, biotin, wherein said first molecule does not interfere with the function of the identifying oligonucleotide, or iv) one predetermined molecule out of a plurality of predetermined molecules comprised of a predetermined number of subunits having the same, or almost the same charge, mass, hydrophobic properties, three dimensional structure, or any other physical or chemical property, or any combination thereof, wherein the different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy, or v) one predetermined dsDNA or ssDNA oligonucleotide out of a plurality of predetermined dsDNA or ssDNA oligonucleotides each having either a different predetermined length, or a different predetermined sequence, optionally chosen from a minimal cross hybridizaton set, or vi) one predetermined peptide out of a plurality of predetermined peptides of a predetermined length or sequence, or vii) one predetermined end of a linarized plasmid out of a plurality of predetermined ends of a linarized plasmids. The other end can either be 3' or 5' overhang or a blunt end, or the linarized plasmid can comprise a set of two overhangs complimentary to each end of an ssDNA tag, that is being cloned into the plasmid, or viii) a molecule comprising one predetermined electromagnetic property out of a plurality of predetermined electromagnetic properties including a paramagnetic property capable of being subjected to magnetic separation, ix) a moiety capable of emitting an one predetermined electromagnetic radiation out of a plurality of predetermined electromagnetic radiations after excitaion, including any fluorescent moiety, including x) any combination of i)–ix), thus making it possible for the skilled person to i) separate, or
ii) manipulate, or
iii) visualize, or
iv) display, or
v) amplify, or
vi) identify, including
vii) any combination thereof the hybrid polynucleotide tag or the chimeric polynucleotide tag formed by said identifying linker oligonucleotide in combination with the ssDNA tag in order to identify the ssDNA tag that is linked to the identifying linker, and optionally quantify said ssDNA tag using the properties of the molecules linked to the identifying linker oligonucleotide. One category of such molecules is "molecular identifiers". Another category is defined as "labels". However, these definitions do not exclude a molecule from belonging to both categories. A label can be separated from the plurality of other labels by using e.g. an optical filter. Manipulation using a molecular identifier can occur without detection, if a downstream detection step is included. A set of two identifying linkers having 3' and 5' overhangs respectively can be a substrate in a ligase chain reaction provided an ssDNA tag is present that is able to hold them in close proximity during the ligation step. In order for the ssDNA tag to function as a catalyzer/modifier in a ligase chain reaction, either the identifying linkers or the ssDNA tag, or both, have to be blocked in the ends that would otherwise link the ssDNA tag to the identifying linkers during the LCR. See e.g. FIGS. 31 through 38 for an example. See also FIG. 14.

Label: Any recognizable feature which is, for example: microscopically distinguishable in shape, size, color, optical density, electromagnetic properties, etc.; differently absorbing or emitting light; chemically reactive; magnetically or electronically encoded; or in some other way distinctively marked with the required information. Examples include, but are not limited to: a fluorochrome/fluorophor, an epitope, an enzyme, a DNA tag, any molecule that is detectable in a mass spectrometer, and a first (small) molecule that can bind to a second (larger) molecule for example, but not limited to, biotin, wherein said first molecule does not interfere with the function of the nucleotide to which the label is attached.

LCR: See Ligase Chain Reaction.

Ligation: Enzymatic reaction carried out by the enzyme ligase. Ligase catalysis the covalent bonding between two nucleotides adjacent to each other. The reaction of ligase is facilitated by a complementary strand holding the two nucleotides in close proximity. The reaction is further facilitated if the two nucleotides comprises the 3' and 5' ends of two polynucleotides that is hold in close proximity to each other by a complementary strand leaving no gaps between the two ends. See "Hybrid oligonucleotide tag". Even if that is the situation the reaction cannot occur if there is no phosphate group on the 5' end or no OH group on the 3' end or if either of the ends are blocked in any other way. Ligation can be carried out using any enzyme capable of ligating nucleotides.

Ligase Chain Reaction: In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA.

Linker: An oligonucleotide, either double stranded or single stranded or comprising both a double stranded and a single stranded part, that link two polynucleotides or a polynucleotide and an oligonucleotide together. An adapter can also function as a linker on top of other functions comprised by the adapter. See also FIG. 14.

Linking: Linking two polynucleotides together means any kind of linking e.g. hydrogen bonding of "sticky ends"; hybridization of a larger overlap between two polynucleotides; covalent bonding after ligation and more.

Methylase: Enzyme capable of performing a site-specific methylation of a nucleotide. Preferred methylases are M.Alw I; M.Bbv I; M.BmrIA; M.BpmI; M.BseRI; M.BsgI; M.BsmF I; M.BspM IA; M.BspMIB; M.Eci I; M.Fau I; M.Fok I; M.Hga IA; M.Hga I B; M.Hph IA; M.Hph IB; M.MboIIA; M.MboIIB; M.MlyI; M.MnII; M.PleI; M.SfaNI.

Methyl-transferase: Enzyme capable of copying the methylation pattern from the old DNA strand to the newly synthesized DNA strand.

Microfluid device: Device manufactured by microfabrication techniques and exploiting a miniaturization of processes involved e.g. in genetic analysis. A representative example of a microfluid device is described in e.g. U.S. Pat. No. 6,168,948.

Molecular identifier: The single stranded polynucleotide tags according to the invention are preferably linked to a suitable label that enables identification of the tag. The linkage may be direct or indirect. When being an indirect linkage, the detectable label may be linked to an identifying linker oligonucleotide to which the single stranded polynucleotide tag is attached by means of e.g. hybridization or ligation. The molecular identifier may facilitate both sorting and/or detection of the tag in question. The sorting may be performed e.g. when a plurality of tags are attached to a plurality of identifying linker oligonucleotides comprising a molecular identifier. Separation preferably occurs by means of differences among molecular identifiers in terms of molecular weight, size, charge, or affinity among predetermined specific binding partners. Accordingly, a molecular identifier is a molecule that a skilled person can use to separate, or manipulate, any molecule attached to said molecular identifier. Normally a molecular identifier has to be linked directly or indirectly to a label in order for a skilled person to track any separation and/or manipulation. Examples of molecular identifiers include, but are not limited to:

i) a predetermined epitope, or
ii) a molecule comprised of a predetermined number of subunits having the same, or almost the same charge, mass, hydrophobic properties, three dimensional structure, or any other physical or chemical property, or any combination thereof, wherein the different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy, or
iii) a predetermined dsDNA or ssDNA oligonucleotide having either a predetermined length, or a predetermined sequence, optionally chosen from a minimal cross hybridization set, or
iv) a peptide of a predetermined length or sequence, or
v) a predetermined first (small) molecule that can bind to a second (larger) molecule for example, but not limited to, biotin, wherein said first molecule does not interfere with the function of the molecular identifier, or
vi) a predetermined end of a linarized plasmid out of a plurality of predetermined ends of a linarized plasmids. The other end can either be 3' or 5' overhang or a blunt end, or the linarized plasmid can comprise a set of two overhangs complimentary to each end of an ssDNA tag, that is being cloned into the plasmid, or
vii) a molecule comprising an electromagnetic property including a paramagnetic property capable of being subjected to magnetic separation,
viii) a moiety capable of emitting an electromagnetic radiation after excitation, including any fluorescent moiety, including
ix) any combination of i)–viii)

The separation and/or manipulation using a molecular identifier can be carried out using antibodies attached to any kind of solid support; for example antibodies attached using a state-of-the-art contacting group to magnetic beads. The separation and/or manipulation using a molecular identifier can also be carried out using a gel like matrix that allows separation according to size; for example when the molecular identifier is dsDNA of a predetermined length that is separated from the plurality of similar molecular identifiers, i.e. dsDNA, by using a polyacrylamide gel. The separation and/or manipulation using a molecular identifier can also be carried out using molecules with paramagnetic properties; for example by passing said molecules with paramagnetic properties through a microfluid device engineered to manipulate such molecules through their paramagnetic properties. In some cases the separation and detection is done in virtually one step. For example, but not limited to, methods outlined in PCT/US 99/02727 and PCT/US 99/02728. In such cases the molecular identifier also functions as a label. The objective of using a molecular identifier in the present context is to use a plurality of molecular identifiers attached using a state-of-the-art contacting group to a plurality of identifying linker oligonucleotides all having a correlation between the sequence of the overhang and the specific molecular identifier attached to the identifying linker oligonucleotide. In other words in this context there is a convergence between the plurality of sequences in the overhang of identifying linker oligonucleotides and the plurality of molecular identifiers attached to said identifying linker oligonucleotides. That way, after forming a chimeric tag out of two identifying linker oligonucleotides and an ssDNA tag, a label originally attached to one of the identifying linker oligonucleotides is now attached to a predetermined molecular identifier originally attached to the other identifying linker oligonucleotide through the ssDNA tag being identified. After separation a quantification of the individual chimeric tags can be carried out. Attaching a plurality of identifying linker oligonucleotides to a grid according to the specific sequence of the overhang will also uniquely identify the linker oligonucleotides according to the sequence of the overhang. It is possible to use as a molecular identifier one end of an extrachromosomal replicon including a plasmid. The other end can either be 3' or 5' overhang or a blunt end. Optionally, the linarized plasmid can comprise a set of two overhangs complimentary to each end of an ssDNA tag that is being cloned into the plasmid.

Monomer: Any member of the set of molecules which can be joined together to form an oligomer or polymer. The set of monomers useful in the present invention includes, but is not restricted to, for the example of oligonucleotide synthesis, the set of nucleotides consisting of adenine, thymine, cytosine, guanine, and uridine (A, T, C, G, and U, respectively) and synthetic analogs thereof. As used herein, monomers refers to any member of a basis set for synthesis of an oligomer. Different basis sets of monomers may be used at successive steps in the synthesis of a polymer.

Messenger RNA: mRNA, a polynucleotide being transcribed only from genes that are actively expressed, where the expressed mRNA codes for a protein.

mRNA: See "messenger RNA".

Nuclear RNA: The group of mRNA consists of both small nuclear RNA and large nuclear RNA transcripts. Different mRNAs can have a variety of functions far beyond the scope of this list.

Nucleoside: A base attached to a ribose ring, as in RNA nucleosides, or a deoxyribose ring, as in DNA nucleosides. See also: "Base".

Nucleotide: Monomer of RNA or DNA. A nucleotide is a ribose or a deoxyribose ring attached to both a base and a phosphate group. Both mono-, di-, and tri-phosphate nucleosides are referred to as nucleotides.

nRNA: See "nuclear RNA".

Oligonucleotide: The oligomer or polymer sequences of the present invention are formed from the chemical or enzymatic addition of monomer subunits. The term "oligonucleotide" as used herein includes linear oligomers of natural or modified monomers or linkages, including deoxyribonucleotides, ribonucleotides, anomeric forms thereof, peptide nucleic acid monomers (PNAs), locked nucleotide acid monomers (LNA), and the like, capable of specifically binding to a single stranded polynucleotide tag by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG," it will be understood that the nucleotides are in 5'→3' order from left to right and the "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise methylated or non-natural nucleotide analogs. Suitable oligonucleotides may be prepared by the phosphoramidite method described by Beaucage and Carruthers (Tetrahedron Lett., 22, 1859–1862, 1981), or by the triester method according to Matteucci, et al. (J. Am. Chem. Soc., 103, 3185, 1981), both incorporated herein by reference, or by other chemical methods using either a commercial automated oligonucleotide synthesizer or VLSIPS.TM. technology. When oligonucleotides are referred to as "double-stranded," it is understood by those of skill in the art that a pair of oligonucleotides exist in a hydrogen-bonded, helical configuration typically associated with, for example, DNA. In addition to the 100% complementary form of double-stranded oligonucleotides, the term "double-stranded" as used herein is also meant to refer to those forms which include such structural features as bulges and loops. For example as described in U.S. Pat. No. 5,770,722 for a unimolecular double-stranded DNA. It is clear to those skilled in the art when oligonucleotides having natural or non-natural nucleotides may be employed, e.g. where processing by enzymes is called for, usually oligonucleotides consisting of natural nucleotides are required. When nucleotides are conjugated together in a string using synthetic procedures, they are always referred to as oligonucleotides.

Polynucleotide: A plurality of individual nucleotides linked together in a single molecule. Polynucleotide covers any derivatized nucleotides such as DNA, RNA, PNA, LNA etc. Any oligonucleotide is also a polynucleotide, but every polynucleotide is not an oligonucleotide.

Predetermined position: The position in a hybridization array occupied by a predetermined, single stranded nucleotide sequence of a first and/or second identifying linker oligonucleotide, or the position in a capilary tube, or any other compartment of a microfluid device, occupied by a predetermined, single stranded nucleotide sequence of a first and/or second identifying linker oligonucleotide. In both cases, the identifying linker oligonucleotide may further comprise a molecular identifier. When this is the case, the single stranded nucleotide sequence of a first and/or second identifying linker oligonucleotide may occupy the predetermined position in the hybridization array or in the capilary tube or in the microfluid device compartment due to the manipulation of the molecular identifier under predetermined conditions.

Ribosomal RNA: rRNA is an integral part of ribozymes. rRNA is also the most abundant RNA species in a living cell.

RNA: ribonucleic acid. Different groups of ribonucleic acids exists: mRNA, tRNA, rRNA and nRNA.

rRNA: See "ribosomal RNA".

Sequence determination: Used interchangeably with "determining a nucleotide sequence" in reference to polynucleotides and includes determination of partial as well as full sequence information of the polynucleotide. That is, the term includes sequence comparisons, fingerprinting, and like levels of information about a target polynucleotide, as well as the express identification and ordering of bases, usually each base, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C)-C . . . " and the like.

Single nucleotide polymorphism: A single nucleotide position in an ordered context, that not constant throughout the population.

Single stranded polynucleotide tag: Consecutive nucleotides linked together and forming a single strand. The number of nucleotides may range from about 6, such as 8, for example 10, such as 12, for example 14 nucleotides, to more than 20 nucleotides,. including tags of more than e.g. 200 nucleotides. In this context a single stranded polynucleotide tag is obtainable from genetic material present in a biological sample.

Single stranded tag source: Ribonucleic acid, including mRNA, which is subsequently converted into a double stranded tag source.

Site-specific cleavage agent: Any agent capable of recognising a predetermined nucleotide motif and cleaving a single stranded nucleotide and/or a double standed nucleotide. The cleavage may occur within the nucleotide motif or at a location either 5' or 3' to the nucleotide motif being recognised.

Site-specific endonuclease: Enzyme capable of recognizing a double stranded polynucleotide and cleaving only one strand of the double stranded polynucleotide, or capable of recognizing a double stranded polynucleotide and cleaving both strands of the double stranded polynucleotide. One group of site-specific endonucleases is blocked in their activity by the presence of methylated bases in specific position in their recognition sequence. Another group of site-specific endonucleases is dependant upon methylated bases in specific position in their recognition sequence. A third group of site-specific endonucleases are oblivious to methylated bases in specific positions in their recognition sequence.

Site-specific Restriction Endonuclease: Enzyme capable of recognizing a double stranded polynucleotide and cleaving both strands of the double stranded polynucleotide. Examples of site-specific restriction endonucleases are shown in New England BioLabs' catalog for 2000-01.

Site-specific Nicking Endonuclease: Enzyme capable of recognizing a double stranded polynucleotide and cleaving only one strand of the double stranded polynucleotide. An example of site-specific nicking endonucleases is shown in New England BioLabs' catalog for 2000-01.

SNP: See: Single nucleotide polymorphism.

Solid support: A material having a rigid or semi-rigid surface. Such materials will preferably take the form of plates or slides, small beads, pellets, disks, capillary tubes or other convenient forms, although other forms may be used. In some embodiments, at least one surface of the solid support will be substantially flat. In other embodiments, a roughly spherical shape is preferred. The solid support may be biological, non-biological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations. For example, the solid support may contain raised or depressed regions on which reactions including, but not limited to, hybridization, ligation, and cleavage takes place. In some embodiments, the solid support will be chosen to provide appropriate light-absorbing characteristics. For example, the support may be a polymerized Langmuir Blodgett film, functionalized glass, Si, Ge, GaAs, GaP, SiO$_2$, SiN$_4$, modified silicon, or any one of a variety of gels or polymers such as (poly)tetrafluoroethylene, (poly)vinyliden-difluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—H functionalities, such as are found on silica surfaces. The solid support is preferably contacted by an array of ordered sets of molecules comprising or essentially consisting of dsDNA and/or ssDNA fragments that are preferably covalently attached to the solid support. In this way the DNA fragments are identified by their two dimensional position in the array.

ssDNA: Single stranded DNA.

sSDNA tag: Single-stranded polynucleotide tag comprising, or essentially consisting of, or consisting exclusively of a single strand of consecutive deoxyribonucleic acids.

Sticky ends: Polynucleotides having complementary 3' and 5' ends that are capable of holding the two polynucleotides linked together by the force of the hydrogen bonds between the complementary overhangs are said to have sticky ends. See FIGS. 10 and 11 for an example of sticky ends.

Strand: Stretch of individual nucleotides linked together and forming an oligonucleotide or a polynucleotide. Normally a strand denotes a single stranded polynucleotide such as ssDNA or RNA. See "Double stranded polynucleotide".

Substantially: Used herein to indicate that numbers or process parameters may deviate from an absolute number or a maximal number under practical circumstances without this deviation being relevant for the technical effect achieved under such circumstances. When used in the context of substantially all of a plurality, it is generally to be understood that the term signifies at least 95% of individual members of such a plurality, such as at least 99% of individual members. Substantially individual linker oligonucleotides refer to any number of one kind of detectable linker oligonucleotides identifiable by their single stranded nucleotide sequence and present among a plurality of different kinds of linker oligonucleotides harbouring different single stranded sequences.

Transfer RNA: tRNA are linked to specific amino acids and subsequently used by the cell as a substrate for the synthesis of protein.

tRNA: See "transfer RNA".

DETAILED DESCRIPTION OF THE INVENTION

The present invention in one preferred embodiment relates to methods for separating, analyzing and optionally quantifying single stranded polynucleotides comprising tags originating at least partly and preferably wholly from a source of DNA and/or RNA including a sample comprising biological cells.

Using at least one cleavage agent capable of recognizing and cleaving at least one strand of double stranded DNA (dsDNA) makes it possible to isolate a single stranded DNA (ssDNA) tag from dsDNA. The dsDNA can either be at least one cDNA molecule as in a number of preferred embodiments of the invention or it can be genomic DNA, extra genomic DNA or amplification product arising from a PCR or an LCR reaction.

Identifying Linker Oligonucleotides

In one preferred embodiment, the population of ssDNA tags are analyzed by annealing and ligating the tags to a set of identifying linker oligonucleotides each having specific 3' and 5' overhangs corresponding to the 3' and 5' end sequences, respectively, of subsets of the ssDNA tag population. The set will be denoted first identifying linker oligonucleotide and second identifying linker oligonucleotide respectively. Both the first and the second identifying linker oligonucleotide can be linked to a solid support in an array in a predetermined position or to a molecular identifier capable of identifying each identifying linker oligonucleotide according to its predetermined overhang. In the former case no separation is necessary after ligation of the ssDNA tag to the first identifying linker oligonucleotide in an array and before the ligation of this chimeric tag to the second identifying linker oligonucleotide. In the latter case a separation of the different identifying linker oligonucleotides is preferably carried out after ligation to the ssDNA tag and before the ligation of this chimeric tag to the second identifying linker oligonucleotide.

The label attached to the identifying linker oligonucleotide for detection of the identified chimeric tag, after ligation between the identifying linker oligonucleotide and one of the ssDNA tags, can be linked to the first or to the second identifying linker oligonucleotide or to both. See FIGS. 15 through 30 and 52 through 63.

Further steps may preferably include, in addition to providing at least one identifying linker oligonucleotide having a 3' or 5' overhang complementary to an ssDNA tag, or a part of an ssDNA tag, the steps of exposing the pool of ssDNA tags being analyzed to the at least one identifying linker oligonucleotide. The contacting and hybridizing of said identifying linker oligonucleotide to an ssDNA tag generates a hybrid oligonucleotide tag.

In yet further steps, the ssDNA tag is preferably ligated to the identifying linker oligonucleotide thereby producing a chimeric polynucleotide tag comprising i) the ssDNA tag derived from a biological sample and ii) the synthetic, partly double stranded identifying linker oligonucleotide. This chimeric polynucleotide will, in one embodiment of the invention, comprise an overhang derived from the ssDNA tag. Such an overhang is capable of being linked to a second identifying linker oligonucleotide having a complementary overhang opposite to that of the overhang of the first identifying linker oligonucleotide, e.g. a 3' overhang when the first identifying linker oligonucleotide has a 5' overhang, and vice versa. See FIGS. 15 and 16.

After contacting, hybridizing and ligating the second identifying linker oligonucleotide to the overhang of the chimeric tag resulting from ligation of the ssDNA tag to the first identifying linker oligonucleotide, the chimeric polynucleotide tag in one preferred embodiment becomes double stranded along the entire length of the original ssDNA tag. See FIGS. 17 and 18.

It is possible to quantify each unique double stranded chimeric tag comprising a unique ssDNA tag by exploiting the physical and/or chemical properties of certain molecules associated with the identifying linker oligonucleotide, including molecules such as e.g. molecular identifiers comprised by the identifying linker oligonucleotides; optionally in combination with the identifying linker oligonucleotide being attached directly or indirectly to a predetermined position in an array.

Furthermore, any identifying linker oligonucleotide may comprise binding/recognition sites for type II or type IIs restriction endonucleases or nicking endonucleases or any combination thereof. The identifying linkers themselves can be blocked in any or both ends of the two DNA strands. For example by not having a 5' PO$_4$ group or a 3' OH group or any combination thereof. If the identifying linker oligonucleotides are blocked in such a way, that they cannot ligate to an ssDNA tag, but, given an ssDNA tag holds them in close proximity, the first identifying linker oligonucleotide and the second identifying linker oligonucleotide can be linked together, and thus undergo any from of LCR, including asymmetric LCR with the ssDNA tag as template. Furthermore the two DNA strands in one linker can be covalently linked together in one end or at any point along the length of the linker. For example by making the linker out of one palindromic DNA strand looping back onto itself. The combined length of the two overhangs can either be equal to or shorter than the ssDNA tag that is being identified by the combination of the two overhangs of the first and second identifying linker oligonucleotide. In some preferred embodiments, the length of the overhang of the first and second identifying linker oligonucleotides is different from each other. See FIGS. 39 through 43 and 52 through 63.

In summary, the identifying linker oligonucleotide is capable of linking the ssDNA tag to a predetermined position in an array and/or to a molecular identifier both capable of identifying the predetermined sequence in the overhang of the linker. The identifying linker oligonucleotide is also capable of linking the ssDNA tag to a label that in some situations are capable of quantifying the relative amount of ssDNA tags linked to that identifying linker. E.g. when the chimeric tag is comprised of a first identifying linker oligonucleotide linked to a predetermined position in an array, an ssDNA tag, and a second identifying linker oligonucleotide linked to a label.

Hybridization Arrays

Figure 44:
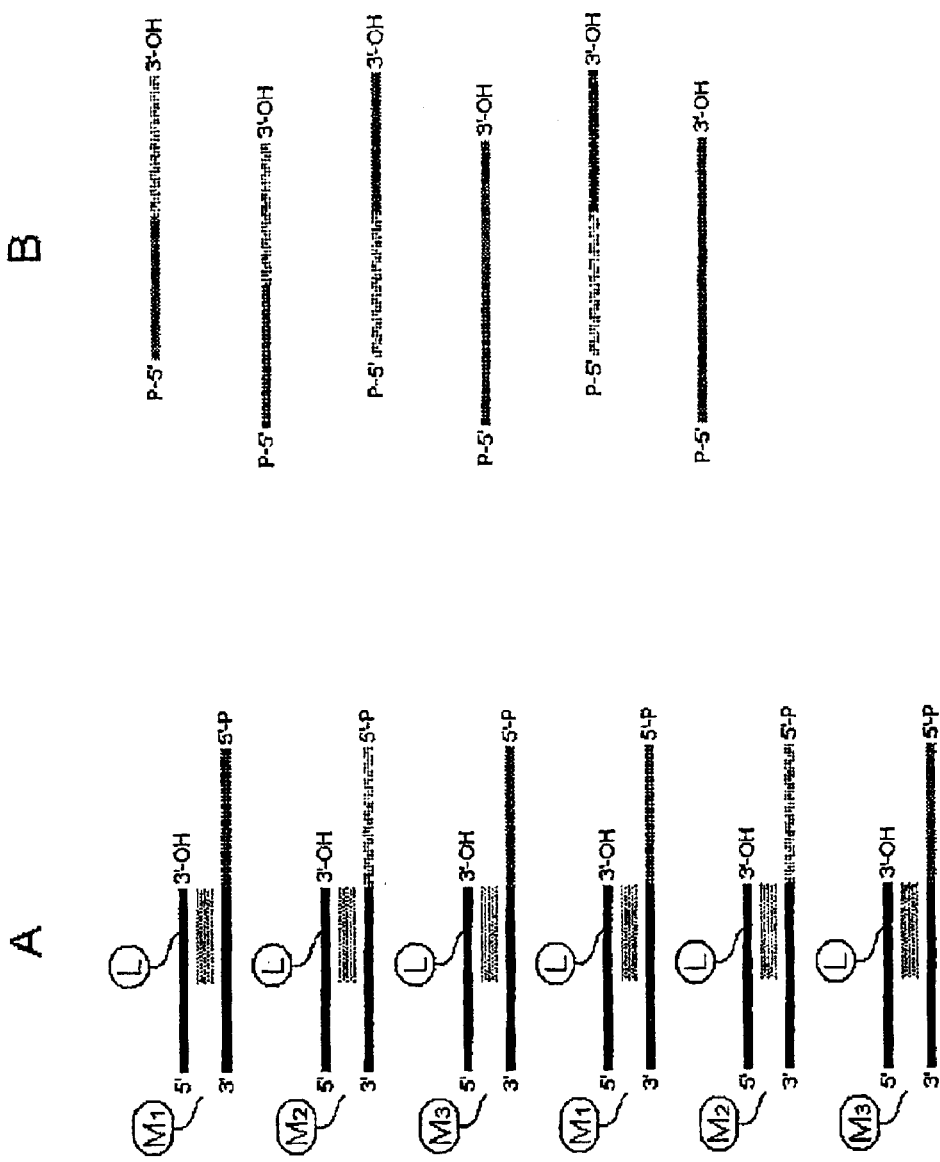
FIG. 44.
Figure 45:
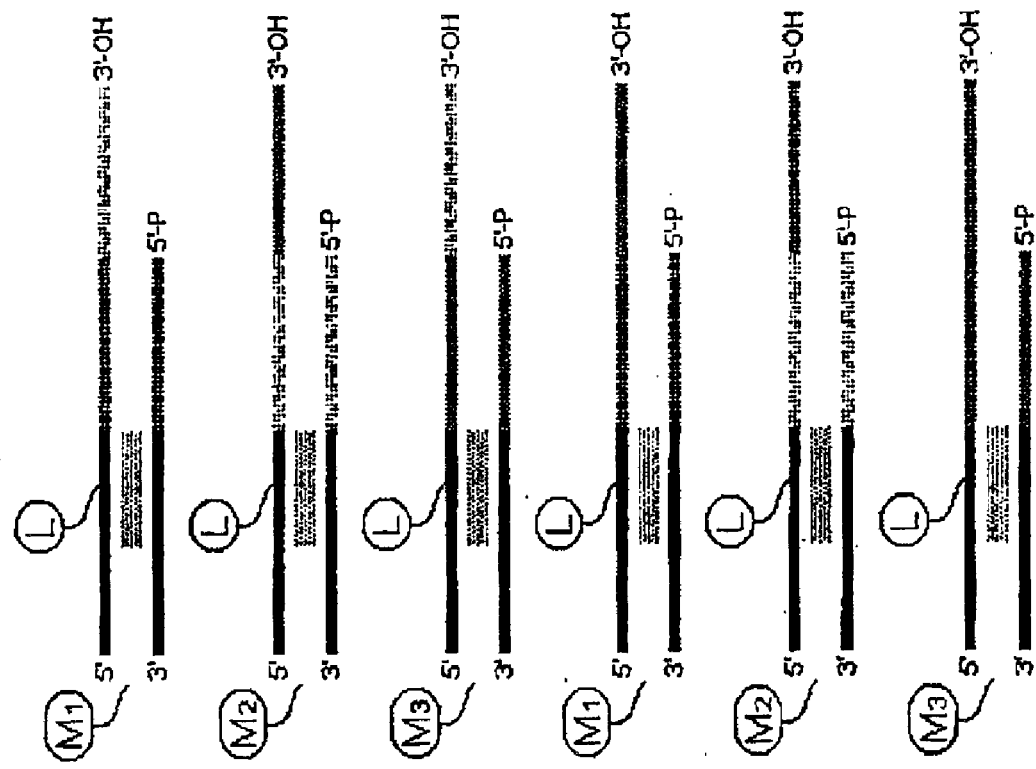
Figure 46:
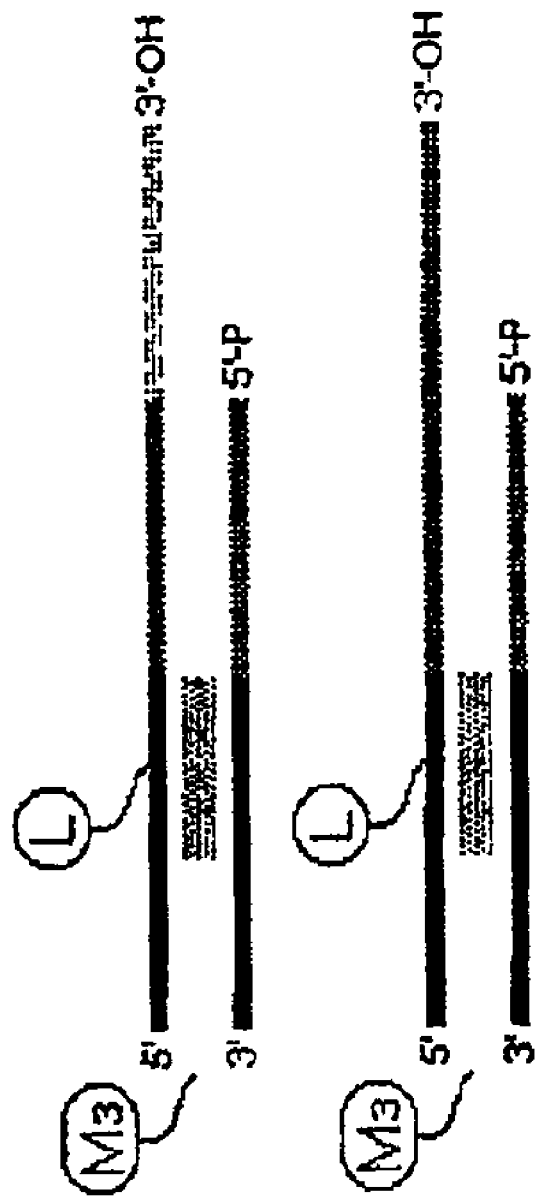
Figure 47:
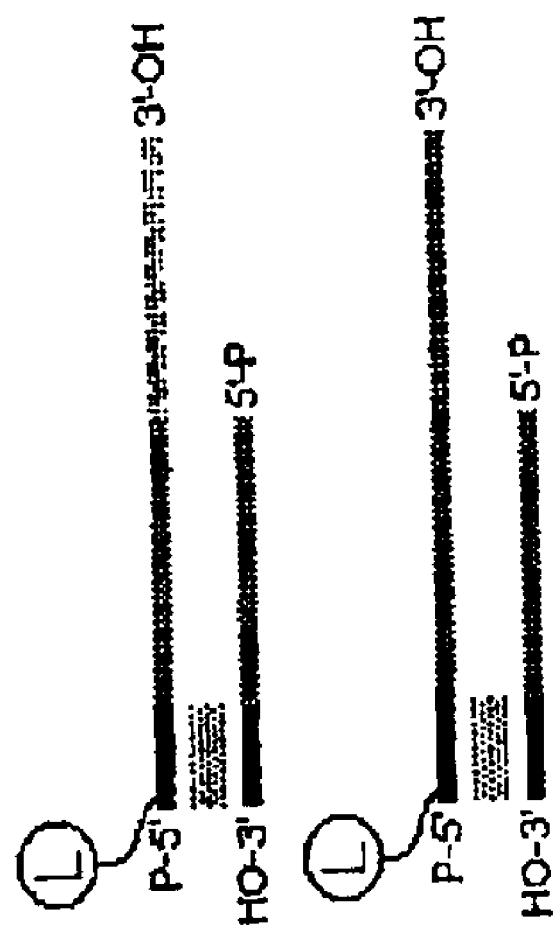
Figure 48:
Figure 49:
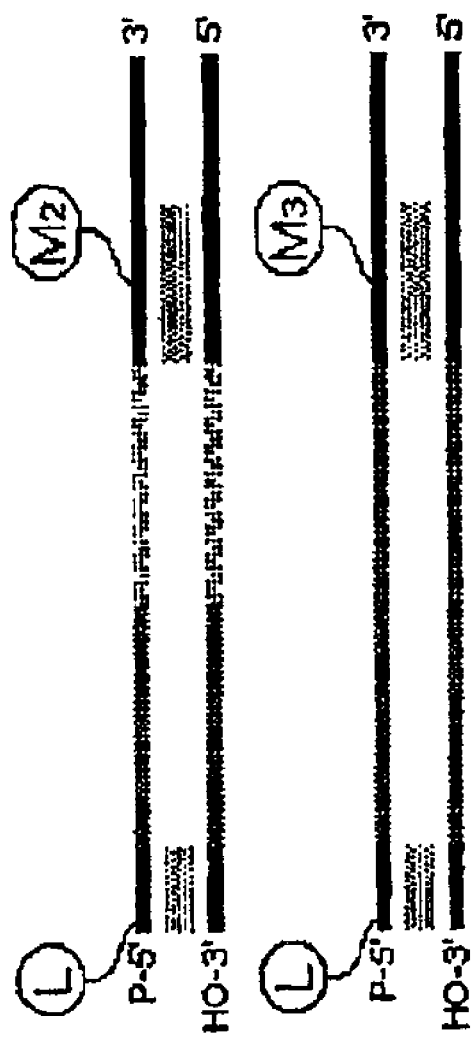
Figure 50:
Figure 51:
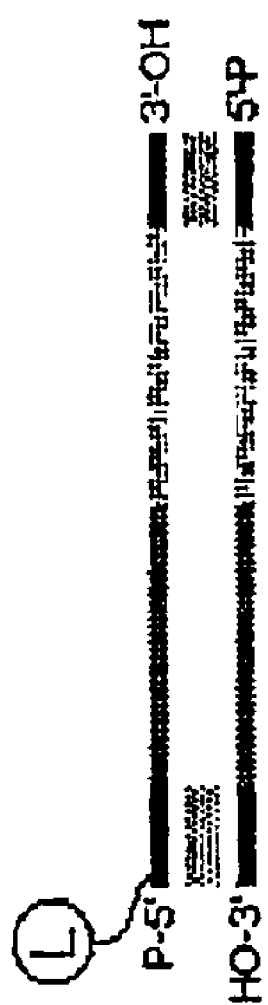
Figure 52:
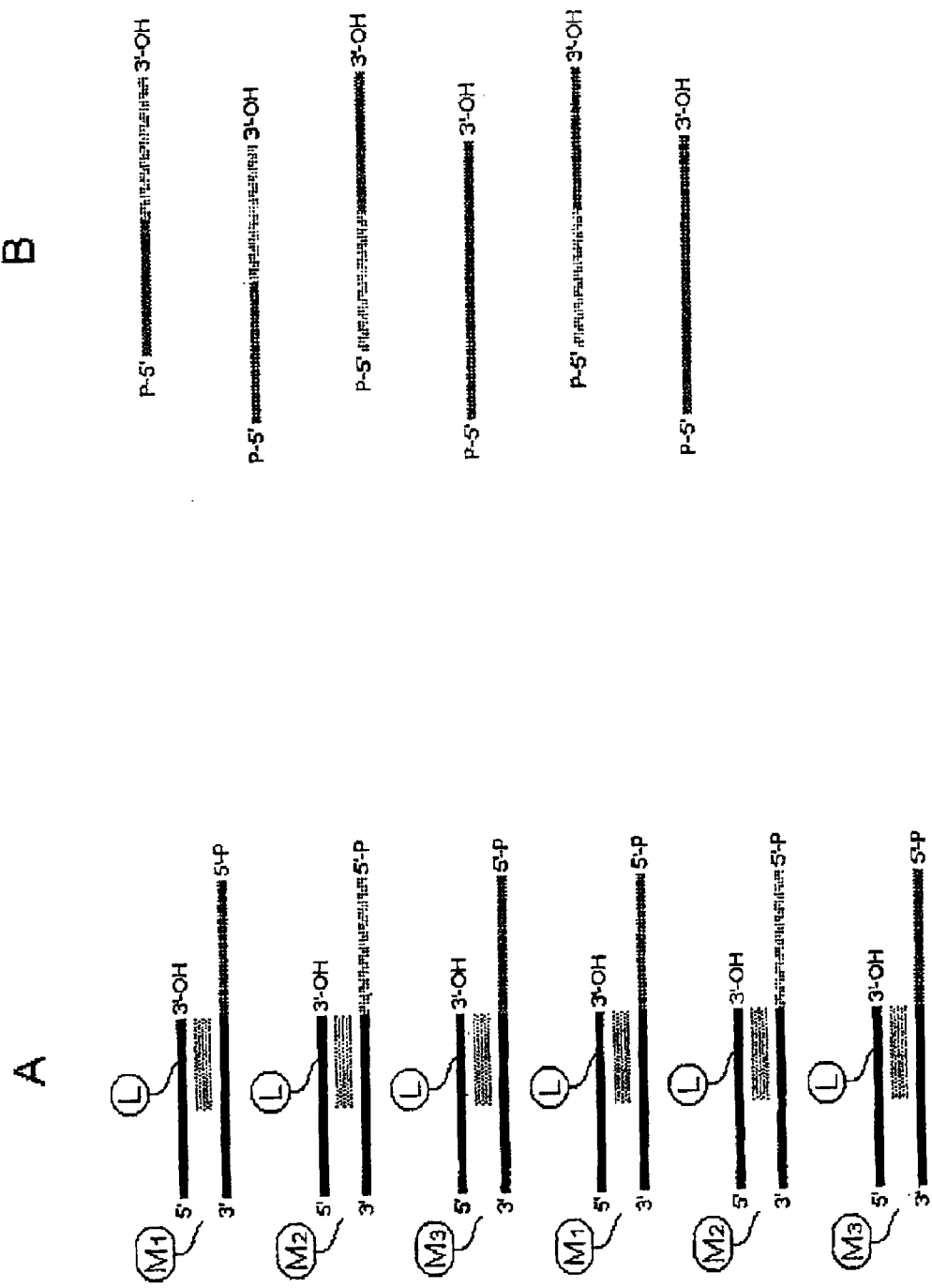
FIG. 52: In one embodiment asymmetric LCR amplification of the signal from each ssDNA tag can be carried out in a microfluid device as illustrated in FIGS. 52 through 63. A complete set of first identifying linker oligonucleotides in solution A) comprising every combination of sequence in the overhang, or a predetermined subset thereof, as illustrated by the different shading of the strands, and comprising a label (L) and a molecular identifier (M) capable of identifying each predetermined overhang of the identifying linker oligonucleotides and also comprising a recognition/ binding site for a site-specific nicking endonuclease (hatched box) is provided. Said identifying linker oligonucleotides are exposed to a sample of ssDNA tags B) The molecular identifier capable of identifying each predetermined overhang of the identifying linker oligonucleotides can be i) a predetermined epitope, or ii) a molecule comprised of a predetermined number of subunits having the same, or almost the same charge, mass, hydrophobic properties, three dimensional structure, or any other physical or chemical property, or any combination thereof, wherein the different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy, or iii) a predetermined dsDNA or ssDNA oligonucleotide having either a different predetermined length, or a different predetermined sequence, optionally chosen from a minimal cross hybridization set, or iv) a peptide of a predetermined length or sequence, or v) a predetermined first (small) molecule capable of binding to a second (larger) molecule, e.g biotin, or vi) any combination of i)–v). In this case 5' overhangs are used, but 3' overhangs may also be used, in both cases along with any suitable plurality of identifying linker oligonucleotides. Complementary sequences are shown with the same shading. Selected 5' $PO_4$ and 3' OH groups are indicated.
Figure 53:
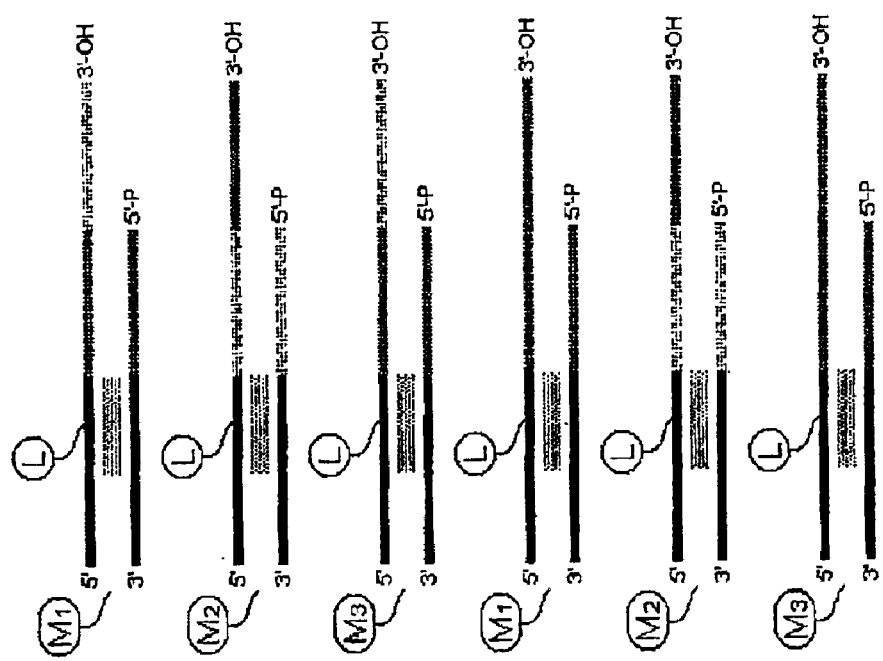
FIG. 53: Following ligation the chimeric dsDNA tags are separated in the microfluid device by using the molecular identifiers capable of identifying each predetermined overhang of the identifying linker oligonucleotides. Different shading of strands illustrates different sequences. Complementary sequences are shown with the same shading. Selected 5' $PO_4$ and 3' OH groups are indicated.
Figure 54:
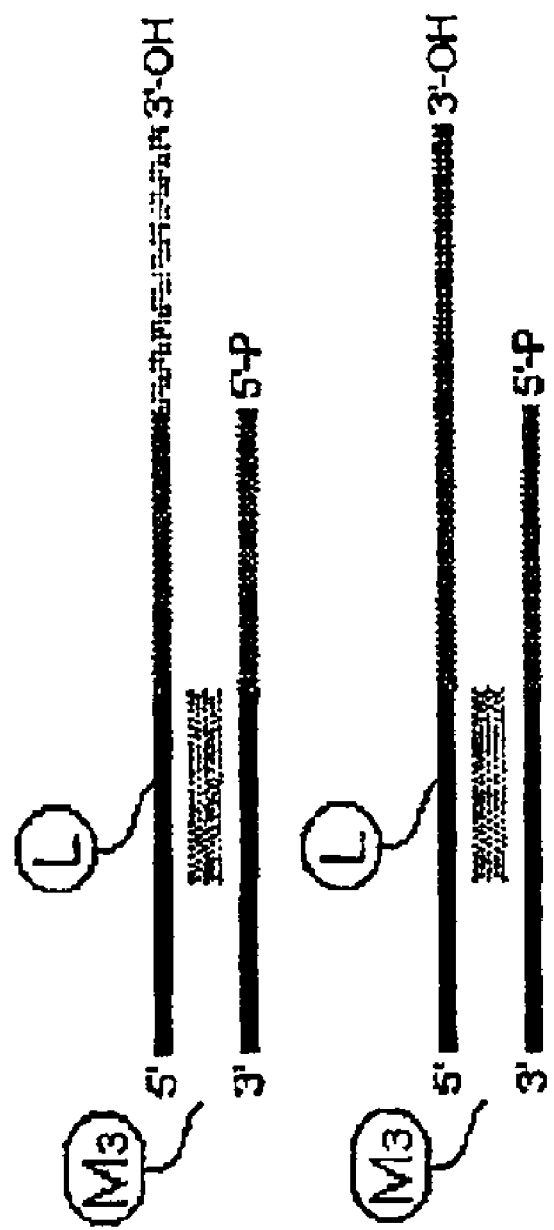
FIG. 54: After separation each pool of separated chimeric dsDNA tags are comprised of chimeric dsDNA tags having a variety of 3' overhangs. The first identifying linker oligonucleotide part of the chimeric dsDNA tags of each pool all had the same sequence in their overhang complementary to one end of the subset of ssDNA tags attached to them before the ligation step. Different shading of strands illustrates different sequences. Complementary sequences are shown with the same shading. Selected 5' $PO_4$ and 3' OH groups are indicated.
Figure 55:
FIG. 55: A site-specific nicking endonuclease is used to separate the first identifying linker oligonucleotides A) from the ssDNA tags B). Different shading of strands illustrates different sequences. Complementary sequences are shown with the same shading. Selected 5' $PO_4$ and 3' OH groups are indicated.
Figure 56:
FIG. 56: After cleavage with a site-specific nicking endonuclease a phosphatase enzyme is employed in order to remove the 5' phosphate from the ssDNA tags. If the first identifying linker oligonucleotides are still in the reaction mixture at this stage they will also have their 5' phosphate groups removed. This, however, does not have any impact on the following steps. Alternatively the 3' end could have been blocked instead if the steps following this step are adapted accordingly. Different shading of strands illustrates different sequences. Complementary sequences are shown with the same shading. Selected 5' $PO_4$ and 3' OH groups are indicated.
Figure 57:
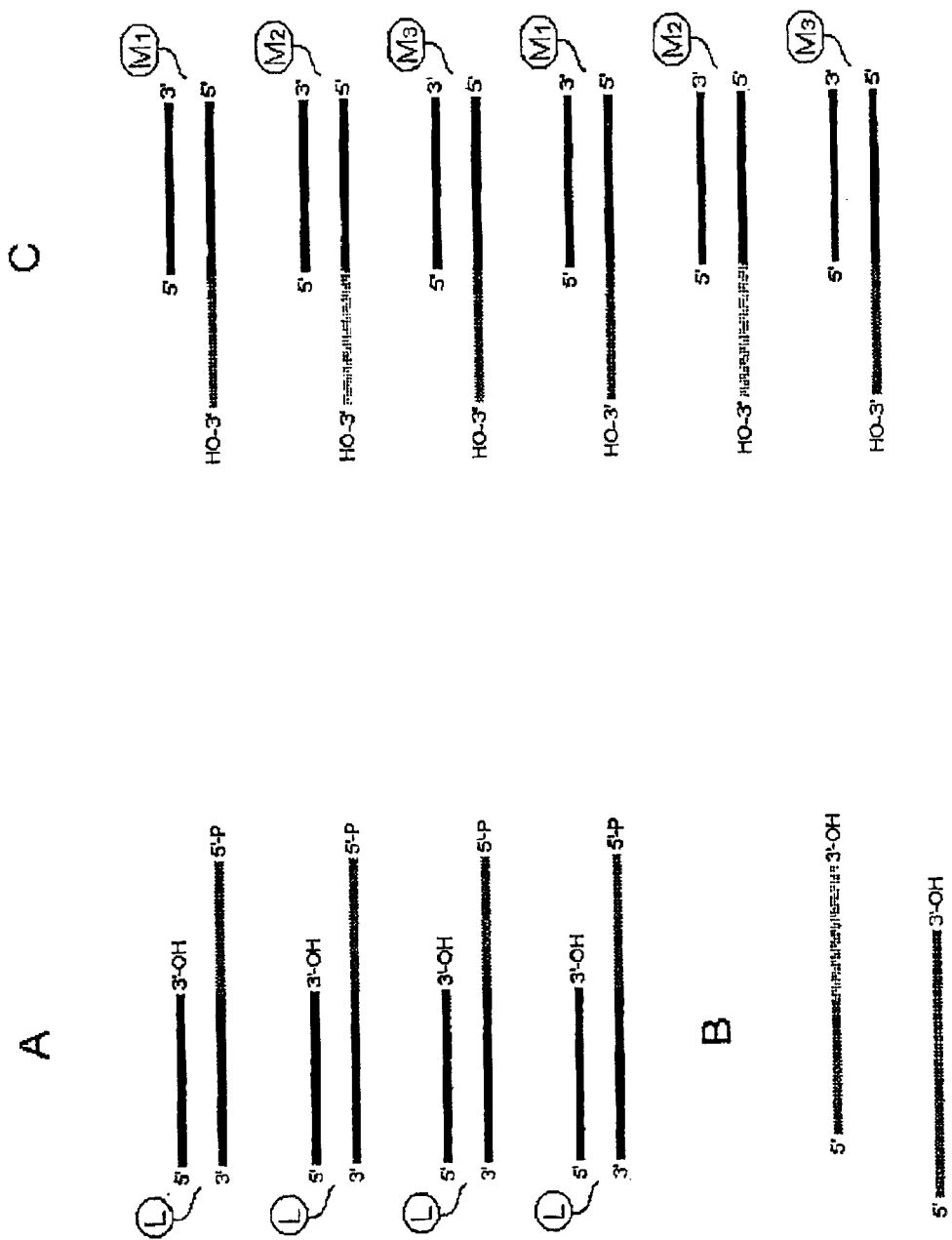
FIG. 57: A new set of first identifying linker oligonucleotides A) comprising a 5' overhang complementary to the 5' end of the specific pool of ssDNA tags having been separated in the previous steps described in FIGS. 52 through 56 and comprising a label are exposed to said pool of ssDNA tags B). A set of second identifying linker oligonucleotides C) with 3' overhangs comprising every combination of sequence in the overhang and comprising a molecular identifier capable of identifying each predetermined overhang of the identifying linker oligonucleotides and lacking the 5' phosphate group next to the overhang are exposed along with A) and B). The molecular identifier capable of identifying each predetermined overhang of the identifying linker oligonucleotides can be i) a predetermined epitope, or ii) a molecule comprised of a predetermined number of subunits having the same, or almost the same charge, mass, hydrophobic properties, three dimensional structure, or any other physical or chemical property, or any combination thereof, wherein the different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy, or iii) a predetermined dsDNA or ssDNA oligonucleotide having either a different predetermined length, or a different predetermined sequence, optionally chosen from a minimal cross hybridization set, or iv) a peptide of a predetermined length or sequence, or v) a predetermined first (small) molecule capable of binding to a second (larger) molecule, e.g biotin, or vi) any combination of i)–v). Different shading of strands illustrates different sequences. Complementary sequences are shown with the same shading. Selected 5' $PO_4$ and 3' OH groups are indicated.
Figure 60:
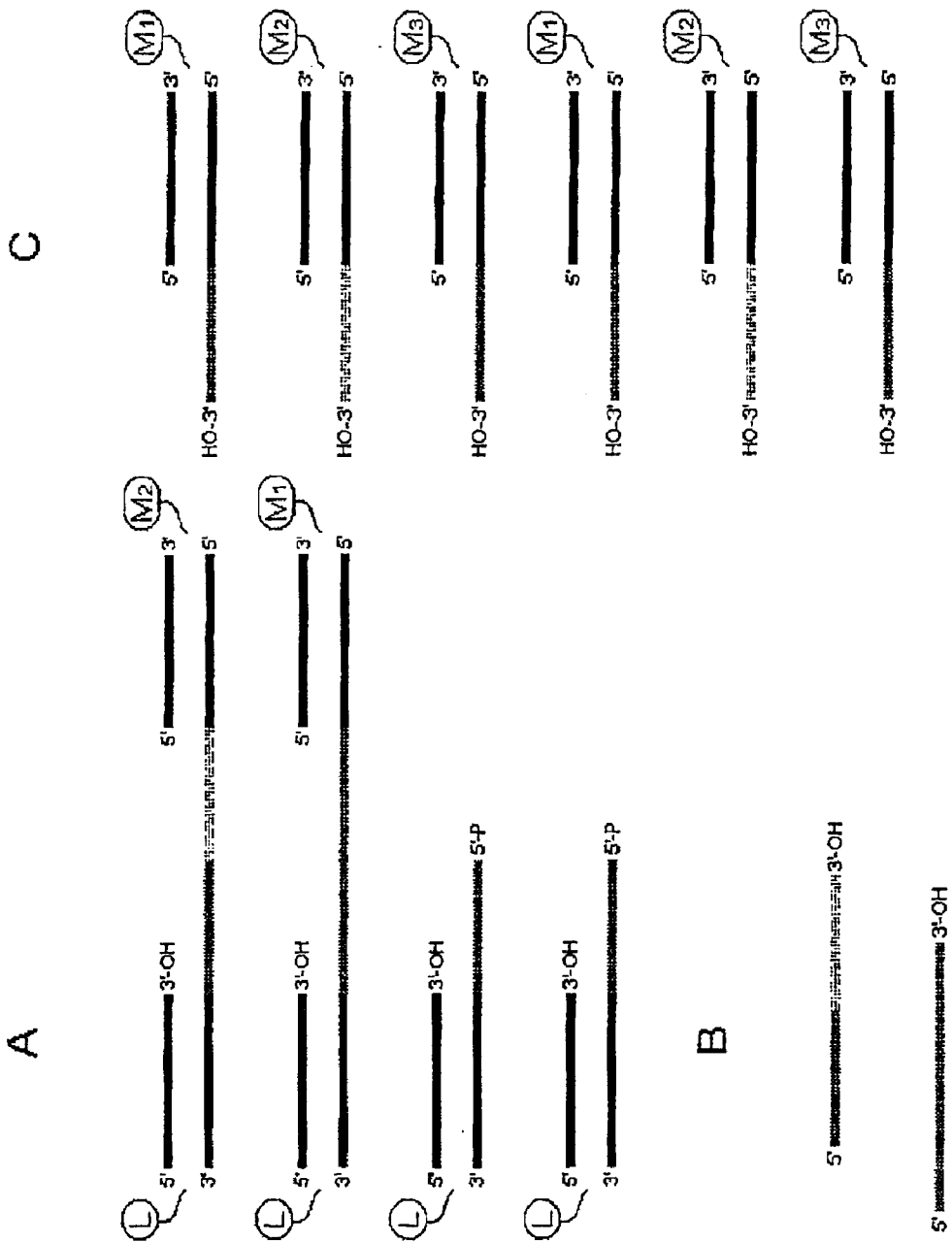
FIG. 60: The conditions are changed again; for example by heating; leaving a number of first and second identifying linker oligonucleotides covalently bound together A). If necessary the concentration of the first and second identifying linker oligonucleotides in solution is adjusted to restore the initial concentration C). The ssDNA tags are restored in solution by the changing of the conditions B). Different shading of strands illustrates different sequences. Complementary sequences are shown with the same shading. Selected 5' $PO_4$ and 3' OH groups are indicated.
Figure 62:
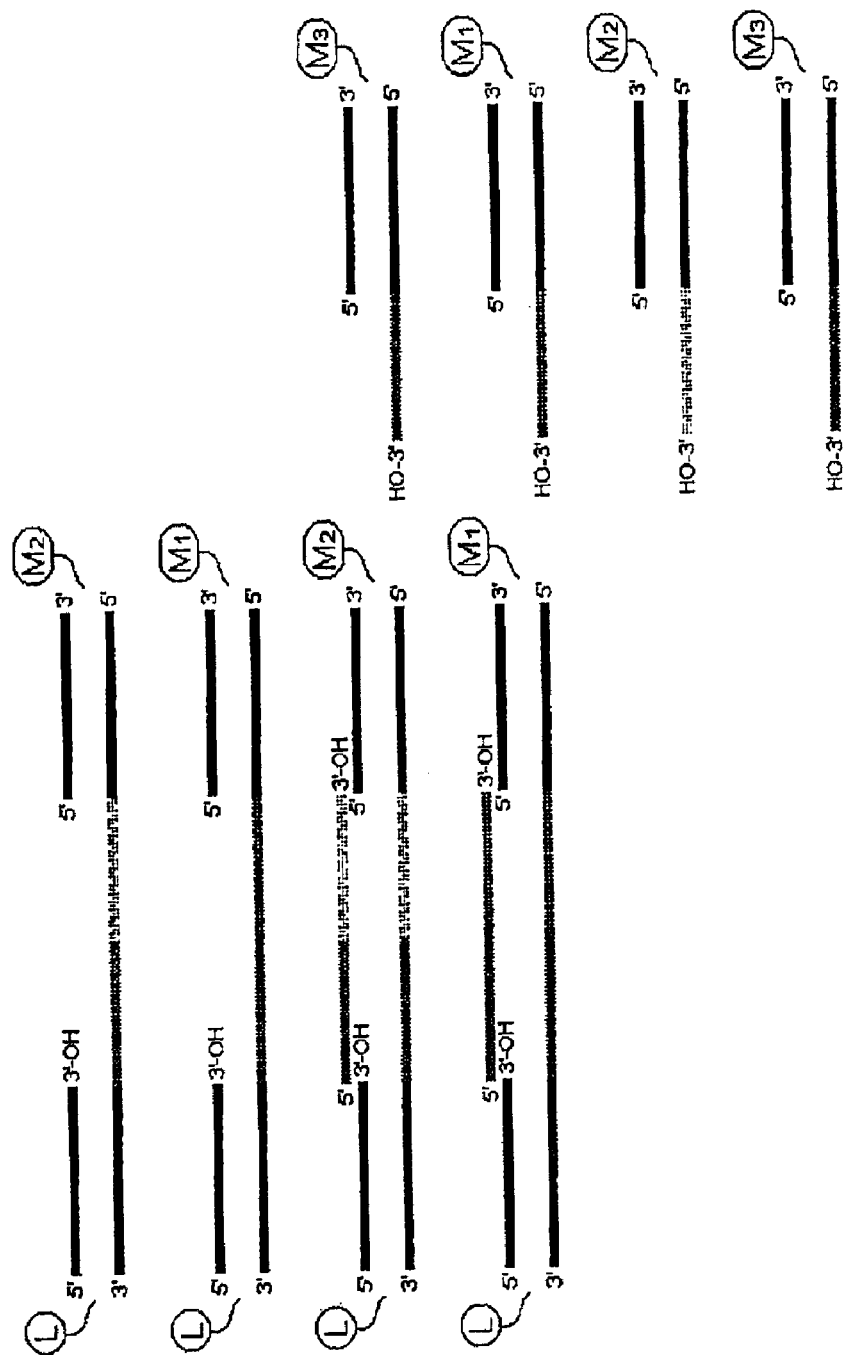
FIG. 62: Concurrently the second identifying linker oligonucleotides comprising a molecular identifier hybridizes to the exposed 3' end of the ssDNA tags hybridized to the first identifying linker oligonucleotides comprising a label. This complex is a substrate for ligase, but because the ssDNA tags and the second identifying linker oligonucleotide in solution had their 5' end blocked only the two identifying linker oligonucleotides can be ligated together. Different shading of strands illustrates different sequences. Complementary sequences are shown with the same shading. Selected 5' $PO_4$ and 3' OH groups are indicated.

In one preferred embodiment, the first identifying linker oligonucleotides of the invention are arranged in an array on a solid support and/or they can comprise any combination of molecules, including molecular identifiers, linked to the 3' or to the 5' end of one or both of the two DNA strands in the identifying linker oligonucleotide or linked to any of the bases or to the backbone structure at any position(s) serving the purpose, or any combination thereof. See FIGS. 15 and 44.

The identifying linker oligonucleotide and/or the molecular identifier may further comprise a label capable of being selectively detected. When detected by any state of the art detection technology, the label provides information of the position and/or presence of a particular identifying linker oligonucleotide and/or a particular molecular identifier. It will be understood that the molecular identifier comprising the label will also provide such information for any identifying linker oligonucleotide when the identifying linker oligonucleotide comprises the molecular identifier comprising the label.

The label thus provides valuable information about the presence and/or position of any identifying linker oligonucleotide. It is possible to correlate a particular selectively detectable label with a particular identifying linker oligonucleotide comprising an overhang comprising a predetermined nucleotide sequence. Accordingly, it is also possible to correlate a particular selectively detectable label with a particular identifying linker oligonucleotide to which a single stranded polynucleotide tag is hybridized. It will be understood that such hybridization occurs at least when the single stranded polynucleotide tag comprises a nucleotide sequence that is complementary to the nucleotide sequence of the overhang of the identifying linker oligonucleotide. As the correlation between the selectively detectable label and the corresponding nucleotide sequence of the overhang of the identifying linker oligonucleotide is known, the label thus also confers information of the sequence of at least part of the single stranded polynucleotide tag that is complementary to the nucleotide sequence of the overhang of the identifying linker oligonucleotide.

When a predetermined first identifying linker oligonucleotide comprising an overhang comprising a predetermined nucleotide sequence is contacting a solid support and is attached thereto in a fixed position by means of a covalent bond or otherwise, a single stranded polynucleotide tag of a predetermined length and comprising a nucleotide sequence complementary to the nucleotide sequence of the overhang of the first identifying linker oligonucleotide may hybridize to the overhang of the first identifying linker oligonucleotide.

The length of the overhang may comprise or essentially consist of e.g. 5 nucleotides, and the length of the single stranded polynucleotide tag may comprise or essentially consist of e.g. 10 nucleotides. It will be understood that all possible sequence permutations, or a subset thereof, may be used in accordance with the present invention. Other lengths of overhangs and tags, respectively, than those exemplified herein above may also be used in accordance with the present invention, such as e.g. an overhang of only 4 nucleotides and a single stranded polynucleotide tag according to the present invention comprising or essentially consisting of 8 nucleotides. In some embodiments, the length of the overhang of the first and second identifying linker oligonucleotides is different from each other.

Once hybridized to the overhang of the first identifying linker oligonucleotide, the remaining e.g. 5 nucleotides of the single stranded polynucleotide tag, i.e. the 5 nucleotides not hybridized, and optionally ligated, to the overhang of the first linker oligonucleotide, may subsequently be identified by introducing at least one or a plurality a second identifying linker oligonucleotides, wherein at least one of said second identifying linker oligonucleotides comprises an overhang of e.g. 5 nucleotides comprising a nucleotide sequence complementary to the part of the single stranded polynucleotide sequence not hybridized, and optionally ligated, to the overhang of the first identifying linker oligonucleotide. See FIGS. 17, 18, 48, and 49.

The at least one second identifying linker oligonucleotide preferably comprises a label capable of being selectively detected at least when the part of the single stranded polynucleotide tag not hybridized to the first identifying linker oligonucleotide is hybridized to the at least one second identifying linker oligonucleotides comprising an overhang of e.g. 5 nucleotides complementary to the part of the single stranded polynucleotide sequence not hybridized to the first identifying linker oligonucleotide.

In one embodiment, the hybridization array comprising a plurality of ordered first and/or second identifying linker oligonucleotides is preferably attached to a substrate, preferably a solid support, said attachment resulting in a large number of positionally distinct identifying linker oligonucleotides attached thereto.

Such hybridization arrays comprising a plurality of ordered first and/or second identifying linker oligonucleotides may, in one embodiment, be "Genechip® arrays," which are well known in the art. Examples are disclosed e.g. in U.S. Pat. No. 5,143,854 and PCT patent publication Nos. WO 90/15070 and 92/10092, all of which are incorporated herein by reference. However, any other suitable commercial hybridization array may also be employed in connection with the present invention.

Such arrays may be produced using mechanical or light directed synthesis methods which incorporate a combination of photolithographic methods and solid phase oligonucleotide synthesis methods. See Fodor et al., Science, 251:767–777 (1991), Pirrung et al., U.S. Pat. No. 5,143,854 (see also PCT Application No. WO 90/15070) and Fodor et al., PCT Publication No. WO 92/10092, all incorporated herein by reference. These references disclose methods of forming vast arrays of peptides, oligonucleotides and other polymer sequences using, for example, light-directed synthesis techniques. Techniques for the synthesis of these arrays using mechanical synthesis strategies are described in, e.g., PCT Publication No. 93/09668 and U.S. Pat. No. 5,384,261, each of which is incorporated herein by reference in its entirety for all purposes. Incorporation of such arrays in injection molded polymeric casings has been described in Published PCT Application No. 95/33846.

In one preferred embodiment, the basic strategy for light directed synthesis of hybridization arrays comprising a plurality of ordered first and/or second identifying linker oligonucleotides is as follows. In a first step, the surface of a solid support, modified with photosensitive protecting groups is illuminated through a photolithographic mask, yielding reactive hydroxyl groups in the illuminated regions.

A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light.

Following capping and oxidation, the substrate is rinsed and the surface is illuminated through a second mask, to expose additional hydroxyl groups for coupling.

A second selected nucleotide (e.g., 5'-protected, 3'-O-phosphoramidite-activated deoxynucleoside) is then presented to the surface. The selective deprotection and coupling cycles are repeated until the desired set of products is obtained. Since photolithography is used, the process can be readily miniaturized to generate high density arrays of oligonucleotide probes. Furthermore, the sequence of the oligonucleotides at each site is known. See, e.g., Pease, et al.: Mechanical synthesis methods are similar to the light directed methods except involving mechanical direction of fluids for deprotection and addition in the synthesis steps.

Typically, the arrays used in the present invention will have a site density of greater than 100 different first and/or second identifying linker oligonucleotides per $cm^2$. Preferably, the arrays will have a site density of greater than $500/cm^2$, more preferably greater than about $1000/cm^2$, and most preferably, greater than about $10,000/cm^2$. Preferably, the arrays will have more than 100 different first and/or second identifying linker oligonucleotides on a single substrate, more preferably greater than about 1000 different first and/or second identifying linker oligonucleotides still more preferably, greater than about 10,000 different first and/or second identifying linker oligonucleotides and most preferably, greater than 100,000 different first and/or second identifying linker oligonucleotides on a single substrate.

For some embodiments, a hybridization array comprising a plurality of ordered first and/or second identifying linker oligonucleotides may be prepared having all possible single stranded first and/or second nucleotide sequences, resepctively, of a given length, such as a length of 3 nucleotides, for example 4 nucleotide, such as 5 nucleotides, for example 6 nucleotides, such as 7 nucleotides, for example 8 nucleotides, such as 9 nucleotides, for example 10 nucleotides, such as 12 nucleotides, for example 14 nucleotides, such as 16 nucleotides, for example 18 nucleotides, such as for example 20 nucleotides.

The length of the single stranded first and/or second nucleotide sequence employed correspond in one embodiment to the expected length of the single stranded polynucleotide tag which may, in preferred embodiments, have a length of for example 4 nucleotide, such as 5 nucleotides, for example 6 nucleotides, such as 7 nucleotides, for example 8 nucleotides, such as 9 nucleotides, for example 10 nucleotides, such as 12 nucleotides, for example 14 nucleotides, such as 16 nucleotides, for example 18 nucleotides, such as for example 20 nucleotides. A length of 10 nucleotides is preferred in one particularly preferred embodiment of the invention.

Hybridization arrays comprising a plurality of ordered first and/or second identifying linker oligonucleotides may be used in such areas as single stranded polynucleotide tag characterization and analysis, including single stranded polynucleotide tag sequencing or sequence checking applications, including any diagnostic application, and the identification in this way of the sequence of a single stranded polynucleotide tag offers substantial benefits over traditional methods.

The use of hybridization arrays in general is described in, e.g., U.S. patent application Ser. No. 08/505,919, filed Jul. 24,1995, now abandoned, and U.S. patent application Ser. No. 08/284,064, filed Aug. 2, 1994, now abandoned, each of which is incorporated herein by reference in its entirety for all purposes.

Determination of Single Stranded Polynucleotide Tags

In one preferred embodiment of the invention it is possible to determine conclusively both i) the position on a solid support of the first identifying linker oligonucleotide comprising an overhang comprising a predetermined, known nucleotide sequence, and ii) the second identifying linker oligonucleotide capable of being selectively detected by detection of the label and/or a molecular identifier attached thereto, wherein the selectively detectable-label and/or molecular identifier is correlated to an overhang comprising a predetermined, known nucleotide sequence hybridising to the part of the single stranded polynucleotide tag that is not hybridized, and optionally ligated, to the overhang of the first identifying linker oligonucleotide.

Both the first and the second identifying linker oligonucleotides will thus be present in the same position in the solid support. This makes it possible to conclusively identify the nucleotide sequences of both of the overhangs of said first and second identifying linker oligonucleotides, and the complementary sequence will thus in one preferred embodiment be identical to the nucleotide sequence of the single stranded polynucleotide tag hybridized to the overhangs.

A label can be any recognizable feature which is, for example: microscopically distinguishable in shape, size, color, optical density, etc.; differently absorbing or emitting of light; chemically reactive; magnetically or electronically encoded; or in some other way distinctively marked with the required information. Examples include, but are not limited to: a fluorochrome/fluorophor, an epitope, an enzyme, a DNA tag, any molecule that is detectable in a mass spectrometer, and a first (small) molecule that can bind to a second (larger) molecule for example, but not limited to, biotin, wherein said first molecule does not interfere with the function of the nucleotide to which the label is attached.

Molecular identifiers can be used for separating and/or manipulating identifying linker oligonucleotides and any ssDNA tag and optionally any additional identifying linker oligonucleotides attached to said ssDNA tag.

Accordingly, a molecular identifier sometimes have a dual role in visualizing and separating the identifying linker oligonucleotides or the chimeric tags. E.g. an epitope has the ability to bind to a specific antigen on a solid support in a separation or manipulation step. The same epitope can also bind to a specific antigen comprising a label with optic properties in the process of quantifying the chimeric tag.

Examples of a molecular identifier are i) a predetermined epitope, or ii) a molecule comprised of a predetermined number of subunits having the same, or substantially the same charge, mass, hydrophobic properties, or any other physical or chemical property, or any combination thereof, or iii) a predetermined dsDNA or ssDNA oligonucleotide having a different predetermined length or a different predetermined sequence, optionally chosen from a minimal cross hybridization set, or iv) a peptide of a predetermined length or sequence, or v) a first (small) molecule that can bind to a second (larger) molecule for example, but not limited to, biotin, wherein said first molecule does not interfere with the function of the molecular identifier, or vi) any combination of i)–v).

It is, possible to use as a molecular identifier one end of an extrachromosomal replicon including a plasmid. The other end can either be 3' or 5' overhang or a blunt end. Optionally, the linarized plasmid can comprise a set of two overhangs complimentary to each end of an ssDNA tag that is being cloned into the plasmid.

Cleavage Agents

Cleavage agents used in connection with the present invention are preferably selected from site-specific endonucleases including site-specific restriction endonucleases of type II and/or site-specific restriction endonucleases of type IIs, and nicking endonucleases. The cleavage agent in question can optionally be sensitive to methylation of the target, or dependant upon methylation of the target.

In a number of preferred embodiments the double stranded DNA carries at least one methylated nucleotide that can either be introduced into the DNA by a cell as is common for genomic DNA or during the cDNA synthesis process by using methylated deoxyribonucleotides in the synthesis reaction. Methylation can also be introduced into double-stranded DNA by applying at least one methylase and/or methyltransferase or any combination thereof. In case extra genomic DNA is being used, the host cell can be engineered to supply the necessary methylase and/or methyltransferase. Methylation of double stranded DNA is used in a number of preferred embodiments of the invention.

Either one of the two identifying linker oligonucleotides, or both of them, may comprise any number of binding/recognition motifs for type II or type IIs restriction endonucleases or nicking endonucleases or any combination thereof. For example a site-specific nicking endonuclease; or a site-specific nicking endonuclease in combination with a site-specific restriction endonuclease of type II; or a site-specific nicking endonuclease in combination with a site-specific restriction endonuclease of type IIs; or a site-specific nicking endonuclease in combination with a site-specific restriction endonuclease of type II and a site-specific restriction endonuclease of type IIs. See FIGS. 39 and 52.

Adapter Oligonucleotides

In one preferred embodiment of the invention the recognition/binding motif or motifs for the cleavage agent or agents are introduced into the double stranded DNA by generating at least one double-stranded DNA fragment by cleaving double-stranded DNA with a cleavage agent and ligating an adapter oligonucleotide onto the end of the double stranded DNA fragment. The adapter comprises a recognition motif for a cleavage agent capable of recognizing a predetermined motif of a double stranded polynucleotide and cleaving only one strand of the double stranded nucleotide. Optionally the adapter oligonucleotide also comprises one or more recognition motifs for one or more cleavage agents capable of cleaving both strands of a double stranded polynucleotide.

The adapter oligonucleotide and the double stranded DNA may be manipulated so that the adapter is preferably ligated to either one of the two ends or to both ends of the double stranded DNA fragment originating from e.g. either cDNA, genomic DNA or extra-genomic DNA. Fragments comprising both an adapter and e.g. cDNA or genomic DNA or extra-genomic DNA are termed chimeric polynucleotide fragments, as only part of the nucleotides originate from the source being subsequently characterized by the single stranded polynucleotide tag of this invention.

Any suitable kind of ligase enzyme can be used for ligating the adapter oligonucleotide and the dsDNA fragment together. The cleavage agent used for cleaving the double stranded DNA in this step can be either a type II or a type IIs restriction endonuclease, and it can optionally be oblivious to methylation, sensitive to methylation or dependant upon methylation.

The adapter oligonucleotide comprises at least one recognition/binding motif for the at least one cleavage agent used in the generation of the ssDNA tag. The cleavage agent or agents includes at least one site-specific nicking endonuclease and optionally one or more site-specific restriction endonuclease of of type II or type IIs.

The adapter oligonucleotide may also comprise a solid support or a first (small) molecule that can bind to a second (larger) molecule for example, but not limited to, biotin, wherein said first molecule does not interfere with the function of the adapter oligonucleotide, and the adapter oligonucleotide may independently thereof further comprise a label for detection of the adapter and/or any tag associated therewith by means of hybridization or otherwise.

The adapter oligonucleotide may further comprise a molecular identifier that is correlated to the overhang of the adapter oligonucleotide. This molecular identifier makes it possible for the skilled person to manipulate with the adapter and anything linked to the adapter. The molecular identifier can either be a predetermined epitope; a molecule comprised of a predetermined number of subunits having the same, or almost the same charge, mass, hydrophobic properties, three dimensional structure, or any other physical or chemical property, or any combination thereof, wherein different molecular identifiers comprise a different number of subunits, and wherein said difference in the number of subunits makes it possible to separate or identify individual molecular identifiers when subjecting these to separation or identification techniques such as e.g. gel electrophoresis or mass spectroscopy; dsDNA of a predetermined length; or ssDNA of a predetermined sequence, optionally chosen from a minimal cross hybridization set; or a peptide of a predetermined length or sequence; including any combination thereof. In one embodiment the adapter is introduced by use of PCR with at leaset one primer comprising the adapter.

Single Stranded Adapter Oligonucleotides

In one preferred embodiment of the invention the adapter oligonucleotide comprising the at least one recognition motif(s) for the cleavage agent or agents are introduced into the double stranded DNA by initially ligating an adapter, preferably a single stranded adapter, to at least one decapped mRNA molecule, reverse transcribing this chimeric mRNA molecule into single stranded cDNA, and then using a polymerase to synthesize the second strand of the cDNA. The cleavage agent or agents includes at least one site-specific nicking endonuclease and optionally one or more site-specific restriction endonuclease of of type II or type IIs.

When the chimera is obtained by ligating an adapter to the 5' end of at least one decapped mRNA molecule, a solid support or a molecular identifier that makes it possible for the skilled person to manipulate with the adapter and anything linked to the adapter is preferably introduced into the chimera with the primer used to synthesize the second strand of the cDNA. It is also possible to put discriminating bases at the 3' end of this primer in order to simplify the analysis by breaking it down into a number of panels. Furthermore it is possible to make sets of ssDNA originating with different offset from the 5' end of the mRNA molecule. In this way it is possible to circumvent any errors introduced due to the specific sequence of a specific ssDNA tag. For example it is possible for palindromic sequences to fold up in a hairpin structure and such a structure will be less likely to hybridize to an identifier linker oligonucleotide. See also FIGS. 12 and 13.

Double Stranded Adapter Oligonucleotides

In another preferred embodiment of the invention, at least one double stranded chimeric polynucleotide is obtained either by ligating an adapter oligonucleotide to dsDNA or by ligating an adapter to the 5' end of at least one decapped mRNA molecule, reverse transcribing this chimeric mRNA molecule or molecules into single stranded cDNA, and using a DNA dependent polymerase to synthesize the second strand of the cDNA.

The chimeric dsDNA is preferably attached to a solid support, or a first (small) molecule that can bind to a second (larger) molecule for example, but not limited to, biotin, wherein said first molecule does not interfere with the function of the chimer, through the adapter oligonucleotide or, in case the chimera is obtained by ligating an adapter to the 5' end of at least one decapped mRNA molecule, the solid support, or the first (small) molecule capable of binding to the second (larger) molecule e.g biotin, is introduced with the primer used to synthesize the second strand of the cDNA. In one preferred embodiment of the invention, the adapter oligonucleotide further comprises at least one recognition motif for a type IIs restriction endonuclease that cleaves from 2 to about 25 bases, preferably about 20 bases, from its recognition/binding motif. At least one set of identifying linker oligonucleotides is used to identify and optionally quantify the generated ssDNA tags.

Initially, the chimeric dsDNA is preferably obtained and cleaved by the type IIs restriction endonuclease. The solid support, or the first (small) molecule capable of binding to a second (larger) molecule, e.g biotin, on the adapter oligonucleotide is then used to separate the distal fragment or fragments from the proximal fragment. The same solid support, or the first (small) molecule capable of binding to a second (larger) molecule, e.g biotin, is then used to separate the two strands of the dsDNA tag after melting of the two strands. This provides at least one ssDNA tag in solution. The at least one ssDNA tag is then ligated to the first identifying linker oligonucleotide, having a sequence in its overhang that correlates to a position in an array whereto it is attached.

A second identifying linker oligonucleotide comprising a label is subsequently ligated to the single stranded overhang produced by forming a chimeric polynucleotide tag comprising the ssDNA tag and the first identifying linker oligonucleotide. The label on the second identifying linker oligonucleotide can optionally be correlated to the sequence of the overhang in this identifying linker oligonucleotide or a panel of identifying linker oligonucleotides with different overhangs can be probed one at the time.

The above-described preferred embodiment of the invention provides at least one ssDNA tag from every chimeric dsDNA used as starting material. The identity and quantity of this at least one ssDNA tag is then assessed. This preferred embodiment can be used e.g. to make expression profiling. It can also be used to track the expression of a selected subset of genes, a commonly used approach in diagnostics. It can also be used to asses the extent of methylation in genomic DNA, provided that the chimeric dsDNA is obtained by cleaving genomic DNA with a methylation sensitive or methylation dependant restriction endonuclease before ligating the fragments onto the adapter oligonucleotide, thereby providing chimeric dsDNA fragments suitable for generating the ssDNA tags according to this invention.

In yet another preferred embodiment of the invention, at least one double stranded chimeric dsDNA is obtained either by ligating an adapter oligonucleotide to dsDNA or by ligating an adapter to the 5' end of at least one decapped mRNA molecule, reverse transcribing this chimeric mRNA molecule or molecules into single stranded cDNA and then using a polymerase to synthesize the second strand of the cDNA, or by introducing an adapter by use of PCR with at leaset one primer comprising the adapter.

The chimeric dsDNA may be attached to a solid support, or the first (small) molecule capable of binding to a second (larger) molecule, e.g biotin, through the adapter oligonucleotide or, in case the chimera is obtained by ligating an adapter to the 5' end of at least one decapped mRNA molecule, the solid support, or the first (small) molecule capable of binding to a second (larger) molecule, e.g biotin, is introduced with the primer used to synthesize the second strand of the cDNA. In this preferred embodiment of the invention, the adapter oligonucleotide comprises one recognition/binding motif for a type IIs restriction endonuclease that cleaves preferably from about 4 to 20 bases from its recognition/binding motif. The adapter oligonucleotide also comprises one recognition/binding motif for a nicking endonuclease that preferably cleaves one of the strands from 0 to 16 bases form its recognition/binding motif. At least one set of identifying linker oligonucleotides is used to identify and optionally quantify the generated ssDNA tag. See also FIGS. 10 and 11.

First the chimeric dsDNA is obtained and then it is cleaved by a type IIs restriction endonuclease. The solid support, or the first (small) molecule capable of binding to a second (larger) molecule, e.g biotin, on the adapter oligonucleotide is then used to separate the distal fragment or fragments from the proximal fragment or fragments. A nicking endonuclease is then used to introduce a single strand break so that a single strand of a fixed length can be melted off and isolated from the rest of the chimeric fragment still attached to the solid support. This gives at least one ssDNA tag in solution. This at least one ssDNA tag is then identified by ligating it to the first identifying linker oligonucleotide, having a sequence in its overhang that correlates to a position in an array whereto it is attached.

The second identifying linker oligonucleotide comprising a label is subsequently ligated to the overhang produced by ligating the ssDNA tag to the first identifying linker oligonucleotide. The label on the second identifying linker oligonucleotide can optionally be correlated to the sequence of the overhang in this identifying linker oligonucleotide or a panel of identifying linker oligonucleotides with different over-hangs can be probed one at the time.

This preferred embodiment of the invention provide an ssDNA tag from every chimeric dsDNA used as starting material. The identity and quantity of this at least one ssDNA tag is then assessed. This preferred embodiment can be used to make expression profiling. It can also be used to track the expression of a selected subset of genes, as is commonly the case in diagnostics. It can also be used to asses the extent of methylation in genomic DNA if the chimeric dsDNA is obtained by cleaving genomic DNA with a methylation sensitive or methylation dependant restriction endonuclease before ligating the fragments onto the adapter oligonucleotide giving the chimeric dsDNA fragments suitable for production of the ssDNA tags according to this invention.

Further Processing Steps in ssDNA Tag Characterization and Identification

Once the at least one ssDNA tag is isolated, its identity and abundance can be assessed. The first step in this process can be, but does not have to be, a blocking of one or both ends of the ssDNA tag. For example by substituting the 5' $PO_4$ group or the 3' OH group, or both of said groups, with a blocking agent that prevents the ligation of the group to another nucleotide.

The combination of at least two identifying linker nucleotides, one having a 5' overhang and the other having a 3' overhang, may be used in the combined processes of identifying and quantifying the at least one ssDNA tag.

The identifying linker nucleotides themselves can be blocked in any end of the two DNA strands, for example by substituting the 5' $PO_4$ group or the 3' OH group, or both of said groups, with a blocking agent that prevents the ligation of the group to another nucleotide. Furthermore the two DNA strands in any one identifying linker oligonucleotide can be covalently linked together in one end, or at any position along the length of the identifying linker nucleotide. For example by making the identifying linker nucleotide out of one palindromic DNA strand looping back onto itself.

The combined length of the two overhangs can either be equal to or shorter than the ssDNA tag that is being identified by the combination of the overhangs from the two identifying linker oligonucleotides. Optionally the identifying linker oligonucleotides can be methylated in any combination of positions. A solid support, a label, a molecular identifier, or any combination thereof, can be linked to the 3' or to the 5' end of one or both of the two DNA strands in one identifying linker oligonucleotide. Or it can be linked to any of the bases, or to the backbone structure at any position(s) serving the purpose or any combination thereof.

The solid support can be either a particle or a predetermined position in an array. It can optionally be correlated to the sequence in the overhang of the identifying linker oligonucleotide.

The label can be any recognizable feature which is, for example: microscopically distinguishable in shape, size, color, optical density, etc.; differently absorbing or emitting of light; chemically reactive; magnetically or electronically encoded; or in some other way distinctively marked with the required information. Examples include, but are not limited to; a fluorochrome/fluorophor, an epitope, an enzyme, a DNA tag, any molecule that is detectable in a mass spectrometer, or a first (small) molecule capable of binding to a second (larger) molecule, e.g biotin. The label can optionally be correlated to the predetermined sequence in the overhang of the identifying linker oligonucleotide.

The molecular identifier correlated to the sequence in the overhang of the identifying linker oligonucleotide can be i) a predetermined epitope, or ii) a molecule comprised of a predetermined number of subunits having the same, or substantially the same charge, mass, hydrophobic properties, or any other physical or chemical property, or any combination thereof, or iii) a predetermined dsDNA or ssDNA oligonucleotide having a different predetermined length or a different predetermined sequence, optionally chosen from a minimal cross hybridization set, or iv) a peptide of a predetermined length or sequence, or v) a predetermined or a first (small) molecule capable of binding to a second (larger) molecule, e.g biotin, including vi) any combination of i)–v).

The identifying linker oligonucleotide may also be a part of a linarized plasmid or an end part thereof. The other end of the linarized plasmid can either be 3' or 5' overhang or a blunt end. Optionally, the linarized plasmid can comprise a set of two identifying overhangs complimentary to the at least one ssDNA tag that is being cloned into the plasmid. Even if the identifying linker oligonucleotide is one end of a linarized plasmid, this embodiment may be combined with using a solid support, a label or a molecular identifier.

In one preferred embodiment, the plasmid comprises an identifier, that is correlated to the sequence of the tag being cloned into that specific plasmid. Said identifier can be a variable stretch of DNA; a gene coding for a specific factor, or a gene coding for a small peptide of variable length, charge or composition, all of which is correlated to the specific sequence of the tag being cloned.

Enhancing the Plurality of ssDNA Tags

In a further preferred embodiment of the invention at least one double stranded chimera is obtained by ligating an adapter oligonucleotide to dsDNA This time the double stranded DNA is cleaved with a type IIs restriction endonuclease leaving 2 to 6 bases of overhang. This gives between 16 and 4096 different sequences of the overhang depending on the number of bases in the overhang. The adapter oligonucleotides that are utilized to obtain the chimeric dsDNA is then identified based upon the sequence of their overhang. This is done by taking one at a time or by applying a label or a molecular identifier or both, that is correlated to the sequence of the overhang of the adapter oligonucleotide. The chimeric dsDNA is then attached to a solid support through the adapter oligonucleotide.

This solid support is engineered so that it can easily be cleaved from the rest of the adapter oligonucleotide if all the 16 to 4096 different chimeric dsDNA fragments are to be separated according to their molecular identifier. In this preferred embodiment of the invention the adapter oligonucleotide comprises one recognition/binding motif for a type IIs restriction endonuclease that cleaves from 4 to 20 bases from its recognition/binding motif. The adapter oligonucleotide also comprises one recognition/binding motif for a nicking endonuclease that cleaves one of the strands from 0 to 16 bases form its recognition/binding motif. At least one set of identifying linker oligonucleotides is used to identify and optionally quantify the generated ssDNA tag.

First the chimeric dsDNA is obtained and then it is cleaved by the type IIs restriction endonuclease. The solid support on the adapter oligonucleotide is then preferably used to separate the distal fragment or fragments from the proximal fragment. A nicking endonuclease is then used to introduce a single strand break so that a single strand of a fixed length can be melted off and isolated from the rest of the chimeric fragment still attached to the solid support. This gives at least one ssDNA tag in solution. This at least one ssDNA tag is then identified by ligating it to the first identifying linker oligonucleotide, having a sequence in its overhang that correlates to a position in an array whereto it is attached.

The second identifying linker oligonucleotide comprising a label is subsequently ligated to the overhang produced by ligating the ssDNA tag to the first identifying linker oligonucleotide. The label on the second identifying linker oligonucleotide can optionally be correlated to the sequence of the overhang in this identifying linker oligonucleotide or a panel of identifying linker oligonucleotides with different overhangs can be probed one at the time.

This preferred embodiment of the invention provide all ssDNA tags from a predetermined subset or panel of chimeric dsDNA used as starting material. The identity and quantity of the ssDNA tags in the panel is then assessed.

This preferred embodiment can be used e.g. to make expression profiling. It can also be used to track the expression of a selected subset of genes, as is commonly the case in diagnostics. It can also be used to asses the extent of methylation in genomic DNA if the chimeric dsDNA is obtained by cleaving genomic DNA with a methylation sensitive or methylation dependant restriction endonuclease before ligating the fragments onto the adapter oligonucleotide giving the chimeric dsDNA fragments used for producing the ssDNA tags. This preferred embodiment is especially useful for identifying a large number of tags because there are up to 4096 panels each giving up to $4^{20}$ or $10^{12}$ different combinations in the sequence of the tags or a total of $4^{26}$ or $4.5 \times 10^{15}$ different combinations.

Generation of cDNA Libraries

The gold standard when doing expression profiling has always been to sequence every clone in a cDNA library. This tedious and laborious task, mainly due to it's complexity, also incorporates some systematic errors. Especially in the process of generating the cDNA libraries. Therefore the status of cDNA library sequencing as a gold standard for expression profiling may not be thoroughly justified. In the following section the whole process of generating these cDNA libraries using different methods are discussed, including the pros and cons involved. Any state of the art method for generating cDNA can be used in accordance with the present invention.

Only a small fraction of the genetic information of an organism is actually used in an individual cell or tissue at any particular point in time. A cDNA library is a type of gene library in which only DNA coding for actively expressed genes is cloned. These active genes can be selectively cloned over silent genes because the DNA of active genes is transcribed into messenger RNA (mRNA) as part of the pathway by which proteins are made. Therefore the expression of mRNA molecules is a bottleneck in the flow of information in a cell, said flow of information going in very general terms from DNA through mRNA to protein and back again to DNA.

RNA molecules are polar by nature; i.e. the constituent nucleoside bases are linked via phosphodiester bonds between the 3' ribosyl position of one nucleoside and the 5' ribosyl position on the following nucleoside. RNA is synthesized in the 5'→3' direction, and mRNAs are translated by ribosomes in the same direction, such that proteins are synthesized from N-terminus to C-terminus.

cDNA libraries have become the standard source from which thousands of genes have been isolated for further study. Accordingly, any conventional method known to the skilled person for converting single stranded messenger RNA (mRNA) into complementary DNA (cDNA) by means of an enzyme comprising reverse transcriptase activity can be employed in accordance with the present invention.

The first step in preparing a cDNA library is to obtain an mRNA fraction by e.g. purifying the mRNA, which usually represents about 1–3% of the total RNA of the cell. The remainder is ribosomal RNA, transfer RNA, and several other RNA species.

Many mRNAs from eukaryotic organisms have a poly(A) "tail". This is a tract of about 50–150 adenosine residues at their 3' ends. A general practice for purifying mRNA from total cellular RNA involves specifically annealing, or binding, the poly(A) tail to oligo(dT), a single stranded DNA molecule of between about 12 and 30 consecutive dT residues. See e.g. Jacobson, A. (Meth. Enzymol. 152, 254, 1987). Total cellular RNA can be incubated with a solid support to which oligo(dT) has been immobilized. Only RNA molecules containing poly(A) tails selectively anneal to the matrix.

Upon purification of poly(A) containing mRNA, a double-stranded complementary DNA (cDNA) copy of this active RNA can be synthesized in vitro by two sequential enzymatic steps. An RNA-dependent DNA polymerase, known as a reverse transcriptase, is used to synthesize the first strand cDNA (complementary DNA), using the RNA as a template. Then, a DNA-dependent DNA polymerase, typically E. coli DNA polymerase I or Taq polymerase, copies the newly synthesized first cDNA strand to form a complementary second cDNA strand. A popular method of second strand synthesis utilizes the enzyme RNaseH to create "nicks" in the mRNA strand. The resulting short mRNA fragments serve as primers for second strand synthesis by the DNA polymerase. See e.g. Gubler, U. (Meth. Enzymol. 152, 330, 1987). Both polymerases synthesize DNA in the 5'→3' direction, reading the template strand from the 3'→5' direction. Double-stranded cDNA thus prepared may be inserted into a prepared cloning vector, or they may be subjected to a series of processing steps according to the invention.

To efficiently process the cDNA or insert the cDNA into a cloning vector, the ends of the insert cDNA, and optionally also the vector DNA molecules, must be prepared in such a way that they are compatible or suitable for processing. Specialized adapter oligonucleotides can be added to the cDNA ends, followed by digestion with a predetermined site-specific restriction endonuclease to cleave the cDNA and optionally also to create single stranded protrusions that will anneal to corresponding ends in the vector. The insert and vector molecules are subsequently ligated together with T4 DNA ligase. The ligated vectors carrying their cDNA molecule inserts are capable of being introduced into any suitable host organism, including e.g. yeast and E. coli.

One way of generating a cDNA library is by using a cDNA primer known as a random primer to produce so-called "random primed libraries." Rather than being a single species, a random primer is, in actuality, a collection or set of primers of a certain length, usually hexameric, wherein the set includes all possible arrangements of the 4 DNA nucleoside bases over the length of the primer. Thus, a random hexamer is actually a collection of $4^6$, or 4096, different primer sequences each of which is capable of annealing specifically with its complementary sequence in mRNA.

Since every possible 6-base long portion of the mRNA has a complement in the set of random hexamer primers, the population of cDNA first strands generated using random primers shares neither a common origin on the mRNA nor a common 3' sequence. The bias for 3' ends is not a problem in random primed libraries because the primer mix of all possible hexamers promotes initiation of cDNA synthesis at any point on the mRNA. No portion of the mRNA molecule is better represented than any other portion in the population of cDNA first strands.

A common practice in the field is to supplement screening of oligo(dT)-primed libraries with random primed libraries to obtain full-length clones. Random-primed libraries have also been used for intentionally cloning cDNA fragments as a means to obtain gene regions encoding DNA binding proteins. See Singh et al., (Cell 52, 415, 1988); Vinson et al., (Genes Dev. 2, 801, 1988). The inability of some mRNAs to be primed with oligo(dT) makes it essential to construct random primed libraries when the mRNA is non-polyadenylated.

One modification of the standard oligo(dT) priming strategy takes advantage of the common 3' ends of the resulting cDNA to allow the cloning of cDNA molecules in a defined orientation (directional cloning) (Ausubel, et al. (eds) in Current Protocols in Molecular Biology, John Wiley & Sons (1995) Supplement 29). Directional cDNA cloning has two major benefits. First, it reduces the amount of work required to retrieve a clone of interest when using any detection scheme based on protein or peptide expression, such as antibody screening. Expression of the desired protein or peptide requires not only that the DNA fragment containing the gene of interest be present, but also that the fragment is provided in the proper orientation and in the correct reading frame to direct the synthesis of that protein. In a non-directional library, statistically only 1 clone in 6 will meet this requirement, since there are two possible orientations and three possible reading frames for every clone. In contrast, directionally cloned cDNA libraries eliminate the orientation variable, thereby doubling the likelihood of successfully expressing a protein from a given clone and effectively reducing by a factor of two the number of clones that must be screened. The immediate result is diminished labor costs.

The second, and perhaps more important, advantage of directional cloning arises in connection with the construction of subtractive cDNA libraries. Subtractive cDNA libraries are collections of cDNA clones from genes expressed in one tissue or during one developmental state, but not in another. Subtractive cDNA libraries are used to rapidly identify genes important in development or progression of a disease, even in the absence of prior information about the genes. For example, a subtractive cDNA library can identify genes that are specifically active in cancer cells. See Scott et al., (Cell 34, 557–567, 1983): Krady et al., (Mol. Brain Res. 7, 287–297, 1990).

Whereas many strategies have been used to create subtractive libraries, one of the most successful is based on the use of directionally cloned cDNA libraries as starting material. See Palazzolo and Meyerowitz, (Gene 52, 197, 1987); Palazzolo et al. (Neuron 3, 527, 1989); Palazzolo et al. (Gene 88, 25, 1990). In this approach, cDNAs prepared from a first source tissue are directionally inserted immediately downstream of a bacteriophage T7 promoter in the vector. Total library DNA is prepared and transcribed in vitro with T7 RNA polymerase to produce large amounts of RNA that correspond to the original mRNA from the first source tissue. Sequences present in both the source tissue and another tissue are subtracted as follows. The in vitro transcribed RNA prepared from the first source is allowed to hybridize with cDNA prepared from either native mRNA or library RNA from the second source tissue.

The complementarity of the cDNA to the RNA makes it possible to remove common sequences as they anneal to each other, allowing the subsequent isolation of unhybridized presumably tissue-specific cDNA. This approach is only possible using directional cDNA libraries, since any cDNA sequence in a non-directional library is as likely to be in the "sense" orientation as the "antisense" direction (sense and antisense are complementary to each other). A cDNA sequence unique to a tissue would not be identifiable during the hybridization procedure due to a low signal to noise ratio if both sense and antisense copies were present.

In one directional cloning strategy, a DNA sequence encoding a specific restriction endonuclease recognition motif (usually 6–10 bases) is provided at the 5' end of the oligo(dT) primer. See Palazzolo and Meyerowitz, (Gene 52, 197, 1987). This relatively short recognition sequence does not affect the annealing of the 12–20 base oligo(dT) primer to the mRNA, so the cDNA second strand synthesized from the first strand template includes the new recognition motif added to the original 3' end of the coding sequence. After second strand cDNA synthesis, a blunt ended adapter oligonucleotide molecule containing a second restriction motif (or a partially double stranded adapter containing a protruding end compatible with a second restriction site) is ligated to both ends of the cDNA. The site encoded by the linker is now on both ends of the cDNA molecule, but only the 3' end of the cDNA has the site introduced by the modified primer. Following the linker ligation step, the product is digested with both restriction enzymes (or, if a partially double stranded linker adapter was ligated onto the cDNA, with only the enzyme that recognizes the modified primer sequence). A population of cDNA molecules results which all have one defined sequence on their 5' end and a different defined sequence on their 3' end.

A related directional cloning strategy developed by Meissner et al. (PNAS USA 84, 4171, 1987), requires no sequence-specific modified primer. Meissner et al. describe a double stranded palindromic BamHI/HindIII directional linker having the sequence d(GCTTGGATCCMGC) (SEQ: ID NO:1), which is ligated to a population of oligo(dT)-primed cDNAs, followed by digestion of the ligation products with BamHI and HindIII. This palindromic linker, when annealed to double stranded form, includes an internal BamHI site (GGATCC) flanked by 4 of the 6 bases that define a HindIII site (AAGCTT). The missing bases needed to complete a HindIII site are d(AA) on the 5' end or d(TT) on the 3' end. Regardless of the sequence to which this directional linker ligates, the internal BamHI site will be present. However, HindIII can only cut the linker if it ligates next to an d(AA):d(TT) dinucleotide base pair. In an oligo (dT)-primed strategy, a HindIII site is always generated at the 3' end of the cDNA after ligation to this directional linker. For cDNAs having the sequence d(TT) at their 5' ends (statistically 1 in 16 molecules), linker addition will also yield a HindIII site at the 5' end. However, because the 5' ends of cDNA are heterogeneous due to the lack of processivity of reverse transcriptases, cDNA products from every gene segment will be represented in the library.

As described above, a major limitation on cDNA cloning technology is imposed by the available priming strategies. Oligo(dT)-primed libraries require poly(A) containing mRNA and generally are deficient in 5' sequences. Random primed cDNA libraries have not found general embodiment, partly due to technical difficulties in their construction, and more recently due to the increasing use of incompatible directional cloning strategies.

A "5' stretch" technique used in some laboratories employs both an oligo(dT) primer and random hexamers for priming two separate first strand cDNA reactions. The discontinuous cDNA fragments are spliced together during second strand synthesis when the two reactions are combined. After second strand synthesis, linkers of the type described above are added, to facilitate directional cloning. The shortcoming of this strategy is that any spliced cDNA molecule that fails to incorporate oligo(dT) at its 3' end is lost from the library because it cannot regenerate the 3' enzyme recognition sequence that must be present to generate a proper end for ligation. This strategy also does not address the inherent problems attributable to the secondary structure of RNA.

Still other techniques involve the use a set of random hexameric primers engineered to also include a common restriction site of six or more bases at one end of each primer. These primers have not been successfully used to prime first strand synthesis. The failure has been attributed to the formation of unstable RNA-primer hybrids. Because the length of the engineered restriction site equals or exceeds the length of the random hexamers, proper hybridization of the random portion of the primers may be energetically unfavorable. Moreover, the presence of six defined bases as part of every primer might bias hybridization toward corresponding complementary portions of the RNA templates.

In spite of the success of cDNA libraries as a resource for studying differential gene expression, several technical difficulties have limited their wider application or have necessitated a large amount of effort to obtain complete gene sequences. One such difficulty concerns the under-representation of the 5' ends of gene sequences obtained from cDNA libraries.

First strand synthesis uses an RNA-dependent DNA polymerase, and no DNA polymerase can start cDNA synthesis de novo. DNA polymerases require a short primer as a starting material upon which to add bases to the 3' end of a nascent cDNA first strand. The simplest primer is an oligo(dT) primer that can anneal specifically to the 3' poly(A) tail found in most mRNA molecules. All cDNAs synthesized with an oligo(dT) primer thus start at the 3' end of the mRNA and share a common 3' sequence (i.e. the $d(A_n:T_n)$ tail).

The major pitfall of oligo(d-T)-primed synthesis is that RNA-dependent DNA polymerases tend to become disengaged from the mRNA template before traversing its entire length. It is thought that this is primarily due to random failure in the elongation process and to specific areas of RNA secondary structure at which the enzyme may pause or stop altogether.

Accordingly, in oligo(dT)-primed libraries, the 3' ends of mRNAs are therefore statistically more likely to be copied than the sequences closer to the 5' end because reverse transcription always commences from the point at which the primer anneals. The resulting cDNA population is therefore biased toward the 3' ends of RNA strands. As might be expected, the effect is particularly noticeable with long mRNAs and results in few or no complete cDNA clones for certain genes in the library. Good quality oligo(dT)-primed cDNA libraries contain some inserts from 4 to 8 kb, but even inserts of this length may not cover the 5' end of a desired gene.

In addition, some mRNAs have a poly(A) tail that is too short to anneal to the oligo(dT) primer, or they have no poly(A) tail at all. See Greenberg, (Biochemistry 15, 3516–3522, 1976); Adesnik and Darnell, (J. Mol. Biol. 67, 397–406, 1982); Houdebine, (FEBS Lett. 66,110–118, 1976).

Estimates of the percent of non-polyadenylated mRNA in different species ranges from 30% Milcarek et al., (Cell 3, 1–10, 1974) to 80% Miller, (Dev. Biol. 64, 118–129, 1978) of mRNA. In a comparison of poly(A) containing mRNA and poly(A) devoid mRNA isolated from mouse brain, Van Ness et al. (Cell 18, 1341–1349, 1979) found that a substantial proportion of non-polyadenylated mRNA contains unique protein-encoding sequences. Therefore, many potentially important genes might be absent in oligo(dT)-primed cDNA libraries.

One preferred method for obtaining randomly primed cDNA is disclosed in U.S. Pat. No. 5,629,179 incorporated herein by reference. U.S. Pat. No. 5,629,179 provide a method for forming cDNA libraries by directional cloning of cDNA molecules formed by random priming. The method differs from other random priming and directional cDNA cloning methods by using a set of oligonucleotides in the form of primers having the sequence of 5'-XXNNNNNN-3' and annealing the primers to a RNA template.

The members of the set of primers are constant in one regard and variable in a second regard. The primers in the set vary in the 3'-most six nucleotides, depicted as NNNNNN, This representation is intended to indicate that A, G, C, or T can appear at any position. Thus, the 3'-most six nucleotides of the primers in the set represent all 4096 ($4^6$) possible hexamers.

All primers in the set contain the same two 5'-most nucleotides, depicted as XX. XX can be any dinucleotide that, when ligated to the 3' terminus of another polynucleotide molecule, forms an endonuclease recognition sequence. The use of a dinucleotide is sterically and energetically acceptable for facilitating primer binding, yet short enough to not bias priming toward any particular sequence on the mRNA templates.

After binding the set of primers to the RNA strand, first and second strand cDNA syntheses are carried out according to any known method. The RNA used as template can be cellular RNA obtained from any biological sample including any organism, such as an animal, including a human being. The RNA can be isolated using known method. One preferred method is that of Chomczynski and Sacchi, (Anal. Biochem, 162, 156–159, 1987). The RNA may, but need not be, poly(A)-enriched. If poly(A) containing RNA is desired, it may be obtained using any method that yields poly(A)-selected RNA.

One preferred method for purifying poly(A)-selected RNA is to pass the total RNA over an oligo(dT)-cellulose matrix, washing unbound RNA from the matrix, and then releasing the poly(A) containing RNA from the oligo(dT)-cellulose under low ionic strength with low salt. More recently developed methods for direct isolation of poly(A) containing RNA from tissues and cells utilizing oligo(dT)-coupled magnetic particles may also be employed.

During copying of the first strand to form the complementary second strand the primer-derived 5'-terminal dinucleotide on the first strand is also copied. Thus, the result of cDNA first and second strand synthesis is a population of fully double-stranded cDNA molecules, each having the same defined dinucleotide at the end corresponding to the 3' (carboxyl-terminal) side of a coding region thus facilitating discrimination between the two ends of the cDNA. In combination with the present invention this enables the isolation of an ssDNA tag from any of the two strands at will.

Another preferred method for obtaining cDNA from the 5' region of RNA is described in Technotes Newsletter 7(3), 1–2, 2000 (published by Ambion) and exploits rapid amplification of cDNA ends (RACE). Common shortcomings of cDNA library synthesis have been discussed earlier. PCR can facilitate isolation of 5'-ends of mRNA by several similar methods collectively termed Rapid Amplification of cDNA Ends, or RACE. RACE involves performing a random-primed reverse transcription (RT) reaction, adding an adapter to the 3'-end of the synthesized cDNA (corresponding to the 5'-end of the gene sequence) by ligation or PCR, and amplifying by PCR with a gene specific primer and a primer that recognizes the adapter sequence.

While RACE can produce results in a relatively short time, the procedure frequently yields sequences exclusively from truncated RT products. This is so partly because it is not a trivial task to prevent premature termination of cDNA synthesis and because PCR will selectively amplify the shortest targets in a mixed population. In order to add selectivity to RACE, several variations to the basic procedure have been developed. The most promising is a method of positive selection for amplification products that contain the true 5'-end of the mRNA. One preferred second-generation RACE-technique is RNA-ligase-mediated RACE, or RLM-RACE (Nucl. Acid Res. 21, 4954–4960, 1993). In RLM-RACE, an RNA sample is first treated with phosphatase, for example Calf Intestine Phosphatase (CIP), to remove the 5'-phosphate from all RNA species except those that have a cap structure.

A cap structure is present on all Pol II transcripts i.e. full-length mRNAs. Molecules that are dephosphorylated by CIP include rRNA, tRNA, DNA, and fragmented mRNA that does not contain the 5'-end. Pyrophosphatase, for example Tobacco Acid Pyrophosphatase (TAP), is then used to remove the cap structure from mRNA. Next a synthetic adapter is ligated to the CIP/TAP treated RNA. The RNA oligonucleotide ligates only to the decapped mRNA—no ligation occurs to dephosphorylated molecules.

The chimeric RNA is then reverse transcribed using random decamers as primers. If the RT extends to the natural 5'-end of an RNA, it will incorporate the adapter sequence into the first-strand cDNA. Next nested PCR using gene specific primers together with adapter primers can be carried out. If using RLM-RACE for preparing cDNA for an expression profiling experiment, second-strand cDNA synthesis can be carried out with an adapter primer conjugated to a solid support or a magnetic bead.

Once a cDNA has been generated it may be subjected to the below described processing steps in order to obtain at least one single stranded polynucleotide tag. In principle, the cDNA can either be subjected to cleavage by at least one cleavage agent, preferably a site-specific nicking endonuclease capable of recognizing a predetermined motif of a double stranded polynucleotide and cleaving only one of said strands, or cloned in a suitable vector prior to such cleavage and generation of a single stranded polynucleotide.

Cloning of cDNA in Suitable Vectors

Various approaches have been used to prepare the cDNA ends for vector insertion. See Kimmel, A. R. and Berger, S. L. (Meth. Enzymol. 152,. 307, 1987). Most have used methods known as "linker" or "adapter" methods. All methods using linkers require an additional step to protect the cDNA from being cleaved at adventitious restriction sites during digestion to create the cohesive ends. See Wu, R., Wu, T. and Ray, A. (Meth. Enzymol. 152, 343, 1987). This protection is accomplished either by treating the cDNA with on site-specific methylases or by substituting a methylated dCTP analog for unmodified dCTP in the synthesis reactions.

The double-stranded cDNA molecules generated as described herein above and in U.S. Pat. No. 5,629,179 may subsequently be joined by ligation to a double-stranded, palindromic linker. Internal to the linker is a palindromic second endonuclease recognition sequence different from the first recognition sequence. At the 3' terminus of each strand of the palindromic linker are at least two nucleotides that form the 5' portion of the first endonuclease recognition sequence, the 3' portion of which is encoded by the dinucleotide that is the constant portion shared by each of the primers in the set. Upon ligation of the mixed population of cDNA molecules to copies of the palindromic linker, the second recognition sequence is formed at the junction in each cDNA molecule.

To obtain a cDNA fragment for directional cloning, the ligated products are cleaved using the first and second endonucleases, thereby generating a first cleavage in the linker 5' to the cDNA and a second cleavage at the 3' end of the cDNA in the site formed at the cDNA-linker junction. As normally practiced, the cDNA can be methylated after synthesis using site-specific enzymes (e.g. EcoRI methylase, AluI methylase, etc.) to protect against digestion at adventitious sites. Alternatively, 5-methyl dCTP can be incorporated during cDNA synthesis to accomplish protection. The directional cDNA fragment thus generated can be ligated directionally into a vector and subsequently prepared as a cDNA library.

It will be understood that "adapter oligonucleotides" according to the present invention may be used either i) for preparing a cDNA for cloning in a suitable vector, or ii) for introducing a predetermined restriction endonuclease recognition motif in conjunction to the cDNA for other purposes than direct cloning into a vector. Examples of such other purposes include the provision of polynucleotide tags obtainable by the methods of the present invention.

Characterizing Single Stranded Polynucleotide Tags From dsDNA

The invention in preferred embodiments relates to methods for obtaining single stranded polynucleotide tags including ssDNA tags from either end of a cDNA, from genomic DNA, or from extra-genomic DNA. The tag may have any desired length ranging from only about 4 or 18 nucleotides to much longer tags containing up to more than several hundred nucleotides.

Accordingly, in preferred embodiments of the present invention there are provided methods for generating short or long tags from either the 5' end or the 3' end of either at least one cDNA or at least one fragment of genomic DNA or at least one fragment of extra-genomic DNA.

In particular, there is provided in one preferred embodiment of the invention a method for obtaining at least one single stranded polynucleotide tag from a biological sample, wherein the method comprises the steps of i) providing at least one double stranded polynucleotide, wherein the polynucleotide is selected from the group of polynucleotides consisting of polynucleotides comprising complementary DNA (cDNA), polynucleotides comprising genomic DNA, and polynucleotides comprising extra-genomic DNA, ii) contacting and cleaving at least one of the complementary strands of the double stranded polynucleotide provided in step i) with at least one cleavage agent capable of recognizing a double stranded polynucleotide comprising complementary polynucleotide strands and cleaving only one of the strands of the polynucleotide provided in step i), and the further step of iii) contacting and cleaving—prior to obtaining at least one single stranded polynucleotide tag—either
   a) the double stranded polynucleotide provided in step i), or
   b) the double stranded polynucleotide of step ii) contacted and cleaved in one strand by the at least one cleavage agent, preferably a site-specific nicking endonuclease, capable of recognizing a double stranded polynucleotide comprising complementary polynucleotide strands and cleaving only one of the strands of the polynucleotide
   with at least one cleavage agent, preferably a site-specific restriction endonuclease, capable of recognizing a double stranded polynucleotide comprising complementary polynucleotide strands and cleaving both of the strands of the polynucleotide,
wherein the cleavage with the cleavage agent capable of cleaving only one strand, and the cleavage with the cleavage agent capable of cleaving both strands, of the double stranded polynucleotide occurs simultaneously, or sequentially in any order, and iv) obtaining at least one single stranded polynucleotide tag.

The single stranded polynucleotide tag preferably comprises or essentially consists of deoxyribonucleic acid, and the biological sample is preferably obtained from an animal, including a human being; or a plant; or a fungus; or a single cellular organism, including bacteria, protozocans; or a virus.

The single stranded polynucleotide tag preferably comprises only a single polynucleotide strand and no complementary strand, or a part thereof, capable of forming with the single stranded polynucleotide tag a double stranded polynucleotide comprising complementary polynucleotides, including any double stranded polynucleotide wherein at least a part of the double stranded polynucleotide consists of single, complementary polynucleotides.

The single stranded polynucleotide tag preferably comprises less than 5000 nucleotides, such as 1000 nucleotides, for example less than 500 nucleotides, such as 100 nucleotides, for example less than 50 nucleotides, such as 40 nucleotides, for example less than 30 nucleotides, such as 25 nucleotides, for example less than 20 nucleotides, such as 19 nucleotides, for example less than 18 nucleotides, such as 17 nucleotides, for example less than 16 nucleotides, such as 15 nucleotides, for example less than 14 nucleotides, such as 13 nucleotides, for example less than 12 nucleotides, such as 11 nucleotides, for example 10 nucleotides, or less than 10 nucleotides, such as 9 nucleotides, for example less than 8 nucleotides, such as 7 nucleotides, for example less than 6 nucleotides, such as 5 nucleotides, for example 4 nucleotides. In one embodiment, tags of less than 20 nucleotides, including tags of 10 nucleotides, is preferred.

It is preferred that all of the nucleotides of the single stranded polynucleotide tag originate from a cDNA obtained from the biological sample, or from genomic DNA obtained from the biological sample, or from extra-genomic DNA obtained from the biological sample.

The cleavage agent capable of recognizing a double stranded polynucleotide comprising complementary polynucleotide strands and cleaving only one of the strands is preferably a site-specific nicking endonuclease, including a site-specific nicking endonuclease catalyzing a single strand cleavage either within the location of the recognition motif recognized by the endonuclease, or at a location beyond the most 5' nucleotide of the recognition motif, such as at least one nucleotide beyond the most 5' nucleotide of the recognition motif, or at a location beyond the most 3' nucleotide of the recognition motif, such as at least one nucleotide beyond the most 3' nucleotide of the recognition motif.

The distance between the location of the site for the single strand cleavage and the nearest nucleotide of the recognition motif is preferably less than about 500 nucleotides, such as about 400 nucleotides, for example less than about 300 nucleotides, such as about 200 nucleotides, for example about 150 nucleotides, such as less than about 100 nucleotides, for example less than about 80 nucleotides, such as about 60 nucleotides, for example less than about 50 nucleotides, such as about 40 nucleotides, for example less than about 30 nucleotides, such as about 25 nucleotides, for example less than 20 nucleotides, such as 19 nucleotides, for example less than 18 nucleotides, such as 17 nucleotides, for example less than 16 nucleotides, such as 15 nucleotides, for example less than 14 nucleotides, such as 13 nucleotides, for example less than 12 nucleotides, such as 11 nucleotides, for example less than 10 nucleotides, such as 9 nucleotides, for example less than 8 nucleotides, such as 7 nucleotides, for example less than 6 nucleotides, such as 5 nucleotides or less, for example 4 nucleotides, or less than 4 nucleotides, such as 3 nucleotides, for example less than 2 nucleotides, such as 1 nucleotide. In one embodiment a distance of 4 nucleotides is preferred.

The site-specific nicking endonuclease preferably recognizes a recognition motif comprising the complementary polynucleotide strands
5'-GAGTC-3'
3'-CTCAG-5'

In one embodiment the site-specific nicking endonuclease is isolated from a strain of *Bacillus stearothermophilus,* including the strain of *Bacillus stearothermophilus* 33M as described by New England Biolabs as a source of N.BstNB I as listed in Catalogue dated 2000-01 under no. R0607S (200 units) or no. R0607L (1000 units), or an isoschizomer thereof.

The cleavage agent capable of recognizing a double stranded polynucleotide comprising complementary polynucleotide strands and cleaving both of the strands of the polynucleotide is preferably a site-specific restriction endonuclease, preferably a site-specific restriction endonuclease selected from the group consisting of site-specific restriction endonucleases of type II recognizing and cleaving a double stranded polynucleotide within the location of a recognition motif producing either 3' or 5' overhangs or blunt ends, and site-specific restriction endonucleases of type IIs recognizing and cleaving a double stranded polynucleotide beyond the location of a recognition motif producing either 3' or 5' overhangs or blunt ends.

The method in one preferred embodiment comprises the further step of providing at least one adapter oligonucleotide comprising at least one recognition motif, or a part thereof, for at least one cleavage agent capable of recognizing a double stranded polynucleotide comprising complementary strands and cleaving a) only one complementary strand, or b) both of the complementary stands of the double stranded polynucleotide.

The adapter oligonucleotide comprises or essentially consists of either complementary strands comprising at least one recognition motif for at least one cleavage agent, wherein said motif comprises complementary polynucleotide strands, or a part of a recognition motif for at least one cleavage agent, wherein said part comprises a single oligonucleotide strand which, together with a complementary strand, forms a recognition motif for at least one cleavage agent.

The adapter oligonucleotide may comprise at least two recognition motifs, or a single stranded part thereof, wherein at least one of said motifs are capable of binding a site-specific nicking endonuclease capable of recognizing a double stranded polynucleotide comprising complementary strands and cleaving only one complementary strand thereof.

The adapter oligonucleotide may further comprise a recognition motif capable of binding a site-specific restriction endonuclease capable of recognizing a double stranded polynucleotide comprising complementary strands and cleaving both of the complementary stands of the double stranded polynucleotide. The recognition motif for the site-specific nicking endonuclease capable of recognizing a double stranded polynucleotide comprising complementary strands and cleaving only one complementary strand thereof may in one embodiment form part of the recognition motif for the site-specific restriction endonuclease capable of recognizing a double stranded polynucleotide comprising complementary strands and cleaving both of the complementary stands of the double stranded polynucleotide.

Preferred Recognition Motifs in Adapter Oligonucleotides

Described herein below are examples of cleavage agents capable of being exploited in connection with the present invention. One preferred site-specific nicking endonuclease is N.BstNB I recognising the illustrated dsDNA sequence and nicking one of the strands at the indicated position (˅).

When used in combination with the recognition motif for at least one additional cleavage agent as illustrated herein below, a number of sequences introduced into the chimeric dsDNA by the adapter oligonucleotide can be generated, as illustrated herein below, wherein each sequence introduced into the chimeric dsDNA by the adapter oligonucleotide comprises the recognition motif for a preferred site-specific nicking endonuclease, including the recognition motif for N.BstNB I, and the recognition motif for a preferred site-specific restriction endonuclease, including the site-specific restriction endonuclease mentioned herein below.

When subjected to both the site-specific nicking endonuclease, including N.BstNB I, and the illustrated site-specific restriction endonucleases listed herein below, an ssDNA tag is generated in each case as illustrated herein below for the respective combination of site-specific nicking endonuclease, including N.BstNB I, and site-specific restriction endonuclease.

N.BstNB I:
5'-GAGTCNNNNN-3' (SEQ ID NO:85)

3'-CTCAGNNNNN-5' (SEQ ID NO:86)

Alw I:
5'-GGATCNNNNNN-3' (SEQ ID NO:103)

3'-CCTAGNNNNNN-5' (SEQ ID NO:104)

Sequence introduced into the chimeric dsDNA by the adapter oligonucleotide (except for any N):
5'-GAGTCGGATCNNNNNN-3' (SEQ ID NO:2)

3'-CTCAGCCTAGNNNNNN-5' (SEQ ID NO:3)

ssDNA tag:
5'-CNNNN-3'

N.BstNB I:
5'-GAGTCNNNNN-3' (SEQ ID NO:85)

3'-CTCAGNNNNN-5' (SEQ ID NO:86)

Bbv I:
5'-GCAGCNNNNNNNNNNNN-3' (SEQ ID NO:105)

3'-CGTCGNNNNNNNNNNNN-5' (SEQ ID NO:106)

Sequence introduced into the chimeric dsDNA by the adapter oligonucleotide (except for any N):
5'-GAGTCGCAGCNNNNNNNNNNNN-3' (SEQ ID NO:4)

3'-CTCAGCGTCGNNNNNNNNNNNN-5' (SEQ ID NO:5)

ssDNA tag:
5'-CNNNNNNNN-3'

N.BstNB I:
5'-GAGTCNNNNN-3' (SEQ ID NO:85)

3'-CTCAGNNNNN-5' (SEQ ID NO:86)

Bci VI:
5'-GTATCCNNNNNNNN-3' (SEQ ID NO:107)

3'-CATAGGNNNNNNNN-5' (SEQ ID NO:108)

Sequence introduced into the chimeric dsDNA by the adapter oligonucleotide (except for any N):
5'-GAGTCGTATCCNNNNNNNN-3' (SEQ ID NO:6)

3'-CTCAGCATAGGNNNNNNNN-5' (SEQ ID NO:7)

ssDNA tag:
5'-CCNNNNNNN-3'

N.BstNB I:
5'-GAGTCNNNNN-3' (SEQ ID NO:85)

3'-CTCAGNNNNN-5' (SEQ ID NO:86)

Bmr I:
5'-ACTGGGNNNNNN-3' (SEQ ID NO:109)

3'-TGACCCNNNNNN-5' (SEQ ID NO:110)

Sequence introduced into the chimeric dsDNA by the adapter oligonucleotide (except for any N):
5'-GAGTCACTGGGNNNNNN-3' (SEQ ID NO:8)

3'-CTCAGTGACCCNNNNNN-5' (SEQ ID NO:9)

ssDNA tag:
5'-GGNNNNN-3'

N.BstNB I:
5'-GAGTCNNNNN-3' (SEQ ID NO:85)

3'-CTCAGNNNNN-5' (SEQ ID NO:86)

Bpm I:
5'-CTGGAGNNNNNNNNNNNNNNNN-3' (SEQ ID NO:111)

3'-GACCTCNNNNNNNNNNNNNNNN-5' (SEQ ID NO:112)

Sequence introduced into the chimeric dsDNA by the adapter oligonucleotide (except for any N) 1:
5'-GAGTCCTGGAGNNNNNNNNNNNNNNNN-3' (SEQ ID NO:10)

3'-CTCAGGACCTCNNNNNNNNNNNNNNNN-5' (SEQ ID NO:11)

ssDNA tag 1:
5'-AGNNNNNNNNNNNNNNNN-3'

Sequence introduced into the chimeric dsDNA by the adapter oligonucleotide (except for any N) 2:
5'-GAGTCTGGAGNNNNNNNNNNNNNNNN-3' (SEQ ID NO:12)

3'-CTCAGACCTCNNNNNNNNNNNNNNNN-5' (SEQ ID NO:13)

ssDNA tag 2:
5'-NNNNNNNNNNNNNNNN-3'

Sequence introduced into the chimeric dsDNA by the adapter oligonucleotide (except for any N) 3:
5'-CTGGAGTCNNNNNNNNNNNNNNNN-3' (SEQ ID NO:113)

3'-GACCTCAGNNNNNNNNNNNNNNNN-5' (SEQ ID NO:114)

```
ssDNA tag 3:
5'-NNNNNNNNNN-3'

N.BstNB I:
5'-GAGTCNNNNN-3'                            (SEQ ID NO:85)

3'-CTCAGNNNNN-5'                            (SEQ ID NO:86)

Bse RI:
5'-GAGGAGNNNNNNNNNNNN-3'                    (SEQ ID NO:115)

3'-CTCCTCNNNNNNNNNNNN-5'                    (SEQ ID NO:116)

Sequence introduced into the
chimeric dsDNA by the adapter
oligonucleotide (except for any N)
1:
5'-GAGTCGAGGAGNNNNNNNNNNN-3'                (SEQ ID NO:14)

3'-CTCAGCTCCTCNNNNNNNNNNN-5'                (SEQ ID NO:15)

ssDNA tag 1:
5'-AGNNNNNNNNNN-3'

Sequence introduced into the
chimeric dsDNA by the adapter
oligonucleotide (except for any N)
2:
5'-GAGGAGTCNNNNNNNNNN-3'                    (SEQ ID NO:117)

3'-CTCCTCAGNNNNNNNNNN-5'                    (SEQ ID NO:118)

ssDNA tag 2:
5'-NNNN-3'

N.BstNB I:
5'-GAGTCNNNNN-3'                            (SEQ ID NO:85)

3'-CTCAGNNNNN-5'                            (SEQ ID NO:86)

Bsg I:
5'-CTGCAGNNNNNNNNNNNNNNNN-3'                (SEQ ID NO:119)

3'-CACGTCNNNNNNNNNNNNNNNN-5'                (SEQ ID NO:120)

Sequence introduced into the
chimeric dsDNA by the adapter
oligonucleotide (except for any N)
1:
5'-GAGTCGTGCAGNNNNNNNNNNNNNNNN-3'           (SEQ ID NO:16)

3'-CTCAGCACGTCNNNNNNNNNNNNNNNN-5'           (SEQ ID NO:17)

ssDNA tag 1:
5'-AGNNNNNNNNNNNNNNNN-3'

Sequence introduced into the
chimeric dsDNA by the adapter
oligonucleotide (except for any N)
2:
5'-GTGCAGGAGTCNNNNNNNNNNNN-3'               (SEQ ID NO:18)

3'-CACGTCCTCAGNNNNNNNNNNNN-5'               (SEQ ID NO:19)

ssDNA tag 2:
5'-NNNNNNN-3'

Sequence introduced into the
chimeric dsDNA by the adapter
oligonucleotide (except for any N)
3:
5'-GTGCAGAGTCNNNNNNNNNNNNN-3'               (SEQ ID NO:20)

3'-CACGTCTCAGNNNNNNNNNNNNN-5'               (SEQ ID NO:21)

ssDNA tag 3:
5'-NNNNNNNN-3'

N.BstNB I:
5'-GAGTCNNNNN-3'                            (SEQ ID NO:85)

3'-CTCAGNNNNN-5'                            (SEQ ID NO:86)

Bsm FI:
5'-GGGACNNNNNNNNNNNNNNNN-3'                 (SEQ ID NO:121)

3'-CCCTGNNNNNNNNNNNNNNNN-5'                 (SEQ ID NO:122)

Sequence introduced into the
chimeric dsDNA by the adapter
oligonucleotide (except for any N):
5'-GAGTCGGGACNNNNNNNNNNNNNNNN-3'            (SEQ ID NO:22)

3'-CTCAGCCCTGNNNNNNNNNNNNNNNN-5'            (SEQ ID NO:23)

ssDNA tag:
5'-CNNNNNNNNNN-3'

N.BstNB I:
5'-GAGTCNNNNN-3'                            (SEQ ID NO:85)

3'-CTCAGNNNNN-5'                            (SEQ ID NO:86)

Bsp MI:
5'-ACCTGCNNNNNNNNNN-3'                      (SEQ ID NO:123)

3'-TGGACGNNNNNNNNNN-5'                      (SEQ ID NO:124)

Sequence introduced into the
chimeric dsDNA by the adapter
oligonucleotide (except for any N):
5'-GAGTCACCTGCNNNNNNNNNN-3'                 (SEQ ID NO:24)

3'-CTCAGTGGACGNNNNNNNNNN-5'                 (SEQ ID NO:25)

ssDNA tag:
5'-GCNNNN-3'

N.BstNB I:
5'-GAGTCNNNNN-3'                            (SEQ ID NO:85)

3'-CTCAGNNNNN-5'                            (SEQ ID NO:86)

Eci I:
5'-GGCGGANNNNNNNNNNNN-3'                    (SEQ ID NO:125)

3'-CCGCCTNNNNNNNNNNNN-5'                    (SEQ ID NO:126)

Sequence introduced into the
chimeric dsDNA by the adapter
oligonucleotide (except for any N):
5'-GAGTCGGCGGANNNNNNNNNNNN-3'               (SEQ ID NO:26)

3'-CTCAGCCGCCTNNNNNNNNNNNN-5'               (SEQ ID NO:27)

ssDNA tag:
5'-GANNNNNNNNNNNN-3'

N.BstNB I:
5'-GAGTCNNNNN-3'                            (SEQ ID NO:85)

3'-CTCAGNNNNN-5'                            (SEQ ID NO:86)

Fau I:
5'-CCCGCNNNNNNN-3'                          (SEQ ID NO:127)

3'-GGGCGNNNNNNN-5'                          (SEQ ID NO:128)

Sequence introduced into the
chimeric dsDNA by the adapter
oligonucleotide (except for any N)
1:
5'-GAGTCCCCGCNNNNNNN-3'                     (SEQ ID NO:28)

3'-CTCAGGGGCGNNNNNNN-5'                     (SEQ ID NO:29)
```

-continued ssDNA tag 1:
5'-CNNNN-3'

Sequence introduced into the
chimeric dsDNA by the adapter
oligonucleotide (except for any N)
2:
5'-GAGTCCCGCNNNNNNNN-3'                     (SEQ ID NO:129)

3'-CTCAGGGCGNNNNNNNN-5'                     (SEQ ID NO:130)

ssDNA tag 2:
5'-NNNNN-3'

N.BstNB I:
5'-GAGTCNNNNN-3'                            (SEQ ID NO:85)

3'-CTCAGNNNNN-5'                            (SEQ ID NO:86)

Fok I:
5'-GGATGNNNNNNNNNNNNNN-3'                   (SEQ ID NO:131)

3'-CCTACNNNNNNNNNNNNNN-5'                   (SEQ ID NO:132)

Sequence introduced into the
chimeric dsDNA by the adapter
oligonucleotide (except for any N):
5'-GAGTCGGATGNNNNNNNNNNNNNN-3'              (SEQ ID NO:30)

3'-CTCAGCCTACNNNNNNNNNNNNNN-5'              (SEQ ID NO:31)

ssDNA tag:
5'-GNNNNNNNNN-3'

N.BstNB I:
5'-GAGTCNNNNN-3'                            (SEQ ID NO:85)

3'-CTCAGNNNNN-5'                            (SEQ ID NO:86)

Hga I:
5'-GACGCNNNNNNNNNNN-3'                      (SEQ ID NO:133)

3'-CTGCGNNNNNNNNNNN-5'                      (SEQ ID NO:134)

Sequence introduced into the
chimeric dsDNA by the adapter
oligonucleotide (except for any N):
5'-GAGTCGACGCNNNNNNNNNNN-3'                 (SEQ ID NO:32)

3'-CTCAGCTGCGNNNNNNNNNNN-5'                 (SEQ ID NO:33)

ssDNA tag:
5'-CNNNNN-3'

N.BstNB I:
5'-GAGTCNNNNN-3'                            (SEQ ID NO:85)

3'-CTCAGNNNNN-5'                            (SEQ ID NO:86)

Hph I:
5'-GGTGANNNNNNNNN-3'                        (SEQ ID NO:135)

3'-CCACTNNNNNNNNN-5'                        (SEQ ID NO:136)

Sequence introduced into the
chimeric dsDNA by the adapter
oligonucleotide (except for any N):
5'-GAGTCGGTGANNNNNNNNN-3'                   (SEQ ID NO:34)

3'-CTCAGCCACTNNNNNNNNN-5'                   (SEQ ID NO:35)

ssDNA tag:
5'-ANNNNNNNN-3'

N.BstNB I:
5'-GAGTCNNNNN-3'                            (SEQ ID NO:85)

3'-CTCAGNNNNN-5'                            (SEQ ID NO:86)

Mbo II:
5'-GAAGANNNNNNNNN-3'                        (SEQ ID NO:137)

3'-CTTCTNNNNNNNNN-5'                        (SEQ ID NO:138)

Sequence introduced into the
chimeric dsDNA by the adapter
oligonucleotide (except for any N):
5'-GAGTCGAAGANNNNNNNNN-3'                   (SEQ ID NO:36)

3'-CTCAGCTTCTNNNNNNNNN-5'                   (SEQ ID NO:37)

ssDNA tag:
5'-ANNNNNNNN-3'

N.BstNB I:
5'-GAGTCNNNNN-3'                            (SEQ ID NO:85)

3'-CTCAGNNNNN-5'                            (SEQ ID NO:86)

Mly I:
5'-GAGTCNNNNN-3'                            (SEQ ID NO:139)

3'-CTCAGNNNNN-5'                            (SEQ ID NO:140)

Sequence introduced into the
chimeric dsDNA by the adapter
oligonucleotide (except for any N):
5'-GAGTCGAGTCNNNNN-3'                       (SEQ ID NO:38)

3'-CTCAGCTCAGNNNNN-5'                       (SEQ ID NO:39)

ssDNA tag:
5'-CNNNNN-3'

N.BstNB I:
5'-GAGTCNNNNN-3'                            (SEQ ID NO:85)

3'-CTCAGNNNNN-5'                            (SEQ ID NO:86)

Mnl I:
5'-CCTCNNNNNNNN-3'                          (SEQ ID NO:141)

3'-GGAGNNNNNNNN-5'                          (SEQ ID NO:142)

Sequence introduced into the
chimeric dsDNA by the adapter
oligonucleotide (except for any N)
1:
5'-GAGTCCCTCNNNNNNNN-3'                     (SEQ ID NO:143)

3'-CTCAGGGAGNNNNNNNN-5'                     (SEQ ID NO:144)

ssDNA tag 1:
5'-NNNNNNN-3'

Sequence introduced into the
chimeric dsDNA by the adapter
oligonucleotide (except for any N)
2:
5'-GAGTCCTCNNNNNNNN-3'                      (SEQ ID NO:145)

3'-CTCAGGAGNNNNNNNN-5'                      (SEQ ID NO:146)

ssDNA tag 2:
5'-NNNNNNN-3'

N.BstNB I:
5'-GAGTCNNNNN-3'                            (SEQ ID NO:85)

3'-CTCAGNNNNN-5'                            (SEQ ID NO:86)

Ple I:
5'-GAGTCNNNNN-3'                            (SEQ ID NO:139)

3'-CTCAGNNNNN-5'                            (SEQ ID NO:140)

Sequence introduced into the
chimeric dsDNA by the adapter

```
-continued
oligonucleotide (except for any N):
5'-GAGTCGAGTCNNNNNN-3'          (SEQ ID NO:40)

3'-CTCAGCTCAGNNNNNN-5'          (SEQ ID NO:41)

ssDNA tag:
5'-CNNNN-3'

N.BstNB I:
5'-GAGTCNNNNN-3'                (SEQ ID NO:85)

3'-CTCAGNNNNN-5'                (SEQ ID NO:86)

Sfa NI:
5'-GCATCNNNNNNNNNNN-3'          (SEQ ID NO:147)

3'-CGTAGNNNNNNNNNNN-5'          (SEQ ID NO:148)

Sequence introduced into the
chimeric dsDNA by the adapter
oligonucleotide (except for any N):
5'-GAGTCGCATCNNNNNNNNNNN-3'     (SEQ ID NO:42)

3'-CTCAGCGTAGNNNNNNNNNNN-5'     (SEQ ID NO:43)

ssDNA tag:
5'-CNNNNN-3'
```

Methods Exploiting Adapter Oligonucleotides for Obtaining a Single Stranded Polynucleotide Tag Adapter oligonucleotides can be exploited in a variety of ways in methods for obtaining single stranded polynucleotide tags. The adapters can thus be used for obtaining tags from a predetermined source. A different class of molecules termed identifying linker oligonucleotides can subsequently be used for isolation and/or sequence determination and/or quantification of such tags.

Figure 64:
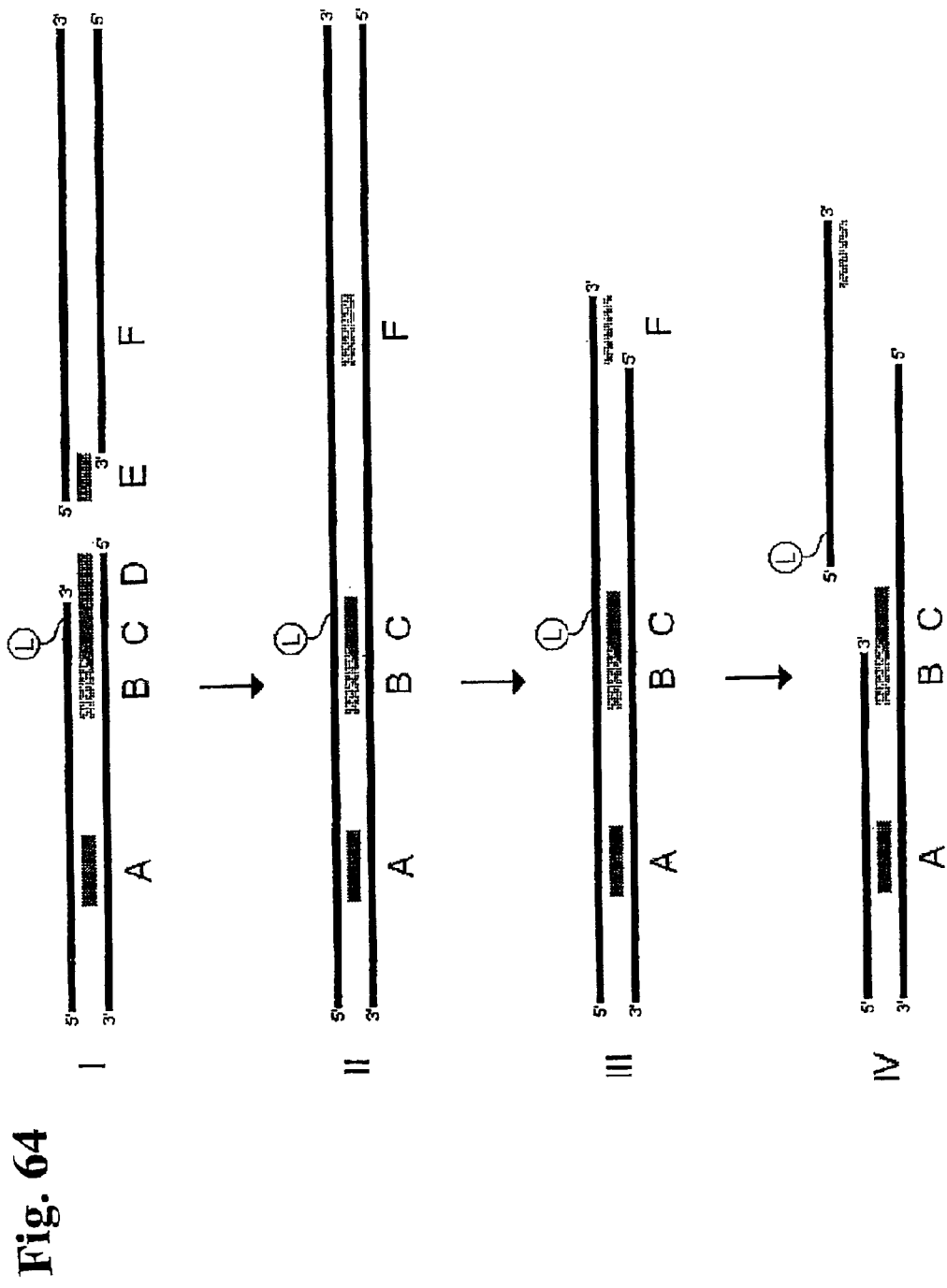
FIG. 64: Concomitant creation and labelling of ssDNA tag. The adapter comprises a nicking endonuclease recognition/binding site, that is situated proximal to a type IIs restriction endonuclease recognition/binding site as the cleavage site for said type IIs restriction endonuclease is distal to the cleavage site for said nicking endonuclease. This is illustrated in FIG. 64 with hatched boxes having different shadings. However, concomitant creation and labelling of the ssDNA tag is also possible when the adapter has a type IIs restriction endonuclease recognition/binding site that is situated proximal to a nicking endonuclease recognition/binding site as the cleavage site for said type IIs restriction endonuclease is distal to said type IIs restriction endonuclease recognition/binding site (not shown). Some of the sites are drawn as if they were overlapping each other. In fact for as long as the general order of the recognition/binding sites and the corresponding cleavage sites is maintained, any number of depicted recognition/binding sites may overlap with neighbouring sites. A) Recognition/binding site for nicking endonuclease. B) Recognition/binding site for type IIs restriction endonuclease. C) Cleavage site for nicking endonuclease. D) Overhang or blunt end of adapter corresponding to the specific cleavage overhang of the type II restriction endonuclease used for cleavage of the dsDNA that is used in the creation of the chimeric dsDNA (only the 5' overhang situation is shown). E) Recognition/binding and cleavage site for type II restriction endonuclease after cleavage of dsDNA. F) Cleavage site for type IIs restriction endonuclease. I) Ligation of adapter carrying a label attached to the non-overhanging 3' end that is to be ligated to the to dsDNA after cleavage of dsDNA with type II restriction endonuclease. The label is attached to one of the nucleotides that are transferred to the end of the ssDNA tag in this process. Therefore the nicking endonuclease and the type IIs restriction endonuclease and their sites in the adaptor are chosen so that at least one nucleotide from the adaptor ends up in one end of the ssDNA tag. The ends of the adaptor and the dsDNA could also have compatible 3' overhangs or blunt ends as long as the resulting chimeric dsDNA has a cleavage site for a nicking endonuclease immediately 3' of a type IIs restriction endonuclease recognition/binding site and a cleavage site for said type IIs restriction endonuclease 3' of the cleavage site for said nicking endonuclease. II) After ligation the chimeric molecule comprises a label inside the sequence. III) After digestion with a type IIs restriction endonuclease down stream fragments are discarded. IV) The remaining fragment is digested with a nicking endonuclease capable of nicking the DNA upstream from the label, so that a ssDNA tag carrying a label in one and can be isolated. 5' $PO_4$ and 3' OH groups are not shown.
Figure 65:
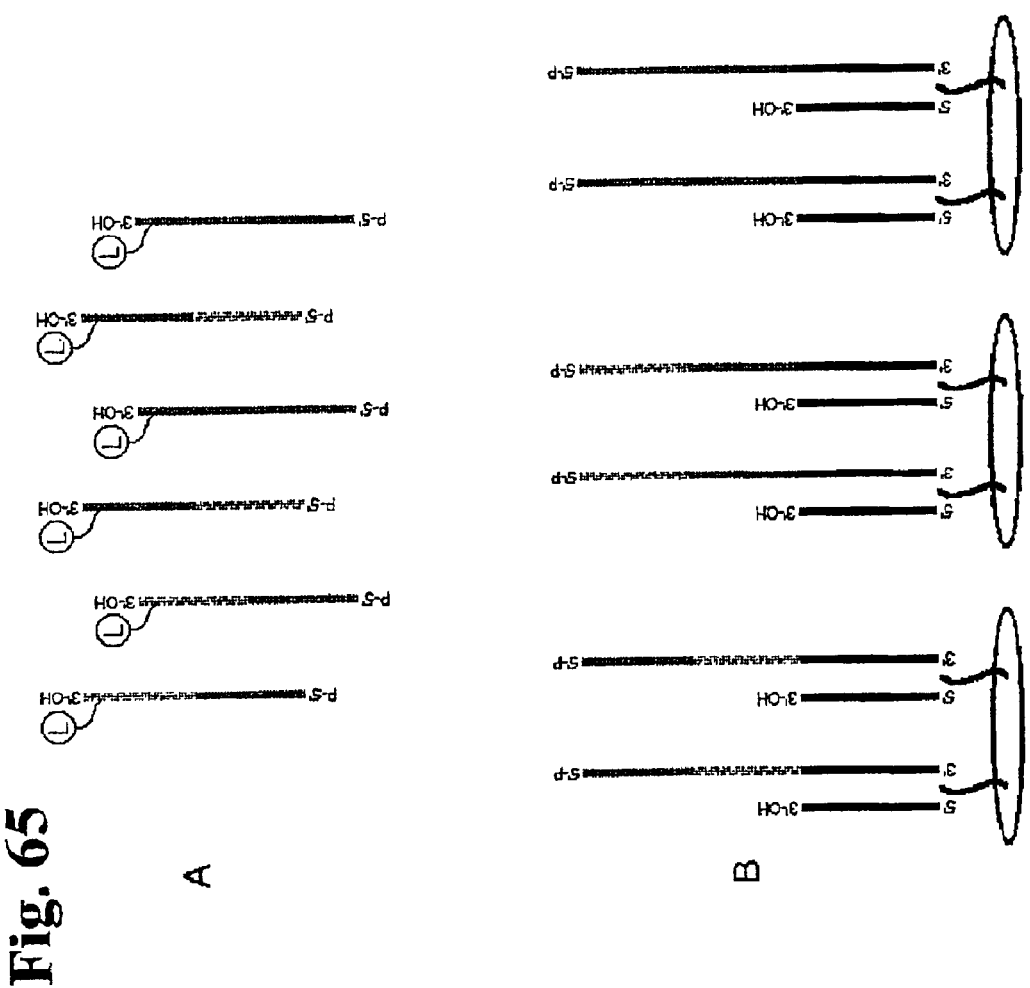
FIG. 65: In a pool of different ssDNA tags created in the process described in FIG. 64, each ssDNA tag will be carrying a label in the same end (here ssDNA tags carrying a label in the 3' end is shown). These tags are ideal for hybridizing to an array. Here an array comprising identifying linker oligonucleotides with 5' overhangs is shown, but 3' overhangs could also work fine.
Figure 66:
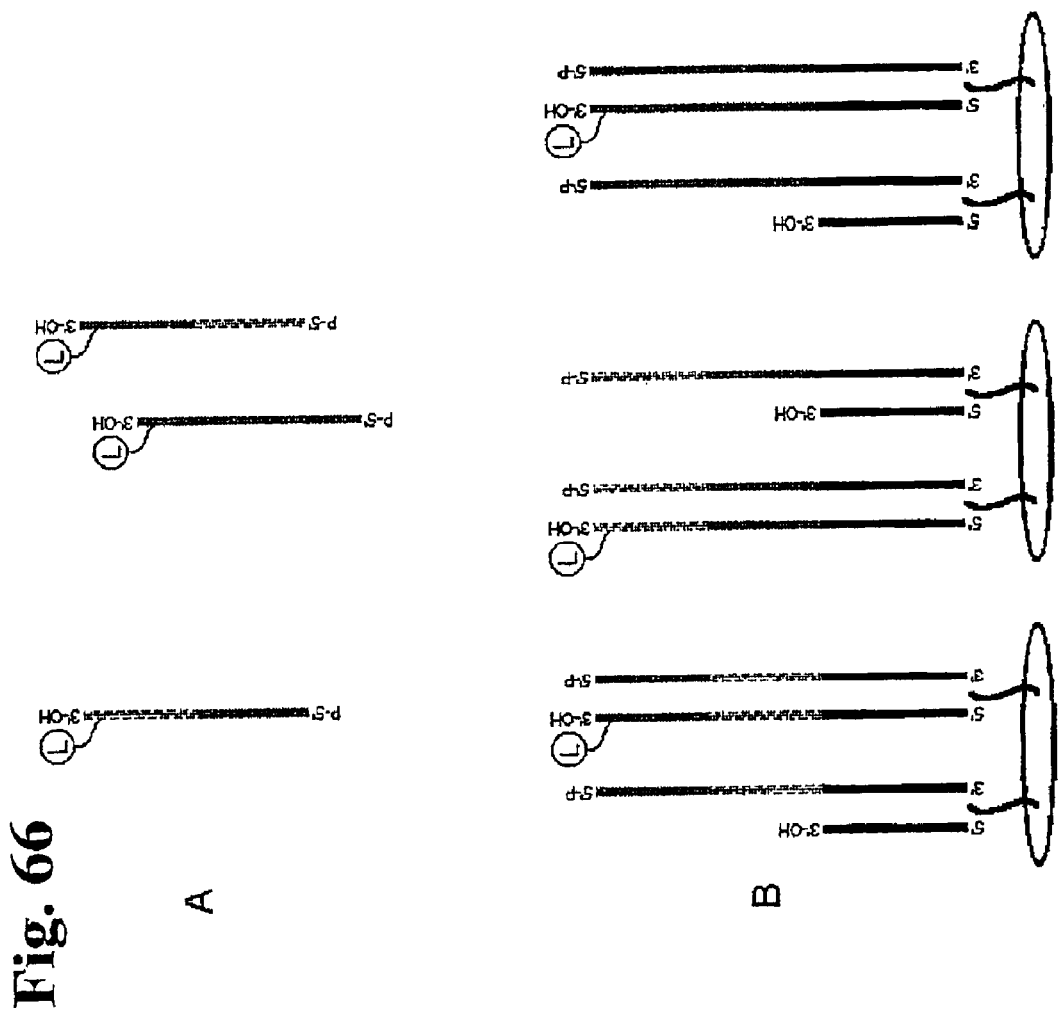
FIG. 66: After hybridizing the ssDNA tags to the overhangs of the identifying linker oligonucleotides in the array the ssDNA tags are optionally ligated to the identifying linker oligonucleotides. The non-hybridized ssDNA tags are washed away before scanning the array.
Figure 67:
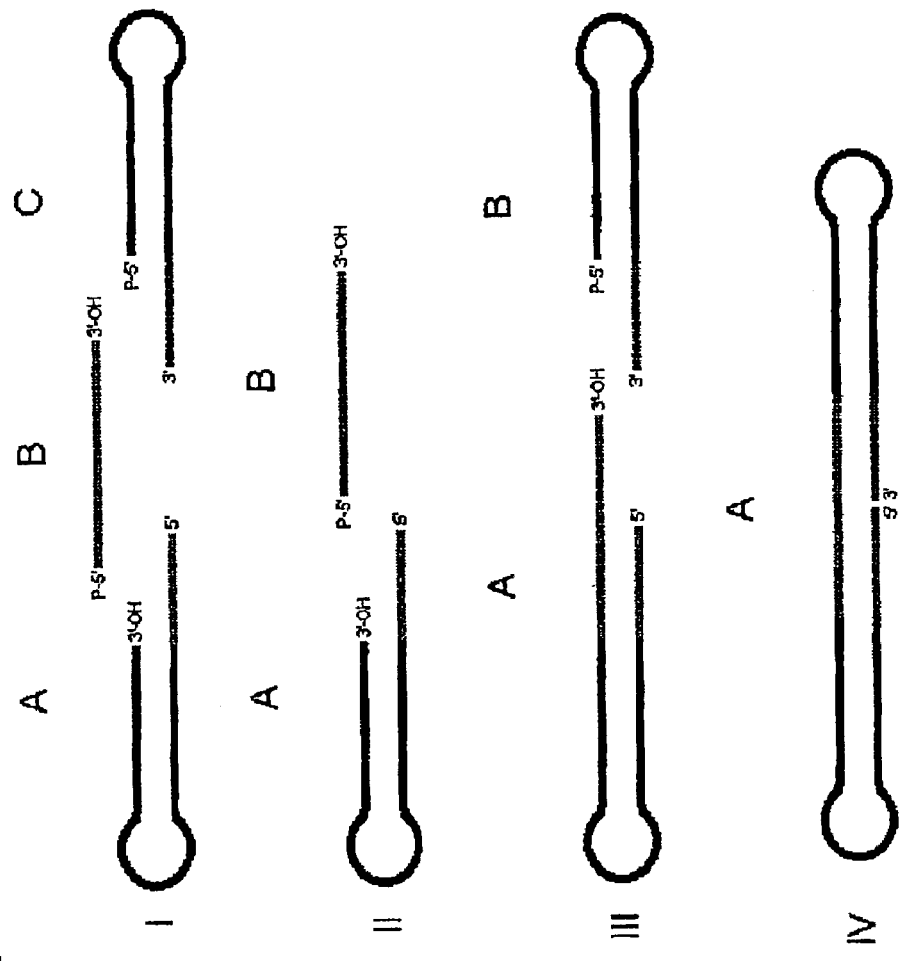
FIG. 67: When using two identifying linker oligonucleotides in solution that are blocked from being ligated together in their overhangs it is possible to create a looped ssDNA string comprising the two identifying linker oligonucleotides and an ssDNA tag. A prerequisite for getting hybridization—and after that, ligation—between the ssDNA tag and the identifying linker oligonucleotides is, of cause, that the sequences of the overhangs of the identifying linker oligonucleotides are complementary to the sequences in the ends of the ssDNA tag.
Figure 68:
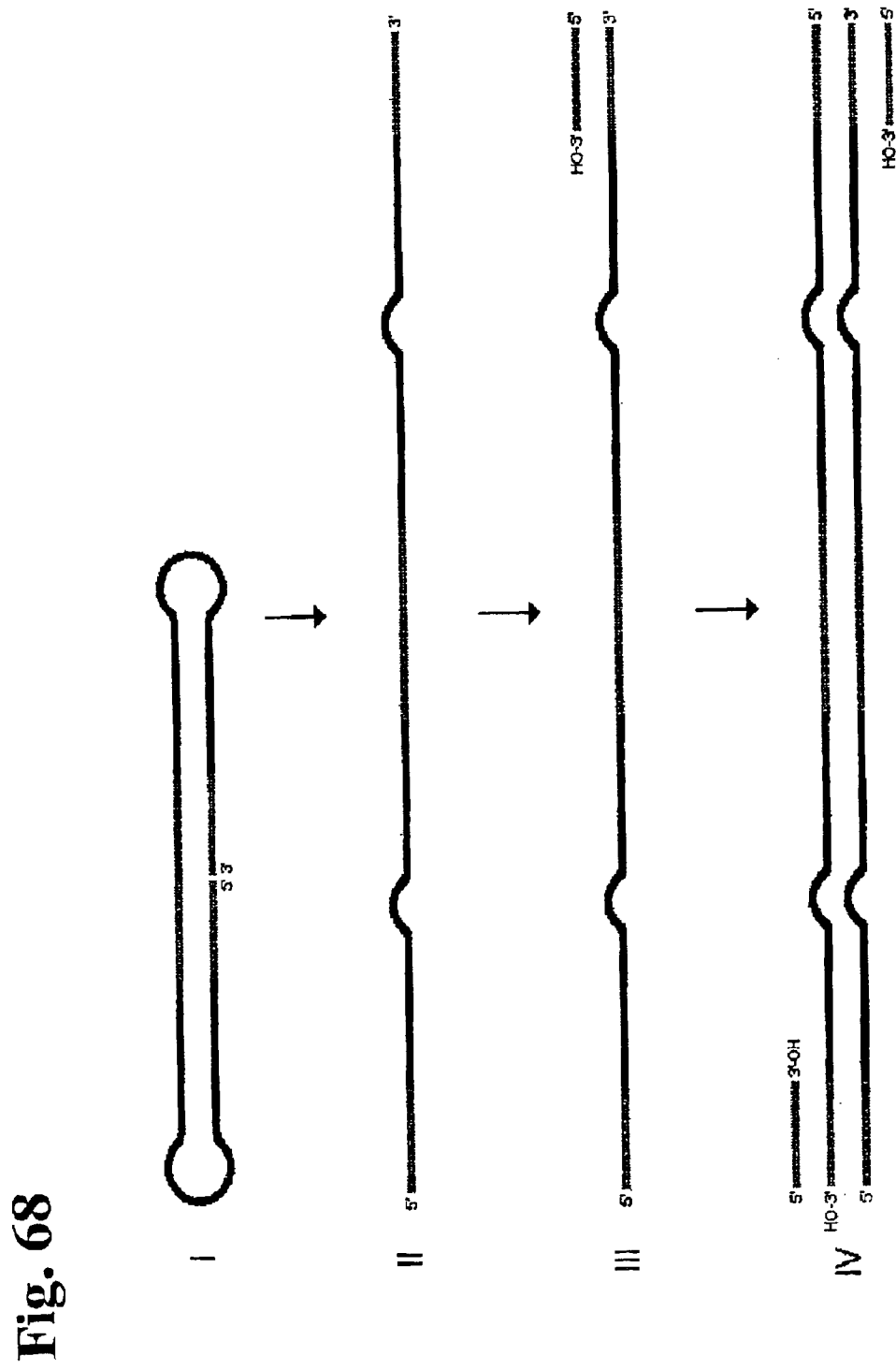
FIG. 68: After creating a looped ssDNA string comprising two identifying linker oligonucleotides and an ssDNA tag as described in FIG. 67 it is possible to detect said molecule in a traditional PCR reaction. I) After ligating together two identifying linker oligonucleotides and an ssDNA tag a looped ssDNA string is created. II) this looped ssDNA string can be melted into an ssDNA string with no loops. III) A second string can be synthesized using a primer complementary to the 3' end of the ssDNA string. IV) Form here on this is equivalent to a traditional PCR reaction. The curved part of the otherwise linear molecule depicts the part of the molecule that ends up in the two loops when the ssDNA molecule folds into its looped configuration.
Figure 69:
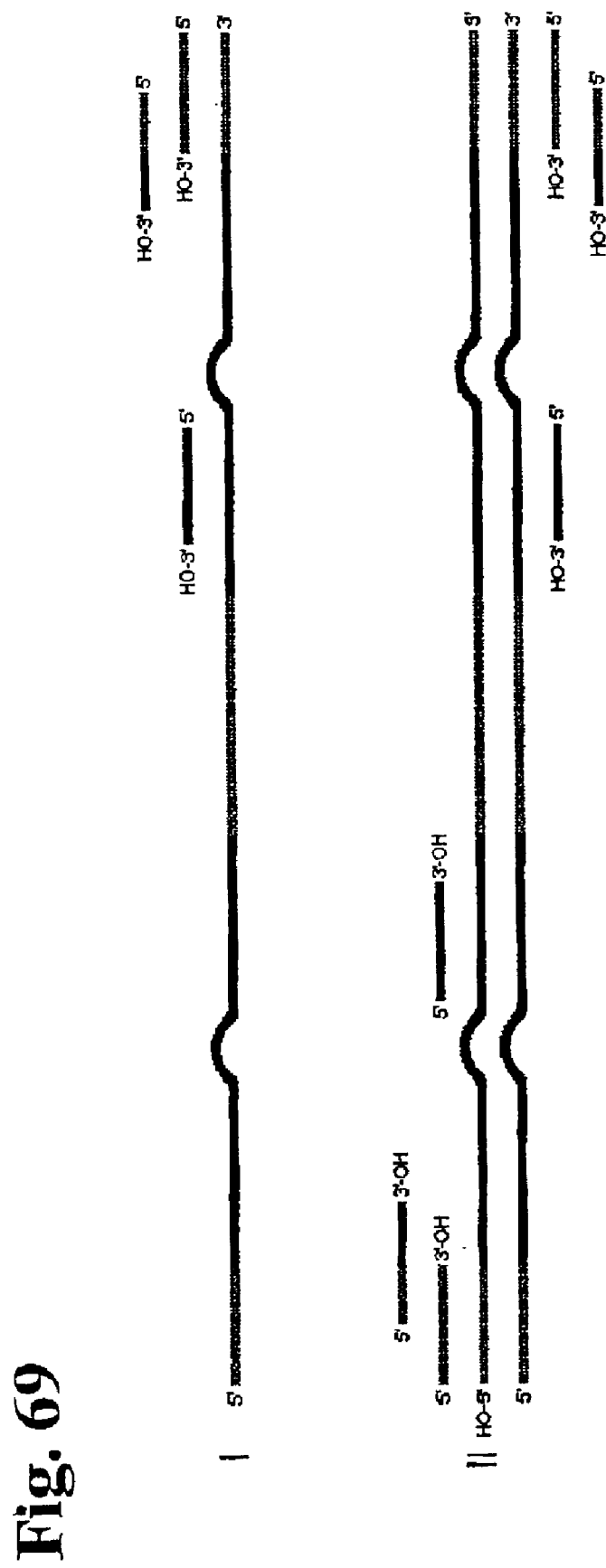
FIG. 69: Both the primers for the second string and for the traditional PCR step can be chosen to be complementary to different sites in the part of the molecule that was the identifying linker oligonucleotides before they were ligated to the ssDNA tag in the middle. I) A number of the different primers that is possible for the second-string synthesis. It is also possible to have primers that are overlapping with the ssDNA tag sequence in the middle of the molecule. II) A number of the different primers that is possible for the traditional PCR reaction. It is also possible to have primers that are overlapping with the ssDNA tag sequence in the middle of the molecule. The curved part of the otherwise linear molecule depicts the part of the molecule that ends up in the two loops when the ssDNA molecule folds into its looped configuration.

The tag sources can be e.g. single stranded RNA, or double stranded cDNA synthesized on the basis thereof. The tag source can also be genomic DNA or extra-genomic DNA, in which case the tag source is preferably also double stranded. It is generally preferred that the tag consists exclusively of a sequence of nucleotides originating from the tag source, although an exemption from this principle is illustrated in FIG. 64. One advantage of obtaining tags consisting exclusively of a sequence of nucleotides originating from the tag source itself is that artificial, non-tag source sequences, such as e.g. sequences originating from adapters, linkers, primers and the like, but not associated with the tag source, do not interfere with the sorting and/or isolation and/or sequence determination and/or quantification of the tag.

When being ligated to single stranded RNA the adapter is preferably in single stranded form. When being ligated to double stranded cDNA or double stranded genomic DNA, or double stranded extra-genomic DNA, the adapter is preferably in double stranded form. The, adapter can in principle be ligated to either the 5' end or the 3' end of the tag source.

Prior to ligation of adapter and double stranded tag source it may be preferred to obtain a fragment of such a tag source. This fragment can be obtained by digesting said double stranded tag source with a cleavage agent capable of providing a fragment thereof. The cleavage agent can be a site specific endonuclease, including a site specific restriction endonuclease of type II or IIs.

The ligation of adapter and tag source can be carried out by using any method known to the skilled person, including methods involving state-of-the-art molecular biology modifications in order to facilitate or optimize ligation of nucleotides.

Ligation of a double stranded adapter and double stranded tag source, or a fragment thereof, results in the formation of a double stranded chimer as defined herein. Likewise, ligation of a single stranded adapter and a single stranded tag source, or a part thereof, results in a single stranded chimer capable of being converted into a double stranded chimer by second strand synthesis using the single stranded chimer as a template.

Accordingly, there is provided in one preferred embodiment of the invention a method for obtaining at least one single stranded polynucleotide tag from a biological sample, said method comprising the steps of
i) providing at least one adapter oligonucleotide comprising
   a) at least one recognition motif for at least one site-specific nicking endonuclease, wherein said motif comprises a double stranded oligonucleotide comprising complementary strands, or
   b) a part of a recognition motif for at least one site-specific nicking endonuclease, wherein said part comprises a single oligonucleotide strand which, together with a complementary strand, forms a recognition motif for at least one site-specific nicking endonuclease,
ii) further providing
   c) at least one ribonucleic acid obtained from the biological sample, or
   d) at least one double stranded polynucleotide fragment comprising complementary polynucleotide strands, wherein said double stranded polynucleotide is obtained by a method comprising the step of using the at least one ribonucleic acid provided in step iic) as a template for the synthesis of a polynucleotide strand complementary to the at least one ribonucleic acid, or
   e) at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide with at least one site-specific restriction endonuclease capable of recognizing a double stranded polynucleotide comprising complementary strands and cleaving both of said strands,
iii) obtaining a double stranded chimeric polynucleotide comprising an adapter oligonucleotide part by
   iiia) linking together
      f) the at least one adapter oligonucleotide of step ia) comprising the at least one recognition motif for the at least one site-specific nicking endonuclease, wherein said motif comprises complementary strands,
   with either
      g) the at least one double stranded polynucleotide comprising complementary polynucleotide strands, wherein said double stranded polynucleotide is obtained by a method comprising the step of using the at least one ribonucleic acid provided in step iic) as a template for the synthesis of a polynucleotide strand complementary to the at least one ribonucleic acid, or
      h) the at least one double stranded genomic polynucleotide or the at least one double stranded extra-genomic polynucleotide of step iie),
   or
   iiib) obtaining a double stranded chimeric polynucleotide comprising an adapter oligonucleotide part by linking together i) at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, with j) the at least one ribonucleic acid obtained from the biological sample, and k) obtaining at least one double stranded chimeric polynucleotide comprising an adapter oligonucleotide part by using the chimeric polynucleotide obtained by linking together the adapter oligonucleotide of step iiibi) with the ribonucleic acid of step iiibj) as a template for the synthesis of a polynucleotide strand complementary to said chimeric polynucleotide, iv) contacting and cleaving the double stranded chimeric polynucleotide obtained in step iiia) or step iiib) with either iva) at least one site-specific nicking endonuclease capable of recognizing a double stranded polynucleotide comprising complementary polynucleotide strands and cleaving only one of said strands, or contacting and cleaving the double stranded chimeric polynucleotide obtained in step iiia) or step iiib) with ivb) a combination of a) at least one site-specific restriction endonuclease capable of recognizing a double stranded polynucleotide comprising complementary strands and cleaving both of said strands, and b) at least one site-specific nicking endonuclease capable of recognizing a double stranded polynucleotide comprising complementary polynucleotide strands and cleaving only one of said strands, wherein the contacting and cleaving of the double stranded chimeric polynucleotide performed with the combination of step ivb) occurs either simultaneously, or sequentially in any order, and v) obtaining at least one single stranded polynucleotide tag.

In the above methods, the fragment of step iid) is preferably obtained by using a site specific restriction endonuclease of type II and/or type IIs. The fragment of step iie) is preferably obtained by using a site specific restriction endonuclease of type II and/or type IIs. The site-specific restriction endonuclease of step ivb) is preferably of type IIs.

In further preferred embodiments there are provided a series of methods comprising some, but not all, of the above method steps. The methods of such embodiments comprise steps:

ia); iid); iiiaf); iiiag); iva); and v),
ia); iid); iiiaf); iiiag); ivb); and v),
ia); iie); iiiaf); iiiah); iva); and v),
ia); iie); iiiaf); iiiah); ivb); and v),
ib); iic); iiibi); iiibj); iiibk); iva); and v), and
ib); iic); iiibi); iiibj); iiibk); ivb); and v), respectively, as described in detail below.

Steps ia); iid); iiiaf); iiiag); iva); and v)

Method for obtaining at least one single stranded polynucleotide tag from a biological sample, said method comprising the steps of i) providing at least one adapter oligonucleotide comprising at least one recognition motif for at least one site-specific nicking endonuclease, wherein said motif comprises a double stranded oligonucleotide comprising complementary strands, ii) further providing at least one ribonucleic acid obtained from a biological sample and at least one double stranded polynucleotide fragment comprising complementary polynucleotide strands, wherein said double stranded polynucleotide is obtained by a method comprising the step of using the at least one ribonucleic acid as a template for the synthesis of a polynucleotide strand complementary to the at least one ribonucleic acid, iii) obtaining a double stranded chimeric polynucleotide comprising an adapter oligonucleotide part by linking together the at least one adapter oligonucleotide of step i) comprising the at least one recognition motif for the at least one site-specific nicking endonuclease, wherein said motif comprises complementary strands, with the at least one double stranded polynucleotide comprising complementary polynucleotide strands, wherein said double stranded polynucleotide is obtained by a method comprising the step of using the at least one ribonucleic acid provided in step ii) as a template for the synthesis of a polynucleotide strand complementary to the at least one ribonucleic acid, iv) contacting and cleaving the double stranded chimeric polynucleotide obtained in step iii) with at least one site-specific nicking endonuclease capable of recognizing a double stranded polynucleotide comprising complementary polynucleotide strands and cleaving only one of said strands, and v) obtaining at least one single stranded polynucleotide tag.

Steps ia); iid); iiiaf); iiia); ivb); and v)

Method for obtaining at least one single stranded polynucleotide tag from a biological sample, said method comprising the steps of i) providing at least one adapter oligonucleotide comprising at least one recognition motif for at least one site-specific nicking endonuclease, wherein said motif comprises a double stranded oligonucleotide comprising complementary strands, ii) further providing at least one ribonucleic acid obtained from a biological sample and at least one double stranded polynucleotide fragment comprising complementary polynucleotide strands, wherein said double stranded polynucleotide is obtained by a method comprising the step of using the at least one ribonucleic acid as a template for the synthesis of a polynucleotide strand complementary to the at least one ribonucleic acid, iii) obtaining a double stranded chimeric polynucleotide comprising an adapter oligonucleotide part by linking together the at least one adapter oligonucleotide of step i) comprising the at least one recognition motif for the at least one site-specific nicking endonuclease, wherein said motif comprises complementary strands, with the at least one double stranded polynucleotide comprising complementary polynucleotide strands, wherein said double stranded polynucleotide is obtained by a method comprising the step of using the at least one ribonucleic acid provided in step ii) as a template for the synthesis of a polynucleotide strand complementary to the at least one ribonucleic acid, iv) contacting and cleaving the double stranded chimeric polynucleotide obtained in step iii) with a combination of a) at least one site-specific restriction endonuclease capable of recognizing a double stranded polynucleotide comprising complementary strands and cleaving both of said strands, and b) at least one site-specific nicking endonuclease capable of recognizing a double stranded polynucleotide comprising complementary polynucleotide strands and cleaving only one of said strands, wherein the contacting and cleaving of the double stranded chimeric polynucleotide performed with said combination occurs either simultaneously, or sequentially in any order, and v) obtaining at least one single stranded polynucleotide tag.

Steps ia); iie); iiiaf); iiiah); iva); and v)

i) providing at least one adapter oligonucleotide comprising at least one recognition motif for at least one site-specific nicking endonuclease, wherein said motif comprises a double stranded oligonucleotide comprising complementary strands, ii) further providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide with at least one site-specific restriction endonuclease capable of recognizing a double stranded polynucleotide comprising complementary strands, and cleaving both of said strands, iii) obtaining a double stranded chimeric polynucleotide comprising an adapter oligonucleotide part by linking together the at least one adapter oligonucleotide of step i) comprising the at least one recognition motif for the at least one site-specific nicking endonuclease, wherein said motif comprises complementary strands, with the the at least one double stranded genomic polynucleotide or the at least one double stranded extra-genomic polynucleotide of step ii), iv) contacting and cleaving the double stranded chimeric polynucleotide obtained in step iii) with at least one site-specific nicking endonuclease capable of recognizing a double stranded polynucleotide comprising complementary polynucleotide strands and cleaving only one of said strands, and v) obtaining at least one single stranded polynucleotide tag.

Steps ia); iie); iiiaf); iiiah); ivb); and v)

i) providing at least one adapter oligonucleotide comprising at least one recognition motif for at least one site-specific nicking endonuclease, wherein said motif comprises a double stranded oligonucleotide comprising complementary strands, ii) further providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide with at least one site-specific restriction endonuclease capable of recognizing a double stranded polynucleotide comprising complementary strands and cleaving both of said strands, iii) obtaining a double stranded chimeric polynucleotide comprising an adapter oligonucleotide part by linking together the at least one adapter oligonucleotide of step i) comprising the at least one recognition motif for the at least one site-specific nicking endonuclease, wherein said motif comprises complementary strands, with the the at least one double stranded genomic polynucleotide or the at least one double stranded extra-genomic polynucleotide of step ii), iv) contacting and cleaving the double stranded chimeric polynucleotide obtained in step iii) with a combination of a) at least one site-specific restriction endonuclease capable of recognizing a double stranded polynucleotide comprising complementary strands and cleaving both of said strands, and b) at least one site-specific nicking endonuclease capable of recognizing a double stranded polynucleotide comprising complementary polynucleotide strands and cleaving only one of said strands, wherein the contacting and cleaving of the double stranded chimeric polynucleotide performed with said combination occurs either simultaneously, or sequentially in any order, and v) obtaining at least one single stranded polynucleotide tag.

Steps ib); iic); iiibJ); iiibi); iiibk); iva); and v)

Method for obtaining at least one single stranded polynucleotide tag from a biological sample, said method comprising the steps of i) providing at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, ii) further providing at least one ribonucleic acid obtained from the biological sample, iii) obtaining a double stranded chimeric polynucleotide comprising an adapter oligonucleotide part by linking together A) at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, with B) the at least one ribonucleic acid obtained from the biological sample, and C) obtaining at least one double stranded chimeric polynucleotide comprising an adapter oligonucleotide part by using the chimeric polynucleotide obtained by linking together the adapter oligonucleotide of step iiiA) with the ribonucleic acid of step iiiB) as a template for the synthesis of a polynucleotide strand complementary to said chimeric polynucleotide, iv) contacting and cleaving the double stranded chimeric polynucleotide obtained in step iii) with at least one site-specific nicking endonuclease capable of recognizing a double stranded polynucleotide comprising complementary polynucleotide strands and cleaving only one of said strands, and v) obtaining at least one single stranded polynucleotide tag.

Steps ib); iic); iibJ); iiibi); iiibk); ivb); and v)

Method for obtaining at least one single stranded polynucleotide tag from a biological sample, said method comprising the steps of i) providing at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, ii) further providing at least one ribonucleic acid obtained from the biological sample, iii) obtaining a double stranded chimeric polynucleotide comprising an adapter oligonucleotide part by linking together A) at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, with B) the at least one ribonucleic acid obtained from the biological sample, and C) obtaining at least one double stranded chimeric polynucleotide comprising an adapter oligonucleotide part by using the chimeric polynucleotide obtained by linking together the adapter oligonucleotide of step iiiA) with the ribonucleic acid of step iiiB) as a template for the synthesis of a polynucleotide strand complementary to said chimeric polynucleotide, iv) contacting and cleaving the double stranded chimeric polynucleotide obtained in step iii) with a combination of at least one site-specific restriction endonuclease capable of recognizing a double stranded polynucleotide comprising complementary strands and cleaving both of said strands, and at least one site-specific nicking endonuclease capable of recognizing a double stranded polynucleotide comprising complementary polynucleotide strands and cleaving only one of said strands, wherein the contacting and cleaving of the double stranded chimeric polynucleotide performed with said combination occurs either simultaneously, or sequentially in any order, and v) obtaining at least one single stranded polynucleotide tag.

It will be clear from the above considerations that the tags provided by the present invention may originate from different parts of a cDNA or a genomic DNA fragment, and that the tag in question will be of different length depending on whether the cDNA or the genomic DNA is cleaved by a nicking endonuclease cleaving one complementary strand only, or cleaved by a nicking endonuclease in combination with a site-specific restriction endonuclease cleaving both of the complementary strands.

Short Tags Obtained from the 5' End of cDNA

There is provided a method for obtaining at least one single stranded polynucleotide tag from a biological sample, said method comprising the steps of i) providing at least one ribonucleic acid from the biological sample ii) providing at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, iii) obtaining at least one chimeric polynucleotide by linking together the at least one ribonucleic acid of step i) with the at least one adapter oligonucleotide of step ii), iv) obtaining at least one double stranded chimeric polynucleotide comprising an adapter oligonucleotide part by using the chimeric polynucleotide of step iii) as a template for the synthesis of a polynucleotide strand complementary to said chimeric polynucleotide, v) providing at least one site-specific restriction endonuclease capable of recognizing a recognition motif comprised in the double stranded polynucleotide comprising complementary strands and cleaving the double stranded polynucleotide obtained in step iv) into at least two fragments, vi) contacting and cleaving the at least one double stranded chimeric polynucleotide obtained in step iv) with the at least one site-specific restriction endonuclease provided in step v), vii) obtaining at least one double stranded chimeric polynucleotide fragment by cleaving the at least one double stranded chimeric polynucleotide contacted with the at least one site-specific restriction endonuclease in step vi), viii) providing at least one site-specific nicking endonuclease capable of recognizing a recognition motif comprised in the double stranded chimeric polynucleotide fragment comprising complementary strands and cleaving only one of the complementary strands of the chimeric polynucleotide fragment obtained in step vii), ix) contacting and cleaving the at least one chimeric polynucleotide fragment obtained in step vii) with the at least one site-specific nicking endonuclease provided in step viii), and x) obtaining at least one single stranded polynucleotide tag.

The site-specific restriction endonuclease of step v) is preferably of type IIs.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

In one embodiment the ribonucleic acid is mRNA that may be polyadenylated or present in mixture with non-polyadenylated ribonucleic acid. The site-specific endonucleases capable of recognizing complementary strands of a double stranded polynucleotide preferably recognize a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, recognition motifs are either recreated or not recreated upon ligation.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.

Long Tags Obtained from the 5' End of cDNA

There is provided a method for obtaining at least one single stranded polynucleotide tag from a biological sample, said method comprising the steps of i) providing at least one ribonucleic acid from the biological sample,
ii) providing at least one adapter oligonucleotide comprising a part of a recognition motif for at least one site-specific nicking endonuclease, wherein said par comprises a single oligonucleotide strand which, together with a complementary strand, forms a recognition motif for at least one site-specific nicking endonuclease,
iii) obtaining at least one chimeric polynucleotide by linking together the at least one ribonucleic acid of step i) with the at least one adapter oligonucleotide of step ii),
iv) obtaining at least one double stranded chimeric polynucleotide comprising an adapter oligonucleotide part by using the chimeric polynucleotide of step iii) as a template for the synthesis of a polynucleotide strand complementary to said chimeric polynucleotide,
v) providing at least one site-specific nicking endonuclease capable of recognizing a recognition motif comprised in the double stranded chimeric polynucleotide comprising complementary strands and cleaving only one of the complementary strands of the chimeric polynucleotide obtained in step iv),
vi) contacting and cleaving the at least one chimeric polynucleotide obtained in step iv) with the at least one site-specific nicking endonuclease provided in step v), and
vii) obtaining at least one single stranded polynucleotide tag.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

In one embodiment the ribonucleic acid is mRNA that may be polyadenylated or present in mixture with non-polyadenylated ribonucleic acid. The site-specific nicking endonuclease capable of recognizing complementary strands of a double stranded polynucleotide preferably recognizes a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, recognition motifs are either recreated or not recreated upon ligation.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.
Short Tags Obtained from the 3' End of cDNA There is provided a method for obtaining at least one single stranded polynucleotide tag from a biological sample, said method comprising the steps of i) providing at least one ribonucleic acid from the biological sample,
ii) obtaining at least one double stranded polynucleotide comprising two complementary strands by using the at least one ribonucleic acid provided in step i) as a template for the synthesis of a polynucleotide strand complementary to the at least one ribonucleic acid,
iii) providing at least one site-specific restriction endonuclease capable of recognizing a recognition motif comprised in the double stranded polynucleotide comprising complementary strands and cleaving the double stranded polynucleotide obtained in step ii) into at least two fragments,
iv) contacting and cleaving the at least one double stranded polynucleotide obtained in step ii) with the at least one site-specific restriction endonuclease provided in step iii),
v) obtaining at least one double stranded polynucleotide fragment by cleaving the at least one double stranded polynucleotide contacted with the at least one site-specific restriction endonuclease in step iv),
vi) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded polynucleotide fragment obtained in step v),
vii) obtaining at least one double stranded chimeric polynucleotide by linking together the at least one double stranded polynucleotide fragment obtained in step v) and the at least one adapter oligonucleotide provided in step vi),
viii) providing at least one further site-specific restriction endonuclease capable of recognizing a recognition motif comprised in the double stranded chimeric polynucleotide comprising complementary strands and cleaving both of the complementary strands of the chimeric polynucleotide provided in step vii),
ix) contacting and cleaving the at least one chimeric polynucleotide obtained in step vii) with the at least one further site-specific restriction endonuclease provided in step viii),
x) obtaining at least one chimeric polynucleotide fragment by cleaving the at least one chimeric polynucleotide contacted with the at least one further site-specific restriction endonuclease in step ix),
xi) providing at least one site-specific nicking endonuclease capable of recognizing a recognition motif comprised in the double stranded chimeric polynucleotide fragment comprising complementary strands and cleaving only one of the complementary strands of the chimeric polynucleotide fragment obtained in step x),
xii) contacting and cleaving the at least one chimeric polynucleotide fragment obtained in step x) with the at least one site-specific nicking endonuclease provided in step xi), and
xiii) obtaining at least one single stranded polynucleotide tag.

The site-specific restriction endonuclease of step iii) is preferably of type II or type IIs. The further site-specific restriction endonuclease of step viii) is preferably of type IIs. The site-specific restriction endonuclease and the further site-specific restriction endonuclease can be the same or different endonucleases.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

In one embodiment the ribonucleic acid is mRNA that may be polyadenylated or present in mixture with non-polyadenylated ribonucleic acid. The site-specific endonucleases capable of recognizing complementary strands of a double stranded polynucleotide preferably recognizes a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, recognition motifs are either recreated or not recreated upon ligation. In one preferred embodiment the cleavage of step iv) and the ligation of step vii) is carried out simultaneously.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.

Long Tags Obtained from the 3' End of cDNA

There is provided a method for obtaining at least one single stranded polynucleotide tag from a biological sample, said method comprising the steps of
i) providing at least one ribonucleic acid from the biological sample,
ii) obtaining at least one double stranded polynucleotide comprising two complementary strands by using the at least one ribonucleic acid provided in step i) as a template for the synthesis of a polynucleotide strand complementary to the at least one ribonucleic acid,
iii) providing at least one site-specific restriction endonuclease capable of recognizing a recognition motif comprised in the double stranded polynucleotide comprising complementary strands and cleaving the double stranded polynucleotide obtained in step ii) into at least two fragments,
iv) contacting and cleaving the at least one double stranded polynucleotide obtained in step ii) with the at least one site-specific restriction endonuclease provided in step iii),
v) obtaining at least one double stranded polynucleotide fragment by cleaving the at least one double stranded polynucleotide contacted with the at least one site-specific restriction endonuclease in step iv),
vi) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded polynucleotide fragment obtained in step v),
vii) obtaining at least one chimeric polynucleotide by linking together the at least one double stranded polynucleotide fragment obtained in step v) and the at least one adapter oligonucleotide provided in step vi),
viii) providing at least one site-specific nicking endonuclease capable of recognizing a recognition motif comprised in the double stranded chimeric polynucleotide comprising complementary strands and cleaving only one of the complementary strands of the chimeric polynucleotide obtained in step vii),
ix) contacting and cleaving the at least one chimeric polynucleotide obtained in step vii) with the at least one site-specific nicking endonuclease provided in step viii), and
x) obtaining at least one single stranded polynucleotide tag.

The site-specific restriction endonuclease of step iii) is preferably of type II or type IIs.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

In one embodiment the ribonucleic acid is mRNA that may be polyadenylated or present in mixture with non-polyadenylated ribonucleic acid. The site-specific endonucleases capable of recognizing complementary strands of a double stranded polynucleotide preferably recognize a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, recognition motifs are either recreated or not recreated upon ligation. In one preferred embodiment the cleavage of step iv) and the ligation of step vii) is carried out simultaneously.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.

Short Tags Obtained from Genomic DNA or Extra-genomic DNA

There is provided a method for obtaining at least one single stranded polynucleotide tag from a biological sample, said method comprising the steps of
i) providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide, respectively, with at least one site-specific restriction endonuclease capable of recognizing a double stranded polynucleotide comprising complementary strands and cleaving both of said strands, ii) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded genomic polynucleotide fragment, or the at least one double stranded extra-genomic polynucleotide fragment, provided in step i), iii) obtaining at least one chimeric polynucleotide by linking together the at least one double stranded-genomic polynucleotide fragment, or the at least one double stranded extra-genomic polynucleotide fragment obtained in step i) and the at least one adapter oligonucleotide provided in step ii), iv) providing at least one further site-specific restriction endonuclease capable of recognizing a double stranded polynucleotide comprising complementary strands and cleaving both of the complementary strands of the at least one chimeric polynucleotide of step iii) obtained by linking together the at least one double stranded genomic polynucleotide fragment, or the at least one double stranded extra-genomic polynucleotide fragment, and the at least one adapter oligonucleotide provided in step ii), v) contacting and cleaving the at least one chimeric polynucleotide obtained in step iii) with the at least one further site-specific restriction endonuclease provided in step iv), vi) obtaining at least one chimeric polynucleotide fragment by cleaving the at least one chimeric polynucleotide contacted with the at least one further site-specific restriction endonuclease in step v), vii) providing at least one site-specific nicking endonuclease capable of recognizing a recognition motif comprised in the double stranded chimeric polynucleotide fragment comprising complementary strands and cleaving only one of the complementary strands of the at least one chimeric polynucleotide fragment obtained in step vi), viii) contacting and cleaving the at least one chimeric polynucleotide fragment obtained in step vi) with the at least one site-specific nicking endonuclease provided in step vii), and ix) obtaining at least one single stranded polynucleotide tag.

The site-specific restriction endonuclease of step i) is preferably of type II or type IIs. The further site-specific restriction endonuclease of step iv) is preferably of type IIs. The site-specific restriction endonuclease and the further site-specific restriction endonuclease can be the same or different endonucleases.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

The site-specific restriction endonuclease capable of recognizing complementary strands of a double stranded polynucleotide preferably recognizes a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, recognition motifs are either recreated or not recreated upon ligation. In one preferred embodiment the cleavage of step i) and the ligation of step iii) is carried out simultaneously.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.

Long Tags Obtained from Genomic DNA or Extra-genomic DNA

There is provided a method for obtaining at least one single stranded polynucleotide tag from a biological sample, said method comprising the steps of i) providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide, respectively, with at least one site-specific restriction endonuclease capable of recognizing a double stranded polynucleotide comprising complementary strands and cleaving both of said strands, ii) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded genomic polynucleotide fragment, or the at least one double stranded extra-genomic polynucleotide fragment, provided in step i), iii) obtaining at least one chimeric polynucleotide by linking together the at least one double stranded genomic polynucleotide fragment, or the at least one double stranded extra-genomic polynucleotide fragment obtained in step i) and the at least one adapter oligonucleotide provided in step ii), iv) providing at least one site-specific nicking endonuclease capable of recognizing a recognition motif comprised in the double stranded polynucleotide comprising complementary strands and cleaving only one of the complementary strands of the at least one chimeric polynucleotide obtained in step iii), v) contacting and cleaving the at least one chimeric polynucleotide obtained in step iii) with the at least one site-specific nicking endonuclease provided in step iv), and vi) obtaining at least one single stranded polynucleotide tag.

The site-specific restriction endonuclease of step iii) is preferably of type II or type IIs.

The tag preferably comprises less than 30 nucleotides, such as less than 20 nucleotides, for example less than 15 nucleotides, such as 10 nucleotides or less than 10 nucleotides. The above method preferably comprises the further steps of isolating the tag and/or determining the sequence of the tag and/or quantifying the tag as compared to the quantification of a predetermined standard.

The site-specific endonucleases capable of recognizing complementary strands of a double stranded polynucleotide preferably recognizes a motif comprising 8 nucleotides, or less than 8 nucleotides, such as 7 nucleotides, or less than 7 nucleotides, such as 6 nucleotides, or less than 6 nucleotides, such as 5 nucleotides, or less than 5 nucleotides, such as 4 nucleotides.

It is much preferred that the chimeric polynucleotide is obtained by means of ligation, and in various embodiments, the recognition motifs are either recreated or not recreated upon ligation. In one preferred embodiment the cleavage of step i) and the ligation of step iii) is carried out simultaneously.

In one embodiment there is provided the further step of contacting the double stranded polynucleotide with a site-specific methylase or methyltransferase. The site-specific methylase or methyltransferase preferably methylates a recognition motif capable of being recognized by at least one of the site-specific endonucleases capable of recognizing a double stranded polynucleotide comprising complementary strands and cleaving either one or both of said strands. In one such embodiment, a methylated dCTP analog is substituted for an unmodified dCTP in the synthesis reaction resulting in the synthesis of a complementary strand to the template. In another embodiment, M.BpmI is used to methylate the target DNA in the motif that BpmI recognizes and binds to.

Methods for Amplification of Isolated Single Stranded Polynucleotide Tags

Various methods are known to the art which may be used to detect and characterize specific polynucleotide tags. Examples include the below-mentioned "signal" amplification methods including the polymerase chain reaction and the ligase chain reaction. In one embodiment of the invention, the amplification step is carried out using PCR techniques that are well known in the art.

The polymerase chain reaction (PCR), as described in U.S. Pat. Nos. 4,683,195 and 4,683,202 to Mullis and Mullis et al. (the disclosures of which are hereby incorporated by reference), is a method for increasing the concentration of a segment of target sequence in a mixture of genomic DNA without cloning or purification. An additional reference guide on PCR is: A Guide to Methods and Applications (Innis, M., Gelfand, D., Sninsky, J. and White, T., eds.) Academic Press (1990), incorporated herein by reference in its entirety for all purposes.

PCR amplification generally involves the use of one strand of the target nucleic acid sequence as a template for producing a large number of complements to that sequence. Generally, two primer sequences complementary to different ends of a segment of the complementary strands of the target sequence hybridize with their respective strands of the target sequence, and in the presence of polymerase enzymes and deoxy-nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as is necessary to obtain the desired amount of amplified nucleic acid.

In PCR methods, strand separation is normally achieved by heating the reaction to a sufficiently high temperature for a sufficient time to cause the denaturation of the duplex but not to cause an irreversible denaturation of the polymerase enzyme (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference). Other embodiments may achieve strand separation by application of electric fields across the sample. For example, Published PCT Application Nos. WO 92/04470 and WO 95/25177, incorporated herein by reference, describe electrochemical methods of denaturing double stranded DNA by application of an electric field to a sample containing the DNA. Structures for carrying out this electrochemical denaturation include a working electrode, counter electrode and reference electrode arranged in a potentiostat arrangement across a reaction chamber (See, Published PCT Application Nos. WO 92/04470 and WO 95/25177, each of which is incorporated herein by reference). Such devices may be readily miniaturized for incorporation into the devices of the present invention utilizing the microfabrication techniques described herein.

Template-dependent extension of primers in PCR is catalyzed by a polymerizing agent in the presence of adequate amounts of at least 4 deoxyribonucleoside triphosphates (typically selected from dATP, dGTP, dCTP, dUTP and dTTP) in a reaction medium which comprises the appropriate salts, metal cations, and pH buffering system. Reaction components and conditions are well known in the art (See PCR Protocols: A Guide to Methods and Applications (Innis, M., Gelfand, D., Sninsky, J. and White, T., eds.) Academic Press (199–0), previously incorporated by reference). Suitable polymerizing agents are enzymes known to catalyze template-dependent DNA synthesis.

In one embodiment, the amplification step is carried out using methods and devices described in published PCT Application No. WO 94/05414, to Northrup and White, and directed to the use of a microPCR chamber which incorporates microheaters and micropumps in the thermal cycling and mixing during the PCR reactions.

Accordingly, PCR technology provides one approach for solving problems of low target sequence concentration, i.e. a low concentration of the source of a single stranded polynucleotide tag to be analysed and/or detected in accordance with the present invention. PCR may thus be used to directly increase the concentration of the target to an easily detectable level.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

The ligase chain reaction (LCR; sometimes referred to as "Ligase Amplification Reaction" (LAR) described by Barany, (PNAS, 88, 189, 1991); (PCR Methods and Applic., 1, 5, 1991); and (Genomics 4, 560, 1989) (all of which are hereby incorporated by reference) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA.

LCR has also been used in combination with PCR to achieve enhanced detection of single-base changes. Segev, PCT Public. No. W09001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

Analysis of ssDNA Tags Obtained According to One Preferred Method of the Present Invention It is possible to divide a sample into a number of panels during the first strand or the second strand synthesis, when making cDNA from RNA. It is preferred to have one or more discriminating bases in the 3' end of the primer used for either the first strand or the second strand synthesis.

When doing RLM-RACE, it is most convenient have any discriminating bases at the 3' end of the primer, that binds to the first strand complementary part of the adapter of the chimeric mRNA molecule. In other instances it might be more convenient to put discriminating bases in the 3' end of the oligo(dT) primer used in the RT-reaction.

Depending on the number of discriminating bases in the 3' end of the oligo(dT) primer, the resulting number of panels is $3 \times 4^{(n-1)}$, where n is the number of discriminating bases. If there is only one discriminating base in the 3' end of an oligo(dT) primer, that base can either be A, G or C—but not T. Hence a degeneracy of 3 in stead of 4 for the first base. When using such panels in the RT reaction, it is possible to create pools of cDNA in a reproducible way. When such pools is combined with extracting an ssDNA tag from the cDNA, then the degeneracy of the ssDNA tag can be combined with the degeneracy of panels from the RT reaction.

An ssDNA tag that is six bases long has a degeneracy of $4^6$, or 4096. If the oligo(dT) primer has three discriminating bases it will divide the cDNA pool into $3 \times 4^2$ or 48 pools. If isolating ssDNA tags form each of the 48 pools, the combined degeneracy is $3 \times 4^2 \times 4^6$ or $48 \times 4096$, or 196.608. In other terms it is possible to identify and quantify 196.608 different transcripts by combining the degeneracy of an oligo(dT) with three discriminating bases in its 3' end and a hexamer ssDNA tag from each cDNA.

In a preferred embodiment of the invention as described herein above, the double stranded DNA is cleaved with a type IIs restriction endonuclease that leads to overhangs of from 2 to 6 bases. This gives between 16 and 4096 different sequences of the overhang depending on the number of bases in the overhang. This approach can naturally also be combined with an oligo(dT) with a number of discriminating bases in its 3' end. If combined with the example above, a type IIs restriction ends nuclease leaving 4 overhanging bases will increase the degeneracy with a factor of $4^4$ or 256 so the total degeneracy in the example reaches 50.331.648— far more than is needed to track the approximately 100.000 transcripts in the human genome.

When using two linkers with 3' and 5' overhangs respectively to analyze the ssDNA tag, the total degeneracy according to preferred embodiments of the invention is selected so that they satisfy the criteria below depending upon the purpose of the analysis:

Every combination of degeneracy where the sum of opportunities satisfies the equation:

$$100 < 4^{L1} \times 4^{L2} < 200.000,$$

where L1 is the number of degenerated bases in linker 1 and where L2 is the number of degenerated bases in linker 2, both L1 and L2 and the sum of the two being shorter than 10 bases long, can be used to make diagnostic tools.

Every combination of degeneracy where the sum of opportunities satisfies the equation:

$$0.1000 < 4^{L1} \times 4^{L2} < 17,000.000,$$

where L1 is the number of degenerated bases in linker 1 and where L2 is the number of degenerated bases in linker 2, both L1 and L2 and the sum of the two being shorter than 13 bases long, can be used to make expression profiling tools.

Every combination of degeneracy where the sum of opportunities satisfies the equation:

$$10.000 < 4^{L1} \times 4^{L2} < 4.500.000,000,$$

where L1 is the number of degenerated bases in linker 1 and where L2 is the number of degenerated bases in linker 2, both L1 and L2 and the sum of the two being shorter than 17 bases long, can be used to make SNP-, methylation-, and expression profiling tools.

Every combination of degeneracy where the sum of opportunities satisfies the equation:
$10,000 < 4^{L1} \times 4^{L2} < 1,2 \times 10^{12}$, where L1 is the number of degenerated bases in linker 1 and where L2 is the number of degenerated bases in linker 2, both L1 and L2 and the sum of the two being shorter than 21 bases long, can be used to make SNP and methylation profiling tools.

Accordingly, there is provided a method of the invention as described herein above and comprising the further step of separating and/or identifying and/or determining the amount of the at least one single stranded polynucleotide tag from other single stranded polynucleotides and/or double stranded polynucleotides.

The method may employ a solid support comprising a hybridization array comprising a plurality of ordered identifying linker oligonucleotides to which at least one single stranded polynucleotide strand may hybridize. In one embodiment, the identifying linker oligonucleotides are identifiable based on their position in the hybridization array.

In another preferred embodiment, the present invention employs a microfluid device for separating and/or identifying and/or determining the amount of the at least one single stranded polynucleotide tag derived from a biological sample. The separation and/or identification and/or determination preferably occurs by separating and/or identifying and/or determining, respectively, a hybrid polynucleotide tag or a chimeric polynucleotide further comprising a molecular identifier and/or a selectively detectable label.

The molecular identifier and/or the selectively detectable label makes it possible to manipulate and/or identify the hybrid polynucleotide tag or a chimeric polynucleotide present within one compartment or present in a plurality of compartments of the microfluid device, wherein the compartments are preferably interconnected.

The manipulation and/or identification is made possible by the ability of, individual molecular identifiers and/or selectively detectable labels to be manipulated and/or identified according to their molecular weight and/or charge and/or a paramagnetic property and/or a fluorescent property or any other capability of emitting electromagnetic radiation when desirably excited by any suitable source of radiation.

Microfluid Device

It is preferred in accordance with one preferred embodiment of the invention to analyse the at least one single stranded polynucleotide tag derived from a biological sample by means of miniaturized, integrated microfluid devices and systems incorporating such devices. The devices of the invention are generally capable of performing one or more sample acquisition and preparation operations, as may be integrated with one or more sample analysis operations. A sample as used herein below shall denote any sample comprising at least one single stranded polynucleotide sample obtained by any method pertaining to the present invention.

For example, the devices can integrate several or all of the operations involved in sample acquisition and storage, sample preparation and sample analysis, within a single, miniaturized, integrated unit. The devices are useful in a variety of applications including single stranded polynucleotide tag manipulation and/or identification, as well as single stranded polynucleotide tag based diagnostic applications.

The devices of the invention will typically be one component of a larger diagnostic system which further preferably includes a reader device for scanning and obtaining data from the device, and a computer based interface for controlling the device and/or interpretation of the data derived from the device.

To carry out their primary functions, one embodiment of the devices of the invention will typically incorporate a plurality of distinct reaction chambers for carrying out the sample acquisition, preparation and analysis operations. In particular, a sample comprising a single stranded polynucleotide tag to be analyzed, including any step involving that the tag is being manipulated and/or separated and/or determined, is preferably introduced into the device whereupon it will be manipulated and delivered to one of the distinct reaction chambers which may, in one embodiment, be designed for carrying out a variety of reactions as a prelude to analysis of the sample. These preparative reactions generally include, e.g., sample extraction, sample processing, including endonuclease digestion, including digestion with a nicking endonuclease and optionally also with a restriction endonuclease, single stranded polynucleotide tag generation, hybrid polynucleotide tag formation, chimeric polynucleotide tag formation, release from the chimeric tag of the single-stranded polynucleotide tag, tag amplification, including PCR amplification and/or LCR amplification, second identifying linker oligonucleotide hybridization to a hybrid polynucleotide tag and/or a chimeric polynucleotide tag.

In one particularly preferred embodiment of this aspect of the invention, there is provided at least one compartment chamber comprising at least one cleavage agent including at least one single stranded nicking endonuclease, wherein the at least one cleavage agent including at least one site-specific nicking endonuclease is preferably bound to a solid support forming part of said chamber.

The chamber comprising the at least one cleavage agent including at least one single stranded nicking endonuclease, or another chamber, may preferably comprise at least one site-specific restriction endonuclease and/or at least one single stranded adapter oligonucleotide and/or at least one double stranded adapter oligonucleotide and/or at least one first and/or second identifying linker oligonucleotide. The at least one adapter oligonucleotide preferably comprises at least one recognition site for a site-specific nicking endonuclease.

In the same or another preferred embodiment as the one described above, there is provided at least one compartment chamber comprising i) at least one or a plurality of first identifying linker oligonucleotides, wherein each or a plurality of first identifying linker oligonucleotides, or a subset thereof, comprise a single stranded, first unique nucleotide sequence forming a 5' overhang, and/or ii) at least one or a plurality of second identifying linker oligonucleotides, wherein each or a plurality of second identifying linker oligonucleotides, or a subset thereof, comprise a single stranded, second unique nucleotide sequence forming a 3' overhang.

At least one or a plurality of said adapter oligonucleotides and/or said first and/or said second identifying linker oligonucleotides, or a subset thereof, preferably comprises one or more of i) a molecular identifier, ii) a selectively identifiable label, and a iii) recognition motif for one or more of a site-specific nicking endonuclease and/or a site-specific restriction endonuclease.

The molecular identifier and/or the selectively identifiable label is in one embodiment preferably attached to a solid support including a hybridization array forming part of a compartment of the microfluid device. Both the molecular identifier and the label may be detachable from the solid support by e.g. cleavage with a cleavage agent including a site-specific restriction endonuclease.

In another preferred embodiment there is provided a microfluid device comprising a solid support comprising at least one hybridization array comprising a plurality of ordered first and/or second identifying linker oligonucleotides, preferably at least one hybridization array comprising a plurality of ordered first identifying linker oligonucleotides, or a subset of such oligonucleotides, and/or at least one hybridization array comprising a plurality of ordered second identifying linker oligonucleotides, or a subset of such oligonucleotides.

Preferably, at least one of said first and/or second identifying linker oligonucleotides comprises a single stranded nucleotide sequence hybridized to at least one single stranded polynucleotide tag comprising a sequence complementary thereto. The single stranded polynucleotide tag is preferably obtained by a method of the invention as described herein. Alternatively, the single stranded polynucleotide tag is obtained by displacement of a double stranded polynucleotide tag comprising polynucleotide strands which are at least partly complementary to one another.

In will be understood that following sample entry into the microfluid device, the sample can be subjected to one or more different analysis operations. A variety of analysis operations may generally be performed, including size or molecular weight based analysis using, e.g., microcapillary electrophoresis, and/or sequence based analysis using first and/or second identifying linker oligonucleotides, hybridization of hybrid polynucleotide tags and/or chimeric polynucleotide tags to e.g. a solid support comprising e.g. a hybridization array including an array comprising first and/or second identifying linker oligonucleotides.

In addition to the various reaction chambers, the device will generally comprise a series of fluid channels which allow for the transportation of the sample, or a portion thereof, among the various reaction chambers. Further chambers and components may also be included to provide reagents, buffers, sample manipulation, e.g., mixing, pumping, fluid direction (i.e., valves) heating and the like.

The below sections describe in more detail preferred integratable operations of a microfluid device according to the present invention.

Sample Acquisition

The sample collection portion of the device of the present invention preferably provides for the identification or nummeration of individual samples, while preventing contamination of the sample by external elements, or contamination of a working environment or an external environment by the sample.

Generally, this is carried out by introducing a sample for analysis, e.g., a biological sample putatively comprising the single stranded polynucleotide tag to be displayed, determined, or identified. The sample may be a preamplified sample, a tissue sample, a blood sample, a saliva sample, etc., directly into a sample collection chamber within the device.

Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. Alternatively, the device may be provided with a hypodermic needle integrated within the device and connected to the sample collection chamber, for direct acquisition of the sample into the sample chamber. This can substantially reduce the opportunity for contamination of the sample.

In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like.

Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Sample Manipulation

In between introducing the sample to be analyzed into the device, and analyzing that sample, e.g., on a hybridization array comprising a plurality of ordered first and/or second identifying linker oligonucleotides such as e.g. a hybridization array comprising an ordered plurality of first and/or second identifying linker oligonucleotides, it will often be desirable to perform one or more initial sample preparation operations upon the sample.

Typically, these sample preparation operations will include such manipulations as extraction of intracellular material, e.g., polynucleotides including nucleic acids from whole cell samples, viruses and the like, and optionally one or more steps preferably including amplification of the extracted nucleic acids, fragmentation by treatment with at least one site-specific endonuclease including at least one site-specific nicking endonuclease, and optionally also a site-specific restriction endonuclease, transcription, including reverse transcription in connection with cDNA synthesis, labeling and/or extension, reactions. One or more of these various operations may be readily incorporated into the microfluid device of the present invention.

Nucleic Acid Extraction from the Biological Sample

For those embodiments where whole cells, viruses or other tissue samples are being analyzed, it will typically be necessary to extract the nucleic acids from the cells or viruses, prior to continuing with the various sample preparation operations. Accordingly, following sample collection, polynucleotides may be liberated from the collected cells, viral coat, etc., into a crude extract, followed by additional treatments to prepare the sample for subsequent operations, e.g., denaturation of contaminating (DNA binding) proteins, purification, filtration, desalting, and the like.

Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within the extraction chamber, a separate accessible chamber or externally introduced.

Alternatively, physical methods may be used to extract the polynucleotides and denature DNA binding proteins. U.S. Pat. No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., employing a channel with restricted cross-sectional dimension which causes cell lysis when the sample is passed through the channel with sufficient flow pressure.

Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to effect cell lysis/extraction, including, e.g., subjecting cells to ultrasonic agitation, or forcing cells through microgeometry apertures, thereby subjecting the cells to high shear stress resulting in rupture.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like, i.e., poly-T oligonucleotides for mRNA purification. This is also preferred when isolating single stranded polynucleotide tags from cDNA synthesised from poly-A containing mRNA.

Alternatively, desalting methods may generally take advantage of the high electrophoretic mobility and negative charge of DNA compared to other elements. Electrophoretic methods may also be utilized in the purification of nucleic acids from other cell contaminants and debris.

In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules.

The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include, e.g., dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow.

Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use.

In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. In some applications, poly-A containing mRNA may be extracted, in other applications, both poly-A containing mRNA and mRNA devoid of a poly-A tail may be extracted.

As such, the device of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself. Immobilization of oligonucleotides on the surface of the chambers or channels may be carried out by methods described herein including, e.g., oxidation and silanation of the surface followed by standard DMT synthesis of the oligonucleotides.

In operation, the lysed sample is introduced into this chamber or channel in an appropriate salt solution for hybridization, whereupon the mRNA will hybridize to the immobilized poly-T. Hybridization may also be enhanced through incorporation of mixing elements, also as described herein. After enough time has elapsed for hybridization, the chamber or channel is washed with clean salt solution.

The mRNA bound to the immobilized poly-T oligonucleotides is then washed free in a low-ionic strength buffer. The surface area upon which the poly-T oligonucleotides are immobilized may be increased through the use of etched structures within the chamber or channel, e.g., ridges, grooves or the like. Such structures also aid in the agitation of the contents of the chamber or channel, as described herein. Alternatively, the poly-T oligonucleotides may be immobilized upon porous surfaces, e.g., porous silicon, zeolites, silica xerogels, cellulose, sintered particles, or other solid supports.

Polynucleotide Amplification and In Vitro Transcription

Following sample collection and nucleic acid extraction, the nucleic acid portion of the sample may be subjected to one or more preparative reactions. These preparative reactions can include in vitro transcription, labeling, fragmentation, amplification and other reactions.

Nucleic acid amplification increases the number of copies of the target nucleic acid sequence of interest. A variety of amplification methods are suitable for use in the methods and device of the present invention, including for example, the polymerase chain reaction method or (PCR), the ligase chain reaction (LCR), self sustained sequence replication (3SR), and nucleic acid based sequence amplification (NASBA).

The latter two amplification methods involve isothermal reactions based on isothermal transcription, which produce both single stranded RNA (ssRNA) and double stranded DNA (dsDNA) as the amplification products in a ratio of approximately 30 or 100 to 1, respectively. As a result, where these latter methods are employed, sequence analysis may be carried out using either type of substrate, i.e., complementary to either DNA or RNA.

In one embodiment, the microfluid device according to the present invention comprises an amplification reaction chamber. The microfluid device preferably comprises a sealable opening for the addition of the various amplification reagents. However, in preferred aspects, the amplification chamber will have an effective amount of the various amplification reagents described above, predisposed within the amplification chamber, or within an associated reagent chamber whereby the reagents can be readily transported to the amplification chamber upon initiation of the amplification operation. By "effective amount" is meant a quantity and/or concentration of reagents required to carry out amplification of a targeted nucleic acid sequence. These amounts are readily determined from known PCR protocols. See, e.g., Sambrook, et al. Molecular Cloning: A Laboratory Manual, (2nd ed.) Vols. 1–3, Cold Spring Harbor Laboratory, (1989) and PCR Protocols: A Guide to Methods and Applications (Innis, M., Geifand, D., Sninsky, J. and White, T., eds.) Academic Press (1990), both of which are incorporated herein by reference for all purposes in their entirety.

For those embodiments where the various reagents are predisposed within the amplification or adjacent chamber, it will often be desirable for these reagents to be in lyophilized forms, to provide maximum shelf life of the overall device. Introduction of the liquid sample to the chamber then reconstitutes the reagents in active form, and the particular reactions may be carried out.

In some aspects, the polymerase enzyme may be present within the amplification chamber, coupled to a suitable solid support, or to the walls and surfaces of the amplification chamber. Suitable solid supports include those that are well known in the art, e.g., agarose, cellulose, silica, divinylbenzene, polystyrene, etc.

Coupling of enzymes to solid supports has been reported to impart stability to the enzyme in question, which allows for storage of days, weeks or even months without a substantial loss in enzyme activity, and without the necessity of lyophilizing the enzyme. The 94 kd, single subunit DNA polymerase from Thermus aquaticus (or taq polymerase) is particularly suited for the PCR based amplification methods used in the present invention, and is generally commercially available from, e.g., Promega, Inc., Madison, Wis. In particular, monoclonal antibodies are available which bind the enzyme without affecting its polymerase activity. Consequently, covalent attachment of the active polymerase enzyme to a solid support, or the walls of the amplification chamber can be carried out by using the antibody as a linker between the enzyme and the support.

In addition to PCR and IVT reactions, the methods and devices of the present invention are also applicable to a number of other reaction types, e.g., reverse transcription, nick translation, cDNA generation, and the like.

In one embodiment, acoustic microstructures may be used for hybridization mixing. A description of an acoustic mixer may be found in X. Zhu and E. S. Kim "Microfluidic Motion Generation With Loosely-Focused Acoustic Waves", 1997 Int'l. Conference on Solid-State Sensors and Actuators, Jun. 16–19, 1997, Chicago, Ill.

Labeling and Fragmentation

Nucleic acids comprising or essentially consisting of the single stranded polynucleotide tag to be analysed and/or determined in the biological sample may, in one embodiment of the present invention, be labeled to facilitate detection in subsequent steps.

The labeling may also comprise labeling of an adapter oligonucleotide, of a first and/or second identifying linker oligonucleotide, of a hybrid or chimeric oligonucleotide tag, of a molecular identifier, or any other molecule used for manipulating and/or identifying the single stranded polynucleotide tag according to the present invention. Labeling reactions are thus not confined to labeling of nucleic acids natively occurring in a biological sample of interest.

Labeling may be carried out prior to, during, and after any amplification step. In particular, amplification, in vitro transcription or nick translation may incorporate a label into the amplified or transcribed sequence, either through the use of labeled primers or the incorporation of labeled dNTPs or NTPs into the amplified sequence. An amplification step, an in vitro transcription step, and/or a nick translation step may thus be employed for generating one or more of e.g. i) an adapter oligonucleotide, ii) an identifying linker oligonucleotide comprising a predetermined single stranded nucleotide sequence, and iii) a chimeric polynucleotide comprising an adapter part.

Labeling may also be carried out by attaching an appropriately labeled (e.g. FICT, or biotin), dNTP to the 3'-end of DNAase fragmented PCR product using terminal deoxytransferase (TdT).

In an alternative embodiment, Poly(A) polymerase will "tail" any RNA molecule with polyA and therefore be used for radiolabeling RNA. Used in conjunction with a biotin-, fluorophore-, gold particle- (or any other detectable moiety)-ATP conjugate, poly (A) polymerase can be used for direct 3'-end labelling of RNA targets for detecting hybridization to DNA probe arrays. The nucleotide conjugate may carry the detectable moiety attached, through a linker (or not) to positions on either the nucleotide base or sugar.

With regard to relative incorporation efficiency, the enzyme may exhibit a preference for one or more of these positions. The nucleotide may be a 2',3'-dideoxynucleotide, in which case only a single label will be added to the 3'-end of the RNA. A preferred format is to tail the RNA with 5-Bromo-UTP, and then detect hybridization indirectly using a labeled ant-bromouridine. This would closely parallel a currently favored assay format used for expression monitoring applications using biotinylated RNA and phycoerythrin-streptavidin "staining".

Alternatively, a polynucleotide and/or any one or more of e.g. i) an adapter oligonucleotide, ii) an identifying linker oligonucleotide comprising a predetermined single stranded nucleotide sequence, and iii) a chimeric polynucleotide comprising an adapter part, may be labeled without any amplification taking place, or following an amplification step involving amplification of natively occurring polynucleotides in the biological sample.

In one such embodiment, the labeling typically involves the covalent attachment of a particular detectable group upon an amplified sequences. Suitable labels or detectable groups include a variety of fluorescent or radioactive labeling groups well known in the art. These labels may also be coupled to the sequences using methods that are well known in the art. See, e.g., Sambrook, et al.

Any one or more of a single stranded polynucleotide tag, an adapter oligonucleotide, an identifying linker oligonucleotide comprising a predetermined single stranded nucleotide sequence, and a chimeric polynucleotide comprising an adapter part may be subjected to one or more further processing steps. For example, in some cases, it may be desirable to further fragment a chimeric polynucleotide or a hybrid polynucleotide tag or a chimeric polynucleotide tag prior to hybridization with a hybridization array, in order to provide segments which are more readily accessible to the identifying linker oligonucleotides comprised in the array. In one embodiment, a further processing step is e.g. a ligation of a single stranded or double stranded adapter oligonucleotide to a single stranded or double stranded polynucleotide, respectively, comprising a single stranded polynucleotide tag, or e.g. a complementary part thereof, as the case may be for some single stranded polynucleotides, wherein said single stranded polynucleotide tag is to be analysed and/or determined according to a method of the present invention, wherein said ligation, preferably a ligation catalysed by an enzyme, generates a chimeric polynucleotide.

Another example of a further processing step is fragmentation of the chimeric polynucleotide by at least one site-specific nicking endonuclease, optionally in combination with a further fragmentation resulting from cleavage of the chimeric polynucleotide by a site-specific restriction endonuclease. The fragmentation generated by the action of the specific nicking endonuclease, and optionally also by the site-specific restriction endonuclease may occur simultaneously, or sequentially, in any order.

Yet further processing steps are steps leading to the formation of hybrid polynucleotide tags and/or chimeric polynucleotide tags. Even further processing steps involve the manipulation or detection of the tags by using e.g. molecular identifiers and/or selectively detectable labels.

In addition to fragmentation of polynucleotides arising from enzymatic treatment, including treatment with site-specific endonucleases, including site-specific nicking endonucleases and optionally also site-specific restriction endonucleases, fragmentation of polynucleotides may also arise from any physical or chemical or enzymatic methods that are known in the art. These additional treatments may be performed within an amplification chamber, or alternatively, they may be carried out in a separate chamber.

For example, physical fragmentation methods may involve moving the sample containing the nucleic acid over pits or spikes in the surface of a reaction chamber or fluid channel. The motion of the fluid sample, in combination with the surface irregularities produces a high shear rate, resulting in fragmentation of the nucleic acids. In one aspect, this may be accomplished in a miniature device by placing a piezoelectric element, e.g., a PZT ceramic element adjacent to a substrate layer that covers a reaction chamber or flow channel, either directly, or through a liquid layer, as described herein. The substrate layer has pits, spikes or apertures manufactured in the surface which are within the chamber or flow channel. By driving the PZT element in the thickness mode, a standing wave is set up within the chamber. Cavitation and/or streaming within the chamber results in substantial shear. Similar shear rates may be achieved by forcing the nucleic acid containing fluid sample through restricted size flow passages, e.g., apertures having a cross-sectional dimension in the micron or submicron scale, thereby producing a high shear rate and fragmenting the nucleic acid.

A number of sample preparation operations may be carried out by adjusting the pH of the sample, such as cell lysis, nucleic acid fragmentation, enzyme denaturation and the like. Similarly, pH control may also play a role in a wide variety of other reactions to be carried out in the device, i.e., for optimizing reaction conditions, neutralizing acid or base additions, denaturing exogenously introduced enzymes, quenching reactions, and the like. Such pH monitoring and control may be readily accomplished using well known methods. For example, pH may be monitored by incorporation of a pH sensor or indicator within a particular chamber. Control may then be carried out by titration of the chamber contents with an appropriate acid or base.

Single Stranded Polynucleotide Tag Analysis

Following the various sample preparation operations, the sample comprising the single stranded polynucleotide tag may in one embodiment be subjected to one or more analysis and/or manipulation operations. Particularly preferred analysis operations include, e.g., sequence based analyses using a hybridization array comprising an ordered plurality of first and/or second identifying linker oligonucleotides and/or an analysis based on separation of single stranded polynucleotide tags comprised in a hybrid polynucleotide tag further comprising a molecular identifier and/or a selectively detectable label or a chimeric polynucleotide tag further comprising a molecular identifier and/or a selectively detectable label, i.e. analyses using, e.g., microcapillary array electrophoresis.

Single Stranded Polynucleotide Tag Analysis Using a Microfluid Device Comprising a Hybridization Array In one embodiment, following sample preparation, the biological sample comprising the single stranded polynucleotide probe is processed and the single stranded polynucleotide tag thus obtained is analysed using a hybridization array comprising a plurality of identifying linker oligonucleotides.

Accordingly, it shall be understood that the below description of single stranded polynucleotide tag characterization using a hybridization array comprising a plurality of ordered first and/or second identifying linker oligonucleotides may take place with or without the use of a microfluid device comprising the array. Furthermore, when sample processing occurs in one microfluid device, the processed sample comprising the at least one single stranded polynucleotide tag may be analysed in said device with or without using a hybridization array comprising an ordered plurality of first and/or second identifying linker oligonucleotides, or the sample may be transferred to another microfluid device comprising a hybridization array comprising an ordered plurality of first and/or second identifying linker oligonucleotides, or the sample may be transferred to a hybridization array that does not form part of a microfluid device. However, in one preferred embodiment of the present invention, a microfluid device, optionally comprising a hybridization array comprising an ordered plurality of first and/or second identifying linker oligonucleotides, is used for sample handling and single stranded polynucleotide tag analysis and characterization.

The method of the present invention for characterizing a single stranded polynucleotide tag employs, in one preferred embodiment, a set of relatively short first and/or second identifying linker oligonucleotides comprising a predetermined, single stranded first and/or second nucleotide sequence, respectively, to search for and identify complementary sequences comprised in a single stranded polynucleotide strand.

The ratio of first and/or second identifying linker oligonucleotides to single stranded polynucleotide tags may differ in various preferred embodiments. When analysing tags of unknown sequence, all possible combinations of single stranded nucleotides sequences comprised in a first and/or second identifying linker oligonucleotide may be employed. The maximum number of possible combinations is in one preferred embodiment given by $4^n$, wherein n denotes the number of nucleotides in the single stranded part of the first and/or second identifying linker oligonucleotide. For other purposes including e.g. diagnostic purposes, the number of first and/or second identifying linker oligonucleotides may be significantly less. This is indicated by stating that a subset of first and/or second identifying linker oligonucleotides are present in the hybridization array. Such a subset may vary in numbers, and it may comprise e.g. numbers corresponding to about 90% of all possible combinations of single stranded nucleotide sequence, such as 80% of such combinations, for example 75% of such combinations, such as 70% of such combinations, for example 65% of such combinations, such as 60% of such combinations, for example 55% of such combinations, such as 50% of such combinations, for example 40% of such combinations, such as 35% of such combinations, for example 30% of such combinations, such as 25% of such combinations, for example 20% of such combinations, or less than about 20% of such combinations.

One strategy of single stranded polynucleotide tag identification can be illustrated by the following example. An ssDNA tag comprising e.g. 10 or more nucleotides is contacted with a hybridization array comprising a complete set of first and/or second identifying linker oligonucleotides, or a subset thereof. Preferably, at least one of the first and/or second identifying linker oligonucleotides will perfectly hybridize to the ssDNA tag sequence. The identity of the first and/or second identifying linker oligonucleotides at each site is known. Thus, by determining the locations at which the tag hybridizes on the array, or the hybridization pattern, one can determine the sequence of the tag sequence.

While first and/or second identifying linker oligonucleotides may be prepared comprising every possible first and/or second single stranded sequence of length n, respectively, it may be desirable, when practicing the present invention, to provide a hybridization array comprising a plurality of ordered first and/or second identifying linker oligonucleotides which is specific and complementary to a particular nucleotide sequence comprised in a predetermined subset of single stranded polynucleotide tags.

For example, in particularly preferred aspects including diagnostic applications, the hybridization array will comprise first and/or second identifying linker oligonucleotides comprising single stranded nucleotide sequences which are complementary to specific, predetermined ssDNA tag sequences, and/or any number or plurality of individual or multiple mutations of these.

Such arrays are particularly useful in the diagnosis of specific disorders which are characterized by the presence of a particular nucleic acid sequence. For example, the tag sequence may be that of a particular exogenous disease causing agent, e.g., human immunodeficiency virus (see, U.S. application Ser. No. 08/284,064, now abandoned, previously incorporated herein by reference), or alternatively, the tag sequence may be that portion of the human genome which is known to be mutated in instances of a particular disorder, i.e., sickle cell anemia (see, e.g., U.S. application Ser. No. 08/082,937, now abandoned, previously incorporated herein by reference) or cystic fibrosis.

For such applications, the array may comprise a plurality of hybridization arrays comprising a plurality of ordered first and/or second identifying linker oligonucleotides, such as two, three, or at least four sets of first and/or second identifying linker oligonucleotides.

A first hybridization array preferebly comprises a first and/or second identifying linker oligonucleotide set comprising a single stranded nucleotide sequence complementary to the nucleotide sequence of the ssDNA tag. Any first and/or second identifying linker oligonucleotide is related to an ssDNA tag comprising a nucleotide sequence complementary to the single stranded part of each first and/or second identifying linker oligonucleotide. Thus, each first and/or second identifying linker oligonucleotide has a position, designated a predetermined position, that is occupied by a nucleotide sequence complementary to the corresponding nucleotide sequence comprised in a single stranded polynucleotide tag capable of hybridizing thereto.

The sample comprising at least one single stranded polynucleotide tag is preferably incubated with the hybridization array comprising a plurality of ordered first and/or second identifying linker oligonucleotides in a hybridization chamber of a microfluid device. Hybridization between the single stranded polynucleotide tag and the first and/or second identifying linker oligonucleotides in the hybridization array is suitably. detected, using, e.g., epifluorescence confocal microscopy.

In one embodiment, the sample comprising at least one single stranded polynucleotide tag is subjected to mixing, e.g. stirring or shaking, when the hybridization is performed. This is to enhance hybridization of ssDNA tag in the sample to first and/or second identifying linker oligonucleotides comprised in the array. Mixing may be carried out by any method described herein, e.g., through the use of piezoelectric elements, electrophoretic methods, or physical mixing by pumping fluids into and out of the hybridization chamber, i.e., into an adjoining chamber.

In one embodiment, the detection operation will be performed using a reader device external to the diagnostic device. However, it may be desirable in some cases, to incorporate the data gathering operation into the diagnostic device itself. Novel systems for direct electronic detection of hybridization/ligation locations on the array will be set forth herein.

The hybridization/ligation data is next analyzed to determine the presence or absence of a particular ssDNA tag sequence within the sample.

In some cases, hybridized oligonucleotides may be labeled following hybridization. For example, where biotin labeled dNTPs are used in, e.g., amplification or transcription, streptavidin linked reporter groups may be used to label hybridized complexes. Such operations are readily integratable into the systems of the present invention, requiring the use of various mixing methods as is necessary.

Capillary Electrophoresis

In some embodiments, it may be desirable to provide an additional, or alternative means for analyzing the nucleic acids from the sample. Accordingly, in one embodiment, the device of the invention will optionally or additionally comprise a micro capillary array for analysis of the nucleic acids obtained from the sample. In this embodiment, the first and/or second identifying linker oligonucleotides preferably further comprises a molecular identifier capable of being manipulated according to size and/or molecular weight and/or charge.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, Proc. Nat'l Acad. Sci. USA (1994) 91:11348–11352. Microcapillary array electrophoresis generally provides a rapid method for size based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods.

Microfabrication of microfluidic devices including microcapillary electrophoretic devices has been discussed in detail in, e.g., Jacobsen, et al., Anal. Chem. (1994) 66:1114–1118, Effenhauser, et al., Anal. Chem. (1994) 66:2949–2953, Harrison, et al., Science (1993) 261:895–897, Effenhauser, et al. Anal. Chem. (1993) 65:2637–2642, and Manz, et al., J. Chromatog. (1992) 593:253–258.

Typically, these methods comprise photolithographic etching of micron scale channels on a silica, silicon or other rigid substrate or chip, and can be readily adapted for use in the miniaturized devices of the present invention. In some embodiments, the capillary arrays may be fabricated from the same polymeric materials described for the fabrication of the body of the device, using the injection molding techniques described herein. In such cases, the capillary and other fluid channels may be molded into a first planar element. A second thin polymeric member having ports corresponding to the termini of the capillary channels disposed therethrough, is laminated or sonically welded onto the first to provide the top surface of these channels. Electrodes for electrophoretic control are disposed within these ports/wells for application of the electrical current to the capillary channels. Through use of a relatively thin sheet as the covering member of the capillary channels, heat generated during electrophoresis can be rapidly dissipated. Additionally, the capillary channels may be coated with more thermally conductive material, e.g., glass or ceramic, to enhance heat dissipation.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Gel matrices may be introduced and polymerized within the capillary channel. However, in some cases, this may result in entrapment of bubbles within the channels which can interfere with sample separations. Accordingly, it is often desirable to place a preformed separation matrix within the capillary channel(s), prior to mating the planar elements of the capillary portion. Fixing the two parts, e.g., through sonic welding, permanently fixes the matrix within the channel. Polymerization outside of the channels helps to ensure that no bubbles are formed. Further, the pressure of the welding process helps to ensure a void-free system. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

Data Gathering and Single Stranded Polynucleotide Tag Analysis

Gathering data from the various analysis operations, e.g., hybridization arrays and/or microcapillary arrays, is carried out using any method known in the art. For example, the arrays may be scanned using lasers to excite fluorescently labeled tags that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Particularly preferred scanning devices are generally described in, e.g., U.S. Pat Nos. 5,143,854 and 5,424,186.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of the single stranded part of first and/or second identifying linker oligonucleotides hybridized to a single stranded polynucleotide tag, normalization of background.

Single Stranded Polynucleotide Tag Characterization for Diagnostic Purposes

When used for diagnostic purposes, the present invention may in one preferred embodiment exploit a microfluid device comprising a part used primarily for sample processing purposes and/or analytical purposes, as well as a part used primarily for diagnostic purposes.

A schematic presentation of a representative microfluid device is disclosed e.g. in U.S. Pat. No. 6,168,948, incorporated herein by reference, wherein the analytical part comprises one or more compartments for sample collection, one or more compartments for sample preparation or sample processing, and one or more compartments for sample analysis, as well as suitable systems for data acquisition, data analysis, and data interpretation. The microfluid device may further comprise a diagnostic part for performing one or more of the operations of sample collection, preparation and/or analysis using, e.g., hybridization and/or separation according to size, molecular weight, or charge, of a molecular identifier.

The diagnostic part of the device can be connected to a reader device in order to detect the hybridization and/or separation information contained in the device. The hybridization and/or separation data is reported from the reader device to a computer which is programmed with appropriate software for interpreting the data obtained by the reader device from the diagnostic device.

Interpretation of the data from the diagnostic device may be used in a variety of ways, including single stranded polynucleotide tag identification and/or nucleic acid sequencing directed towards a particular disease or a particular disease causing agent, such as viral or bacterial infections, e.g., AIDS, malaria, etc., or genetic disorders, e.g., sickle cell anemia, cystic fibrosis, Fragile X syndrome, Duchenner muscular dystrophy, gene expression and the like.

When used for diagnostic and/or analytical purposes, including single stranded polynucleotide tag characterization and/or sequence determination, the device generally comprises a number of discrete reaction, storage and/or analytical chambers disposed within a single unit or body. While referred to herein as a "diagnostic device," those of skill in the art will appreciate that the device of the invention wilt have a variety of applications outside the scope of diagnostics, alone. Such applications include sample identification and characterization applications (for, e.g., taxonomic studies, forensic applications, i.e., criminal investigations, and the like).

Typically, the body of the device defines the various reaction chambers and fluid passages in which the above described operations are carried out. Fabrication of the body, and thus the various chambers and channels disposed within the body may generally be carried out using one or a combination of a variety of well known manufacturing techniques and materials. Generally, the material from which the body is fabricated will be selected so as to provide maximum resistance to the full range of conditions to which the device will be exposed, e.g., extremes of temperature, salt, pH, application of electric fields and the like, and will also be selected for compatibility with other materials used in the device. Additional components may be later introduced, as necessary, into the body. Alternatively, the device may be formed from a plurality of distinct parts that are later assembled or mated. For example, separate and individual chambers and fluid passages may be assembled to provide the various chambers of the device.

As a miniaturized device, the body of the microfluid device as described herein will typically be approximately 1 to 20 cm in length by about 1 to 10 cm in width by about 0.1 cm to about 2 cm thick. Although indicative of a rectangular shape, it will be readily appreciated that the devices of the invention may be embodied in any number of shapes depending upon the particular need. Additionally, these dimensions will typically vary depending upon the number of operations to be performed by the device, the complexity of these operations and the like. As a result, these dimensions are provided as a general indication of the size of the device.

The number and size of the reaction chambers included within the device will also vary depending upon the specific application for which the device is to be used. Generally, the device will include at least two distinct reaction chambers, and preferably, at least three, four or five distinct reaction chambers, all integrated within a single body. Individual reaction chambers will also vary in size and shape according to the specific function of the reaction chamber.

For example, in some cases, circular reaction chambers may be employed. Alternatively, elongate reaction chambers may be used. In general however, the reaction chambers will be from about 0.05 mm to about 20 mm in width or diameter, preferably from about 0.1 mm to about 2.0 mm in width or diameter and about 0.05 mm to about 5 mm deep, and preferably 0.05 mm to about 1 mm deep. For elongate chambers, length will also typically vary along these same ranges.

Microfluid channels, on the other hand, are typically distinguished from chambers in having smaller dimensions relative to the chambers, and will typically range from about 10 $\mu$m to about 1000 $\mu$m wide, preferably, 100 $\mu$m to 500 $\mu$m wide and about 1 $\mu$m to 500 $\mu$m deep. Although described in terms of reaction chambers, it will be appreciated that these chambers may perform a number of varied functions, e.g., as storage chambers, incubation chambers, mixing chambers and the like.

In some cases, a separate chamber or chambers may be used as volumetric chambers, e.g., to precisely measure fluid volumes for introduction into a subsequent reaction chamber. In such cases, the volume of the chamber will be dictated by volumetric needs of a given reaction. Further, the device may be fabricated to include a range of volumetric chambers having varied, but known volumes or volume ratios (e.g., in comparison to a reaction chamber or other volumetric chambers).

As described above, the body of the device is generally fabricated using one or more of a variety of methods and materials suitable for microfabrication techniques. For example, in preferred aspects, the body of the device may comprise a number of planar members that may individually be injection molded parts fabricated from a variety of polymeric materials, or may be silicon, glass, or the like. In the case of substrates like silica, glass or silicon, methods for etching, milling, drilling, etc., may be used to produce wells and depressions which make up the various reaction chambers and fluid channels within the device.

Microfabrication techniques, such as those regularly used in the semiconductor and microelectronics industries are particularly suited to these materials and methods. These techniques include, e.g., electrodeposition, low-pressure vapor deposition, photolithography, wet chemical etching, reactive ion etching (RIE), laser drilling, and the like. Where these methods are used, it will generally be desirable to fabricate the planar members of the device from materials similar to those used in the semiconductor industry, i.e., silica, silicon, gallium arsenide, polyimide substrates. U.S. Pat. No. 5,252,294, to Kroy, et al., incorporated herein by reference in its entirety for all purposes, reports the fabrication of a silicon based multiwell apparatus for sample handling in biotechnology applications.

Photolithographic methods of etching substrates are particularly well suited for the microfabrication of these substrates and are well known in the art. For example, the first sheet of a substrate may be overlaid with a photoresist. An electromagnetic radiation source may then be shone through a photolithographic mask to expose the photoresist in a pattern which reflects the pattern of chambers and/or channels on the surface of the sheet. After removing the exposed photoresist, the exposed substrate may be etched to produce the desired wells and channels. Generally preferred photoresists include those used extensively in the semiconductor industry. Such materials include polymethyl methacrylate (PMMA) and its derivatives, and electron beam resists such as poly(olefin sulfones) and the like (more fully discussed in, e.g., Ghandi, "VLSI Fabrication Principles," Wiley (1983) Chapter 10, incorporated herein by reference in its entirety for all purposes).

As an example, the wells manufactured into the surface of one planar member make up the various reaction chambers of the device. Channels manufactured into the surface of this or another planar member make up fluid channels which are used to fluidly connect the various reaction chambers. Another planar member is then placed over and bonded to the first, whereby the wells in the first planar member define cavities within the body of the device which cavities are the various reaction chambers of the device. Similarly, fluid channels manufactured in the surface of one planar member, when covered with a second planar member define fluid passages through the body of the device. These planar members are bonded together or laminated to produce a fluid tight body of the device.

Bonding of the planar members of the device may generally be carried out using a variety of methods known in the art and which may vary depending upon the materials used. For example, adhesives may generally be used to bond the planar members together. Where the planar members are, e.g., glass, silicon or combinations thereof, thermal bonding, anodic/electrostatic or silicon fusion bonding methods may be applied. For polymeric parts, a similar variety of methods may be employed in coupling substrate parts together, e.g., heat with pressure, solvent based bonding. Generally, acoustic welding techniques are generally preferred. In a related aspect, adhesive tapes may be employed as one portion of the device forming a thin wall of the reaction chamber/channel structures.

Although primarily described in terms of producing a fully integrated body of the device, the above described methods can also be used to fabricate individual discrete components of the device which are later assembled into the body of the device.

In additional embodiments, the body may comprise a combination of materials and manufacturing techniques described above. In some cases, the body may include some parts of injection molded plastics, and the like, while other portions of the body may comprise etched silica or silicon planar members, and the like. For example, injection molding techniques may be used to form a number of discrete cavities in a planar surface which define the various reaction chambers, whereas additional components, e.g., fluid channels, arrays, etc, may be fabricated on a planar glass, silica or silicon chip or substrate. Lamination of one set of parts to the other will then result in the formation of the various reaction chambers, interconnected by the appropriate fluid channels.

In particularly preferred embodiments, the body of the device is made from at least one injection molded, press molded or machined polymeric part that has one or more wells or depressions manufactured into its surface to define several of the walls of the reaction chamber or chambers. Molds or mold faces for producing these injection molded parts may generally be fabricated using the methods described herein for, e.g., conventional machining or silicon molds. Examples of suitable polymers for injection molding or machining include, e.g., polycarbonate, polystyrene, polypropylene, polyethylene, acrylic, and commercial polymers such as Kapton, Valox, Teflon, ABS, Delrin and the like. A second part that is similarly planar in shape is mated to the surface of the polymeric part to define the remaining wall of the reaction chamber(s). Published PCT Application No. 95/33846, incorporated herein by reference, describes a device that is used to package individual hybridization array comprising a plurality of ordered first and/or second identifying linker oligonucleotides. The device includes a hybridization chamber disposed within a planar body. The chamber is fluidly connected to an inlet port and an outlet port via flow channels in the body of the device. The body includes a plurality of injection molded planar parts that are mated to form the body of the device, and which define the flow channels and hybridization chamber.

The surfaces of the fluid channels and reaction chambers which contact the samples and reagents may also be modified to better accommodate a desired reaction. Surfaces may be made more hydrophobic or more hydrophilic depending upon the particular application. Alternatively, surfaces may be coated with any number of materials in order to make the overall system more compatible to the reactions being carried out. For example, in the case of nucleic acid analyses, it may be desirable to coat the surfaces with a non-stick coating, e.g., a Teflon, parylene or silicon, to prevent adhesion of nucleic acids to the surface. Additionally, insulator coatings may also be desirable in those instances where electrical leads are placed in contact with fluids, to prevent shorting out, or excess gas formation from electrolysis. Such insulators may include those well known in the art, e.g., silicon oxide, ceramics or the like.

Below is illustrated preferred embodiments of the present invention related to single stranded polynucleotide tag analysis and characterization. The analysis and characterization, including characterizations for diagnostic purposes, includes in preferred embodiment of using microfluid devices and hybridization arrays as described herein above.

Method for Generating a Hybrid Polynucleotide Tag

When it is desirable to i) characterise and/or ii) separate and/or identify a single stranded polynucleotide tag according to the present invention, or desirable to determine the amount of the at least one single stranded polynucleotide tag, the present invention in one preferred embodiment provides a method for generating a hybrid polynucleotide tag by hybridizing a single stranded polynucleotide tag to a first and/or second identifying linker oligonucleotide. The hybrid polynucleotide tag may subsequently be subjected to a ligation, preferably an enzymatic ligation, resulting in the ligation of the single stranded polynucleotide tag to the first and/or second identifying linker oligonucleotide in the form of a chimeric polynucleotide tag.

Accordingly, the method comprises the step of forming a hybrid polynucleotide tag and/or a chimeric polynucleotide tag between at least one single stranded polynucleotide tag and a complementary, single stranded first unique nucleotide sequence of a first identifying linker oligonucleotide, said method comprising the steps of i) providing a sample preferably comprising at least one single stranded polynucleotide tag, or a plurality of samples obtained by dividing a composition comprising a plurality of single stranded polynucleotide tags into at least about 4 samples, for example at least about 16 samples, such as at least about 256 samples, for example at least about 1024 samples, such as at least about 4096 samples, ii) contacting each of the plurality of samples, or a subset thereof, provided in step i) with at least one first identifying linker oligonucleotide, or a plurality of first identifying linker oligonucleotides, wherein each first identifying linker oligonucleotide comprises a single stranded first unique nucleotide sequence, wherein the at least one single stranded polynucleotide tag, or each of the plurality of single stranded polynucleotide tags, or a subset thereof, in each of the samples is contacted with essentially only one first identifying linker oligonucleotide comprising a single stranded first unique nucleotide sequence, wherein preferably each sample is contacted with essentially all possible combinations of single stranded first unique nucleotide sequences of the first identifying linker oligonucleotide, or a predetermined subset of such combinations, wherein at least one single stranded polynucleotide tag in each sample comprises a polynucleotide sequence, or a part thereof, complementary to a single stranded first unique nucleotide sequence of at least one first identifying linker oligonucleotide contacting the sample, wherein the contacting of each of the plurality of samples, or a subset thereof provided in step i), with at least one or a plurality of first identifying linker oligonucleotides, occurs under conditions allowing a hybridization to occur between a) at least one first identifying linker oligonucleotide comprising a single stranded first unique nucleotide sequence, and b) at least one single stranded polynucleotide tag complementary to the single stranded first unique nucleotide sequence, and optionally iii) removing by means of one or more washing steps any unhybridized material from the hybrid polynucleotide tags and/or the chimeric polynucleotide tags formed between the single stranded polynucleotide tag and the complementary, single stranded first unique nucleotide sequence of the first identifying linker oligonucleotide.

The plurality or subset of first identifying linker oligonucleotides will typically comprise a molecular identifier and/or be attached to a solid support, preferably a solid support comprising a hybridization array in the form of an ordered plurality of first identifying linker oligonucleotides.

Accordingly, substantially each of the plurality or subset of first identifying linker oligonucleotides may further comprise a molecular identifier capable of characterizing and/or separating the linker oligonucleotides and/or hybrid oligonucleotide tags according to i) the molecular weight and/or ii) charge and/or iii) an electromagnetic property and/or iv) an ability to emit electromagnetic radiation after excitation of individual linker oligonucleotides comprising individual molecular identifiers.

Substantially each of the plurality or subset of first identifying linker oligonucleotides may also comprise, or comprise in addition to a molecular identifier, a selectively detectable label capable of identifying substantially individual identifying linker oligonucleotides and/or hybrid oligonucleotide tags forming part of a plurality of such oligonucleotides, or a subset thereof.

In one embodiment, the maximum number of combinations of single stranded first unique nucleotide sequences is $4^n$, wherein n denotes the number of nucleotides in the unique, single stranded nucleotide sequence comprised in the identifying linker oligonucleotides.

In one embodiment, substantially each single stranded polynucleotide tag is ligated to a first identifying linker oligonucleotide hybridized thereto, preferably by means of an enzyme catalysed ligation.

Each sample comprising the at least one single stranded polynucleotide tag may be located in the same compartment, or located in separate containers.

The at least one or a plurality of first identifying linker oligonucleotides may preferably comprise a recognition motif for a site-specific restriction endonuclease, wherein the recognition motif is correlated to the sequence of nucleotides in the single stranded first, unique nucleotide sequence. For such identifying linker oligonucleotides, there is provided the embodiment of i) obtaining at least one or a plurality of chimeric polynucleotide tags comprising a first identifying linker oligonucleotide,
ii) contacting and cleaving the at least one or a plurality of chimeric polynucleotide tags comprising
  a) a single stranded polynucleotide tag and
  b) a complementary, single stranded first unique nucleotide sequence of a first identifying linker oligonucleotide
  with a site-specific restriction endonuclease capable of recognising the recognition motif, and
iii) obtaining at least one or a plurality of chimeric polynucleotide tag fragments, and optionally
iv) substituting a phosphate group and/or an OH-group at one or both ends of the single stranded polynucleotide tag with a molecular moiety preventing the substituted, single stranded polynucleotide tag from participating in a ligase reaction including a ligase chain reaction, and further optionally,
v) contacting at least one or a plurality of second identifying linker oligonucleotides each comprising a single stranded, unique second nucleotide sequence with the at least one or a plurality of chimeric polynucleotide tag fragments obtained in step iii).

Each recognition motif may be recognised by a different site-specific restriction endonuclease or by the same site-specific restriction endonuclease. In a further step the method involves contacting the at least one or a plurality of chimeric polynucleotide tags with a site-specific nicking endonuclease capable of recognising a recognition motif of the chimeric polynucleotide tag fragment and cleaving a single strand of said fragment and providing a single stranded polynucleotide tag.

In another embodiment, there is provided a method wherein the at least one or a plurality of first identifying linker oligonucleotides comprises a recognition motif for a site-specific nicking endonuclease, wherein the recognition motif is correlated to the sequence of nucleotides in the single stranded first, unique nucleotide sequence. In this embodiment, the method comprises the further steps of i) obtaining at least one or a plurality of chimeric polynucleotide tags comprising a first identifying linker oligonucleotide,
ii) contacting and cleaving the at least one or a plurality of chimeric polynucleotide tags comprising
  a) a single stranded polynucleotide tag and
  b) a complementary, single stranded first unique nucleotide sequence of a first identifying linker oligonucleotide
  with a site-specific nicking endonuclease capable of recognising the recognition motif, and
iii) obtaining at least one or a plurality of single stranded polynucleotide tags, and optionally
iv) substituting a phosphate group and/or an OH-group at one or both ends of the single stranded polynucleotide tag with a molecular moiety preventing the substituted, single stranded polynucleotide tag from participating in a ligase reaction including a ligase chain reaction, and further optionally,
v) contacting at least one or a plurality of second identifying linker oligonucleotides each comprising a single stranded, unique second nucleotide sequence with the at least one or a plurality of single stranded polynucleotide tags obtained in step iii).

Each recognition motif may be recognised by a different site-specific nicking endonuclease or by the same site-specific nicking endonuclease. The method pertaining to this embodiment may comprise the further step of contacting the at least one or a plurality of chimeric polynucleotide tags with a site-specific restriction endonuclease capable of recognising a recognition motif of the chimeric polynucleotide tag fragment and cleaving said fragment.

When involving the step of contacting second identifying linker oligonucleotides, the plurality or subset of second identifying linker oligonucleotides may comprise a molecular identifier or be attached to a solid support including a hybridization array in the form of an ordered plurality of second identifying linker oligonucleotides.

In one preferred embodiment, substantially each chimeric polynucleotide tag fragment is subsequently ligated to a second identifying linker oligonucleotide hybridized thereto, preferably by means of an enzyme catalysed ligation.

In one embodiment, it is preferred that substantially each of the plurality or subset of second identifying linker oligonucleotides further comprises a molecular identifier capable of characterizing and/or separating the linker oligonucleotides and/or hybrid oligonucleotide tags and/or chimeric polynucleotide tags according to individual linker oligonucleotides properties such as e.g. i) the molecular weight and/or ii) charge and/or iii) an electromagnetic property and/or iv) an ability to emit electromagnetic radiation after excitation of individual linker oligonucleotides comprising individual molecular identifiers.

In the same embodiment, or in another embodiment, substantially each of the plurality or subset of second identifying linker oligonucleotides further comprises a selectively detectable label capable of identifying substantially individual identifying linker oligonucleotides and/or hybrid oligonucleotide tags and/or chimeric oligonucleotide tags forming part of a plurality of such oligonucleotides, or a subset thereof.

In one embodiment, the maximum number of combinations of single stranded second unique nucleotide sequences is $4^n$, wherein n denotes the number of nucleotides in the unique nucleotide sequence comprised in a first and/or second identifying linker oligonucleotide. Each sample comprising the at least one single stranded polynucleotide tag is preferably located in the same container or in separate containers.

Method for Sequence Determination of at Least a Part of a Single Stranded Polynucleotide Tag In another preferred embodiment of the present invention there is provided a method for determining at least part of the sequence of a single stranded polynucleotide tag hybridized or ligated to an identifying linker oligonucleotide, said method comprising the further steps of i) contacting
  a) a solid support comprising a hybridization array comprising an ordered plurality of first identifying linker oligonucleotides comprising a single stranded first unique oligonucleotide sequence, with
  b) a sample comprising at least one single stranded polynucleotide tag, or a plurality of samples obtained by dividing a composition comprising a plurality of single stranded polynucleotide tags into at least about 4 samples, for example at least about 16 samples, such as at least about 256 samples, for example at least about 1024 samples, such as at least about 4096 samples,
  wherein each set of first identifying linker oligonucleotides comprising a single stranded first unique oligonucleotide sequence is identifiable by their location in the hybridization array,
  wherein essentially all possible combinations of single stranded first unique nucleotide sequences of first identifying linker oligonucleotides, or a subset of such combinations, are represented in the array,
  wherein at least one single stranded polynucleotide tag comprised in the sample is hybridized to a complementary single stranded first unique nucleotide sequences of a first identifying linker oligonucleotide,
  wherein the hybridization of the at least one single stranded polynucleotide tag to a complementary single stranded first unique nucleotide sequence occurs at an identifiable position in the hybridization array,
  wherein said hybridization generates a hybrid nucleotide tag comprising the at least one single stranded polynucleotide tag hybridized to a complementary single stranded first unique nucleotide sequence of a first identifying linker oligonucleotide, and optionally
ii) determining the position in the hybridization array of the hybrid polynucleotide tag, by
iii) correlating the position in the hybridization array of the hybrid polynucleotide tag with the corresponding single stranded first unique nucleotide sequence, and
iv) determining the sequence of the part of the single stranded polynucleotide tag that is hybridized to the complementary single stranded first unique nucleotide sequence at the determined position in the hybridization array.

In one preferred embodiment, substantially each tag is ligated to the first identifying linker oligonucleotide hybridized thereto, preferably by means of an enzyme catalysed ligation.

Substantially each of the plurality or subset of first identifying linker oligonucleotides may preferably further comprise a molecular identifier capable of characterizing and/or separating the linker oligonucleotides and/or hybrid oligonucleotide tags and/or chimeric oligonucleotide tags according to properties of individual molecular identifiers such as e.g. i) the molecular weight and/or ii) charge and/or iii) an electromagnetic property and/or iv) an ability to emit electromagnetic radiation after excitation of individual linker oligonucleotides comprising individual molecular identifiers.

In the same or in another embodiment,.substantially each of the plurality or subset of first identifying linker oligonucleotides may further comprise a selectively detectable label capable of identifying substantially individual identifying linker oligonucleotides and/or hybrid oligonucleotide tags and/or chimeric oligonucleotides forming part of a plurality of such oligonucleotides, or a subset thereof.

The maximum number of combinations of single stranded first unique nucleotide sequences is preferably $4^n$, wherein n denotes the number of nucleotides in the unique nucleotide sequence, and each sample comprising the at least one single stranded polynucleotide tag is located in the same or separate containers.

Method for Determining the Sequence of a Single Stranded Polynucleotide Tag

Having determined at least a part of the nucleotide sequence of a single stranded polynucleotide tag as described herein immediately above, the present invention further relates to a method comprising the further steps of determining at least part of the sequence of the tag not hybridized to the single stranded, first unique nucleotide sequence of a first identifying linker oligonucleotide, said method comprising the further steps of i) contacting at least one or a plurality of hybrid or chimeric polynucleotide tags, each comprising a single stranded polynucleotide tag, with at least one or a plurality of second identifying linker oligonucleotides,
  wherein each second identifying linker oligonucleotide comprises a single stranded, second unique oligonucleotide sequence,
  wherein the single stranded, unique second nucleotide sequence of each second identifying linker oligonucleotide comprises essentially all possible combinations of second oligonucleotide sequences, or a subset of such sequences,
  wherein each second identifying linker oligonucleotide further comprises at least one molecular identifier and/or at least one selectively detectable label capable of identifying the second identifying linker oligonucleotide,
  wherein the contacting of step i) occurs under conditions allowing a hybridization to occur between at least one of second identifying linker oligonucleotide and at least one hybrid polynucleotide tag, and optionally removing any unhybridized second identifying linker oligonucleotide,
ii) determining the presence and/or amount of any hybridized second identifying linker oligonucleotide comprising a second unique oligonucleotide sequence by means of detection of the label and/or the molecular identifier, and optionally
iii) repeating steps i) and/or ii) until substantially all of the second identifying linker oligonucleotides in the hybridization array, or a predetermined subset thereof, have been tested.

In the above described methods, any hybridization step is preferably followed by or performed simultaneously with a ligation step, including any ligation step catalysed by a ligase enzyme.

Method for Amplification of a Hybrid Polynucleotide Tag or a Chimeric Polynucleotide Tag In one embodiment it may be desirable to amplify a hybrid or chimeric polynucleotide tag. Accordingly, there is provided method for amplification of a hybrid polynucleotide tag or a chimeric polynucleotide tag obtainable by any of the method according to the present invention claims, said method comprising the steps of i) obtaining at least one hybrid polynucleotide tag or at least one chimeric polynucleotide tag comprising
   a) a single stranded polynucleotide tag hybridized or ligated to one or both of
   b) a first identifying linker oligonucleotide comprising a single stranded, first unique oligonucleotide sequence, and
   c) a second identifying linker oligonucleotide comprising a single stranded, second unique oligonucleotide sequence
   wherein said first identifying linker oligonucleotide and said second idnetifying linker oligonucleotide comprises single stranded nucleotide sequences complementary to at least a part of the nucleotide sequence of the single stranded polynucleotide tag, and
ii) amplifying the at least one hybrid or chimeric polynucleotide tag.

The amplification preferably comprises an amplification step comprising a polymerase chain reaction (PCR) step, including an asymmetric PCR step, and/or a ligase chain reaction (LCR) step, including an asymmetric LCR step.

Method for Identifying a cDNA in a Biological Sample

In a further preferred preferred embodiment there is provided a method for identifying a cDNA in a biological sample, said method comprising the steps of any of the methods for obtaining and characterizing a single stranded polynucleotide tag as described herein above, as well as the further steps of i) comparing for at least one of a plurality of predetermined positions in a hybridization array, or for at least one of a plurality of predetermined positions in a capilary tube of a microfluid device,
   a) the sequence of the at least one single stranded polynucleotide tag and/or the amount of the at least one single stranded polynucleotide tag with
   b) the sequence and/or amount of a predetermined polynucleotide tag obtained from a predetermined cDNA, and
ii) identifying a cDNA present in the biological sample.

Method for Diagnosing a Clinical Condition

In a yet further preferred embodiment of the present invention, there is provided a method for diagnosing a clinical condition in an individual, preferably a human being, said method comprising the steps of i) determining for at least one of a plurality of predetermined positions in a hybridization array, or for at least one of a plurality of predetermined positions in a capilary tube of a microfluid device, at least one predetermined cDNA in a biological sample by performing a method of the present invention as described herein above,
   wherein each of the first identifying linker oligonucleotides comprises a predetermined single stranded, first unique oligonucleotide sequence,
   wherein each of the second identifying linker oligonucleotides comprises a predetermined single stranded, second unique oligonucleotide sequence,
   wherein at least one of said first and second identifying linker oligonucleotides comprises at least one selectively detectable molecular identifier and/or at least one selectively detectable label,
   wherein the predetermined cDNA is determined by assaying for a predetermined polynucleotide tag originating from said predetermined cDNA,
   wherein the predetermined polynucleotide tag originating from said predetermined cDNA comprises a nucleotide sequence complementary to the sequence of the first and second identifying linker oligonucleotides,
   wherein the at least one predetermined position in the hybridization array, or the at least one predetermined position in the capilary tube of a microfluid device, in combination with the determination of the at least one selectively detectable molecular identifier and/or the at least one selectively detectable label comprised by at least one of said first and second identifying linker oligonucleotides, is positively correlated with the presence in the biological sample of the at least one predetermined cDNA, and
ii) diagnosing the clinical condition.

Preferably, in any one of the above methods, at least one cleavage agent including at least one site-specific nicking endonuclease is attached to a solid support. The solid support may be a compartment of a microfluid device, including a capilary tube. The ligation steps are also preferably carried out by a ligase attached to a solid support, including be a compartment of a microfluid device, including a capilary tube. When the solid support is a capilary tube the diameter of said tube is preferably less than 1 mm, such as less than 0.1 mm.

In yet another preferred embodiment there is provided the method of using a single stranded polynucleotide tag obtained according to the present invention in the preparative steps of the method of U.S. Pat. No. 6,013,445 pertaining to a method of nucleic acid sequence analysis based on the ligation of one or more sets of encoded adapters to at least the terminus of a single stranded polynucleotide tag according to the present invention. Encoded adapters whose protruding strands form perfectly matched duplexes with at least the complementary protruding strands of the single stranded polynucleotide tag are ligated, and the identity of the nucleotides in the protruding strands is determined by an oligonucleotide tag carried by the encoded adapter. Such determination, or "decoding" is carried out by specifically hybridizing a labeled tag complement to its corresponding tag on the ligated adapter.

Accordingly, there is provided a method of nucleic acid sequence analysis based on the ligation of one or more sets of encoded adapters to a single stranded polynucleotide tag according to the present invention (or to multiple single stranded polynucleotide tags according to the present inventions when used in a parallel sequencing operation). Each encoded adapter comprises a protruding strand and an oligonucleotide tag selected from a minimally cross-hybridizing set of oligonucleotides. Encoded adapters whose protruding stands form perfectly matched duplexes with the single stranded polynucleotide tag according to the present invention, or a part thereof, are ligated. After ligation, the identity and ordering of the nucleotides in he protruding strands are determined, or "decoded," by specifically hybridizing a labeled tag complement to its corresponding tag on the ligated adapter.

For example, if an encoded adapter with a protruding strand of four nucleotides, say 5'-AGGT, form a perfectly matched duplex with the complementary protruding strand of a single stranded polynucleotide tag according to the present invention and is ligated, the four complementary nucleotides, 3'-TCCA, on the polynucleotide may be identified by a unique oligonucleotide tag selected form a set of 256 such tags, one for every possible four nucleotide sequence of the protruding strands. Tag complements are applied to the ligated adapters under conditions which allow specific hybridization of only those tag complements that form perfectly matched duplexes (or triplexes) with the oligonucleotide tags of the ligated adapters. The tag complements may be applied individually or as one or more mixtures to determine the identity of the oligonucleotide tags, and therefore, the sequences of the protruding strands.

The encoded adapters may be used in sequence analysis either i) to identify one or more nucleotides as a step of a process that involves repeated cycles of ligation, identification, and cleavage, as described in Brenner U.S. Pat. No. 5,599,675, or ii) as a "stand alone" identification method, wherein sets of encoded adapters are applied to single stranded polynucleotide tags according to the present inventions such that each set is capable of identifying the nucleotide sequence of a different portion of a single stranded polynucleotide tag according to the present invention; that is, in the latter embodiment, sequence analysis is carried out with a single ligation for each set followed by identification.

An important feature of the encoded adapters is the use of oligonucleotide tags that are members of a minimally cross-hybridizing set of oligonucleotides, e.g; as described in International patent applications PCT/US95/12791 and PCT/US96/09513. The sequences of oligonucleotides of such a set differ from the sequences of every other member of the same set by at least two nucleotides. Thus, each member of such a set cannot form a duplex (or triplex) with the complement of any other member with less than two mismatches. Preferably, each member of a minimally cross-hybridizing set differs from every other member by as much nucleotides as possible consistent with the size of set required for a particular application. For example, where longer oligonucleotide tags are used, such as 12- to 20-mers for delivering labels to encoded adapters, then the difference between members of a minimally cross-hybridizing set is preferably significantly greater than two. Preferably, each member of such a set differs from every other member by at least four nucleotides. More preferably, each member of such a set differs from every other member by at least six nucleotides. Complements of oligonucleotide tags of the invention are referred to herein as "tag complements."

Oligonucleotide tags may be single stranded and be designed for specific hybridization to single stranded tag complements by duplex formation. Oligonucleotide tags may also be double stranded and be designed for specific hybridization to single stranded tag complements by triplex formation. Preferably, the oligonucleotide tags of the encoded adapters are double stranded and their tag complements are single stranded, such that specific hybridization of a tag with its complements occurs through the formation of a triplex structure.

Preferably, the method of the invention comprises the following steps: (a) ligating an encoded adapter to an end of a polynucleotide, the adapter having an oligonucleotide tag selected from a minimally cross-hybridizing set of oligonucleotides and a protruding strand complementary to a protruding strand of the polynucleotide; and (b) identifying one or more nucleotides in the protruding strand of the polynucleotide by specifically hybridizing a tag complement to the oligonucleotide tag of the encoded adapter.

Kit for Performing or Assaying Expression Profiling

There is also provided a kit for performing or assaying expression profiling and comprising at least one cleavage agent including at least one site-specific nicking endonuclease, at least one adapter oligonucleotide, and at least one identifying linker oligonucleotide.

In another embodiment, there is provided a kit for performing or assaying expression profiling and comprising a first identifying linker oligonucleotide comprising a single stranded part forming a 5' overhang, and a second identifying linker oligonucleotide comprising a single stranded part forming a 3' overhang. This kit may further comprise an adapter oligonucleotide.

When comprising an adapter oligonucleotide, such an adapter oligonucleotide preferably comprises at least one recognition motif for a site-specific nicking endonuclease.

The kits may further comprise at least one adapter oligonucleotide and/or at least one first and/or said second identifying linker oligonucleotide comprising one or more of i) a molecular identifier, ii) a selectively identifiable label, and a iii) recognition motif for a site-specific nicking endonuclease. One or more of said molecular identifier and said selectively identifiable label are preferably attached to a solid support including a hybridization array.

Solid Support Comprising a Hybridization Array

In a still further embodiment of the present invention there is provided a solid support, preferably a solid support comprising an array in the form of an ordered set of molecules comprising or essentially consisting of dsDNA and/or ssDNA fragments comprising permutated nucleotide sequences, wherein the solid support further comprises at least one single stranded polynucleotide tag according to the present invention.

The dsDNA and/or ssDNA fragments are preferably covalently attached to the solid support so that the DNA fragments are identified by their two dimensional position in the array. The array may also comprise an ordered set of e.g. identifying linkers covalently attached to an ordered set of molecular identifiers.

In one particularly preferred embodiment, there is provided a solid support comprising a hybridization array comprising a plurality of ordered first identifying linker oligonucleotides, or a subset of such oligonucleotides, wherein at least one of said first identifying linker oligonucleotides comprises a single stranded nucleotide sequence hybridized to at least one single stranded polynucleotide tag, and preferably only one such tag, comprising a sequence complementary thereto.

The single stranded polynucleotide tag is preferably obtained by any method of the invention as described herein. Alternatively, the single stranded polynucleotide tag is obtained by displacement of a double stranded polynucleotide tag comprising at least partly complementary nucleotide strands.

The solid support may be biological, non-biological, organic, inorganic, or a combination of any of these, existing as particles, strands, precipitates, gels, sheets, tubing, spheres, containers, capillaries, pads, slices, films, plates, slides, etc. The solid support is preferably flat but may take on alternative surface configurations.

The support may be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface Si—H functionalities, such as are found on silica surfaces.

In yet another preferred embodiment there is provided a kit comprising cleavage agents, adapter oligonucleotides, and molecular "identifiers" according to the invention for performing expression profiling.

EXAMPLE

The present example illustrates how three different plasmids can be used to simulate tag analysis in more complex biological systems. The example demonstrates the principles of how one would obtain and detect a single stranded polynucleotide tag. In a first step specific test RNA molecules are produced. A second step is concerned with the synthesis of custom oligos on magnetic beads. In step three, the test RNA molecules are used as templates for second strand synthesis. A single stranded tag comprising a sequence of 10 nucleotides is isolated in step four, and the single stranded tags are detected as described in step five.

". . ." as used herein below denotes an intervening sequence of varying length. "I" as used herein below indicates a 5'-3' bond in a hair-pin type structure, when connecting two nucleotides in a sequence printed over two lines.
Step 1: Production of Specific Test RNA Molecules:

PCR fragments from CTR1 (GenEMBL acc #U83460), CTR2 (GenEMBL acc #U83461), and HAH1 (GenEMBL acc #U70660), were amplified from human genomic DNA using the primers:

```
CTR1, BamHI, KOZAK                 (SEQ ID NO:44)
5'-CGCGGATCCGCCGCCATGGATCATTCCCACCATAT-3'

CTR1, Xba I                        (SEQ ID NO:45)
5'-GCTCTAGAACTGCAATCGATAAGGCCACGC-3'

CTR2, BamHI, KOZAK                 (SEQ ID NO:46)
5'-CGCGGATCCGCCGCCATGGCGATGCATTTCATCT-3'

CTR2, Xba I                        (SEQ ID NO:47)
5'-GCTCTAGAGCTTCAGCTCAAAGTTTCCAGG-3'

HAH1, BamHI, KOZAK                 (SEQ ID NO:48)
5'-CGCGGATCCGCCGCCATGCCGAAGCACGAGTTC-3'

HAH1 Xba I                         (SEQ ID NO:49)
5'-GCTCTAGAACTGCCAAGTCCCAGGTCTGTC-3'
```

Respectively, and cloned into the Bam HI and Xba I sites of the vector pcDNA3.1+ from Invitrogen. The three plasmids were named pCTR1, pCTR2, and pHAH respectively.

Using the ampcillin resistance marker on the plasmids, they were amplified in *E. coli* using standard procedures.

Using the two primers:

```
pcDNA3s
5'-ACCCACTGTTTACTGGCTTATC-3'       (SEQ ID NO:50)

pcDNA3c
5'-GAGGGGCAAACAGATGGC-3'           (SEQ ID NO:51)
```

PCR and cycle sequencing was carried out on each of the plasmids in order to verify and compare the sequence with the public database.

In separate tubes the three plasmids were digested with Dra III and the linearized plasmids were purified on a 0,7% agarose gel.

The purified linearized plasmids were used as templates in PCR reactions using as primes pcDNA3s and pcDNA3c.

The resulting PCR products were used as templates in a MAXI-script RNA transcription reaction using the T7 RNA polymerase.
Step 2: Production of Sera-Mag Beads with Custom Oligos Outlined below is the production of magnetic beads carrying the RT-primer.

Steps involved in creating specific RT primer attached to bead or solid support (–[1):

```
A:                       (SEQ ID NO:52; SEQ ID NO:53)
5'-
CCATCTGTTGTTTGCCCCTCAAAAAAAAAAAAAAAAAAAAAAAAA-3'

3'-TTTTTTTTTTTTTTTTTTTTTTTTT-5'-
[1
```

A: Primer Comprising a 5' end complementary to desired sequence and a 3' poly d(A) tail is annealed to a poly d(T) primer already attached to a bead or a solid support (–[1).

```
B:                       (SEQ ID NO:52; SEQ ID NO:54)
5'-CCATCTGTTGTTTGCCCCTCAAAAAAAAAAAAAAAAAAAAAAAAA-
3'

3'-GGTAGACAACAAACGGGGAGTTTTTTTTTTTTTTTTTTTTTTTTT-
5'-[1
```

B: A DNA polymerase elongates the poly d(T) primer.

```
C:                                      (SEQ ID NO:54)
3'-
CGTAGACAACAAACGGGGAGTTTTTTTTTTTTTTTTTTTTTTTTT-
5'-[1
```

C: The two strands are separated and isolated.
Step 3: Revers Transcriptase, and 2, Strand Synthesis.

Using the test RNA molecules described in step 1 as templates a revers transcriptase reaction was carried out using the RT-primer on Sera-Mag beads described in step 2. After melting the template RNA off the newly formed 1. strand, the second strand was synthesized using one of the following primes according to the origin of the test RNA (pCTR1, pCTR2, or pHAH).

```
CTR1, BamHI, KOZAK                 (SEQ ID NO:44)
5'-CGCGGATCCGCCGCCATGGATCATTCCCACCATAT-3'

CTR2, BamHI, KOZAK                 (SEQ ID NO:46)
5'-CGCGGATCCGCCGCCATGGCGATGCATTTCATCT-3'

HAH1, BamHI, KOZAK                 (SEQ ID NO:48)
5'-CGCGGATCCGCCGCCATGCCGAAGCACGAGTTC-3'
```

Step 4: Isolation of a 10-mer ss DNA Tag From cDNA Tracing Back to CTR1.

The dsDNA on the beads from step 3 was digested with Dde I followed by the ligation of the first adapter. The first adapter comprises two oligos hybridised together. One of them, 1. adap. B. has a biotin in the 5'-end. The first adapter comprises sites for Bpm I and N.Bst NB I and has a 5' overhang compatible with Dde I, and a biotin moiety (B) in the opposite end.

```
1st adap A                         (SEQ ID NO:55)
5'-TCAGACTCCAGACACCCACACAACCACAA-3'

1st adap B                         (SEQ ID NO:56)
(B)-5'-TTTTTTTTGTGGTTGTGTGGGTGTCTGGAGTC-3'
```

In the following example the steps involved in isolation of a 10-mer ssDNA tag from CTR1 in vitro transcribed and reverse transcribed ds cDNA is illustrated:

```
D:  5'-TGAGCTTTCCTCACCTCCTGCAAACAGTGCTGCACATCATC............TAGTTG-
    3'-CGAAAGGAGTGGAGGACGTTTGTCACGACGTGTAGTAG............ATCAAC-

CCAGCCATCTGTTGTTGCCCCTCCCCCGTGCCTT-3'
    GGTCGGTAGACAACAAACGGGGAGTTTTTTTTTTTTTTTTTTTTTTTT-5'-[1
(SEQ ID NO:57; SEQ ID NO:58; SEQ ID NO:59; SEQ ID NO:60)
```

D: After 1. and 2. strand synthesis the cDNA is digested with Dde I.

```
                               (SEQ ID NO:89)
E:  (B)-5'-TTTTTTTTGTGGTTGTGTGGGTGTCTGGAGTC-3'
                               (SEQ ID NO:90)
           3'-AACACCAACACACCCACACACCTCAGACT-5'
```

E: The first adapter.

```
F:  (B)-5'-TTTTTTTTGTGGTTGTGTGGGTGTCTGGAGTCTGAGCTTTCCTCACCTCCTGCA . . .
           3'-AACACCAACACACCCACACACCTCAGACTCGAAAGGAGTGGAGGACGT . . .

. . . AACAGTGCTGCCAGCCATCTGTTGTTTGCCCCTCCCCCGTGCCTT-3'
. . . TTGTCACGACGGTCGGTAGACAACAAACGGGGAGTTTTTTTTTTTTTTTTTTTTTTTTT-5'-[1
(SEQ ID NO:61; SEQ ID NO:62; SEQ ID NO:63; SEQ ID NO:64)
```

F: The adapter from E is ligated to digested cDNA from D.

```
H:
(B)-5'-TTTTTTTTGTGGTTGTGTGGGTGTCTGGAGTCTGAGCTTTCCT
                                                 CAC-3'
3'-AACACCAACACACCCACACACCTCAGACTCGAAAGGAG-5'
(SEQ ID NO:65; SEQ ID NO:66)
```

H: The resulting molecule is digested with Bpm I and the free fragment is isolated on a solid support coated with streptavidine.

```
I:  (B)-5'-TTTTTTTTGTGGTTGTGTGGGTGTCTGGAGTCTGAG-3'    5'-CTTTCCTCAC-3'
           3'-AACACCAACACACCCACACACCTCAGACTCGAAAGGAG-5'
(SEQ ID NO:66; SEQ ID NO:67; SEQ ID NO:68)
```

I: The molecule is now digested with N.BstNB I and the resulting ssDNA 10-mer is isolated.

Using the same approach the ssDNA 10-mer 5'-GCTGGAGGGA-3' ((SEQ ID NO:69) is isolated when RNA tracing back to pCTR2 is used, and the ssDNA 10-mer 5'-CACAGCATGG-3' (SEQ ID NO:70) is isolated when RNA tracing back to pHAH is used.

Step 5: Detection of ssDNA Tags.

Steps involved in creation of the immobilized discriminating adapters.

```
                                          (SEQ ID NO:71; SEQ ID NO:72; SEQ ID NO:73)
J:  CTR1 ID B  5'-CTCACTAAGGTTCAAAGGTTCAAACGGATCCAAAAAAAAAAAAAAAAAAAAAAAA-3'

CTR2 ID B  5'-AGGGATAAGGTTCAAAGGTTCAAACGGATCCAAAAAAAAAAAAAAAAAAAAAAAA-3'

HAH  ID B  5'-CATCGTAAGGTTCAAAGGTTCAAACGGATCCAAAAAAAAAAAAAAAAAAAAAAAA-3'
```

J: Just as when producing RT-primer on Sera-Mag beads in A, B, and C, primers comprising a 5' end complementary to desired sequence and a 3' poly d(A) tail is annealed to a poly d(T) primer already attached to a bead or a solid support. A DNA polymerase elongates the poly d(T) primer, and the two strands are separated and isolated. Individual 5' ends are selected that are identical to the 5' ends of the 10-mers isolated from CTR1, CTR2, and HAH1. A sequence separates the poly d(A) tail from the said 5' sequence. The only function of this middle sequence is to provide a spacer and a digestion site for Bam HI.

(SEQ ID NO:74)
K: 5'-TAAGGTTCAAAGGTTCAAACGGATCCAAAAAAA-3'

K: A common sequence only covering the common sequence of the three different 3' ends provided in J is annealed to the single stranded DNA molecules on Sera-Mag beads provided in J. But first this oligo is radiolabled for later detection using standard procedures.

L:
CTR1
```
     5'-TAAGGTTCAAAGGTTCAAACGGATCCAAAAAAA-3'
3'-GAGTGATTCCAAGTTTCCAAGTTTGCCTAGGTTTTTTTTTTTTTTT
                                  TTTTTTTTTT-5'-[1
```
(SEQ ID NO:75;.SEQ ID NO:76)

CTR2
```
     5'-TAAGGTTCAAAGGTTCAAACGGATCCAAAAAAA-3'
3'-TCCCTATTCCAAGTTTCCAAGTTTGCCTAGGTTTTTTTTTTTTTTTT
                                   TTTTTTTTT-5'-[1
```
(SEQ ID NO:77; SEQ ID NO:78)

HAH1
```
     5'-TAAGGTTCAAAGGTTCAAACGGATCCAAAAAAA-3'
3'-GTACCATTCCAAGTTTCCAAGTTTGCCTAGGTTTTTTTTTTTTTTTT
                                   TTTTTTTTT-5'-[1
```
(SEQ ID NO:79; SEQ ID NO:80)

L: The resulting adapters provide 3' overhangs capable of hybridising to a specific 10-mer and compatible for ligation of that 10-mer.

-continued
TTTT-ACACGAAATTGGGACCAAACCTTCC-3'

(SEQ ID NO:94)
|TTT-TCTGCTTTAACCCTGGTTTGGAAGG-CGACC-5'

HAH (SEQ ID NO:83)
5'-CTGTGGGTGTTGTGTGGAATTTCGTGTAAGGTCCCTTTTTTTGGGAC
CTTACACGAAATTCCACACAACACC-3'

(SEQ ID NO:95)
TTTT-GGGACCTTACACGAAATTCCACACAACACC-3'

(SEQ ID NO:96)
|TTT-CCCTGGAATGTGCTTTAAGGTGTGTTGTGG-GTGTC-5'

M: Three adapters of different length and capable of forming a hair-pin structure and having 5' ends complementary to the 3' ends of the 10-mers isolated from CTR1, CTR2, and HAH1 are synthesized with a 5' phosphate group.

The actual detection (illustrated with CTR1):

N:

```
5'-CTTTCCTCAC-3' 5'-TAAGGTTCAAAGGTTCAAACGGATCCAAAAAAA-3'
           3'-GAGTGATTCCAAGTTTCCAAGTTTGCCTAGGTTTTTTTTTTTTTTTTTTTTTTTTT-5'-[1
```
(SEQ ID NO:76; SEQ ID NO:97; SEQ ID NO:98)

Steps involved in creation of the discriminating adapters in solution.

N: The ssDNA 10-mer and the immobilized discriminating adapter are ligated together.

O:

```
5'-CTTTCCTCACTAAGGTTCAAAGGTTCAAACGGATCCAAAAAAA-3'
           3'-GAGTGATTCCAAGTTTCCAAGTTTGCCTAGGTTTTTTTTTTTTTTTTTTTTTTTTT-5'-[1
```
(SEQ ID NO:76; SEQ ID NO:84)

M:
CTR1
(SEQ ID NO:81)
5'-GAAAGTCCCTGGAATGCCGGTTTCGTTTTTTTCGAAACCTTCATTCC
ATGGGA-3'

(SEQ ID NO:91)
TTTT-CGAAACCTTCATTCCAGGGA-3'

(SEQ ID NO:92)
|TTT-GCTTTGGAAGTAAGGTCCCT GAAAG-5'

CTR2
(SEQ ID NO:82)
5'-CCAGCGGAAGGTTTGGTCCCAATTTCGTGTTTTTTTACACGAAATT
GGGACCAAACCTTCC-3'

(SEQ ID NO:93)

O: The molecule resulting from ligating the ssDNA 10-mer and the immobilized discriminating adapter together.

```
TTTT-CGAAACCTTCATTCCAGGGA-3'
|TTT-GCTTTGGAAGTAAGGTCCCT-GAAAG-5'
```

(SEQ ID NO:91; SEQ ID NO:92)

```
5'-CTTTCCTCACTAAGGTTCAAAGGTTCAAACGGATCCAAAAAAA-3'
   3'-GAGTGATTCCAAGTTTCCAAGTTTGCCTAGGTTTTTTTTTTTTTTTTTTTTTTTTT-5'-[1
```

(SEQ ID NO:76; SEQ ID NO:84)

P: The discriminating adapter in solution is ligated to the molecule from O.

```
Q:
TTTTT-CGAAACCTTCATTCCAGGGACTTTCCTCACTAAGGTTCAAAGGTTCAAACGGATCAAAAAAA-3'

|TTT-GCTTTGGAAGTAAGGTCCCTGAAAGGAGTGATTCCAAGTTTCCAAGTTTGCCTAGGTTTTTT . . .TTTTT-5'-[1
```
(SEQ ID NO:87, composed of SEQ ID NO:100 (bottom sequence above), 5' to 3', and SEQ ID NO:99, top sequence above)

Q: The molecule resulting from ligating the discriminating adapter in solution to the molecule from O. This molecule is digested with Bam HI.

R:

(SEQ ID NO:101; SEQ ID NO:102)
```
TTTT-CGAAACCTTCATTCCAGGGACTTTCCTCACTAAGGTTCAAAGGTT
CAAACG-3'

|TTT-GCTTTGGAAGTAAGGTCCCTGAAAGGAGTGATTCCAAGTTTCCAA
GTTTGCCTAG 5'
```

(SEQ ID NO:88)
```
5'-GATCCGTTTG  AACCTTTGAA  CCTTAGTGAG  GAAAGTCCCT
   GGAATGAAGG  TTTCGTTTTT  TTCGAAACC   TTCATTCCAG
   GGACTTTCCT  CACTAAGGTT  CAAAGGTTCA  AACG-3'
```

R: After digestion with Bam HI a 114 bp molecule can be separated for polyacrylamide gel detection and quantification. When using identifying linkers with overhangs complementary to the ssDNA 10-mer tags tracing back to CTR2 and HAH the length of the molecules after this last digestion with Bam HI is 124, and 134 respectively.

What is claimed is:

1. Method for obtaining at least one single stranded polynucleotide tag from a biological sample, in a form suitable for further use of said tag, said method comprising the steps of
   i) providing at least one double stranded polynucleotide, wherein the polynucleotide is selected from the group of polynucleotides consisting of polynucleotides comprising complementary DNA (cDNA), polynucleotides comprising genomic DNA, and polynucleotides comprising extra-g-enomic DNA,
   ii) contacting and cleaving at least one of the complementary strands of the double stranded polynucleotide provided in step i) with at least one cleavage agent capable of recognizing a double stranded polynucleotide comprising complementary polynucleotide strands and cleaving only one of the strands of the polynucleotide provided in step i), thereby obtaining a nicked double stranded polynucleotide which comprises a single stranded polynucleotide tag, and thus obtaining at least one single stranded polynucleotide tag,
   (iii) isolating the tag, and retaining said tag for further use.

2. The method of claim 1, further comprising at least one of the following steps
   a) determining the sequence of the tag by direct analysis of said tag, or
   b) quantifying said tag; or
   c) hybridizing and/or ligating said tag to a polynucleotide molecule.

3. Method of claim 2, comprising the use of said tag in the further step of determining the sequence of the tag by direct analysis of the tag.

4. Method of claim 2, comprising the use of said tag in the further step of quantifying the tag.

5. Method of claim 1, wherein the single stranded polynucleotide tag comprises or essentially consists of deoxyribonucleic acid.

6. Method of claim 1, wherein the single stranded polynucleotide tag comprises only a single polynucleotide strand and no complementary strand, or a part thereof, capable of forming with the single stranded polynucleotide tag a double stranded polynucleotide comprising complementary polynucleotides, including any double stranded polynucleotide wherein at least a part of the double stranded polynucleotide consists of single, complementary polynucleotides.

7. Method of claim 1, wherein the single stranded polynucleotide tag comprises less than 20 nucleotides.

8. Method of claim 1, wherein the single stranded polynucleotide tag comprises 10 nucleotides.

9. Method of claim 7, wherein all of said nucleotides of the single stranded polynucleotide tag originate from a cDNA obtained from a biological sample, or from genomic DNA obtained from a biological sample, or from extragenomic DNA obtained from the biological sample.

10. Method of claim 1, wherein the cleavage agent capable of recognizing a double stranded polynucleotide comprising complementary polynucleotide strands and cleaving only one of the strands is a site-specific nicking endonuclease.

11. Method of claim 10, wherein the site-specific nicking endonuclease recognizes a recognition motif comprising the complementary polynucleotide strands 5'-GAGTC-3' 3'-CTCAG-5'.

12. Method of claim 10, wherein the site-specific nicking endonuclease is isolated from a strain of *Bacillus stearotherophilus*.

13. Method of claim 10, wherein the site-specific nicking endonuclease is isolated from a strain of *Bacillus stearothermophilus* 33M as provided by New England Biolabs.

14. Method of claim 1 for obtaining at least one single stranded polynucleotide tag from a biological sample, wherein the method comprises, prior to the step of obtaining at least one single stranded polynucleotide tag, the further step of contacting and cleaving
   a) the double stranded polynucleotide provided in step i), or
   b) the double stranded polynucleotide of step ii) contacted and cleaved in one strand by the at least one first cleavage agent, capable of recognizing a double stranded polynucleotide comprising complementary polynucleotide strands and cleaving only one of the strands of the polynucleotide with at least one second cleavage agent, capable of recognizing a double stranded polynucleotide comprising complementary polynucleotide strands and cleaving both of the strands of the polynucleotide, wherein the cleavage of only one strand, or both strands, of the double stranded polynucleotide occurs simultaneously, or sequentially in any order.

15. Method of claim 14, wherein the cleavage agent capable of recognizing a double stranded polynucleotide comprising complementary polynucleotide strands and cleaving both of the strands of the polynucleotide is a site-specific restriction endonuclease.

16. Method of claim 15, wherein the site-specific restriction endonuclease is selected from the group consisting of site-specific restriction endonucleases of type II recognizing and cleaving a double stranded polynucleotide within the location of a recognition motif.

17. Method of claim 15, wherein the site-specific restriction endonuclease is selected from the group consisting of site-specific restriction endonucleases of type IIs recognizing and cleaving a double stranded polynucleotide beyond the location of a recognition motif producing either 3' or 5' overhangs or blunt ends.

18. Method of claim 6, wherein the method comprises the further step of providing at least one adapter oligonucleotide comprising at least one recognition motif, or a part thereof, for at least one cleavage agent capable of recognizing a double stranded polynucleotide comprising complementary strands and cleaving a) only one complementary strand, or b) both of the complementary stands of the double stranded polynucleotide.

19. Method of claim 18, wherein the adapter oligonucleotide comprises or essentially consists of complementary strands comprising at least one recognition motif for at least on cleavage agent, wherein said motif comprises complementary polynucleotide strands.

20. Method of claim 18, wherein the adapter oligonucleotide comprises or essentially consists of a part of a recognition motif for at least one cleavage agent, wherein said part comprises a single oligonucleotide strand which, together with a complementary strand, forms a recognition motif for at least one cleavage agent.

21. Method of claim 18, wherein the adapter comprises at least two recognition motifs, or a single stranded part thereof, wherein at least one of said motifs are capable of binding a site-specific nicking endonuclease capable of recognizing a double stranded polynucleotide comprising complementary strands and cleaving only one complementary strand thereof.

22. Method of claim 21, wherein the adapter further comprises a recognition motif capable of binding a site-specific restriction endonuclease capable of recognizing a double stranded polynucleotide comprising complementary strands and cleaving both of the complementary stands of the double stranded polynucleotide.

23. Method of claim 22, wherein the recognition motif for the site-specific nicking endonuclease capable of recognizing a double stranded polynucleotide comprising complementary strands and cleaving only one complementary strand thereof forms part of the recognition motif for the site-specific restriction endonuclease capable of recognizing a double stranded polynucleotide comprising complementary strands and cleaving both of the complementary stands of the double stranded polynucleotide.

24. Method of claim 18 for obtaining at least one single stranded polynucleotide tag from biological sample, said method comprising the steps of
   i) providing at least one adapter oligonucleotide comprising
      a) at least one recognition motif for a least one site-specific nicking endonuclease, wherein said motif comprises a double stranded polyucleotide comprising complementary polynucleotide strands, or
      b) a part of a recognition motif for a least one site-specific nicking endonuclease, wherein said part comprises a single polynucleotide strand which, together with a complementary polynucleotide strand, forms a recognition motif for at least one site-specific nicking endonuclease,
   ii) further providing
      c) at least one ribonucleic acid obtained from the biological sample, or
      d) at least one double stranded polynucleotide fragment comprising complementary polynucleotide strands, wherein said double stranded polynucleotide is obtained by a method comprising the step of using the at least one ribonucleic acid provided in step iic) as a template for the synthesis of a polynucleotid strand complementary to the at least one ribonucleic acid, or
      e) at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide with at least one site-specific restriction endonuclease capable of recognizing a double stranded polynucleotide comprising complementary strands and cleaving both of said strands,
   iii) obtaining a double stranded chimeric polynucleotide comprising an adapter oligonucleotide part by
      iiia) linking together
         f) the at least one adapter oligonucleotide of step ia) comprising the at least one recognition motif for the at least one site-specific nicking endonuclease, wherein said motif comprises complementary strands,
      with either
         g) the at least one double stranded polynucleotide comprising complementary polynucleotide strands, wherein said double stranded polynucleotide is obtained by a method comprising the step of using the at least one ribonucleic acid provided in step iic) as a template for the synthesis of a polynucleotide strand complementary to the at least one ribonucleic acid, or
         h) the at least one double stranded genomic polynucleotide or the at least one double stranded extra-genomic polynucleotide of step iie),
   or
      iiib) obtaining a double stranded chimeric polynucleotide comprising an adapter oligonucleotide part by linking together
         i) at least one adapter oligonucleotide comprising a part of a recognition motif for a least one site-specific nicking endonuclease, wherein said part comprises a single oligonucleotide strand which, together with a complementary strand, forms a recognition motif for at least one site-specific nicking endonuclease,
      with
         j) the at least one ribonucleic acid obtained from the biological sample,
      and
         k) obtaining at least one double stranded chimeric polynucleotide comprising an adapter oligonucleotide part by using the chimeric polynucleotide obtained by linking together the adapter oligonucleotide of step iiibi) with the ribonucleic acid of step iiibj) as a template for the synthesis of a polynucleotide strand complementary to said chimeric polynucleotide, iv) contacting and cleaving the double stranded chimeric polynucleotide obtained in step iiia) or step iiib) with either iva) at least one site-specific nicking endonuclease capable of recognizing a double stranded polynucleotide comprising complementary polynucleotide strands and cleaving only one of said strands, or contacting and cleaving the double stranded chimeric polynucleotide obtained in step iiia) or step iiib) with ivb) a combination of
  a) at least one site-specific restriction endonuclease capable of recognizing a double stranded polynucleotide comprising complementary strands and cleaving both of said strands, and
  b) at least one site-specific nicking endonuclease capable of recognizing a double stranded polynucleotide comprising complementary polynucleotide strands and cleaving only one of said strands, wherein the contacting and cleaving of the double stranded chimeric polynucleotide performed with the combination of step ivb) occurs either simultaneously, or sequentially in any order, and v) isolating at least one single stranded polynucleotide tag.

25. Method of claim 24 for obtaining at least one single stranded polynucleotide tag from a biological sample, said method comprising the steps of i) providing at least one ribonucleic acid from the biological sample, ii) obtaining at least one double stranded polynucleotide comprising two complementary strands by using the at least one ribonucleic acid provided in step i) as a template for the synthesis of a polynucleotide strand complementary to the at least one ribonucleic acid, iii) providing at least one site-specific restriction endonuclease capable of recognizing a recognition motif comprised in the double stranded polynucleotide comprising complementary strands and cleaving the double stranded polynucleotide obtained in step ii) into at least two fragments, iv) contacting and cleaving the at least one double stranded polynucleotide obtained in step ii) with the at least one site-specific restriction endonuclease provided in step iii), v) obtaining at least one double stranded polynucleotide fragment by cleaving the at least one double stranded polynucleotide contacted with the at least one site-specific restriction endonuclease in step iv), vi) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded polynucleotide if fragment obtained in step v), vii) obtaining at least one chimeric polynucleotide by linking together the at least one double stranded polynucleotide fragment obtained in step v) and the at least one adapter oligonucleotide provided in step vi)

viii) providing at least one site-specific nicking endonuclease capable of recognizing a recognition motif comprised in the double stranded chimeric polynucleotide comprising complementary strands and cleaving only one of the complementary strands of the chimeric polynucleotide obtained in step vii), ix) contacting and cleaving the at least one chimeric polynucleotide obtained in step vii) with the at least one site-specific nicking endonuclease provided in step viii), and x) isolating at least one single stranded polynucleotide tag.

26. Method of claim 24 for obtaining at least one single stranded polynucleotide tag from a biological sample, said method comprising the steps of i) providing at least one ribonucleic acid from the biological sample, ii) obtaining at least one double stranded polynucleotide comprising two complementary strands by using the at least one ribonucleic acid provided in step i) as a template for the synthesis of a polynucleotide strand complementary to the at least one ribonucleic acid, iii) providing at least one site-specific restriction endonuclease capable of recognizing a recognition motif comprised in the double stranded polynucleotide comprising complementary strands and cleaving the double stranded polynucleotide obtained in step ii) into at least two fragments, iv) contacting and cleaving the at least one double stranded polynucleotide obtained in step ii) with the at least one site-specific restriction endonuclease provided in step iii), v) obtaining at least one double stranded polynucleotide fragment by cleaving the at least one double stranded polynucleotide contacted with the at least one site-specific restriction endonuclease in step iv), vi) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded polynucleotide fragment obtained in step v), vii) obtaining at least one double stranded chimeric polynucleotide by linking together the at least one double stranded polynucleotide fragment obtained in step v) and the at least one adapter oligonucleotide provided in step vi), viii) providing at least one further site-specific restriction endonuclease capable of recognizing a recognition motif comprised in the double stranded chimeric polynucleotide comprising complementary strands and cleaving both of the complementary strands of the chimeric polynucleotide provided in step vii), ix) contacting and cleaving the at least on chimeric polynucleotide obtained in step vii) with the at least one further site-specific restriction endonuclease provided in step viii), x) obtaining at least one chimeric polnucleotide fragment by cleaving the at least one chimeric polynucleotide contacted with the at least one further site-specific restriction endonuclease in step ix), xi) providing at least one site-specific nicking endonuclease capable of recognizing a recognition motif comprised in the double stranded chimeric polynucleotide fragment comprising complementary strands and cleaving only one of the complementary strands of the chimeric polynucleotide fragment obtained in step x), xii) contacting and cleaving the at least one chimeric polynucleotide fragment obtained in step x) with the at least one site-specific nicking endonuclease provided in step xi), and xiii) isolating at least one single stranded polynucleotide tag.

27. Method of claim 24 for obtaining at least one single stranded polynucleotide tag from biological sample, said method comprising the steps of i) providing at least one ribonucleic acid from the biological sample ii) providing at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, iii) obtaining at least one chimeric polynucleotide by linking together the at least one ribonucleic acid of step i) with the at least one adapter oligonucleotide of step ii)

iv) obtaining at least one double stranded chimeric polynucleotide comprising an adapter oligonucleotide part by using the chimeric polynucleotide of step iii) as a template for the synthesis of a polynucleotide strand complementary to said chimeric polynucleotide, v) providing at least one site-specific restriction endonuclease capable of recognizing a recognition motif comprised in the double stranded polynucleotide comprising complementary strands and cleaving the double stranded polynucleotide obtained in step iv) into at least two fragments, vi) contacting and cleaving the at least one double stranded chimeric polynucleotide obtained in step iv) with the at least one site-specific restriction endonuclease provided in step v), vii) obtaining at least one double stranded chimeric polynucleotide fragment by cleaving the at least one double stranded chimeric polynucleotide contacted with the at least one site-specific restriction endonuclease in step vi), viii) providing at least one site-specific nicking endonuclease capable of recognizing a recognition motif comprised in the double stranded chimeric polynucleotide fragment comprising complementary strands and cleaving only one of the complementary strands of the chimeric polynucleotide fragment obtained in step vii), ix) contacting and cleaving the at least one chimeric polynucleotide fragment obtained in step vii) with the at least one site-specific nicking endonuclease provided in step viii), and x) isolating at least one single stranded polynucleotide tag.

28. Method of claim 24 for obtaining at least one single stranded polynucleotide tag from a biological sample, said method comprising the steps of i) providing at least one ribonucleic acid from the biological sample, ii) providing at least one adapter oligonucleotide comprising a part of a recognition motif for at least one site-specific nicking endonuclease, wherein said part comprises a single oligonucleotide strand which, together with a complementary strand, forms a recognition motif for at least one site-specific nicking endonuclease, iii) obtaining at least one chimeric polynucleotide by linking together the at least one ribonucleic acid of step i) with the at least one adapter oligonucleotide of step ii), iv) obtaining at least one double stranded chimeric polynucleotide comprising an adapter oligonucleotide part by using the chimeric polynucleotide of step iii) as a template for the synthesis of a polynucleotide strand complementary to said chimeric polynucleotide, v) providing at least one site-specific nicking endonuclease capable of recognizing a recognition motif comprised in the double stranded chimeric polynucleotide comprising complementary strands and cleaving only one of the complementary strands of the chimeric polynucleotide obtained in step iv), vi) contacting and cleaving the at least on chimeric polynucleotide obtained in step iv) with the at least one site-specific nicking endonuclease provided in step v), and vii) isolating at least one single stranded polynucleotide tag.

29. Method of claim 24 for obtaining at least one single stranded polynucleotide tag from a biological sample, said method comprising the steps of i) providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide, respectively, with at least one site-specific restriction endonuclease capable of recognizing a double stranded polynucleotide comprising complementary strands and cleaving both of said strands, ii) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded genomic polynucleotide fragment, or the at least one double stranded extra-genomic polynucleotide fragment, provided in step i), iii) obtaining at least one chimeric polynucleotide by linking together the at least one double stranded genomic polynucleotide fragment, or the at least one double stranded extra-genomic polynucleotide fragment obtained in step i) and the at least one adapter oligonucleotide provided in step ii), iv) providing at least one site-specific nicking endonuclease capable of recognizing a recognition motif comprised in the double stranded polynucleotide comprising complementary strands and cleaving only one of the complementary strands of the at least one chimeric polynucleotide obtained in step iii), v) contacting and cleaving the at least one chimeric polynucleotide obtained in step iii) with the at least one site-specific nicking endonuclease provided in step iv), and vi) isolating at least one single stranded polynucleotide tag.

30. Method of claim 24 for obtaining at least one single stranded polynucleotide tag from a biological sample, said method comprising the steps of
  i) providing at least one double stranded genomic polynucleotide fragment, or at least one double stranded extra-genomic polynucleotide fragment, wherein said genomic polynucleotide fragment or extra-genomic polynucleotide fragment is obtained by cleaving a genomic polynucleotide or an extra-genomic polynucleotide, respectively, with at least one site-specific restriction endonuclease capable of recognizing a double stranded polynucleotide comprising complementary strands and cleaving both of said strands,
  ii) providing at least one adapter oligonucleotide comprising at least one recognition motif for at least one site-specific nicking endonuclease, wherein said motif comprises a double stranded oligonucleotide comprising complementary strands, wherein the adapter is capable of being linked together with the at least one double stranded genomic polynucleotide fragment, or the at least one double stranded extra-genomic polynucleotide fragment, provided in step i),
  iii) obtaining at least one chimeric polynucleotide by linking together the at least one double stranded genomic polynucleotide fragment, or the at least one double stranded extra-genomic polynucleotide fragment obtained in step i) and the at least one adapter oligonucleotide provided in step ii),
  iv) providing at least one further site-specific rrestriction endonuclease capable of recognizing a recognition motif comprised in the double stranded polynucleotide comprising complementary strands and cleaving both of the complementary strand of the at least one chimeric polynucleotide of step iii) obtained by linking together the at least one double stranded genomic polynucleotide fragment, or the at least one double stranded extra-genomic polynucleotide fragment, and the at least one adapter oligonucleotide provided in step ii),
  v) contacting and cleaving the at least one chimeric polynucleotide obtained in step iii) with the at least one further site-specific restriction endonuclease provided in step iv),
  vi) obtaining at least one chimeric polynucleotide fragment by cleaving the at least one chimeric polynucleotide contacted with the at least one further site-specific restriction endonuclease in step v),
  vii) providing at least one site-specific nicking endonuclease capable of recognizing a recognition motif comprised in the double stranded polynucleotide comprising complementary strands and cleaving only one of the complementary strands of the at least one chimeric polynucleotide fragment obtained in step vi),
  viii) contacting and cleaving the at least one chimeric polynucleotide fragment obtained in step vi) with the at least one site-specific nicking endonuclease provided in step vii), and
  ix) isolating at least one single stranded polynucleotide tag.

31. Method of claim 24, wherein the ribonucleic acid comprises mRNA.

32. Method of claim 31, wherein the ribonucleic acid comprises mRNA that is polyadenylated.

33. Method of claim 31, wherein the mRNA is present in mixture with nonpolyadenylated ribonucleic acids.

34. Method of claim 24, wherein the site-specific restriction endonuclease capable of recognizing complementary strands of a double stranded polynucleotide recognizes a motif comprising less than 7 nucleotides.

35. Method of claim 24, wherein the chimeric polynucleotide is obtained by means of ligation.

36. Method of claim 24 comprising the further step of contacting the double stranded polynucleotide with a site-specific methylase or methyltransferase.

37. Method of claim 36, wherein the site-specific methylase or methyltransferase methylates a recognition motif capable of being recognized by at least one of the site-specific endonucleases capable of recognizing a double stranded polynucleotide comprising complementary strands and cleaving either one or both of said strands.

38. Method of claim 24, wherein a methylated dCTP analog is substituted for an unmodifed dCTP in the synthesis reaction resulting in the synthesis of a complementary strand to the template.

39. Method of claim 1 comprising the further step of separating at least one single stranded polynucleotide tag from other single stranded polynucleotides and/or double stranded polynucleotides.

40. Method of claim 39 comprising the further steps of separating the at least one single stranded polynucleotide tag by forming a hybrid polynucleotide tag and/or a chimeric polynucleotide tag between at least one single stranded polynucleotide tag and a complementary, single stranded first unique nucleotide sequence of a first identifying linker oligonucleotide, said method comprising the steps of
  i) providing a sample, or a plurality of samples obtained by dividing a composition comprising a plurality of single stranded polynucleotide tags into at least about 16 samples,
  ii) contacting each of the plurality of samples, or a subset thereof, provided in step i) with a least one first identifying linker oligonucleotide, or a plurality of first identifying linker oligonucleotides,
    wherein each first identifying linker oligonucleotide comprises a single stranded first unique nucleotide sequence,
    wherein the at least one single stranded polynucleotide tag, or each of the plurality of single stranded polynucleotide tags, or a subset thereof, in each of the samples is contacted with essentially only one first identifying linker oligonucleotide comprising a single stranded first unique nucleotide sequence,
    wherein at least one single stranded polynucleotide tag in each sample comprises a polynucleotide sequence, or a part thereof, complementary to a single stranded first unique nucleotide sequence of at least one first identifying linker oligonucleotide contacting the sample,
    wherein the contacting of each of the plurality of samples, or a subset thereof provided in step i), with at least one or a plurality of first identifying linker oligonucleotides, occurs under conditions allowing a hybridization to occur between
      a) at least one first identifying linker oligonucleotide comprising a single stranded first unique nucleotide sequence, and
      b) at least one single stranded polynucleotide tag complementary to the single stranded first unique nucleotide sequence, and optionally
  iii) removing by means of one or more washing steps any unhybridized material from the hybrid polynucleotide tags and/or the chimeric polynucleotide tags formed between the single stranded polynucleotide tag and the complementary, single stranded first unique nucleotide sequence of the first identifying linker oligonucleotide.

41. Method of claim 40, wherein the plurality or subset of first identifying linker oligonucleotides is attached to a solid support.

42. Method of claim 41, wherein the solid support comprises a hybridization array in the form of an ordered plurality of first identifying linker oligonucleotides.

43. Method of claim 40, wherein substantially each tag is ligated to the first identifying linker oligonucleotide hybridized thereto.

44. Method of claim 43, wherein the ligation is an enzyme catalysed ligation.

45. Method of claim 40, wherein substantially each of the plurality or subset of first identifying linker oligonucleotides further comprises a molecular identifier capable of characterizing and/or separating the linker oligonucleotides and/or hybrid oligonucleotide tags according to i) the molecular weight and/or ii) charge and/or iii) an electromagnetic property and/or iv) an ability to emit electromagnetic radiation after excitation of individual linker oligonucleotides comprising individual molecular identifiers.

46. Method of claim 40, wherein substantially each of the plurality or subset of first identifying linker oligonucleotides further comprises a selectively detectable label capable of identifying substantially individual identifying linker oligonucleotides and/or hybrid oligonucleotide tags forming part of a plurality of such oligonucleotides, or a subset thereof.

47. Method of claim 40, wherein the maximum number of combinations of single stranded first unique nucleotide sequences is $4^n$, wherein n denotes the number of nucleotides in the unique nucleotide sequence.

48. Method of claim 40, wherein each sample comprising the at least one single stranded polynucleotide tag is located in a separate container.

49. Method of claim 40, wherein the at least one or a plurality of first identifying linker oligonucleotides comprises a recognition motif for a site-specific restriction endonuclease, wherein the recognition motif is correlated to the sequence of nucleotides in the single stranded first, unique nucleotide sequence.

50. Method of claim 49 comprising the further steps of
i) obtaining at least one or a plurality of chimeric polynucleotide tags comprising a first identifying linker oligonucleotide,
ii) contacting and cleaving the at least one or a plurality of chimeric polynucleotide tags comprising
   a) a single stranded polynucleotide tag and
   b) a complementary, single stranded first unique nucleotide sequence of a first identifying linker oligonucleotide with a site-specific restriction endonuclease capable of recognising the recognition motif, and
iii) obtaining at least one or a plurality of chimeric polynucleotide tag fragments, and optionally
iv) substituting a phosphate group and/or an OH-group at one or both ends of the single stranded polynucleotide tag with a molecular moiety preventing the substituted, single stranded polynucleotide tag from participating in a ligase reaction including a ligase chain reaction, and further optionally,
v) contacting at least one or a plurality of second identifying linker oligonucleotides each comprising a single stranded, unique second nucleotide sequence with the at least one or a plurality of chimeric polynucleotide tag fragments obtained in step iii).

51. Method of claim 50, wherein each recognition motif is recognised by a different site-specific restriction endonuclease.

52. Method of claim 50, wherein each recognition motif is recognised by the same site-specific restriction endonuclease.

53. Method of claim 50 and comprising the further step of contacting the at least one or a plurality of chimeric polynucleotide tags with a site-specific nicking endonuclease capable of recognising a recognition motif of the chimeric polynucleotide tag fragment and cleaving a single strand of said fragment and providing a single stranded polynucleotide tag.

54. Method of claim 40, wherein the at least one or a plurality of first identifying linker oligonucleotides comprises a recognition motif for a site-specific nicking endonuclease, wherein the recognition motif is correlated to the sequence of nucleotides in the single stranded first, unique nucleotide sequence.

55. Method of claim 54 comprising the further steps of
i) obtaining at least one or a plurality of chimeric polynucleotide tags comprising a first identifying linker oligonucleotide,
ii) contacting and cleaving the at least one or a plurality of chimeric polynucleotide tags comprising
   a) a single stranded polynucleotide tag and
   b) a complementary, single stranded first unique nucleotide sequence of a first identifying linker oligonucleotide with a site-specific nicking endonuclease capable of recognising the recognition motif, and
iii) obtaining at least one or a plurality of single stranded polynucleotide tags, and optionally
iv) substituting a phosphate group and/or an OH-group at one or both ends of the single stranded polynucleotide tag with a molecular moiety preventing the substituted, single stranded polynucleotide tag from participating in a ligase reaction including a ligase chain reaction, and further optionally,
v) contacting at least one or a plurality of second identifying linker oligonucleotides each comprising a single stranded, unique second nucleotide sequence with the at least one or a plurality of single stranded polynucleotide tags obtained in step iii).

56. Method of claim 55, wherein each recognition motif is recognised by a different site-specific nicking endonuclease.

57. Method of claim 55, wherein each recognition motif is recognised by the same site-specific nicking endonuclease.

58. Method of claim 55 and comprising the further step of contacting the at least one or a plurality of chimeric polynucleotide tags with a site-specific restriction endonuclease capable of recognising a recognition motif of the chimeric polynucleotide tag fragment and cleaving said fragment.

59. Method of claim 50, wherein the plurality or subset of second identifying linker oligonucleotides is attached to a solid support.

60. Method of claim 59, wherein the solid support comprises a hybridization array in the form of an ordered plurality of second identifying linker oligonucleotides.

61. Method of claim 50, wherein substantially each chimeric polynucleotide tag fragment is ligated to the second identifying linker oligonucleotide hybridized thereto.

62. Method of claim 61, wherein the ligation is an enzyme catalysed ligation.

63. Method of claim 50, wherein substantially each of the plurality or subset of second identifying linker oligonucleotides further comprises molecular identifier capable of characterizing and/or separating the linker oligonucleotides and/or hybrid oligonucleotide tags according to i) the molecular weight and/or ii) charge and/or iii) an electromagnetic property and/or iv) an ability to emit electromagnetic radiation after excitation of individual linker oligonucleotides comprising individual molecular identifiers.

64. Method of claim 50, wherein substantially each of the plurality or subset of second identifying linker oligonucleotides further comprises a selectively detectable label capable of identifying substantially individual identifying linker oligonucleotides and/or hybrid oligonucleotide tags and/or chimeric oligonucleotide tags forming part of a plurality of such oligonucleotides, or a subset thereof.

65. Method of claim 50, wherein the maximum number of combinations of single stranded second unique nucleotide sequences is $4^n$, wherein n denotes the number of nucleotides in the unique nucleotide sequence.

66. Method of claim 50, wherein each sample comprising the at least one single stranded polynucleotide tag is located in a separate container.

67. Method of claim 43 for determining the sequence of a part of a single stranded polynucleotide tag hybridized or ligated to an identifying linker oligonucleotide, said method comprising the further steps of i) contacting
  a) a solid support comprising a hybridization array comprising an ordered plurality of first identifying linker oligonucleotides comprising a single stranded first unique oligonucleotide sequence, with
  b) a sample comprising at least one single stranded polynucleotide tag, or a plurality of samples obtained by dividing a composition comprising a plurality of single stranded polynucleotide tags into at least about 16 samples,
  wherein each set of first identifying linker oligonucleotides comprising a single stranded first unique oligonucleotide sequence is identifiable by their location in the hybridization array,
  wherein essentially all possible combinations of single stranded first unique nucleotide sequences of first identifying linker oligonucleotides, or a subset of such combinations, are represented in the array,
  wherein at least one single stranded polynucleotide tag comprised in the sample is hybridized to a complementary single stranded first unique nucleotide sequences of a first identifying linker oligonucleotide,
  wherein the hybridization of the at least one single stranded polynucleotide tag to a complementary single stranded first unique nucleotide sequence occurs at an identifiable position in the hybridization array,
  wherein said hybridization generates a hybrid nucleotide tag comprising the at least one single stranded polynucleotide tag hybridized to a complementary single stranded first unique nucleotide sequence of a first identifying linker oligonucleotide, and optionally ii) determining the position in the hybridization array of the hybrid polynucleotide tag, by iii) correlating the position in the hybridization array of the hybrid polynucleotide tag with the corresponding single stranded first unique nucleotide sequence, and iv) determining the sequence of the part of the single stranded polynucleotide tag that is hybridized to the complementary single stranded first unique nucleotide sequence at the determined position in the hybridization array.

68. Method of claim 67, wherein substantially each tag is ligated to the first identifying linker oligonucleotide hybridized thereto.

69. Method of claim 68, wherein the ligation is an enzyme catalysed ligation.

70. Method of claim 67, wherein substantially each of the plurality or subset of first identifying linker oligonucleotides further comprises a molecular identifier capable of characterizing and/or separating the linker oligonucleotides and/or hybrid oligonucleotide tags and/or chimeric oligonucleotide tags according to i) the molecular weight and/or ii) charge and/or iii) an electromagnetic property and/or iv) an ability to emit electromagnetic radiation after excitation of individual linker oligonucleotides comprising individual molecular identifiers.

71. Method of claim 67, wherein substantially each of the plurality or subset of first identifying linker oligonucleotides further comprises a selectively detectable label capable of identifying substantially individual identifying linker oligonucleotides and/or hybrid oligonucleotide tags and/or chimeric oligonucleotides forming part of a plurality of such oligonucleotides, or a subset thereof.

72. Method of claim 67, wherein the maximum number of combinations of single stranded first unique nucleotide sequences is $4^n$, wherein n denotes the number of nucleotides in the unique nucleotide sequence.

73. Method of claim 67, wherein each sample comprising the at least one single stranded polynucleotide tag is located in a separate container.

74. Method of claim 43, wherein the method comprises the further steps of determining at least part of the sequence of the tag not hybridized to the single stranded, first unique nucleotide sequence of a first identifying linker oligonucleotide, said method comprising i) contacting at least one or a plurality of said hybrid or chimeric polynucleotide tags with at least one or a plurality of second identifying linker oligonucleotides,
  wherein each second identifying linker oligonucleotide comprises a single stranded, second unique oligonucleotide sequence,
  wherein the single stranded, unique second nucleotide sequence of each second identifying linker oligonucleotide comprises essentially all possible combinations of second oligonucleotide sequences, or a subset of such sequences,
  wherein each second identifying linker oligonucleotide further comprises at least one molecular identifier and/or at least one selectively detectable label capable of identifying the second identifying linker oligonucleotide,
  wherein the contacting of step i) occurs under conditions allowing a hybridization to occur between at least one of the second identifying linker oligonucleotides and at least one hybrid polynucleotide tag, and optionally removing any unhybridized second identifying linker oligonucleotide, ii) determining the presence and/or amount of any hybridized second identifying linker oligonucleotide comprising a second unique oligonucleotide sequence by means of detection of the label and/or the molecular identifier, and optionally iii) repeating steps i) and/or ii) until substantially all of the second identifying linker oligonucleotides in the hybridization array, or a predetermined subset thereof, have been tested.

75. Method of claim 40, wherein any hybridization step is followed by or performed simultaneously with a ligation step.

76. Method of claim 75, wherein the ligation is an enzyme catalysed ligation.

77. Method for amplification of a hybrid polynucleotide tag obtainable by claim 40, wherein the method comprises the steps of
  i) obtaining at least one hybrid polynucleotide tag or at least one chimeric polynucleotide tag comprising
    a) a single stranded polynucleotide tag hybridized or ligated to one or both of
    b) a first identifying linker oligonucleotide comprising a single stranded, first unique oligonucleotide sequence, and
    c) a second identifying linker oligonucleotide comprising a single stranded, second unique oligonucleotide sequence
    wherein said first identifying linker oligonucleotide and said second identifying linker olignucleotide comprises single stranded nucleotide sequences complementary to at least a part of the nucleotide sequence of the single stranded polynucleotide tag, and
  ii) amplifying the at least one hybrid or chimeric polynucleotide tag.

78. Method of claim 77, wherein the amplification comprises a polymerase chain reaction (PCR) step, including a reaction step comprising an asymmetric PCR, and/or a ligase chain reaction (LCR) step, including a reaction step comprising an asymmetric LCR.

79. Method for identifying a cDNA in a biological sample, said method comprising the steps of any of the methods for obtaining and characterizing a single stranded polynucleotide tag according to claim 40, said method comprising the further steps of
  i) comparing for at least one of a plurality of predetermined positions in a hybridization array, or for at least one of a plurality of predetermined positions in a capilary tube of a microfluid device,
    a) the sequence of the at least one single stranded polynucleotide tag and/or the amount of the at least one single stranded polynucleotide tag with
    b) the sequence and/or amount of a predetermined polynucleotide tag obtained from a predetermined cDNA, and
  ii) identifying a cDNA present in the biological sample.

80. A method for diagnosing a clinical condition, said method comprising the step of
  i) determining for at least one of a plurality of predetermined positions in a hybridization array, or for at least one of a plurality of predetermined positions in a capilary tube of a microfluid device, at least one predetermined cDNA in a biological sample by performing a method according to claim 40,
    wherein each of the first identifying linker oligonucleotides comprises a predetermined single stranded, first unique oligonucleotide sequence,
    wherein each of the second identifying linker oligonucleotides comprises a predetermined single stranded, second unique oligonucleotide sequence,
    wherein at least one of said first and second identifying linker oligonucleotides comprises at least one selectively detectable molecular identifier and/or at least one selectively detectable label,
    wherein the predetermined cDNA is determined by assaying for a predetermined polynucleotide tag originating from said predetermined cDNA,
    wherein the predetermined polynucleotide tag originating from said predetermined cDNA comprises a nucleotide sequence complementary to the sequence of the first and second identifying linker oligonucleotides,
    wherein the at least one predetermined postion in the hybridization array, or the at least one predetermined position in the capilary tube of a microfluid device, in combination with the determination of the at least one selectively detectable molecular identifier and/or the at least one selectively detectable label comprised by at least one of said first and second identifying linker oligonucleotides, is positively correlated with the presence in the biological sample of the at least one predetermined cDNA, and
  ii) diagnosing the clinical condition.

81. Method of claim 1, wherein at least one cleavage agent is attached to a solid support.

82. Method of claim 35, wherein a ligation step is carried out by using a ligase that is attached to a solid support.

83. Method of claim 81, wherein solid support is a capillary tube with a diameter of less than 1 mm.

84. Method of claim 83, wherein the solid support is a capillary tube with a diameter less than 0.1 mm.

85. Method of claim 81 wherein the solid support forms part of the inside of a chamber of a microfluid device.

86. Method of claim 55, wherein the plurality or subset of second identifying linker oligonucleotides is attached to a solid support.

87. Method of claim 55, wherein the solid support comprises a hybridization array in the form of an ordered plurality of second identifying linker oligonucleotides.

88. Method of claim 55, wherein substantially each chimeric polynucleotide tag fragment is ligated to the second identifying linker oligonucleotide hybridized thereto.

89. Method of claim 55, wherein the ligation is an enzyme catalysed ligation.

90. Method of claim 55, wherein substantially each of the plurality or subset of second identifying linker oligonucleotides further comprises a molecular identifier capable of characterizing and/or separating the linker oligonucleotides and/or hybrid oligonucleotide tags according to i) the molecular weight and/or ii) charge and/or iii) an electromagnetic property and/or iv) an ability to emit electromagnetic radiation after excitation of individual linker oligonucleotides comprising individual molecular identifiers.

91. Method of claim 55, wherein substantially each of the plurality or subset of second identifying linker oligonucleotides further comprises a selectively detectable label capable of identifying substantially individual identifying linker oligonucleotides and/or hybrid oligonucleotide tags and/or chimeric oligonucleotide tags forming part of a plurality of such oligonucleotides, or a subset thereof.

92. Method of claim 55, wherein the maximum number of combinations of single stranded second unique nucleotide sequences is $4^n$, wherein n denotes the number of nucleotides in the unique nucleotide sequence.

93. Method of claim 55, wherein each sample comprising the at least one single stranded polynucleotide tag is located in a separate container.

94. Method of claim 2, comprising the further step of quantifying the tag.

95. Method of claim 3, comprising the further step of quantifying the tag.

96. Method of claim 82, wherein the solid support forms part of the inside of a chamber of a microfluid device.

97. Method of claim 8, wherein all of said nucleotides of the single stranded polynucleotide tag originate from a cDNA obtained from the biological sample, or from genomic DNA obtained from the biological sample, or from extra-genomic DNA obtained from the biological sample.

98. Method of claim 15 in which the first cleavage agent is a site specific nicking endonuclease.

99. The method according to claim 40, wherein the sample comprises at least one single stranded polynucleotide tag.

100. Method of claim 99 wherein each sample is contacted with essentially all possible combinations of single stranded first unique nucleotide sequences of the first identifying linker oligonucleotide, or a predetermined subset of such combinations.

* * * * *